(12) United States Patent
Tobin et al.

(10) Patent No.: US 12,359,212 B2
(45) Date of Patent: Jul. 15, 2025

(54) RECOMBINANT MICELLE AND METHOD OF IN VIVO ASSEMBLY

(71) Applicant: Mozza Foods, Inc., Los Angeles, CA (US)

(72) Inventors: Cory J. Tobin, Pasadena, CA (US); Noah Brookes, Los Angeles, CA (US)

(73) Assignee: Mozza Foods, Inc., Los Angeles, CA (US)

( * ) Notice: Subject to any disclaimer, the term of this patent is extended or adjusted under 35 U.S.C. 154(b) by 395 days.

(21) Appl. No.: 17/826,021

(22) Filed: May 26, 2022

(65) Prior Publication Data

US 2022/0290167 A1 Sep. 15, 2022

Related U.S. Application Data

(63) Continuation-in-part of application No. 17/717,000, filed on Apr. 8, 2022, now Pat. No. 11,718,856, which is a continuation of application No. 16/741,680, filed on Jan. 13, 2020, now Pat. No. 11,326,176.

(60) Provisional application No. 63/281,069, filed on Nov. 18, 2021, provisional application No. 62/939,247, filed on Nov. 22, 2019.

(51) Int. Cl.
*C12N 15/82* (2006.01)
*B01D 61/14* (2006.01)

(52) U.S. Cl.
CPC ....... *C12N 15/8202* (2013.01); *B01D 61/145* (2013.01); *B01D 61/146* (2022.08); *B01D 61/147* (2013.01); *C12N 15/8218* (2013.01); *B01D 2315/16* (2013.01)

(58) Field of Classification Search
CPC .................................................. B01D 61/146
See application file for complete search history.

(56) References Cited

U.S. PATENT DOCUMENTS

| | | | |
|---|---|---|---|
| 4,518,616 A | 5/1985 | Czulak | |
| 5,015,580 A | 5/1991 | Christou et al. | |
| 5,159,135 A | 10/1992 | Umbeck | |
| 5,378,619 A | 1/1995 | Rogers | |
| 5,491,084 A | 2/1996 | Chalfie et al. | |
| 5,538,880 A | 7/1996 | Lundquist et al. | |
| 5,547,870 A | 8/1996 | Datta et al. | |
| 5,550,318 A | 8/1996 | Adams et al. | |
| 5,591,616 A | 1/1997 | Hiei et al. | |
| 5,599,670 A | 2/1997 | Jefferson | |
| 5,633,435 A | 5/1997 | Barry et al. | |
| 5,780,708 A | 7/1998 | Lundquist et al. | |
| 5,824,877 A | 10/1998 | Hinchee et al. | |
| 6,118,047 A | 9/2000 | Anderson et al. | |
| 6,153,812 A | 11/2000 | Fry et al. | |
| 6,160,202 A | 12/2000 | Bustos et al. | |
| 6,160,208 A | 12/2000 | Lundquist et al. | |
| 6,194,636 B1 | 2/2001 | McElroy et al. | |
| 6,232,526 B1 | 5/2001 | McElroy et al. | |
| 6,288,312 B1 | 9/2001 | Christou et al. | |
| 6,384,301 B1 | 5/2002 | Martinell et al. | |
| 6,399,861 B1 | 6/2002 | Anderson et al. | |
| 6,541,682 B1 | 4/2003 | Nehra et al. | |
| 6,603,061 B1 | 8/2003 | Armstrong et al. | |
| 6,632,468 B2 | 10/2003 | Morgan et al. | |
| 7,417,178 B2 | 8/2008 | Huang et al. | |
| 9,924,728 B2 | 3/2018 | Pandya et al. | |
| 10,894,812 B1 | 1/2021 | Lanquar et al. | |
| 10,947,552 B1 | 3/2021 | Lanquar et al. | |
| 10,988,521 B1 | 4/2021 | Lanquar et al. | |
| 11,034,743 B1 | 6/2021 | Lanquar et al. | |
| 11,072,797 B1 | 7/2021 | Lanquar et al. | |
| 11,076,615 B2 | 8/2021 | Pandya et al. | |
| 11,142,555 B1 | 10/2021 | Lanquar et al. | |
| 11,172,691 B2 | 11/2021 | Kizer et al. | |
| 11,326,176 B2 | 5/2022 | Tobin | |
| 11,401,526 B2 | 8/2022 | Lanquar et al. | |
| 11,457,649 B2 | 10/2022 | Pandya et al. | |
| 2003/0044503 A1 | 3/2003 | Morgan et al. | |
| 2004/0111766 A1 | 6/2004 | Huang et al. | |
| 2004/0172682 A1 | 9/2004 | Kinney et al. | |
| 2004/0216189 A1 | 10/2004 | Houmard et al. | |
| 2005/0166289 A1 | 7/2005 | Chuan Chiang et al. | |
| 2005/0172356 A1 | 8/2005 | Christeller et al. | |
| 2010/0048464 A1 | 2/2010 | Recio Sanchez et al. | |
| 2010/0223682 A1 | 9/2010 | Katz et al. | |
| 2010/0313307 A1 | 12/2010 | Herman et al. | |

(Continued)

FOREIGN PATENT DOCUMENTS

| | | |
|---|---|---|
| CN | 101305017 A | 11/2008 |
| CN | 101600358 A | 12/2009 |

(Continued)

OTHER PUBLICATIONS

Zhang et al Secretory kinase Fam20C tunes endoplasmic reticulum redox state via phosphorylation of Ero1alpha The EMBO Journal 37:1-16 (Year: 2018).*
Philip et al.: Processing and localization of bovine beta-casein expressed in transgenic soybean seeds under control of a soybean lectin expression cassette. Plant Sci. 161(2):323-335 doi:10.1016/s0168-9452(01)00420-4 (2001).
U.S. Appl. No. 17/717,000 Non-Final Office Action dated Feb. 1, 2023.
Co-pending U.S. Appl. No. 17/717,000, filed Apr. 8, 2022.
PCT/US2020/056449 International Search Report and Written Opinion dated Feb. 3, 2021.
Co-pending U.S. Appl. No. 17/890,172, inventor Tarshis; Adam, filed Aug. 17, 2022.
Hettinga et al.: Can recombinant milk proteins replace those produced by animals? Current Opinion in Biotechnology 75:102690; pp. 1-6 (2022).

(Continued)

Primary Examiner — Brent T Page

(57) ABSTRACT

A plant cell co-expressing at least one casein protein and at least one kinase. The at least one casein protein is phosphorylated by the at least one kinase in vivo. Casein micelles comprising phosphorylated κ-casein and at least one of αS1-casein, αS2-casein, and β-casein can be made in vivo and/or in vitro. The casein micelles can be used to make food products including milk and cheese.

7 Claims, 22 Drawing Sheets

Specification includes a Sequence Listing.

(56) References Cited

U.S. PATENT DOCUMENTS

| | | |
|---|---|---|
| 2011/0293813 A1 | 12/2011 | Cavallini et al. |
| 2012/0219600 A1 | 8/2012 | Perumal et al. |
| 2013/0065824 A1 | 3/2013 | De Kort et al. |
| 2013/0295646 A1 | 11/2013 | Lejars et al. |
| 2014/0127358 A1 | 5/2014 | Brown et al. |
| 2014/0366218 A1 | 12/2014 | Li |
| 2014/0370110 A1 | 12/2014 | Perumal et al. |
| 2016/0168198 A1 | 6/2016 | Govindappa et al. |
| 2016/0257730 A1 | 9/2016 | Mayfield et al. |
| 2017/0164632 A1 | 6/2017 | Pandya et al. |
| 2017/0273328 A1 | 9/2017 | Pandya et al. |
| 2018/0291392 A1* | 10/2018 | El-Richani ............... A23J 1/00 |
| 2019/0216106 A1 | 7/2019 | Geistlinger et al. |
| 2019/0382781 A1 | 12/2019 | Shoseyov et al. |
| 2021/0010017 A1 | 1/2021 | El-Richani et al. |
| 2021/0030014 A1 | 2/2021 | Brown et al. |
| 2021/0037849 A1 | 2/2021 | Pandya et al. |
| 2021/0115456 A1 | 4/2021 | Mason et al. |
| 2021/0198693 A1 | 7/2021 | Mason et al. |
| 2021/0235714 A1 | 8/2021 | Geistlinger et al. |
| 2022/0098259 A1 | 3/2022 | Lanquar et al. |
| 2022/0169690 A1 | 6/2022 | Lanquar et al. |
| 2022/0211061 A1* | 7/2022 | Geistlinger ............ A61P 37/00 |
| 2022/0372504 A1 | 11/2022 | Lanquar et al. |
| 2022/0378058 A1 | 12/2022 | Ghandi et al. |
| 2022/0378723 A1 | 12/2022 | Wang et al. |
| 2023/0000100 A1 | 1/2023 | Zahn et al. |
| 2023/0034320 A1 | 2/2023 | Aharoni et al. |
| 2023/0141532 A1 | 5/2023 | Gibson et al. |
| 2023/0203556 A1 | 6/2023 | Lanquar et al. |
| 2023/0212594 A1 | 7/2023 | Tobin |
| 2023/0407319 A1 | 12/2023 | Tobin |

FOREIGN PATENT DOCUMENTS

| | | |
|---|---|---|
| CN | 102883623 A | 1/2013 |
| EP | 4060045 A1 | 9/2022 |
| WO | WO-2013148331 A1 | 10/2013 |
| WO | WO-2021050759 A2 | 3/2021 |
| WO | WO-2021101647 A1 | 5/2021 |
| WO | WO-2023002061 A2 | 1/2023 |

OTHER PUBLICATIONS

Kim et al.: Effects of proteome rebalancing and sulfur nutrition on the accumulation of methionine rich σ-zein in transgenic soybeans. Frontiers in Plant Science, vol. 5 Article 633 (1- 12) 2014.QI: Studies of casein micelle structure: the past and the present. Lait 87 (2007) 363-383 (2007) [Article published by EDP Sciences and available at http://www.lelait-journal.org ].

Sood et al.: Formation of Reconstituted Casein Micelles with Human β-Caseins and Bovine κ-Casein. J. Dairy Sci. 85:472-477 (2002).

U.S. Appl. No. 17/717,000 Final Office Action dated May 10, 2023.

U.S. Appl. No. 63/281,069, inventors Tobin; Cory J. et al., filed Nov. 18, 2021.

U.S. Appl. No. 63/331,460, inventors T; Cory J. et al., filed Apr. 15, 2022.

U.S. Appl. No. 63/376,223, inventors Johnson; Brady et al., filed Sep. 19, 2022.

U.S. Appl. No. 17/717,000 Notice of Allowance dated Jun. 14, 2023.

U.S. Appl. No. 18/456,080 Office Action dated Nov. 7, 2023.

Philip et al.: Processing and localization of bovine beta-casein expressed in transgenic soybean seeds under control of a soybean lectin expression cassette. Plant Sci. [Abstract Only] 161(2):323-335 doi:10.1016/s0168-9452(01)00420-4 (2001).

* cited by examiner

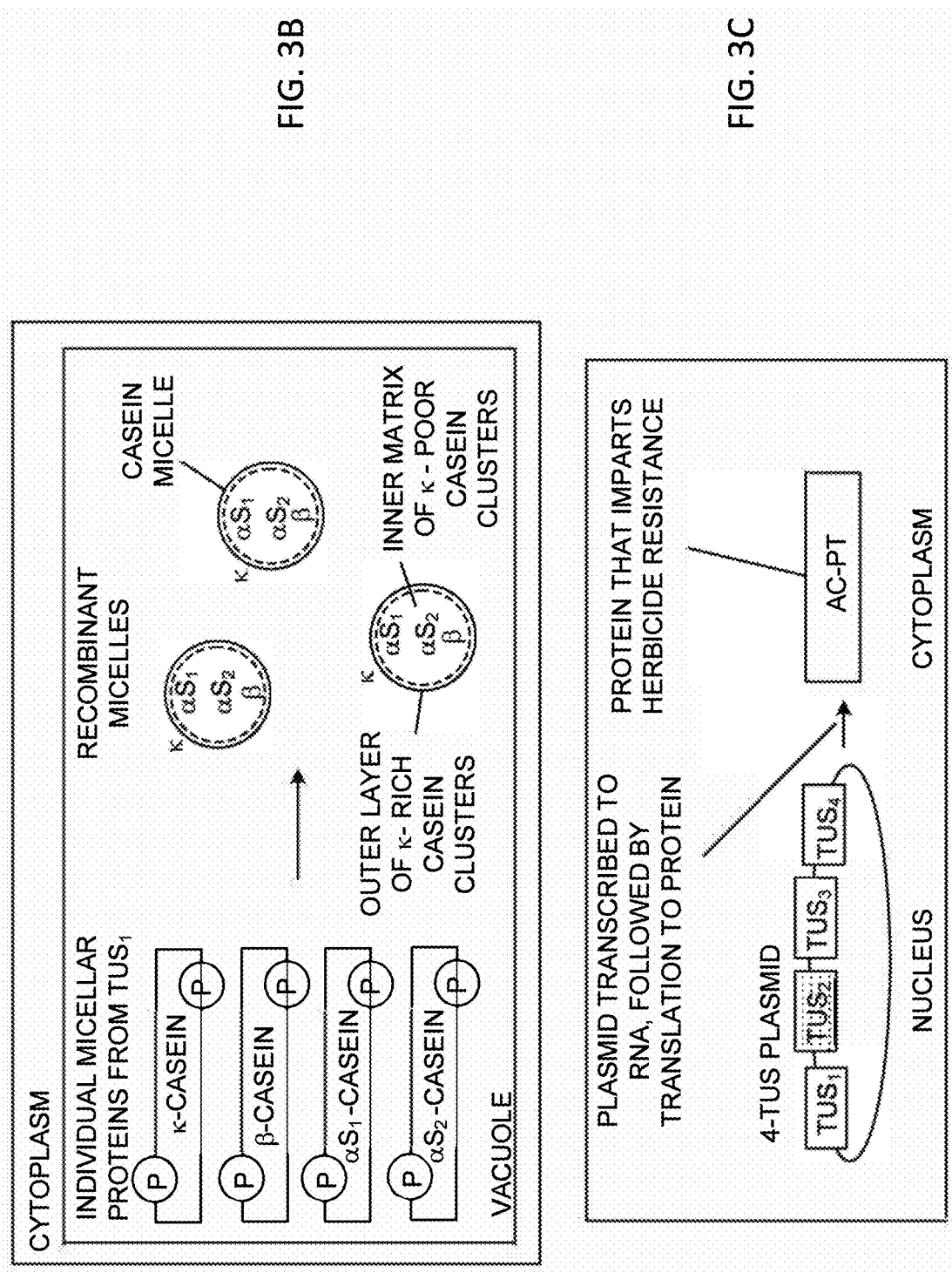

SEQUENCE LISTING

```
<160> NUMBER OF SEQ ID NOS: 96

<210> SEQ ID NO 1
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Codon optimized

<400> SEQUENCE: 1
aggcccaagc acccatcaa gcatcagggg ttgccacagg aagtcctcaa tgaaaatctg      60
ctgaggttct tcgtggctcc tttcccagaa gttttcggaa aggaaaaagt taacgagctc    120
agcaaagaca tcggctctga atccaccgaa gaccaagcaa tggaggacat taagcaaatg    180
gaagctgaga gtatatcctc atccgaagaa atcgtcccaa acagcgtaga acaaaagcat    240
attcagaaag aagatgttcc tagtgaaaga tacctcgggt atttggagca acttctgaga    300
ctgaaaaagt acaaagtgcc ccagctcgag atcgttccaa actccgccga agaacgtctg    360
catagtatga aggaggggat acatgcacaa cagaaggaac ccatgatcgg agttaaccag    420
gaactcgctt acttctaccc tgaactcttc aggcagtttt atcagcttga cgcttatccc    480
tccggtgctt ggtactatgt accacttgga acacaataca cagacgcacc atcattttct    540
gacataccca accctatcgg gtctgagaac agtgaaaaaa caacaatgcc tctgtggtaa    600

<210> SEQ ID NO 2
<211> LENGTH: 510
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Codon optimized
```

<400> SEQUENCE: 2

```
caggagcaga accaagaaca acctatcagg tgcgaaaagg atgagaggtt cttttccgat    60
aaaattgcaa agtacattcc tattcaatat gtactgtctc gctacccag ttatggactt    120
aactactacc aacagaaacc cgttgccctt ataaacaatc agttcctccc ttatccttac    180
tatgcaaagc tgctgccgt gcgtagtccc gcacagattc tccagtggca ggttctcagc    240
aatactgttc ccgcaaaaag ctgtcaggct caacctacta ctatggcacg tcatcctcac    300
ccccatttga gctttatggc catccctcca agaagaacc aagataagac tgaaatccca    360
actataaaca caatcgcatc cggggagcct acctctactc ccactattga ggctgtcgaa    420
tctactgttg caactttgga agctagtccc gaagtcaccg agagcccccc tgagatcaac    480
accgtacagg ttacatctac cgctgtatga                                     510
```

<210> SEQ ID NO 3
<211> LENGTH: 630
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Codon optimized

<400> SEQUENCE: 3

```
agggagctgg aagagctgaa cgtccctggc gaaatagtag agtccctcag ctcatcagaa    60
gagtccatta ctcgtattaa caaaaagatt gaaaagtttc agtcagaaga gcaacaacag    120
actgaggacg aactccaaga caagattcac cctttcgcac agacacagag tctggtctac    180
ccatttcctg gtcctattcc caattccctt ccccagaata tacctcccct cacccagact    240
cctgtggtgg tccccccatt cctccaacca gaggttatgg gtgtttctaa agtcaaagaa    300
gcaatggccc ctaagcacaa agagatgcca ttccccaagt atcccgttga gcccttacc    360
gagtctcaga gccttacact gaccgacgta gaaaatctcc atctcccact cccattgttg    420
caatcttgga tgcaccagcc ccatcagcct ttgcccccta ctgtcatgtt ccccccccag    480
agtgttctgt ccttgagcca agcaaagtg ctccctgtgc cccagaaagc cgtaccttat    540
ccccaaagag acatgccaat acaggccttt tgctctacc aggagcctgt tctcggtccc    600
gtaagaggcc ctttccctat catcgtgtag                                     630
```

<210> SEQ ID NO 4
<211> LENGTH: 624
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Codon optimized

<400> SEQUENCE: 4

```
aaaaacacta tggagcacgt aagctcatcc gaggagagta taatctccca ggaaacatat    60
aaacaagaaa aaatatggc aattaaccca tccaaggaaa acctgtgttc cacctttttgt   120
aaggaagtcg tgcgtaatgc taatgaagaa gagtattcaa tcggctccag ttcagaggag    180
tctgcagaag tagccacaga ggaggttaag attactgttg atgataaaca ctaccaaaag    240
gcccttaacg agataaatca gttctatcaa aaatttcctc aatatttgca atacttgtat    300
```

```
cagggaccta ttgttctcaa tccttgggat caggttaagc gtaacgccgt accaattaca    360
ccaactctca acagggagca gctcagcacc tccgaggaaa actccaaaaa gacagtggat    420
atggagtcaa ctgaggtctt cacaaaaaag acaaagctca ccgaggaaga aagaacaga    480 ctcaactttt tgaaaaaaat atcacaaaga taccaaaagt ttgcactgcc ccaatatctc    540
aagactgttt accaacacca aaaggctatg aagccctgga ttcaaccaaa gaccaaagtc    600 atacccctacg tgaggtattt gtaa                                         624
```

```
<210> SEQ ID NO 5
<211> LENGTH: 612
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Codon optimized

<400> SEQUENCE: 5
cgtccgaaac atccaatcaa gcaccaaggc ctcccacagg aggtcctcaa cgaaaacctt    60
ttacgttttt ttgtggcacc cttccctgag gtcttcggaa aggaaaaagt gaatgaactt    120
tcaaaggaca ttggcagcga atccacggaa gaccaggcga tggaggatat taagcagatg    180
gaggctgaaa gtattagctc ttccgaggag atagttccta attccgtgga acaaaagcac    240
attcaaaaag aggatgtccc gagtgagaga tacctgggct atctcgaaca gcttctgaga    300
ctaaaaaagt ataaggtccc gcaactggaa attgttccaa atagcgccga agaaaggtta    360
cattccatga agaaggcat tcatgctcag caaaaggaac ctatgatcgg agtaaaccag    420
gaacttgcct atttttaccc ggagttgttc cgtcagttct atcagttgga tgcatacca    480 tcaggggcat ggtactatgt acctctcggt acccaataca cggacgctcc ttctttctcc    540 gatatacccca atcccatagg tagcgaaaac tctgagaaaa caactatgcc cctctggcat    600
gacgaacttt ag                                                       612
```

```
<210> SEQ ID NO 6
<211> LENGTH: 522
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Codon optimized

<400> SEQUENCE: 6
caagaacaga atcaggagca acccattagg tgtgagaagg acgaaaggtt ttttttcagac    60 aaaatcgcga aatacatacc tattcagtac gttctcagca gatacccag ttatggactt    120 aactactacc agcaaaagcc tgtggcattg ataaataacc agttccttcc gtacccgtac    180
tatgcgaaac cggcagcggt acgaagccca gcccagattt gcaatggca ggtattgagt    240 aacaccgtcc cggcgaaaag ttgtcaagcg caaccgacca caatggcccg acaccccgcat    300 ccacatctca gcttcatggc aatcccaccc aagaaaaacc aagataaaac tgaaataccg    360
acaataaaca ctatagcttc aggcgagcca actagcacac ccactattga agcggtagag    420
agtacggtcg caaccctaga ggcaagcccg gaagtgactg aatctccgcc ggaaattaac    480
accgtccagg taacctcaac agcggttcat gacgaactct ag                       522
```

<210> SEQ ID NO 7
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Codon optimized

<400> SEQUENCE: 7

```
cgtgaactag aagagcttaa tgtgcctggt gagatagtcg aaagtttgtc cagctcagaa      60
gaatcaatta cacgtatcaa caaaaaaata gaaaagtttc aatctgagga acaacaacag     120
acagaggacg aattacaaga taaaatacac ccatttgctc agacgcaaag cttagtctat     180
ccattcccag gaccaattcc gaatagctta cctcaaaaca tcccgccgct cacgcagacc     240
cctgtagtcg tgccgccgtt tttacaaccc gaggtcatgg gcgtcagcaa ggtaaaagag     300
gcaatggctc ctaagcataa ggagatgcct ttccctaaat atcccgtcga gcctttcacc     360
gagagccaat ctttaacctt aacggacgta gagaacctac atcttcctct accactgtta     420
caatcctgga tgcatcagcc gcaccaacct cttcccccta cagtaatgtt cccccccgcag    480 tccgtcctat ctctctctca atccaaggtc ctaccagttc ctcagaaggc tgtcccctac     540
cctcagcgag acatgccgat ccaggctttc ttgctatacc aagagccggt actaggccct     600
gtccgagggc cgtttccgat aattgtccac gatgaactt                            639
```

<210> SEQ ID NO 8
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Codon optimized

<400> SEQUENCE: 8

```
aaaaacacta tggagcatgt gagcagctct gaggagtcca ttatatccca ggaaacatat      60
aaacaagaaa agaacatggc tattaacccg tcaaaggaga atctgtgttc cacgttctgt     120
aaggaagtgg tgaggaacgc taatgaggaa gagtactcaa tcggcagttc atccgaagaa     180
tctgctgagg tggcgacaga agaagttaag attactgtcg acgacaaaca ctaccagaag     240
gccctaaatg agataaatca attttatcag aagttcccgc agtatttgca atatctatat     300
caggggccaa tcgttctcaa tccatgggat caggtgaaaa gaaacgcagt acctatcaca     360
cctacgctga acagggaaca actgagcacc tctgaggaaa actcaaaaaa gaccgtagac     420
atggagtcca ctgaggtctt taccaagaaa acaaagctaa cagaggagga gaaaaatcga     480
ctgaattttc tgaagaaaat cagccagcgt tatcaaaagt tcgctctccc tcagtaccta     540
aagacggtat atcaacacca aaaagctatg aagccgtgga tacagcccaa gacgaaagtg     600
attccatacg tgcgttatct tcacgatgaa ttatag                               636
```

<210> SEQ ID NO 9
<211> LENGTH: 675
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Codon optimized

<400> SEQUENCE: 9

```
atgggttact ctaagacact ggttgctggc ctgtttgcca cacttctgct ggctcccgtg      60
gtgttggcca ctgatcccga tccacttcaa gacttctgcg tagctgacct cgatggtaaa     120
gctgtaagtg tcaacggcca tccttgcaag ccaatgtcaa aagcagggga cgatttcttg     180
ttttcctcta aactggctaa agctggtaac acttccaccc ctaatggtag tgctgtgaca     240
gagcttgacg ttgcagaatg gcccggaact aacactttgg gagtcagtat gaaccgtgtc     300
gattttgccc tgggggggac aaatccacct catattcacc cacgtgccac agaaattggc     360
atagtcatga agggcgaact tctcgtgggc atccttggca gcttggactc aggcaataaa     420
ctttattccc gcgtagtcag ggccggtgag actttcttga ttcccagggg actgatgcac     480
ctgcagttca acgtaggaaa aactgaagcc agtatggtag tctccttcaa ttctcaaaat     540
cccggtattg tgttcgtccc cctcactctg ttctcctcta acccccccaat cccaactccc    600
gtacttacca aggctcttag agtcgaggct ggagttgtag agctgttgaa gtcaaagttt     660
gcagccggat tttaa                                                      675
```

<210> SEQ ID NO 10
<211> LENGTH: 176
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: This sequence has elements from Arabidopsis thaliana and Glycine max.

<400> SEQUENCE: 10

```
agagccagag agcagcctca gcaaaacagg tcgtgatatg attcaattag cttccgactc      60
attcatccaa ataccgagtc gccaaaattc aaactagact cgttaaatga atgaatgatg     120
cggtagacaa attggatcat tgattctctt tgatttgctg aggctgctct ctggct         176
```

<210> SEQ ID NO 11
<211> LENGTH: 1644
<212> TYPE: DNA
<213> ORGANISM: Glycine max

<400> SEQUENCE: 11

```
atggcgtcaa ttacttttttc tcttcttcaa tttcatcgtg ctcctattct tctgctaatt      60
ctgctcgcgg gtttcggtca ctgccatatt ccgtcaaccc tcgaaggtcc ctttgatccc     120
gtcaccgttc cgttcgaccc cgccttgcgc ggcgtcgccg tcgacttgcc ggaaaccgat     180
cctcgagttc gccgccgcgt ccgggggttt c gagcccgaac agatttcggt ttctctctct     240
acctcccatg actccgtttg gatatcttgg gttacagggg agttccaaat aggtctcgac     300
atcaagccctt tagaccctaa aactgtatca agtgttgttc aatatggaac ttcaagattt     360
gaattagtgc atgaagctag aggccagtct ctcatctaca accagctcta tccttttgaa     420
ggccttcaga attacacatc tggaatcatc catcacgttc aactcaaagg attggaacca     480
agcacactat actattatca atgtggagat ccttcattgc aagccatgag tgatatatac     540
tatttcagga ccatgccaat ttctggttca aagagctacc caggcaaagt agctgtagta     600
ggagatcttg gtcttactta taatacaact actaccatcg gtcacctgac tagtaatgaa     660
cctgatcttc ttctattgat tggtgatgta acctacgcga atctgtacct cacaaatgga     720
```

```
actggctctg attgttatag ttgctcgttt ccactaactc ctatacatga aacctaccag    780
cctcgatggg attattgggg aaggtttatg cagaatctag tttctaacgt tccaataatg    840
gtggtagaag gaaatcatga aatagaaaaa caggctgaaa acaggacatt tgtggcctac    900
agttctaggt ttgcattccc ctctcaagaa agtggatctt catctacatt ctactattct    960
ttcaatgctg gaggcattca tttatattatg cttggggctt atattaacta tgataaaacg   1020
gctgaacaat acaagtggtt ggagagagat ctggaaaatg ttgatagatc aataactccc   1080
tggcttgtag ttacttggca tccaccatgg tatagttctt atgaagccca ttacagagaa   1140
gcagagtgca tgagggtgga gatggaggac ctattatacg catatggtgt ggatataata   1200
tttaatggac atgttcatgc ctatgagagg tcaaaccgag tttacaatta caatttagat   1260
ccatgtggtc ctgtatatat tacagttggg gatggggggca acagagagaa gatggcaatc   1320
aaattcgcag acgagcctgg tcattgtccc gatccattaa gtactcctga tccttatatg   1380
ggtggctttt gtgcaacaaa ttttacgttt ggtacaaaag tgagtaagtt ttgttgggat   1440
cgccagccag attacagtgc tttcagagaa agtagctttg ctatgggat  tctagaggtg    1500 aaaaatgaaa cttgggcttt gtggagttgg tatcgtaatc aggactctta caaggaagtt   1560
ggggatcaaa tttacatagt gagacaacct gatatatgcc ccatccatca aagggtgaac   1620
atagattgca ttgcttcgat ataa                                           1644
```

<210> SEQ ID NO 12  
<211> LENGTH: 1284  
<212> TYPE: DNA  
<213> ORGANISM: Artificial Sequence  
<220> FEATURE:  
<223> OTHER INFORMATION: Description of Artificial Sequence: Synthetic polynucleotide  
<220> FEATURE:  
<223> OTHER INFORMATION: Codon optimized

<400> SEQUENCE: 12

```
atggtcccac ttgcaagtac caccaccggc accgggaccg ctaccggtac atcaactgca     60
gccgaacctt ccgccactgt gccatttgca agtacagatc caaacccccgt cctctggaat   120 gaaacatcag atccagcact tgtgaagcct gagcgcaata agctcggggc tactatccag   180
ggtcctgata atctgcctat cgatttgcag aacccagatc tgttggctcc tcctaccact   240
gaccatggtt ttgtagggaa tgcaaagtgg ccattctcat ttagcaaaca aagacttcaa   300
accggcgggt gggcaagaca gcaaaatgaa gtcgttcttc ctctcgctac caatctcgct   360
tgtactaata tgaggctgga agccggggca attagagagc tccattggca taaaaacgcc   420
gaatgggctt acgtgttgaa aggtagtacc cagatttccg ctgtggacaa tgagggaagg   480
aactacatca gtactgtcgg tccaggcgat ctgtggtatt tcccccctgg aatccccac    540 tcccttcaag ccaccgccga cgaccctgag gggtccgagt tcattttggt gtttgatagt   600
ggagccttca atgatgacgg aaccttttctt ctcaccgact ggctgagtca cgtccctatg   660
gaagtcattc tgaaaaattt tagggccaag aaccccgctg cttggtccca tatacccgcc   720
cagcagttgt atatttttccc cagtgagcct cccgccgata accagccaga ccccgtcagt   780
ccccagggaa ccgtccccct cccatattcc tttaatttct caagtgtgga acctacccag   840
tactcagggg gtaccgccaa aattgccgat agtacaactt ttaatattag tgtcgcaatc    900
gcagtggcag aagtaacagt tgagcctgga gcactcagaa acttcattg caccccacc    960 gaagatgagt ggacattctt catctcaggc aacgcacgcg tgactatttt cgcagcacaa  1020
```

| | |
|---|---:|
| agtgtagcca gtacttttga ttaccagggc ggagatatag catatgttcc cgccagtatg | 1080 |
| ggccactacg tcgagaacat agggaatact accttgacct accttgaagt gttcaacaca | 1140 |
| gacagattcg ccgacgtgag tcttagccag tggctggccc tcacacctcc atccgttgtt | 1200 |
| caagcacacc tgaacctcga tgacgaaact ctggccgaac ttaagcagtt cgccaccaag | 1260 |
| gctacagtag tgggccccgt gaat | 1284 |

```
<210> SEQ ID NO 13
<211> LENGTH: 1024
<212> TYPE: DNA
<213> ORGANISM: Glycine max

<400> SEQUENCE: 13
```

| | |
|---|---:|
| aaagaagtaa atcatgagct tttccaactc aacatctatt ttttttctct caacctttt | 60 |
| cacatcttaa gtagtctcac cctttatata tataacttat ttcttacctt ttacattatg | 120 |
| taactttat caccaaaacc aacaacttta aaattttatt aaatagactc cacaagtaac | 180 |
| ttgacactct tacattcatc gacattaact tttatctgtt ttataaatat tattgtgata | 240 |
| taatttaatc aaaataacca caaactttca taaaaggttc ttattaagca tggcatttaa | 300 |
| taagcaaaaa caactcaatc actttcatat aggaggtagc ctaagtacgt actcaaaatg | 360 |
| ccaacaaata aaaaaaagt tgctttaata atgccaaaac aaattaataa aacacttaca | 420 |
| acaccggatt ttttttaatt aaaatgtgcc atttaggata aatagttaat atttttaata | 480 |
| attatttaaa aagccgtatc tactaaaatg attttttattt ggttgaaaat attaatatgt | 540 |
| ttaaatcaac acaatctatc aaaattaaac taaaaaaaaa ataagtgtac gtggttaaca | 600 |
| ttagtacagt aatataagag gaaaatgaga aattaagaaa ttgaaagcga gtctaatttt | 660 |
| taaattatga acctgcatat ataaaaggaa agaaagaatc caggaagaaa agaaatgaaa | 720 |
| ccatgcatgg tcccctcgtc atcacgagtt tctgccattt gcaatagaaa cactgaaaca | 780 |
| cctttctctt tgtcacttaa ttgagatgcc gaagccacct cacaccatga acttcatgag | 840 |
| gtgtagcacc caaggcttcc atagccatgc atactgaaga atgtctcaag ctcagcaccc | 900 |
| tacttctgtg acgtgtccct cattcacctt cctctcttcc ctataaataa ccacgcctca | 960 |
| ggttctccgc ttcacaactc aaacattctc tccattggtc cttaaacact catcagtcat | 1020 |
| cacc | 1024 |

```
<210> SEQ ID NO 14
<211> LENGTH: 1055
<212> TYPE: DNA
<213> ORGANISM: Glycine max

<400> SEQUENCE: 14
```

| | |
|---|---:|
| tttacaataa atactcaatt tatctttcac aatcaaaaga ttgagatgtt gtaagatctc | 60 |
| cgataatata cttatatctt ttcatttatt acgttttcaa atttgaattt taatgtgtgt | 120 |
| tgtaagtata aatttaaaat aaaaataaaa acaattatta tatcaaaatg gcaaaaacat | 180 |
| ttaatacgta ttatttaaga aaaaaatatg taataatata tttatatttt aatatctatt | 240 |
| cttatgtatt tttaaaaat ctattatata ttgatcaact aaaatatttt tatatctaca | 300 |
| cttattttgc attttttatca attttcttgc gttttttggc atatttaata atgactattc | 360 |
| tttaataatc aatcattatt cttacatggt acatattgtt ggaaccatat gaagtgtcca | 420 |
| ttgcatttga ctatgtggat agtgttttga tccaggcctc catttgccgc ttattaatta | 480 |
| atttggtaac agtccgtact aatcagttac ttatccttcc tccatcataa ttaatcttgg | 540 |

```
tagtctcgaa tgccacaaca ctgactagtc tcttggatca taagaaaaag ccaaggaaca      600
aaagaagaca aaacacaatg agagtatcct ttgcatagca atgtctaagt tcataaaatt      660
caaacaaaaa cgcaatcaca cacagtggac atcacttatc cactagctga tcaggatcgc      720
cgcgtcaaga aaaaaaaact ggaccccaaa agccatgcac aacaacacgt actcacaaag      780
gtgtcaatcg agcagcccaa acattcacc aactcaaccc atcatgagcc cacacatttg       840
ttgtttctaa cccaacctca aactcgtatt ctcttccgcc acctcatttt tgtttatttc      900
aacacccgtc aaactgcatg ccaccccgtg gccaaatgtc catgcatgtt aacaagacct      960
atgactataa atatctgcaa tctcggccca ggttttcatc atcaagaacc agttcaatat     1020
cctagtacac cgtattaaag aatttaagat atact                                1055
```

<210> SEQ ID NO 15
<211> LENGTH: 1045
<212> TYPE: DNA
<213> ORGANISM: Glycine max

<400> SEQUENCE: 15

```
ccttctcatc ctctctgaat attttgagtg ctcttcctag ttatctagta atgcatgaaa       60
ttaaacttac taaatgtttc ttcaatttaa agaataatt gtttatctgt ttcaatttt        120 ttaagagaat tttaaaaaga taattgtttc ggggagagag atataaaaaa gaaaagggag      180
aaatattaaa atgtactaaa taatatgata agaaagaga gaaaaataaa agagaaaatt      240
tgtatatagt tataattatt catgtaataa ggattcatct ctcaactgaa atatacttta     300
atgcagaaga aaaaatcatt atttacaaac gttgagtctt gagtgggaaa agaggaggcg      360
ccgttactat acaatataag atcatagtac tgacaaaatg cacagtaaaa cagttcaaat     420
tgagaaggat tcttaacaca ccatagtatt taatatatat ctttacagag acaattatgc     480
tggaggattc aggcaaagat tatatattgt ggatttgttt tttaataatt aacgcatcat     540
atgaaagatc gatgatatat actaatggtt ataagaaaaa tatttaacag tttctataac     600 cttttttcttt tatcttttac tgtaatatta tttattttat ttcacatttt taatcagctt    660
atctcattta taaacgaaat tgtataaaaa tatacatgat gaactgaata gaacaatatt     720
gatctgatat tctcatattg tataagagga tagactttga gacgcggaga atctgtagga     780
ggggaccatt cagagtgcct ccaatttttgg tgttgttcat tgtaccattg caaatataaa    840
cgaagcatgc atgcttatgt atgaggtgta acaaaattgg aaacaatagc catgcaaggt     900
gaagaatgtc acaaactcag caacccttat tcattgacgt gtccctcagt cactctcctc     960
tcatacctat aaatcaccac tcctcatgtt ctttccaatt caccaactcc ttcaaactta    1020
attattaaca cttccttagt tcaat                                          1045
```

<210> SEQ ID NO 16
<211> LENGTH: 1186
<212> TYPE: DNA
<213> ORGANISM: Glycine max

<400> SEQUENCE: 16

```
gtctatttgc atgttcttct gcatggtatt aagaagttct tagagaatta atctaagtac       60
attttttttg gtctggatca gacatcatat ggatgctttc aaattcatgc gttggagatt      120
aattttactc ataataggta attatattaa ttaaagaaa ttttacataa aaatacaaca       180
taaattattc cattaaatat attattccct gtgactacaa tgagataatc taagtgtatt      240
```

| | |
|---|---:|
| tgaaagtgga acagtagaaa ttataaaaat tgcaatgagt tgaataaaaa aggttggatt | 300 |
| aagaaagtaa tctaagtaca tttggaagtg gaatagtaga aataaaatta aatgagttga | 360 |
| aattgaaaat aattaaaaaa agtagggcta agaaatttct ccttcaactt catgatagca | 420 |
| aatattccat taggccattt gtagtttatg aatgagtata tataatcatg attttaggaa | 480 |
| ttcgatctgc tcgacacaac cgtgttacac tttttttaaa atgtcatcat aaaaataaaa | 540 |
| aataaaagac atgttataat taagaataag gtgatcagta taaaaataag taattttggg | 600 |
| aaatattaaa gttcaaaaaa gaactattga aagaaagaat attattattt aaaaagagaa | 660 |
| aagaaaatga tgaaatgcta ttttcagtta aagaaaataa gaaaaaaaaa tacaaagaat | 720 |
| aattcaatgc tggggctgta tatatgttta agatgataat taatttttt ttaaaaaaaa | 780 |
| gataagaatt aaatattttc tccttaatt tctgaatcac ggttttggtt ctgataagac | 840 |
| actgattagt cacccatcaa ataataataa ctaattctcc tattctattt caaaattttg | 900 |
| attatactta gattaatttt ctaatatact tggacctgtt tttcatgcag aagatgcaga | 960 |
| tatagctaga cagcacctag taatcgtgga accaacacca atgtccatat catgcatgtg | 1020 |
| tgccaccttt caaatgtaat ccagtagtaa aaaaagccat gacatgtaac tccacgacag | 1080 |
| agtaaaactc tcagaagtac ctctcgtttc atatctgcaa atcctctaat ataaataact | 1140 |
| cacttcacgg gttctttct cttcacagca aaacaatta ataaag | 1186 |

<210> SEQ ID NO 17
<211> LENGTH: 179
<212> TYPE: DNA
<213> ORGANISM: Glycine max

<400> SEQUENCE: 17

| | |
|---|---:|
| ctacgaaggg cgttgcggtt gagggtgcag cgagagaggg caacaccggc acactggaat | 60 |
| ggcttgttgt tagggttcca tgtctcaatg agccctcctt ctgactctat acggttatcc | 120 |
| ggtttgaggg cattgagttt ttggatctgg cactcgtttt gctgaggctg ctctctgga | 179 |

<210> SEQ ID NO 18
<211> LENGTH: 1000
<212> TYPE: DNA
<213> ORGANISM: Glycine max

<400> SEQUENCE: 18

| | |
|---|---:|
| aaaatagtgt ttgatttttt gacacattat taagtgtttt attttaagt ttaaaagcat | 60 |
| tggtatcctt tcataaaagg aggtaatctt atttaagtca aggagaatta ttatgggaaa | 120 |
| taaaaccttt tttttaaag tgtttaatat aattatatac tcaaaattcg atttatgatt | 180 |
| aaatctaagt gacattaaa aaaaattagt gtgaaaataa tttatatata attttgaaaa | 240 |
| atttatcatt aatttttttt tataaataaa tgttaattta ttagtttta ttataaatgt | 300 |
| gaatagaatg gattcgaagc agcaattct ctctttctcc ttttccatgc caaccttata | 360 |
| tatggtgacg aactgcatat acagtaaaac agttcaaatt gagaaagatt ttaaacatca | 420 |
| tagtatttga tatatatctt ttacagagac aattatgctg caggagttag ataagattat | 480 |
| tgtggatgtc atttttctttt taatatttta acgcattata taaagatga tatagtatgg | 540 |
| ttataaaaaa attatttaac agtttataaa accttttttt ttatctttta cagtaatatt | 600 |
| atttatttta tttcacattt ttttcatatc cttatctcat ttataaagga aattaattgt | 660 |
| ataaaaaaaa tatgatgcac tgaatagaat gctgatctta ttgtataagg aggatagaat | 720 |
| ttgagacgcg gagaatctgt agaggggac cattcagggt gcctgcaatt tggtgttgt | 780 |

| | |
|---|---|
| tcatgtacgg ttgcagatat aaacgaagca tagcttatgt atgaggtgta acaaaattgg | 840 |
| aaacaatagc catgcaaggt gaagaatgtc accaactcag aaaccttcct tcattgacgt | 900 |
| gtccctcact cactctcctc tcttcactat aaatcgccac tcttcgtgtt ctccacttca | 960 |
| ccaactcctt caaacttatt aacactttcc ttagttcaat | 1000 |

<210> SEQ ID NO 19
<211> LENGTH: 146
<212> TYPE: DNA
<213> ORGANISM: Glycine max

<400> SEQUENCE: 19

| | |
|---|---|
| tttctgtctc atttggcatt gcgtattggg aaaagcagaa ccccagtcac aacaagtgcc | 60 |
| tccgaagttg caatagcgag aaagactcct acaggaacca agcatgccac gctcgttgca | 120 |
| acctccttaa ggtggaggaa gaagaa | 146 |

<210> SEQ ID NO 20
<211> LENGTH: 150
<212> TYPE: DNA
<213> ORGANISM: Glycine max

<400> SEQUENCE: 20

| | |
|---|---|
| ttcttcttcc tccaccttaa ggaggttgca acgagcgtgg catgcttggt tcctgtagga | 60 |
| gtctttctcg ctattgcaac ttcggaggca cttgttgtga ctggggttct gcttttccca | 120 |
| atacgcaatg ccaaatgaga cagaaactga | 150 |

<210> SEQ ID NO 21
<211> LENGTH: 114
<212> TYPE: DNA
<213> ORGANISM: Glycine max

<400> SEQUENCE: 21

| | |
|---|---|
| atcgagaatt ttaaggttga gtgtcctaat gtgaagtaca ccgagactga gattcagtcc | 60 |
| gtgtacaact acgaaaccac cgaacttgtt cacgagaaca ggaatggcac ctat | 114 |

<210> SEQ ID NO 22
<211> LENGTH: 114
<212> TYPE: DNA
<213> ORGANISM: Glycine max

<400> SEQUENCE: 22

| | |
|---|---|
| ataggtgcca ttcctgttct cgtgaacaag ttcggtggtt tcgtagttgt acacggactg | 60 |
| aatctcagtc tcggtgtact tcacattagg acactcaacc ttaaaattct cgat | 114 |

<210> SEQ ID NO 23
<211> LENGTH: 1081
<212> TYPE: DNA
<213> ORGANISM: Glycine max

<400> SEQUENCE: 23

| | |
|---|---|
| acaaaattaa gaactgatac atcttgtttt ttgtcactga agataaacac gtgatctttg | 60 |
| gcaaaacata aaggccaaca aaacaaactt gtctcatccc tgaatgattc gaatgccatc | 120 |
| gtatgcgtgt cacaaagtgg aatacagcaa tgaacaaatg ctatcctctt gagaaaagtg | 180 |
| aatgcagcag cagcagcaga ctagagtgct acaaatgctt atcctcttga gaaagtgaa | 240 |
| tgcagcggca gcagacctga gtgctatata caattagaca cagggtctat taattgaaat | 300 |

```
tgtcttatta ttaaatattt cgtttatat taatttttta aattttaatt aaatttatat    360
atattatatt taagacagat atatttattt gtgattataa atgtgtcact ttttctttta    420
gtccatgtat tcttctattt tttcaattta acttttatt tttattttta agtcactctt     480
gatcaagaaa acattgttga cataaaacta ttaacataaa attatgttaa catgtgataa    540
catcatattt tactaatata acgtcgcatt ttaacgtttt tttaacaaat atcgactgta    600
agagtaaaaa tgaaatgttt gaaaaggtta attgcatact aactattttt tttcctataa    660
gtaatctttt ttgggatcaa ttgtatatca ttgagatacg atattaaata tgggtacctt    720
ttcacaaaac ctaacccttg ttagtcaaac cacacataag agaggatgga tttaaaccag    780
tcagcaccgt aagtatatag tgaagaaggc tgataacaca ctctattatt gttagtacgt    840
acgtatttcc ttttttgttt agtttttgaa tttaattaat taaatatat atgctaacaa     900 cattaaattt taaatttacg tctaattata tattgtgatg tataataaat tgtcaacctt    960
taaaaattat aaaagaaata ttaatttga taaacaactt ttgaaaagta cccaataatg     1020
ctagtataaa tagggggcatg actccccatg catcacagtg caatttagct gaagcaaagc    1080
a                                                                    1081

<210> SEQ ID NO 24
<211> LENGTH: 179
<212> TYPE: DNA
<213> ORGANISM: Glycine max

<400> SEQUENCE: 24
tccagagagc agcctcagca aaacgagtgc cagatccaaa aactcaatgc cctcaaaccg    60
gataaccgta tagagtcaga aggagggctc attgagacat ggaaccctaa caacaagcca    120
ttccagtgtg ccggtgttgc cctctctcgc tgcacccctca accgcaacgc ccttcgtag    179

<210> SEQ ID NO 25
<211> LENGTH: 211
<212> TYPE: DNA
<213> ORGANISM: Solanum tuberosum

<400> SEQUENCE: 25
ccaattggta agtttctgct tctacctttg atatatatat aataattatc attaattagt    60
agtaatataa tatttcaaat attttttttca aaataaaaga atgtagtata tagcaattgc   120
ttttctgtag tttataagtg tgtatatttt aatttataac ttttctaata tatgaccaaa    180
atttgttgat gtgcagttgg gaaattgggt t                                    211

<210> SEQ ID NO 26
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Codon optimized

<400> SEQUENCE: 26
atggctaagt tggttttttc tctctgtttt ttgctctttt ccggctgttg ctttgca       57

<210> SEQ ID NO 27
<211> LENGTH: 63
<212> TYPE: DNA
<213> ORGANISM: Arabidopsis thaliana
```

<400> SEQUENCE: 27

```
atggactcta aaagtttcct cctgctgttg ctccttttt gcttcttatt tttgcacgac    60
gca                                                                63
```

<210> SEQ ID NO 28
<211> LENGTH: 221
<212> TYPE: DNA
<213> ORGANISM: Unknown
<220> FEATURE:
<223> OTHER INFORMATION: Description of Unknown:
      Agrobacterium tumefaciens sequence

<400> SEQUENCE: 28

```
gaaccgcaac gttgaaggag ccactgagcc gcgggtttct ggagtttaat gagctaagca    60
catacgtcag aaaccattat tgcgcgttca aaagtcgcct aaggtcacta tcagctagca   120
aatatttctt gtcaaaaatg ctccactgac gttccataaa ttccctcgg tatccaatta   180 gagtctcata ttcactctca actcgatcga ggggatctac c                       221
```

<210> SEQ ID NO 29
<211> LENGTH: 403
<212> TYPE: DNA
<213> ORGANISM: Cauliflower mosaic virus

<400> SEQUENCE: 29

```
tgagactttt caacaaagga taatttcggg aaacctcctc ggattccatt gcccagctat    60
ctgtcacttc atcgaaagga cagtagaaaa ggaaggtggc tcctacaaat gccatcattg   120
cgataaagga aaggctatca ttcaagatct ctctgccgac agtggtccca agatggacc   180 cccacccacg aggagcatcg tggaaaaaga agaggttcca accacgtcta caaagcaagt   240
ggattgatgt gacatctcca ctgacgtaag ggatgacgca caatcccact atccttcgca   300
agacccttcc tctatataag gaagttcatt tcatttggag aggacaacaa ttaccaacaa   360
caacaaacaa caaacaacat tacaattact atttacaatt aca                    403
```

<210> SEQ ID NO 30
<211> LENGTH: 1014
<212> TYPE: DNA
<213> ORGANISM: Glycine max

<400> SEQUENCE: 30

```
atcagaatta aactttaatt ctagttaatt agaaaatttt aggtttaaat acaacttcag    60
tgatcttatt ttatttattc tgtaatttta gtctcttat tttgaaataa aaattttgat   120
ccttcaattt taaaaaattc acaattaatt ttgatttcat tttcaatttt gtcatttatt   180
tattttattt cttatatttt aattgaacaa ataatttatt gatgacactt taaatgaatt   240
ttttaggttt aagattaagt taaattaaaa taaaaagcat aaaacataaa taaaattgag   300
aactaaacta aaattatatt ttttaaaata aaaaaatctc tatttctgaa ataggtgaac   360
taaaattacc aatagaaaaa aataattaaa tgataaactt tgaataatc tcactaatca   420 cttttaagat ctcttattca ataaattttt cttttacatt catagaactc atatccgaaa   480
cctaaggacc gaatcaatac cactcgatat gttgataaat aataattatt ttaaaatcta   540
aatctagtta aaataatttt tatttggttg aaaatgttaa tatctttata aaagtacagt   600
attacaagaa caaaatgaga aagaaattga aattcagtct aatttataaa taatcaacct   660
gcatgtaaaa ggaaagaaag aagcgagcag gaagaaaaga aatgaaacca tgcatggtcc   720
```

```
ccccaccccc aggacatcat gggtttctgc catttgcaat acaaacactg aaacaccttt    780
ctctttgtca cgtaatcgag attccgaagc caccttacac cattaactta atgaggtgta    840
agacagaagg gttccatagc catgcatact gaagaatgtc ttaagctcag cacccacctt    900
ctgagacgtg tccctcattc accttcctct cttccctata aataaccacg cctcaggttc    960
tccgcttcac aacacaaaca ttctctccat tgtccttga atataatact cagc           1014
```

<210> SEQ ID NO 31
<211> LENGTH: 403
<212> TYPE: DNA
<213> ORGANISM: Cauliflower mosaic virus

<400> SEQUENCE: 31

```
tgagactttt caacaaagga taatttcggg aaacctcctc ggattccatt gcccagctat     60
ctgtcacttc atcgaaagga cagtagaaaa ggaaggtggc tcctacaaat gccatcattg    120
cgataaagga aaggctatca ttcaagatct ctctgccgac agtggtccca agatggacc    180 cccacccacg aggagcatcg tggaaaaaga agaggttcca accacgtcta caaagcaagt    240
ggattgatgt gacatctcca ctgacgtaag ggatgacgca caatcccact atccttcgca    300
agacccttcc tctatataag gaagttcatt tcatttggag aggacaacaa ttaccaacaa    360
caacaaacaa caaacaacat tacaattact atttacaatt aca                      403
```

<210> SEQ ID NO 32
<211> LENGTH: 382
<212> TYPE: DNA
<213> ORGANISM: Unknown
<220> FEATURE:
<223> OTHER INFORMATION: Description of Unknown:
      Agrobacterium tumefaciens sequence

<400> SEQUENCE: 32

```
ttttcaaatc agtgcgcaag acgtgacgta agtatccgag tcagttttta ttttttctact     60 aatttggtcg tttatttcgg cgtgtaggac atggcaaccg ggcctgaatt tcgcgggtat    120
tctgtttcta ttccaacttt ttcttgatcc gcagccatta cgactttgt aatagatacg    180 ctgacacgcc aagcctcgct agtcaaaagt gtaccaaaca acgctttaca gcaagaacgg    240
aatgcgcgtg acgctcgcgg tgacgccatt tcgccttttc agaaatggat aaatagcctt    300
gcttcctatt atatcttccc aaattaccaa tacattacac tagcatctga atttcataac    360
caatctcgat acaccaaatc ga                                             382
```

<210> SEQ ID NO 33
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Original GFP sequence was from jellyfish. This
      has changes that increase the fluorescence of the protein as well
      as codon optimizations for expression in plants.

<400> SEQUENCE: 33

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca cccttcagcta cggcgtgcag tgcttcagcc gctacccccga ccacatgaag    240
```

```
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actcacggca tggacgagct gtacaagtaa    720
```

<210> SEQ ID NO 34
<211> LENGTH: 552
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Codon optimized

<400> SEQUENCE: 34

```
atgagcccag aacgacgccc ggccgacatc cgccgtgcca ccgaggcgga catgccggcg     60
gtctgcacca tcgtcaacca ctacatcgag acaagcacgg tcaacttccg taccgagccg    120
caggaaccgc aggagtggac ggacgacctc gtccgtctgc gggagcgcta tccctggctc    180
gtcgccgagg tggacggcga ggtcgccggc atcgcctacg cgggtccctg gaaggcacgc    240
aacgcctacg actggacggc cgagtcgacc gtgtacgtct ccccccgcca ccagcggacg    300
ggactgggct ccacgctcta cacccacctg ctgaagtccc tggaggcaca gggcttcaag    360
agcgtggtcg ctgtcatcgg gctgcccaac gacccgagcg tgcgcatgca cgaggcgctc    420
ggatatgccc ccgcggcat gctgcgggcg gccggcttca gcacgggaa ctggcatgac    480 gtgggtttct ggcagctgga cttcagcctg ccggtgccgc ccgtccggt cctgcccgtc    540 accgaaatct ga                                                       552
```

<210> SEQ ID NO 35
<211> LENGTH: 253
<212> TYPE: DNA
<213> ORGANISM: Unknown
<220> FEATURE:
<223> OTHER INFORMATION: Description of Unknown:
      Agrobacterium tumefaciens sequence

<400> SEQUENCE: 35

```
gatcgttcaa acatttggca ataaagtttc ttaagattga atcctgttgc cggtcttgcg     60
atgattatca tataatttct gttgaattac gttaagcatg taataattaa catgtaatgc    120
atgacgttat ttatgagatg gtttttatg attagagtcc cgcaattata catttaatac    180
gcgatagaaa acaaaatata gcgcgcaaac taggataaat tatcgcgcgc ggtgtcatct    240
atgttactag atc                                                      253
```

<210> SEQ ID NO 36
<211> LENGTH: 190
<212> TYPE: PRT
<213> ORGANISM: Bos taurus

<400> SEQUENCE: 36

```
Met Met Lys Ser Phe Phe Leu Val Val Thr Ile Leu Ala Leu Thr Leu
1               5                   10                  15

Pro Phe Leu Gly Ala Gln Glu Gln Asn Gln Glu Gln Pro Ile Arg Cys
                20                  25                  30

Glu Lys Asp Glu Arg Phe Phe Ser Asp Lys Ile Ala Lys Tyr Ile Pro
            35                  40                  45

Ile Gln Tyr Val Leu Ser Arg Tyr Pro Ser Tyr Gly Leu Asn Tyr Tyr
    50                  55                  60

Gln Gln Lys Pro Val Ala Leu Ile Asn Asn Gln Phe Leu Pro Tyr Pro
65                  70                  75                  80

Tyr Tyr Ala Lys Pro Ala Ala Val Arg Ser Pro Ala Gln Ile Leu Gln
                85                  90                  95

Trp Gln Val Leu Ser Asn Thr Val Pro Ala Lys Ser Cys Gln Ala Gln
                100                 105                 110

Pro Thr Thr Met Ala Arg His Pro His Pro His Leu Ser Phe Met Ala
            115                 120                 125

Ile Pro Pro Lys Lys Asn Gln Asp Lys Thr Glu Ile Pro Thr Ile Asn
    130                 135                 140

Thr Ile Ala Ser Gly Glu Pro Thr Ser Thr Pro Thr Thr Glu Ala Val
145                 150                 155                 160

Glu Ser Thr Val Ala Thr Leu Glu Asp Ser Pro Glu Val Ile Glu Ser
                165                 170                 175

Pro Pro Glu Ile Asn Thr Val Gln Val Thr Ser Thr Ala Val
            180                 185                 190
```

<210> SEQ ID NO 37
<211> LENGTH: 214
<212> TYPE: PRT
<213> ORGANISM: Bos taurus

<400> SEQUENCE: 37

```
Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
                20                  25                  30

Glu Asn Leu Leu Arg Phe Phe Val Ala Pro Phe Pro Glu Val Phe Gly
            35                  40                  45

Lys Glu Lys Val Asn Glu Leu Ser Lys Asp Ile Gly Ser Glu Ser Thr
    50                  55                  60

Glu Asp Gln Ala Met Glu Asp Ile Lys Gln Met Glu Ala Glu Ser Ile
65                  70                  75                  80

Ser Ser Ser Glu Glu Ile Val Pro Asn Ser Val Glu Gln Lys His Ile
                85                  90                  95

Gln Lys Glu Asp Val Pro Ser Glu Arg Tyr Leu Gly Tyr Leu Glu Gln
            100                 105                 110

Leu Leu Arg Leu Lys Lys Tyr Lys Val Pro Gln Leu Glu Ile Val Pro
    115                 120                 125

Asn Ser Ala Glu Glu Arg Leu His Ser Met Lys Glu Gly Ile His Ala
    130                 135                 140

Gln Gln Lys Glu Pro Met Ile Gly Val Asn Gln Glu Leu Ala Tyr Phe
145                 150                 155                 160

Tyr Pro Glu Leu Phe Arg Gln Phe Tyr Gln Leu Asp Ala Tyr Pro Ser
                165                 170                 175
```

Gly Ala Trp Tyr Tyr Val Pro Leu Gly Thr Gln Tyr Thr Asp Ala Pro
            180                 185                 190

Ser Phe Ser Asp Ile Pro Asn Pro Ile Gly Ser Glu Asn Ser Glu Lys
        195                 200                 205

Thr Thr Met Pro Leu Trp
    210

<210> SEQ ID NO 38
<211> LENGTH: 222
<212> TYPE: PRT
<213> ORGANISM: Bos taurus

<400> SEQUENCE: 38

Met Lys Phe Phe Ile Phe Thr Cys Leu Leu Ala Val Ala Leu Ala Lys
1               5                   10                  15

Asn Thr Met Glu His Val Ser Ser Ser Glu Glu Ser Ile Ile Ser Gln
            20                  25                  30

Glu Thr Tyr Lys Gln Glu Lys Asn Met Ala Ile Asn Pro Ser Lys Glu
        35                  40                  45

Asn Leu Cys Ser Thr Phe Cys Lys Glu Val Val Arg Asn Ala Asn Glu
    50                  55                  60

Glu Glu Tyr Ser Ile Gly Ser Ser Glu Glu Ser Ala Glu Val Ala
65                  70                  75                  80

Thr Glu Glu Val Lys Ile Thr Val Asp Asp Lys His Tyr Gln Lys Ala
                85                  90                  95

Leu Asn Glu Ile Asn Gln Phe Tyr Gln Lys Phe Pro Gln Tyr Leu Gln
            100                 105                 110

Tyr Leu Tyr Gln Gly Pro Ile Val Leu Asn Pro Trp Asp Gln Val Lys
        115                 120                 125

Arg Asn Ala Val Pro Ile Thr Pro Thr Leu Asn Arg Glu Gln Leu Ser
130                 135                 140

Thr Ser Glu Glu Asn Ser Lys Lys Thr Val Asp Met Glu Ser Thr Glu
145                 150                 155                 160

Val Phe Thr Lys Lys Thr Lys Leu Thr Glu Glu Glu Lys Asn Arg Leu
                165                 170                 175

Asn Phe Leu Lys Lys Ile Ser Gln Arg Tyr Gln Lys Phe Ala Leu Pro
            180                 185                 190

Gln Tyr Leu Lys Thr Val Tyr Gln His Gln Lys Ala Met Lys Pro Trp
        195                 200                 205

Ile Gln Pro Lys Thr Lys Val Ile Pro Tyr Val Arg Tyr Leu
210                 215                 220

<210> SEQ ID NO 39
<211> LENGTH: 224
<212> TYPE: PRT
<213> ORGANISM: Bos taurus

<400> SEQUENCE: 39

Met Lys Val Leu Ile Leu Ala Cys Leu Val Ala Leu Ala Leu Ala Arg
1               5                   10                  15

Glu Leu Glu Glu Leu Asn Val Pro Gly Glu Ile Val Glu Ser Leu Ser
            20                  25                  30

Ser Ser Glu Glu Ser Ile Thr Arg Ile Asn Lys Lys Ile Glu Lys Phe
        35                  40                  45

Gln Ser Glu Glu Gln Gln Gln Thr Glu Asp Glu Leu Gln Asp Lys Ile
    50                  55                  60

```
His Pro Phe Ala Gln Thr Gln Ser Leu Val Tyr Pro Phe Pro Gly Pro
 65                  70                  75                  80

Ile Pro Asn Ser Leu Pro Gln Asn Ile Pro Pro Leu Thr Gln Thr Pro
                 85                  90                  95

Val Val Val Pro Pro Phe Leu Gln Pro Glu Val Met Gly Val Ser Lys
            100                 105                 110

Val Lys Glu Ala Met Ala Pro Lys His Lys Glu Met Pro Phe Pro Lys
        115                 120                 125

Tyr Pro Val Glu Pro Phe Thr Glu Ser Gln Ser Leu Thr Leu Thr Asp
130                 135                 140

Val Glu Asn Leu His Leu Pro Leu Pro Leu Leu Gln Ser Trp Met His
145                 150                 155                 160

Gln Pro His Gln Pro Leu Pro Pro Thr Val Met Phe Pro Pro Gln Ser
                165                 170                 175

Val Leu Ser Leu Ser Gln Ser Lys Val Leu Pro Val Pro Gln Lys Ala
            180                 185                 190

Val Pro Tyr Pro Gln Arg Asp Met Pro Ile Gln Ala Phe Leu Leu Tyr
        195                 200                 205

Gln Glu Pro Val Leu Gly Pro Val Arg Gly Pro Phe Pro Ile Ile Val
210                 215                 220
```

<210> SEQ ID NO 40
<211> LENGTH: 536
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Met Ser Ser Ser Phe Leu Ser Ser Thr Ala Phe Phe Leu Leu Leu Cys
1               5                   10                  15

Leu Gly Phe Cys His Val Ser Ser Gln Leu Arg Pro Arg Glu Arg Pro
            20                  25                  30

Arg Gly Cys Pro Cys Thr Gly Arg Ala Ser Ser Leu Ala Arg Asp Ser
        35                  40                  45

Ala Ala Ala Ala Ser Asp Pro Gly Thr Ile Val His Asn Phe Ser Arg
    50                  55                  60

Thr Glu Pro Arg Thr Glu Pro Ala Gly Gly Ser His Ser Gly Ser Ser
65                  70                  75                  80

Ser Lys Leu Gln Ala Leu Phe Ala His Pro Leu Tyr Asn Val Pro Glu
                85                  90                  95

Glu Pro Pro Leu Leu Gly Ala Glu Asp Ser Leu Leu Ala Ser Gln Glu
            100                 105                 110

Ala Leu Arg Tyr Tyr Arg Arg Lys Val Ala Arg Trp Asn Arg Arg His
        115                 120                 125

Lys Met Tyr Arg Glu Gln Met Asn Leu Thr Ser Leu Asp Pro Pro Leu
130                 135                 140

Gln Leu Arg Leu Glu Ala Ser Trp Val Gln Phe His Leu Gly Ile Asn
145                 150                 155                 160

Arg His Gly Leu Tyr Ser Arg Ser Ser Pro Val Val Ser Lys Leu Leu
                165                 170                 175

Gln Asp Met Arg His Phe Pro Thr Ile Ser Ala Asp Tyr Ser Gln Asp
            180                 185                 190
```

Glu Lys Ala Leu Leu Gly Ala Cys Asp Cys Thr Gln Ile Val Lys Pro
195                 200                 205

Ser Gly Val His Leu Lys Leu Val Leu Arg Phe Ser Asp Phe Gly Lys
210                 215                 220

Ala Met Phe Lys Pro Met Arg Gln Gln Arg Asp Glu Glu Thr Pro Val
225                 230                 235                 240

Asp Phe Phe Tyr Phe Ile Asp Phe Gln Arg His Asn Ala Glu Ile Ala
            245                 250                 255

Ala Phe His Leu Asp Arg Ile Leu Asp Phe Arg Arg Val Pro Pro Thr
            260                 265                 270

Val Gly Arg Ile Val Asn Val Thr Lys Glu Ile Leu Glu Val Thr Lys
        275                 280                 285

Asn Glu Ile Leu Gln Ser Val Phe Phe Val Ser Pro Ala Ser Asn Val
        290                 295                 300

Cys Phe Phe Ala Lys Cys Pro Tyr Met Cys Lys Thr Glu Tyr Ala Val
305                 310                 315                 320

Cys Gly Asn Pro His Leu Leu Glu Gly Ser Leu Ser Ala Phe Leu Pro
            325                 330                 335

Ser Leu Asn Leu Ala Pro Arg Leu Ser Val Pro Asn Pro Trp Ile Arg
            340                 345                 350

Ser Tyr Thr Leu Ala Gly Lys Glu Glu Trp Glu Val Asn Pro Leu Tyr
            355                 360                 365

Cys Asp Thr Val Lys Gln Ile Tyr Pro Tyr Asn Asn Ser Gln Arg Leu
370                 375                 380

Leu Asn Val Ile Asp Met Ala Ile Phe Asp Phe Leu Ile Gly Asn Met
385                 390                 395                 400

Asp Arg His His Tyr Glu Met Phe Thr Lys Phe Gly Asp Asp Gly Phe
            405                 410                 415

Leu Ile His Leu Asp Asn Ala Arg Gly Phe Gly Arg His Ser His Asp
            420                 425                 430

Glu Ile Ser Ile Leu Ser Pro Leu Ser Gln Cys Cys Met Ile Lys Lys
            435                 440                 445

Lys Thr Leu Leu His Leu Gln Leu Leu Ala Gln Ala Asp Tyr Arg Leu
450                 455                 460

Ser Asp Val Met Arg Glu Ser Leu Leu Glu Asp Gln Leu Ser Pro Val
465                 470                 475                 480

Leu Thr Glu Pro His Leu Leu Ala Leu Asp Arg Arg Leu Gln Thr Ile
            485                 490                 495

Leu Arg Thr Val Glu Gly Cys Ile Val Ala His Gly Gln Gln Ser Val
            500                 505                 510

Ile Val Asp Gly Pro Val Glu Gln Leu Ala Pro Asp Ser Gly Gln Ala
            515                 520                 525

Asn Leu Thr Ser His Asp Glu Leu
530                 535

<210> SEQ ID NO 41
<211> LENGTH: 586
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Met Ser Ser Ser Phe Leu Ser Ser Thr Ala Phe Phe Leu Leu Leu Cys
1               5                   10                  15

Leu Gly Phe Cys His Val Ser Ser Leu Asp Leu Leu Pro Arg Leu Glu
            20                  25                  30

Arg Arg Gly Ala Arg Pro Ser Gly Glu Pro Gly Cys Ser Cys Ala Gln
        35                  40                  45

Pro Ala Ala Glu Val Ala Ala Pro Gly Trp Ala Gln Val Arg Gly Arg
    50                  55                  60

Pro Gly Glu Pro Pro Ala Ala Ser Ser Ala Ala Gly Asp Ala Gly Trp
65                  70                  75                  80

Pro Asn Lys His Thr Leu Arg Ile Leu Gln Asp Phe Ser Ser Asp Pro
                85                  90                  95

Ser Ser Asn Leu Ser Ser His Ser Leu Glu Lys Leu Pro Pro Ala Ala
            100                 105                 110

Glu Pro Ala Glu Arg Ala Leu Arg Gly Arg Asp Pro Gly Ala Leu Arg
        115                 120                 125

Pro His Asp Pro Ala His Arg Pro Leu Leu Arg Asp Pro Gly Pro Arg
    130                 135                 140

Arg Ser Glu Ser Pro Pro Gly Pro Gly Gly Asp Ala Ser Leu Leu Ala
145                 150                 155                 160

Arg Leu Phe Glu His Pro Leu Tyr Arg Val Ala Val Pro Pro Leu Thr
                165                 170                 175

Glu Glu Asp Val Leu Phe Asn Val Asn Ser Asp Thr Arg Leu Ser Pro
            180                 185                 190

Lys Ala Ala Glu Asn Pro Asp Trp Pro His Ala Gly Ala Glu Gly Ala
        195                 200                 205

Glu Phe Leu Ser Pro Gly Glu Ala Ala Val Asp Ser Tyr Pro Asn Trp
    210                 215                 220

Leu Lys Phe His Ile Gly Ile Asn Arg Tyr Glu Leu Tyr Ser Arg His
225                 230                 235                 240

Asn Pro Ala Ile Glu Ala Leu Leu His Asp Leu Ser Ser Gln Arg Ile
                245                 250                 255

Thr Ser Val Ala Met Lys Ser Gly Gly Thr Gln Leu Lys Leu Ile Met
            260                 265                 270

Thr Phe Gln Asn Tyr Gly Gln Ala Leu Phe Lys Pro Met Lys Gln Thr
        275                 280                 285

Arg Glu Gln Glu Thr Pro Pro Asp Phe Phe Tyr Phe Ser Asp Tyr Glu
    290                 295                 300

Arg His Asn Ala Glu Ile Ala Ala Phe His Leu Asp Arg Ile Leu Asp
305                 310                 315                 320

Phe Arg Arg Val Pro Pro Val Ala Gly Arg Met Val Asn Met Thr Lys
                325                 330                 335

Glu Ile Arg Asp Val Thr Arg Asp Lys Lys Leu Trp Arg Thr Phe Phe
            340                 345                 350

Ile Ser Pro Ala Asn Asn Ile Cys Phe Tyr Gly Glu Cys Ser Tyr Tyr
        355                 360                 365

Cys Ser Thr Glu His Ala Leu Cys Gly Lys Pro Asp Gln Ile Glu Gly
    370                 375                 380

Ser Leu Ala Ala Phe Leu Pro Asp Leu Ser Leu Ala Lys Arg Lys Thr
385                 390                 395                 400
```

```
Trp Arg Asn Pro Trp Arg Arg Ser Tyr His Lys Arg Lys Ala Glu
            405                 410                 415

Trp Glu Val Asp Pro Asp Tyr Cys Glu Val Lys Gln Thr Pro Pro
            420                 425                 430

Tyr Asp Ser Ser His Arg Ile Leu Asp Val Met Asp Met Thr Ile Phe
            435                 440             445

Asp Phe Leu Met Gly Asn Met Asp Arg His His Tyr Glu Thr Phe Glu
450                 455                 460

Lys Phe Gly Asn Glu Thr Phe Ile Ile His Leu Asp Asn Gly Arg Gly
465                 470                 475                 480

Phe Gly Lys Tyr Ser His Asp Glu Leu Ser Ile Leu Val Pro Leu Gln
            485                 490                 495

Gln Cys Cys Arg Ile Arg Lys Ser Thr Tyr Leu Arg Leu Gln Leu Leu
            500                 505                 510

Ala Lys Glu Glu Tyr Lys Leu Ser Leu Leu Met Ala Glu Ser Leu Arg
            515                 520                 525

Gly Asp Gln Val Ala Pro Val Leu Tyr Gln Pro His Leu Glu Ala Leu
            530                 535                 540

Asp Arg Arg Leu Arg Val Val Leu Lys Ala Val Arg Asp Cys Val Glu
545                 550                 555                 560

Arg Asn Gly Leu His Ser Val Val Asp Asp Leu Asp Thr Glu His
            565                 570                 575

Arg Ala Ala Ser Ala Arg His Asp Glu Leu
            580                 585

<210> SEQ ID NO 42
<211> LENGTH: 426
<212> TYPE: DNA
<213> ORGANISM: Cauliflower mosaic virus

<400> SEQUENCE: 42
gtcaacatgg tggagcacga cactctggtc tactccaaaa atgtcaaaga tacagtctca      60
gaagatcaaa gggctattga gacttttcaa caaaggataa tttcgggaaa cctcctcgga     120
ttccattgcc cagctatctg tcacttcatc gaaaggacag tagaaaagga aggtggctcc     180
tacaaatgcc atcattgcga taaggaaag gctatcattc aagatctctc tgccgacagt      240
ggtcccaaag atgaccccc acccacgagg agcatcgtgg aaaaagaaga ggttccaacc     300
acgtctacaa agcaagtgga ttgatgtgac atctccactg acgtaaggga tgacgcacaa     360
tcccactatc cttcgcaaga cccttcctct atataaggaa gttcatttca tttggagagg     420
acacgc                                                                426

<210> SEQ ID NO 43
<211> LENGTH: 391
<212> TYPE: PRT
<213> ORGANISM: Homo sapiens

<400> SEQUENCE: 43

Met Ser Gly Pro Val Pro Ser Arg Ala Arg Val Tyr Thr Asp Val Asn
1               5                   10                  15

Thr His Arg Pro Arg Glu Tyr Trp Asp Tyr Glu Ser His Val Val Glu
            20                  25                  30

Trp Gly Asn Gln Asp Asp Tyr Gln Leu Val Arg Lys Leu Gly Arg Gly
            35                  40                  45
```

Lys Tyr Ser Glu Val Phe Glu Ala Ile Asn Ile Thr Asn Asn Glu Lys
           50                  55                  60

Val Val Val Lys Ile Leu Lys Pro Val Lys Lys Lys Ile Lys Arg
 65                  70                  75                  80

Glu Ile Lys Ile Leu Glu Asn Leu Arg Gly Gly Pro Asn Ile Ile Thr
                     85                  90                  95

Leu Ala Asp Ile Val Lys Asp Pro Val Ser Arg Thr Pro Ala Leu Val
                100                 105                 110

Phe Glu His Val Asn Asn Thr Asp Phe Lys Gln Leu Tyr Gln Thr Leu
                115                 120                 125

Thr Asp Tyr Asp Ile Arg Phe Tyr Met Tyr Glu Ile Leu Lys Ala Leu
130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175

Gly Leu Ala Glu Phe Tyr His Pro Gly Gln Glu Tyr Asn Val Arg Val
                180                 185                 190

Ala Ser Arg Tyr Phe Lys Gly Pro Glu Leu Leu Val Asp Tyr Gln Met
                195                 200                 205

Tyr Asp Tyr Ser Leu Asp Met Trp Ser Leu Gly Cys Met Leu Ala Ser
                210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
                245                 250                 255

Tyr Ile Asp Lys Tyr Asn Ile Glu Leu Asp Pro Arg Phe Asn Asp Ile
                260                 265                 270

Leu Gly Arg His Ser Arg Lys Arg Trp Glu Arg Phe Val His Ser Glu
                275                 280                 285

Asn Gln His Leu Val Ser Pro Glu Ala Leu Asp Phe Leu Asp Lys Leu
                290                 295                 300

Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
                325                 330                 335

Ser Ser Met Pro Gly Gly Ser Thr Pro Val Ser Ser Ala Asn Met Met
                340                 345                 350

Ser Gly Ile Ser Ser Val Pro Thr Pro Ser Pro Leu Gly Pro Leu Ala
                355                 360                 365

Gly Ser Pro Val Ile Ala Ala Asn Pro Leu Gly Met Pro Val Pro
                370                 375                 380

Ala Ala Ala Gly Ala Gln Gln
385                 390

<210> SEQ ID NO 44
<211> LENGTH: 714
<212> TYPE: DNA
<213> ORGANISM: Unknown
<220> FEATURE:
<223> OTHER INFORMATION: Description of Unknown:
      Agrobacterium tumefaciens sequence

<400> SEQUENCE: 44

```
gtcctgcttt aatgagatat gcgagaagcc tatgatcgca tgatatttgc tttcaattct      60
gttgtgcacg ttgtaaaaaa cctgagcatg tgtagctcag atccttaccg ccggtttcgg     120
ttcattctaa tgaatatatc acccgttact atcgtatttt tatgaataat attctccgtt     180
caatttactg attgtaccct actacttata tgtacaatat taaaatgaaa acaatatatt     240
gtgctgaata ggtttatagc gacatctatg atagagcgcc acaataacaa acaattgcgt     300
tttattatta caaatccaat tttaaaaaaa gcggcagaac cggtcaaacc taaaagactg     360
attacataaa tcttattcaa atttcaaaag tgccccaggg gctagtatct acgacacacc     420
gagcggcgaa ctaataacgc tcactgaagg gaactccggt tccccgccgg cgcgcatggg     480
tgagattcct tgaagttgag tattggccgt ccgctctacc gaaagttacg ggcaccattc     540
aacccggtcc agcacggcgg ccgggtaacc gacttgctgc cccgagaatt atgcagcatt     600
tttttggtgt atgtgggccc caaatgaagt gcaggtcaaa ccttgacagt gacgacaaat     660
cgttgggcgg gtccagggcg aattttgcga caacatgtcg aggctcagca ggac          714
```

<210> SEQ ID NO 45
<211> LENGTH: 386
<212> TYPE: PRT
<213> ORGANISM: Gallus gallus

<400> SEQUENCE: 45

```
Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
            20                  25                  30

Ile Ala Ile Met Ser Ala Leu Ala Met Val Tyr Leu Gly Ala Lys Asp
        35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
        115                 120                 125

Gly Leu Glu Pro Ile Asn Phe Gln Thr Ala Ala Asp Gln Ala Arg Glu
    130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
225                 230                 235                 240
```

```
Ser Met Leu Val Leu Leu Pro Asp Glu Val Ser Gly Leu Glu Gln Leu
            245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
            275                 280                 285

Glu Glu Lys Tyr Asn Leu Thr Ser Val Leu Met Ala Met Gly Ile Thr
            290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
            325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
            355                 360                 365

Ile Lys His Ile Ala Thr Asn Ala Val Leu Phe Phe Gly Arg Cys Val
            370                 375                 380

Ser Pro
385

<210> SEQ ID NO 46
<211> LENGTH: 705
<212> TYPE: PRT
<213> ORGANISM: Gallus gallus

<400> SEQUENCE: 46

Met Lys Leu Ile Leu Cys Thr Val Leu Ser Leu Gly Ile Ala Ala Val
1               5                   10                  15

Cys Phe Ala Ala Pro Pro Lys Ser Val Ile Arg Trp Cys Thr Ile Ser
            20                  25                  30

Ser Pro Glu Glu Lys Lys Cys Asn Asn Leu Arg Asp Leu Thr Gln Gln
            35                  40                  45

Glu Arg Ile Ser Leu Thr Cys Val Gln Lys Ala Thr Tyr Leu Asp Cys
        50                  55                  60

Ile Lys Ala Ile Ala Asn Asn Glu Ala Asp Ala Ile Ser Leu Asp Gly
65                  70                  75                  80

Gly Gln Ala Phe Glu Ala Gly Leu Ala Pro Tyr Lys Leu Lys Pro Ile
            85                  90                  95

Ala Ala Glu Val Tyr Glu His Thr Glu Gly Ser Thr Thr Ser Tyr Tyr
            100                 105                 110

Ala Val Ala Val Val Lys Lys Gly Thr Glu Phe Thr Val Asn Asp Leu
            115                 120                 125

Gln Gly Lys Thr Ser Cys His Thr Gly Leu Gly Arg Ser Ala Gly Trp
        130                 135                 140

Asn Ile Pro Ile Gly Thr Leu Leu His Arg Gly Ala Ile Glu Trp Glu
145                 150                 155                 160

Gly Ile Glu Ser Gly Ser Val Glu Gln Ala Val Ala Lys Phe Phe Ser
            165                 170                 175

Ala Ser Cys Val Pro Gly Ala Thr Ile Glu Gln Lys Leu Cys Arg Gln
            180                 185                 190

Cys Lys Gly Asp Pro Lys Thr Lys Cys Ala Arg Asn Ala Pro Tyr Ser
            195                 200                 205
```

```
Gly Tyr Ser Gly Ala Phe His Cys Leu Lys Asp Gly Lys Asp Val
    210                 215                 220

Ala Phe Val Lys His Thr Thr Val Asn Glu Asn Ala Pro Asp Gln Lys
225                 230                 235                 240

Asp Glu Tyr Glu Leu Leu Cys Leu Asp Gly Ser Arg Gln Pro Val Asp
                245                 250                 255

Asn Tyr Lys Thr Cys Asn Trp Ala Arg Val Ala Ala His Ala Val Val
                260                 265                 270

Ala Arg Asp Asp Asn Lys Val Glu Asp Ile Trp Ser Phe Leu Ser Lys
            275                 280                 285

Ala Gln Ser Asp Phe Gly Val Asp Thr Lys Ser Asp Phe His Leu Phe
        290                 295                 300

Gly Pro Pro Gly Lys Lys Asp Pro Val Leu Lys Asp Leu Leu Phe Lys
305                 310                 315                 320

Asp Ser Ala Ile Met Leu Lys Arg Val Pro Ser Leu Met Asp Ser Gln
                325                 330                 335

Leu Tyr Leu Gly Phe Glu Tyr Tyr Ser Ala Ile Gln Ser Met Arg Lys
                340                 345                 350

Asp Gln Leu Thr Pro Ser Pro Arg Glu Asn Arg Ile Gln Trp Cys Ala
            355                 360                 365

Val Gly Lys Asp Glu Lys Ser Lys Cys Asp Arg Trp Ser Val Val Ser
    370                 375                 380

Asn Gly Asp Val Glu Cys Thr Val Val Asp Glu Thr Lys Asp Cys Ile
385                 390                 395                 400

Ile Lys Ile Met Lys Gly Glu Ala Asp Ala Val Ala Leu Asp Gly Gly
                405                 410                 415

Leu Val Tyr Thr Ala Gly Val Cys Gly Leu Val Pro Val Met Ala Glu
            420                 425                 430

Arg Tyr Asp Asp Glu Ser Gln Cys Ser Lys Thr Asp Glu Arg Pro Ala
        435                 440                 445

Ser Tyr Phe Ala Val Ala Val Ala Arg Lys Asp Ser Asn Val Asn Trp
    450                 455                 460

Asn Asn Leu Lys Gly Lys Lys Ser Cys His Thr Ala Val Gly Arg Thr
465                 470                 475                 480

Ala Gly Trp Val Ile Pro Met Gly Leu Ile His Asn Arg Thr Gly Thr
                485                 490                 495

Cys Asn Phe Asp Glu Tyr Phe Ser Glu Gly Cys Ala Pro Gly Ser Pro
                500                 505                 510

Pro Asn Ser Arg Leu Cys Gln Leu Cys Gln Gly Ser Gly Ile Pro
            515                 520                 525

Pro Glu Lys Cys Val Ala Ser Ser His Glu Lys Tyr Phe Gly Tyr Thr
    530                 535                 540

Gly Ala Leu Arg Cys Leu Val Glu Lys Gly Asp Val Ala Phe Ile Gln
545                 550                 555                 560

His Ser Thr Val Glu Glu Asn Thr Gly Gly Lys Asn Lys Ala Asp Trp
                565                 570                 575

Ala Lys Asn Leu Gln Met Asp Asp Phe Glu Leu Leu Cys Thr Asp Gly
            580                 585                 590

Arg Arg Ala Asn Val Met Asp Tyr Arg Glu Cys Asn Leu Ala Glu Val
        595                 600                 605

Pro Thr His Ala Val Val Arg Pro Glu Lys Ala Asn Lys Ile Arg
    610                 615                 620
```

```
Asp Leu Leu Glu Arg Gln Glu Lys Arg Phe Gly Val Asn Gly Ser Glu
625                 630                 635                 640

Lys Ser Lys Phe Met Met Phe Glu Ser Gln Asn Lys Asp Leu Leu Phe
            645                 650                 655

Lys Asp Leu Thr Lys Cys Leu Phe Lys Val Arg Glu Gly Thr Thr Tyr
            660                 665                 670

Lys Glu Phe Leu Gly Asp Lys Phe Tyr Thr Val Ile Ser Ser Leu Lys
        675                 680                 685

Thr Cys Asn Pro Ser Asp Ile Leu Gln Met Cys Ser Phe Leu Glu Gly
        690                 695                 700

Lys
705

<210> SEQ ID NO 47
<211> LENGTH: 210
<212> TYPE: PRT
<213> ORGANISM: Gallus gallus

<400> SEQUENCE: 47

Met Ala Met Ala Gly Val Phe Val Leu Phe Ser Phe Val Leu Cys Gly
1               5                   10                  15

Phe Leu Pro Asp Ala Ala Phe Gly Ala Glu Val Asp Cys Ser Arg Phe
            20                  25                  30

Pro Asn Ala Thr Asp Lys Glu Gly Lys Asp Val Leu Val Cys Asn Lys
        35                  40                  45

Asp Leu Arg Pro Ile Cys Gly Thr Asp Gly Val Thr Tyr Thr Asn Asp
    50                  55                  60

Cys Leu Leu Cys Ala Tyr Ser Ile Glu Phe Gly Thr Asn Ile Ser Lys
65                  70                  75                  80

Glu His Asp Gly Glu Cys Lys Glu Thr Val Pro Met Asn Cys Ser Ser
                85                  90                  95

Tyr Ala Asn Thr Thr Ser Glu Asp Gly Lys Val Met Val Leu Cys Asn
            100                 105                 110

Arg Ala Phe Asn Pro Val Cys Gly Thr Asp Gly Val Thr Tyr Asp Asn
        115                 120                 125

Glu Cys Leu Leu Cys Ala His Lys Val Glu Gln Gly Ala Ser Val Asp
    130                 135                 140

Lys Arg His Asp Gly Gly Cys Arg Lys Glu Leu Ala Ala Val Ser Val
145                 150                 155                 160

Asp Cys Ser Glu Tyr Pro Lys Pro Asp Cys Thr Ala Glu Asp Arg Pro
                165                 170                 175

Leu Cys Gly Ser Asp Asn Lys Thr Tyr Gly Asn Lys Cys Asn Phe Cys
            180                 185                 190

Asn Ala Val Val Glu Ser Asn Gly Thr Leu Thr Leu Ser His Phe Gly
        195                 200                 205

Lys Cys
    210

<210> SEQ ID NO 48
<211> LENGTH: 439
<212> TYPE: PRT
<213> ORGANISM: Gallus gallus

<400> SEQUENCE: 48

Met Gly Ala Leu Leu Ala Leu Leu Asp Pro Val Gln Pro Thr Arg Ala
1               5                   10                  15
```

```
Pro Asp Cys Gly Gly Ile Leu Thr Pro Leu Gly Leu Ser Tyr Leu Ala
         20                  25                  30

Glu Val Ser Lys Pro His Ala Glu Val Val Leu Arg Gln Asp Leu Met
         35                  40                  45

Ala Gln Arg Ala Ser Asp Leu Phe Leu Gly Ser Met Glu Pro Ser Arg
 50                  55                  60

Asn Arg Ile Thr Ser Val Lys Val Ala Asp Leu Trp Leu Ser Val Ile
 65                  70                  75                  80

Pro Glu Ala Gly Leu Arg Leu Gly Ile Glu Val Glu Leu Arg Val Ala
             85                  90                  95

Pro Leu His Ala Val Pro Met Pro Val Arg Ile Ser Ile Arg Ala Asp
            100                 105                 110

Leu His Val Asp Met Gly Pro Asp Gly Asn Leu Gln Leu Leu Thr Ser
            115                 120                 125

Ala Cys Arg Pro Thr Val Gln Ala Gln Ser Thr Arg Glu Ala Glu Ser
            130                 135                 140

Lys Ser Ser Arg Ser Ile Leu Asp Lys Val Val Asp Val Asp Lys Leu
145                 150                 155                 160

Cys Leu Asp Val Ser Lys Leu Leu Phe Pro Asn Glu Gln Leu Met
                165                 170                 175

Ser Leu Thr Ala Leu Phe Pro Val Thr Pro Asn Cys Gln Leu Gln Tyr
            180                 185                 190

Leu Pro Leu Ala Ala Pro Val Phe Ser Lys Gln Gly Ile Ala Leu Ser
            195                 200                 205

Leu Gln Thr Thr Phe Gln Val Ala Gly Ala Val Val Pro Val Pro Val
            210                 215                 220

Ser Pro Val Pro Phe Ser Met Pro Glu Leu Ala Ser Thr Ser Thr Ser
225                 230                 235                 240

His Leu Ile Leu Ala Leu Ser Glu His Phe Tyr Thr Ser Leu Tyr Phe
            245                 250                 255

Thr Leu Glu Arg Ala Gly Ala Phe Asn Met Thr Ile Pro Ser Met Leu
            260                 265                 270

Thr Thr Ala Thr Leu Ala Gln Lys Ile Thr Gln Val Gly Ser Leu Tyr
            275                 280                 285

His Glu Asp Leu Pro Ile Thr Leu Ser Ala Ala Leu Arg Ser Ser Pro
            290                 295                 300

Arg Val Val Leu Glu Glu Gly Arg Ala Ala Leu Lys Leu Phe Leu Thr
305                 310                 315                 320

Val His Ile Gly Ala Gly Ser Pro Asp Phe Gln Ser Phe Leu Ser Val
            325                 330                 335

Ser Ala Asp Val Thr Ala Gly Leu Gln Leu Ser Val Ser Asp Thr Arg
            340                 345                 350

Met Met Ile Ser Thr Ala Val Ile Glu Asp Ala Glu Leu Ser Leu Ala
            355                 360                 365

Ala Ser Asn Val Gly Leu Val Arg Ala Ala Leu Leu Glu Glu Leu Phe
            370                 375                 380

Leu Ala Pro Val Cys Gln Gln Val Pro Ala Trp Met Asp Asp Val Leu
385                 390                 395                 400

Arg Glu Gly Val His Leu Pro His Leu Ser His Phe Thr Tyr Thr Asp
            405                 410                 415

Val Ser Val Val Val His Lys Asp Tyr Val Leu Val Pro Cys Lys Leu
            420                 425                 430
```

Lys Leu Arg Ser Thr Met Ala
        435

<210> SEQ ID NO 49
<211> LENGTH: 1463
<212> TYPE: PRT
<213> ORGANISM: Bos taurus

<400> SEQUENCE: 49

Met Phe Ser Phe Val Asp Leu Arg Leu Leu Leu Leu Ala Ala Thr
1               5                   10                  15

Ala Leu Leu Thr His Gly Gln Glu Gly Gln Glu Glu Gly Gln Glu
            20                  25                  30

Glu Asp Ile Pro Pro Val Thr Cys Val Gln Asn Gly Leu Arg Tyr His
            35                  40                  45

Asp Arg Asp Val Trp Lys Pro Val Pro Cys Gln Ile Cys Val Cys Asp
        50                  55                  60

Asn Gly Asn Val Leu Cys Asp Asp Val Ile Cys Asp Glu Leu Lys Asp
65                  70                  75                  80

Cys Pro Asn Ala Lys Val Pro Thr Asp Glu Cys Cys Pro Val Cys Pro
                85                  90                  95

Glu Gly Gln Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
        115                 120                 125

Pro Gly Arg Asp Gly Ile Pro Gly Gln Pro Gly Leu Pro Gly Pro Pro
    130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Ile Ser Val
                165                 170                 175

Pro Gly Pro Met Gly Pro Ser Gly Pro Arg Gly Leu Pro Gly Pro Pro
            180                 185                 190

Gly Ala Pro Gly Pro Gln Gly Phe Gln Gly Pro Pro Gly Glu Pro Gly
        195                 200                 205

Glu Pro Gly Ala Ser Gly Pro Met Gly Pro Arg Gly Pro Pro Gly Pro
    210                 215                 220

Pro Gly Lys Asn Gly Asp Asp Gly Glu Ala Gly Lys Pro Gly Arg Pro
225                 230                 235                 240

Gly Glu Arg Gly Pro Pro Gly Pro Gln Gly Ala Arg Gly Leu Pro Gly
                245                 250                 255

Thr Ala Gly Leu Pro Gly Met Lys Gly His Arg Gly Phe Ser Gly Leu
            260                 265                 270

Asp Gly Ala Lys Gly Asp Ala Gly Pro Ala Gly Pro Lys Gly Glu Pro
        275                 280                 285

Gly Ser Pro Gly Glu Asn Gly Ala Pro Gly Gln Met Gly Pro Arg Gly
    290                 295                 300

Leu Pro Gly Glu Arg Gly Arg Pro Gly Ala Pro Gly Pro Ala Gly Ala
305                 310                 315                 320

Arg Gly Asn Asp Gly Ala Thr Gly Ala Ala Gly Pro Pro Gly Pro Thr
                325                 330                 335

Gly Pro Ala Gly Pro Pro Gly Phe Pro Gly Ala Val Gly Ala Lys Gly
            340                 345                 350

```
        Glu Gly Gly Pro Gln Gly Pro Arg Gly Ser Glu Gly Pro Gln Gly Val
                355                 360                 365

Arg Gly Glu Pro Gly Pro Pro Gly Pro Ala Gly Ala Ala Gly Pro Ala
            370                 375                 380

Gly Asn Pro Gly Ala Asp Gly Gln Pro Gly Ala Lys Gly Ala Asn Gly
        385                 390                 395                 400

Ala Pro Gly Ile Ala Gly Ala Pro Gly Phe Pro Gly Ala Arg Gly Pro
                    405                 410                 415

Ser Gly Pro Gln Gly Pro Ser Gly Pro Pro Gly Pro Lys Gly Asn Ser
                        420                 425                 430

Gly Glu Pro Gly Ala Pro Gly Ser Lys Gly Asp Thr Gly Ala Lys Gly
                    435                 440                 445

Glu Pro Gly Pro Thr Gly Ile Gln Gly Pro Pro Gly Pro Ala Gly Glu
                450                 455                 460

Glu Gly Lys Arg Gly Ala Arg Gly Glu Pro Gly Pro Ala Gly Leu Pro
        465                 470                 475                 480

Gly Pro Pro Gly Glu Arg Gly Gly Pro Gly Ser Arg Gly Phe Pro Gly
                            485                 490                 495

Ala Asp Gly Val Ala Gly Pro Lys Gly Pro Ala Gly Glu Arg Gly Ala
                        500                 505                 510

Pro Gly Pro Ala Gly Pro Lys Gly Ser Pro Gly Glu Ala Gly Arg Pro
                    515                 520                 525

Gly Glu Ala Gly Leu Pro Gly Ala Lys Gly Leu Thr Gly Ser Pro Gly
                530                 535                 540

Ser Pro Gly Pro Asp Gly Lys Thr Gly Pro Pro Gly Pro Ala Gly Gln
        545                 550                 555                 560

Asp Gly Arg Pro Gly Pro Pro Gly Pro Pro Gly Ala Arg Gly Gln Ala
                            565                 570                 575

Gly Val Met Gly Phe Pro Gly Pro Lys Gly Ala Ala Gly Glu Pro Gly
                        580                 585                 590

Lys Ala Gly Glu Arg Gly Val Pro Gly Pro Pro Gly Ala Val Gly Pro
                    595                 600                 605

Ala Gly Lys Asp Gly Glu Ala Gly Ala Gln Gly Pro Pro Gly Pro Ala
                610                 615                 620

Gly Pro Ala Gly Glu Arg Gly Glu Gln Gly Pro Ala Gly Ser Pro Gly
        625                 630                 635                 640

Phe Gln Gly Leu Pro Gly Pro Ala Gly Pro Pro Gly Glu Ala Gly Lys
                            645                 650                 655

Pro Gly Glu Gln Gly Val Pro Gly Asp Leu Gly Ala Pro Gly Pro Ser
                        660                 665                 670

Gly Ala Arg Gly Glu Arg Gly Phe Pro Gly Glu Arg Gly Val Gln Gly
                    675                 680                 685

Pro Pro Gly Pro Ala Gly Pro Arg Gly Ala Asn Gly Ala Pro Gly Asn
                690                 695                 700

Asp Gly Ala Lys Gly Asp Ala Gly Ala Pro Gly Ala Pro Gly Ser Gln
        705                 710                 715                 720

Gly Ala Pro Gly Leu Gln Gly Met Pro Gly Glu Arg Gly Ala Ala Gly
                            725                 730                 735

Leu Pro Gly Pro Lys Gly Asp Arg Gly Asp Ala Gly Pro Lys Gly Ala
                        740                 745                 750

Asp Gly Ala Pro Gly Lys Asp Gly Val Arg Gly Leu Thr Gly Pro Ile
                    755                 760                 765
```

```
Gly Pro Pro Gly Pro Ala Gly Ala Pro Gly Asp Lys Gly Glu Ala Gly
        770                 775                 780

Pro Ser Gly Pro Ala Gly Pro Thr Gly Ala Arg Gly Ala Pro Gly Asp
785                 790                 795                 800

Arg Gly Glu Pro Gly Pro Gly Pro Ala Gly Phe Ala Gly Pro Pro
            805                 810                 815

Gly Ala Asp Gly Gln Pro Gly Ala Lys Gly Glu Pro Gly Asp Ala Gly
                820                 825                 830

Ala Lys Gly Asp Ala Gly Pro Pro Gly Pro Ala Gly Pro Ala Gly Pro
        835                 840                 845

Pro Gly Pro Ile Gly Asn Val Gly Ala Pro Gly Pro Lys Gly Ala Arg
        850                 855                 860

Gly Ser Ala Gly Pro Pro Gly Ala Thr Gly Phe Pro Gly Ala Ala Gly
865                 870                 875                 880

Arg Val Gly Pro Pro Gly Pro Ser Gly Asn Ala Gly Pro Pro Gly Pro
                885                 890                 895

Pro Gly Pro Ala Gly Lys Glu Gly Ser Lys Gly Pro Arg Gly Glu Thr
        900                 905                 910

Gly Pro Ala Gly Arg Pro Gly Glu Val Gly Pro Pro Gly Pro Pro Gly
        915                 920                 925

Pro Ala Gly Glu Lys Gly Ala Pro Gly Ala Asp Gly Pro Ala Gly Ala
        930                 935                 940

Pro Gly Thr Pro Gly Pro Gln Gly Ile Ala Gly Gln Arg Gly Val Val
945                 950                 955                 960

Gly Leu Pro Gly Gln Arg Gly Glu Arg Gly Phe Pro Gly Leu Pro Gly
                965                 970                 975

Pro Ser Gly Glu Pro Gly Lys Gln Gly Pro Ser Gly Ala Ser Gly Glu
        980                 985                 990

Arg Gly Pro Pro Gly Pro Met Gly Pro Pro Gly Leu Ala Gly Pro Pro
        995                 1000                1005

Gly Glu Ser Gly Arg Glu Gly Ala Pro Gly Ala Glu Gly Ser Pro
        1010                1015                1020

Gly Arg Asp Gly Ser Pro Gly Ala Lys Gly Asp Arg Gly Glu Thr
        1025                1030                1035

Gly Pro Ala Gly Pro Pro Gly Ala Pro Gly Ala Pro Gly Ala Pro
        1040                1045                1050

Gly Pro Val Gly Pro Ala Gly Lys Ser Gly Asp Arg Gly Glu Thr
        1055                1060                1065

Gly Pro Ala Gly Pro Ala Gly Pro Ile Gly Pro Val Gly Ala Arg
        1070                1075                1080

Gly Pro Ala Gly Pro Gln Gly Pro Arg Gly Asp Lys Gly Glu Thr
        1085                1090                1095

Gly Glu Gln Gly Asp Arg Gly Ile Lys Gly His Arg Gly Phe Ser
        1100                1105                1110

Gly Leu Gln Gly Pro Pro Gly Pro Pro Gly Ser Pro Gly Glu Gln
        1115                1120                1125

Gly Pro Ser Gly Ala Ser Gly Pro Ala Gly Pro Arg Gly Pro Pro
        1130                1135                1140

Gly Ser Ala Gly Ser Pro Gly Lys Asp Gly Leu Asn Gly Leu Pro
        1145                1150                1155

Gly Pro Ile Gly Pro Pro Gly Pro Arg Gly Arg Thr Gly Asp Ala
        1160                1165                1170
```

Gly Pro Ala Gly Pro Pro Gly Pro Pro Gly Pro Pro
    1175             1180             1185

Gly Pro Pro Ser Gly Gly Tyr Asp Leu Ser Phe Leu Pro Gln Pro
    1190             1195             1200

Pro Gln Glu Lys Ala His Asp Gly Gly Arg Tyr Tyr Arg Ala Asp
    1205             1210             1215

Asp Ala Asn Val Val Arg Asp Arg Asp Leu Glu Val Asp Thr Thr
    1220             1225             1230

Leu Lys Ser Leu Ser Gln Gln Ile Glu Asn Ile Arg Ser Pro Glu
    1235             1240             1245

Gly Ser Arg Lys Asn Pro Ala Arg Thr Cys Arg Asp Leu Lys Met
    1250             1255             1260

Cys His Ser Asp Trp Lys Ser Gly Glu Tyr Trp Ile Asp Pro Asn
    1265             1270             1275

Gln Gly Cys Asn Leu Asp Ala Ile Lys Val Phe Cys Asn Met Glu
    1280             1285             1290

Thr Gly Glu Thr Cys Val Tyr Pro Thr Gln Pro Ser Val Ala Gln
    1295             1300             1305

Lys Asn Trp Tyr Ile Ser Lys Asn Pro Lys Glu Lys Arg His Val
    1310             1315             1320

Trp Tyr Gly Glu Ser Met Thr Gly Gly Phe Gln Phe Glu Tyr Gly
    1325             1330             1335

Gly Gln Gly Ser Asp Pro Ala Asp Val Ala Ile Gln Leu Thr Phe
    1340             1345             1350

Leu Arg Leu Met Ser Thr Glu Ala Ser Gln Asn Ile Thr Tyr His
    1355             1360             1365

Cys Lys Asn Ser Val Ala Tyr Met Asp Gln Gln Thr Gly Asn Leu
    1370             1375             1380

Lys Lys Ala Leu Leu Leu Gln Gly Ser Asn Glu Ile Glu Ile Arg
    1385             1390             1395

Ala Glu Gly Asn Ser Arg Phe Thr Tyr Ser Val Thr Tyr Asp Gly
    1400             1405             1410

Cys Thr Ser His Thr Gly Ala Trp Gly Lys Thr Val Ile Glu Tyr
    1415             1420             1425

Lys Thr Thr Lys Thr Ser Arg Leu Pro Ile Ile Asp Val Ala Pro
    1430             1435             1440

Leu Asp Val Gly Ala Pro Asp Gln Glu Phe Gly Phe Asp Val Gly
    1445             1450             1455

Pro Ala Cys Phe Leu
    1460

<210> SEQ ID NO 50
<211> LENGTH: 1341
<212> TYPE: DNA
<213> ORGANISM: Glycine max

<400> SEQUENCE: 50
ggttcaacaa cacaagcttc aagttttaaa aggaaaaatg tcagccaaaa actttaaata    60
aaatggtaac aaggaaatta ttcaaaaatt acaaacctcg tcaaaatagg aaagaaaaaa   120
agtttaggga tttagaaaaa acatcaatct agttccacct tattttatag agagaagaaa   180
ctaatatata agaactaaaa aacagaagaa tagaaaaaaa aagtattgac aggaaagaaa   240
aagtagctgt atgcttataa gtactttgag gatttgaatt ctctcttata aaacacaaac   300

```
acaattttta gattttattt aaataatcat caatccgatt ataattattt atatatttt       360
ctattttcaa agaagtaaat catgagcttt tccaactcaa catctatttt ttttctctca       420
acctttttca catcttaagt agtctcaccc tttatatata taacttattt cttaccttt        480
acattatgta actttatca ccaaaaccaa caacttaaa attttattaa atagactcca         540
caagtaactt gacactctta cattcatcga cattaacttt tatctgtttt ataaatatta      600
ttgtgatata atttaatcaa aataaccaca aactttcata aaaggttctt attaagcatg       660
gcatttaata agcaaaaaca actcaatcac tttcatatag gaggtagcct aagtacgtac       720
tcaaaatgcc aacaaataaa aaaaagttg ctttaataat gccaaaacaa attaataaaa        780
cacttacaac accggatttt ttttaattaa aatgtgccat ttaggataaa tagttaatat      840
ttttaataat tatttaaaaa gccgtatcta ctaaaatgat ttttatttgg ttgaaaatat      900
taatatgttt aaatcaacac aatctatcaa aattaaacta aaaaaaaaat aagtgtacgt      960
ggttaacatt agtacagtaa tataagagga aaatgagaaa ttaagaaatt gaaagcgagt     1020
ctaattttta aattatgaac ctgcatatat aaaaggaaag aaagaatcca ggaagaaaag     1080
aaatgaaacc atgcatggtc ccctcgtcat cacgagtttc tgccatttgc aatagaaaca     1140
ctgaaacacc tttctctttg tcacttaatt gagatgccga agccacctca caccatgaac     1200
ttcatgaggt gtagcaccca aggcttccat agccatgcat actgaagaat gtctcaagct     1260
cagcacccta cttctgtgac gtgtccctca ttcaccttcc tctcttccct ataaataacc     1320
acgcctcagg ttctccgctt c                                                1341
```

<210> SEQ ID NO 51
<211> LENGTH: 147
<212> TYPE: PRT
<213> ORGANISM: Gallus gallus

<400> SEQUENCE: 51

```
Met Arg Ser Leu Leu Ile Leu Val Leu Cys Phe Leu Pro Leu Ala Ala
1               5                   10                  15

Leu Gly Lys Val Phe Gly Arg Cys Glu Leu Ala Ala Ala Met Lys Arg
            20                  25                  30

His Gly Leu Asp Asn Tyr Arg Gly Tyr Ser Leu Gly Asn Trp Val Cys
        35                  40                  45

Ala Ala Lys Phe Glu Ser Asn Phe Asn Thr Gln Ala Thr Asn Arg Asn
    50                  55                  60

Thr Asp Gly Ser Thr Asp Tyr Gly Ile Leu Gln Ile Asn Ser Arg Trp
65                  70                  75                  80

Trp Cys Asn Asp Gly Arg Thr Pro Gly Ser Arg Asn Leu Cys Asn Ile
                85                  90                  95

Pro Cys Ser Ala Leu Leu Ser Ser Asp Ile Thr Ala Ser Val Asn Cys
            100                 105                 110

Ala Lys Lys Ile Val Ser Asp Gly Asn Gly Met Asn Ala Trp Val Ala
        115                 120                 125

Trp Arg Asn Arg Cys Lys Gly Thr Asp Val Gln Ala Trp Ile Arg Gly
    130                 135                 140

Cys Arg Leu
145
```

<210> SEQ ID NO 52
<211> LENGTH: 517
<212> TYPE: PRT
<213> ORGANISM: Gallus gallus

<400> SEQUENCE: 52

```
Met Thr Asp Trp Val Leu His His Lys Val Gly Pro Leu Asp Met Thr
1               5                   10                  15

Thr Arg Tyr Ile Phe Pro Leu Leu Pro Leu Pro Phe Leu Pro His Ser
            20                  25                  30

Glu Ser Lys Arg Ala Val Cys Ala Pro Arg Cys Ser Ala Met Arg Thr
        35                  40                  45

Ala Arg Gln Phe Val Gln Val Ala Leu Ala Leu Cys Cys Phe Ala Asp
    50                  55                  60

Ile Ala Phe Gly Ile Glu Val Asn Cys Ser Leu Tyr Ala Ser Gly Ile
65              70                  75                  80

Gly Lys Asp Gly Thr Ser Trp Val Ala Cys Pro Arg Asn Leu Lys Pro
                85                  90                  95

Val Cys Gly Thr Asp Gly Ser Thr Tyr Ser Asn Glu Cys Gly Ile Cys
            100                 105                 110

Leu Tyr Asn Arg Glu His Gly Ala Asn Val Lys Glu Tyr Asp Gly
        115                 120                 125

Glu Cys Arg Pro Lys His Val Thr Ile Asp Cys Ser Pro Tyr Leu Gln
    130                 135                 140

Val Val Arg Asp Gly Asn Thr Met Val Ala Cys Pro Arg Ile Leu Lys
145                 150                 155                 160

Pro Val Cys Gly Ser Asp Ser Phe Thr Tyr Asp Asn Glu Cys Gly Ile
            165                 170                 175

Cys Ala Tyr Asn Ala Glu His His Thr Asn Ile Ser Lys Leu His Asp
        180                 185                 190

Gly Glu Cys Lys Leu Glu Ile Gly Ser Val Asp Cys Ser Lys Tyr Pro
    195                 200                 205

Ser Thr Val Ser Lys Asp Gly Arg Thr Leu Val Ala Cys Pro Arg Ile
210                 215                 220

Leu Ser Pro Val Cys Gly Thr Asp Gly Phe Thr Tyr Asp Asn Glu Cys
225                 230                 235                 240

Gly Ile Cys Ala His Asn Ala Glu Gln Arg Thr His Val Ser Lys Lys
            245                 250                 255

His Asp Gly Lys Cys Arg Gln Glu Ile Pro Glu Ile Asp Cys Asp Gln
        260                 265                 270

Tyr Pro Thr Arg Lys Thr Thr Gly Gly Lys Leu Leu Val Arg Cys Pro
    275                 280                 285

Arg Ile Leu Leu Pro Val Cys Gly Thr Asp Gly Phe Thr Tyr Asp Asn
290                 295                 300

Glu Cys Gly Ile Cys Ala His Asn Ala Gln His Gly Thr Glu Val Lys
305                 310                 315                 320

Lys Ser His Asp Gly Arg Cys Lys Glu Arg Ser Thr Pro Leu Asp Cys
            325                 330                 335

Thr Gln Tyr Leu Ser Asn Thr Gln Asn Gly Glu Ala Ile Thr Ala Cys
        340                 345                 350

Pro Phe Ile Leu Gln Glu Val Cys Gly Thr Asp Gly Val Thr Tyr Ser
    355                 360                 365

Asn Asp Cys Ser Leu Cys Ala His Asn Ile Glu Leu Gly Thr Ser Val
370                 375                 380

Ala Lys Lys His Asp Gly Arg Cys Arg Glu Glu Val Pro Glu Leu Asp
385                 390                 395                 400
```

```
Cys Ser Lys Tyr Lys Thr Ser Thr Leu Lys Asp Gly Arg Gln Val Val
            405                 410                 415

Ala Cys Thr Met Ile Tyr Asp Pro Val Cys Ala Thr Asn Gly Val Thr
            420                 425                 430

Tyr Ala Ser Glu Cys Thr Leu Cys Ala His Asn Leu Glu Gln Arg Thr
            435                 440                 445

Asn Leu Gly Lys Arg Lys Asn Gly Arg Cys Glu Glu Asp Ile Thr Lys
            450                 455                 460

Glu His Cys Arg Glu Phe Gln Lys Val Ser Pro Ile Cys Thr Met Glu
465                 470                 475                 480

Tyr Val Pro His Cys Gly Ser Asp Gly Val Thr Tyr Ser Asn Arg Cys
            485                 490                 495

Phe Phe Cys Asn Ala Tyr Val Gln Ser Asn Arg Thr Leu Asn Leu Val
            500                 505                 510

Ser Met Ala Ala Cys
            515

<210> SEQ ID NO 53
<211> LENGTH: 225
<212> TYPE: PRT
<213> ORGANISM: Gallus gallus

<400> SEQUENCE: 53

Val Val Ser Thr Ala Ala Pro Thr Asp Pro Arg Arg Arg Met Ala Val
1               5                   10                  15

Ser Val Leu Leu Phe Ile Ser Val Ala Leu Ala Gly Val Leu Ser Thr
            20                  25                  30

Ala Ser Gln Ala Cys Lys Leu Glu Pro Val Lys Ile Asp Leu Ala Asn
            35                  40                  45

Pro Gln Leu Ala Gly Lys Trp Tyr Phe Ile Gln Val Ala Thr Glu Val
        50                  55                  60

Glu Leu Tyr Gln Ala Arg Phe Ala Asn Ile Asp Asn Ser Tyr Phe Ile
65                  70                  75                  80

Ser Thr Pro Asp Val Lys Leu Asn Lys Thr Asn Ile Lys Glu Tyr Ser
                85                  90                  95

Gln Leu Gly Asp Leu Cys Leu Ser Thr Asn Thr Asp Tyr Val Val Leu
            100                 105                 110

Glu Asn Gly Tyr Glu Phe Thr Asp Gly Ala Lys Asn Ile Asn Asn Phe
        115                 120                 125

Arg Ile Ile Lys Ser Lys Ile Asp Asn Met Leu Ile Ile Asp Tyr Gln
130                 135                 140

Tyr Gln Ile Glu Lys Met Asp Tyr His Met Leu Thr Leu Phe Lys Arg
145                 150                 155                 160

Asn Pro Thr Ala Ser Lys Glu Glu Met Glu Ile Phe Glu Ser Tyr Thr
                165                 170                 175

Lys Cys Leu Gly Leu Asp Lys Asp Lys Ile Lys Ala Phe Pro Arg Asn
            180                 185                 190

Lys Ser Glu Cys Lys Glu Glu Lys Gln Ile Asn Ser Phe Asn Ala Thr
            195                 200                 205

Thr Gln Ala Gln Asp Phe Leu Glu Glu Lys Val Leu Gln Asn Arg Asn
        210                 215                 220

Ile
225
```

<210> SEQ ID NO 54
<211> LENGTH: 886
<212> TYPE: DNA
<213> ORGANISM: Glycine max

<400> SEQUENCE: 54

```
gtgtgttgta agtataaatt taaaataaaa ataaaaacaa ttattatatc aaaatggcaa      60
aaacatttaa tacgtattat ttaagaaaaa aatatgtaat aatatattta tattttaata     120
tctattctta tgtattttt aaaaatctat tatatattga tcaactaaaa tattttata       180
tctacactta ttttgcattt ttatcaattt tcttgcgttt tttggcatat ttaataatga    240
ctattcttta ataatcaatc attattctta catggtacat attgttggaa ccatatgaag    300
tgtccattgc atttgactat gtggatagtg ttttgatcca ggcctccatt tgccgcttat   360
taattaattt ggtaacagtc cgtactaatc agttacttat ccttcctcca tcataattaa   420
tcttggtagt ctcgaatgcc acaacactga ctagtctctt ggatcataag aaaaagccaa   480
ggaacaaaag atcacaaaac acaatgagag tatcctttgc atagcaatgt ctaagttcat   540
aaaattcaaa caaaaacgca atcacacaca gtggacatca cttatccact agctgatcag   600
gatcgccgcg tcaagaaaaa aaaactggac cccaaaagcc atgcacaaca acacgtactc   660
acaaaggtgt caatcgagca gcccaaaaca ttcaccaact caacccatca tgagcccaca   720
catttgttgt ttctaaccca acctcaaact cgtattctct tccgccacct cattttgtt    780
tatttcaaca cccgtcaaac tgcatgccac cccgtggcca aatgtccatg catgttaaca   840
agacctatga ctataaatat ctgcaatctc ggcccaggtt ttcatc                   886
```

<210> SEQ ID NO 55
<211> LENGTH: 208
<212> TYPE: PRT
<213> ORGANISM: Gallus gallus

<400> SEQUENCE: 55

```
Ala Leu Thr Ser Gly Leu Gly Pro Asp Val Tyr Gln Phe Leu Gln Asp
1               5                   10                  15

Met Gly Met Lys Phe Phe Thr Asn Ser Lys Ile Arg Gln Pro Thr Val
            20                  25                  30

Cys Thr Arg Glu Thr Val Arg Pro Pro Ser Tyr Phe Leu Asn Ala Gly
        35                  40                  45

Phe Thr Ala Ser Thr His His Val Lys Leu Ser Ala Glu Val Ala Arg
    50                  55                  60

Glu Glu Arg Gly Lys Arg His Ile Leu Glu Thr Ile Arg Glu Phe Phe
65                  70                  75                  80

Pro Glu Thr Trp Ile Trp Asp Ile Ile Leu Ile Asn Ser Thr Gly Lys
                85                  90                  95

Ala Ser Val Ser Tyr Thr Ile Pro Asp Thr Ile Thr Glu Trp Lys Ala
            100                 105                 110

Ser Ala Phe Cys Val Leu Pro Pro Asn Val Val Glu Glu Ser Ala Arg
        115                 120                 125

Ala Ser Val Ser Val Leu Gly Asp Ile Leu Gly Ser Ala Met Gln Asn
    130                 135                 140

Thr Gln Asn Leu Leu Gln Met Pro Tyr Gly Cys Gly Glu Gln Asn Met
145                 150                 155                 160

Val Leu Phe Ala Pro Asn Ile Tyr Val Leu Asp Tyr Leu Asn Glu Thr
                165                 170                 175
```

```
Gln Gln Leu Ser Glu Asp Met Lys Ser Lys Thr Ile Gly Tyr Leu Glu
                180                 185                 190

Ser Gly Tyr Gln Lys Gln Leu Ser Tyr Lys His Pro Asp Gly Ser Tyr
            195                 200                 205

<210> SEQ ID NO 56
<211> LENGTH: 152
<212> TYPE: PRT
<213> ORGANISM: Gallus gallus

<400> SEQUENCE: 56

Met Val His Ala Thr Ser Pro Leu Leu Leu Leu Leu Leu Ser Leu
1               5                   10                  15

Ala Leu Val Ala Pro Gly Leu Ser Ala Arg Lys Cys Ser Leu Thr Gly
                20                  25                  30

Lys Trp Thr Asn Asp Leu Gly Ser Asn Met Thr Ile Gly Ala Val Asn
                35                  40                  45

Ser Arg Gly Glu Phe Thr Gly Thr Tyr Ile Thr Ala Val Thr Ala Thr
            50                  55                  60

Ser Asn Glu Ile Lys Glu Ser Pro Leu His Gly Thr Gln Asn Thr Ile
65                  70                  75                  80

Asn Lys Arg Thr Gln Pro Thr Phe Gly Phe Thr Val Asn Trp Lys Phe
                85                  90                  95

Ser Glu Ser Thr Thr Val Phe Thr Gly Gln Cys Phe Ile Asp Arg Asn
                100                 105                 110

Gly Lys Glu Val Leu Lys Thr Met Trp Leu Leu Arg Ser Ser Val Asn
                115                 120                 125

Asp Ile Gly Asp Asp Trp Lys Ala Thr Arg Val Gly Ile Asn Ile Phe
            130                 135                 140

Thr Arg Leu Arg Thr Gln Lys Glu
145                 150

<210> SEQ ID NO 57
<211> LENGTH: 148
<212> TYPE: PRT
<213> ORGANISM: Gallus gallus

<400> SEQUENCE: 57

Met Val Gly Ser Pro Arg Ala Pro Leu Leu Leu Ala Ser Leu Ile
1               5                   10                  15

Val Ala Leu Ala Leu Ala Leu Ala Val Ser Pro Ala Ala Gln Gly
                20                  25                  30

Pro Arg Lys Gly Arg Leu Leu Gly Gly Leu Met Glu Ala Asp Val Asn
                35                  40                  45

Glu Glu Gly Val Gln Glu Ala Leu Ser Phe Ala Val Ser Glu Phe Asn
            50                  55                  60

Lys Arg Ser Asn Asp Ala Tyr Gln Ser Arg Val Val Arg Val Arg
65                  70                  75                  80

Ala Arg Lys Gln Val Val Ser Gly Met Asn Tyr Phe Leu Asp Val Glu
                85                  90                  95

Leu Gly Arg Thr Thr Cys Thr Lys Ser Gln Ala Asn Leu Asp Ser Cys
                100                 105                 110

Pro Phe His Asn Gln Pro His Leu Lys Arg Glu Lys Leu Cys Ser Phe
            115                 120                 125

Gln Val Tyr Val Val Pro Trp Met Asn Thr Ile Asn Leu Val Lys Phe
            130                 135                 140
```

```
<210> SEQ ID NO 58
<211> LENGTH: 62
<212> TYPE: DNA
<213> ORGANISM: Tobacco mosaic virus

<400> SEQUENCE: 58 attttttacaa caattaccaa caacaacaaa caacaaacaa cattacaatt acatttacaa    60
tt                                                                    62

<210> SEQ ID NO 59
<211> LENGTH: 739
<212> TYPE: DNA
<213> ORGANISM: Arabidopsis thaliana

<400> SEQUENCE: 59
ttgcttcttc tctctttttt tggttcaata tgaacctttt gatgtccact atcctttat     60 ataatgaaat gataaggttt ttgatatgtt atgtggttct tgataacatt atacaattac    120
ttaatatcta catatgaaag gttggaattt ttttaagtc accacaatag aggtgacacg     180
tgtaagcacc tcgttaatct tatctcatcc aagatggggg taggaagagg atatgaatgt    240
atgattgagg ttggttttga gttttttttt tttttttttt tgagtccttc aacttgttat    300 tttaatttt tttggtggg ggaggagggg ggttgaaata tttatcatat agtagtccaa      360
agtaaattga tagctagagt acttgtttgc ttgcttatat tgtcctcaac tttatgtaat    420
accatgattc caacttagac actcttttaa gttgtaatt tcattatttt ctttttttag     480
agttttatgt tgaattcgca taattttcaa tcggataata caagaaaaat aatattttag    540
tataatttta tacatgaaat ttcgggaagg taggatatac ggattgtttg tcggatcaga    600
gactttactc gtacctttgt aactgttgat cccaaataca gatagtgact ccagagttat    660
atattatacc tatagagact aatatgattt agtgttatta aaattagtat tactaattaa    720
ttgtaatgcc ccatgaatt                                                  739

<210> SEQ ID NO 60
<211> LENGTH: 4968
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
tctgtgaaga caaactagaa ttcgagctcg gagtgagacc gcagctggca cgacaggttt    60
gccgactgga aagcgggcag tgagcgcaac gcaattaatg tgagttagct cactcattag    120 gcacccagg ctttacactt tatgcttccg gctcgtatgt tgtgtggaat tgtgagcgga     180
taacaatttc acacaggaaa cagctatgac catgattacg ccaagcttgc atgcctgcag    240
gtcgactcta gaggatcccc gggtaccgag ctcgaattca ctggccgtcg ttttacaacg    300
tcgtgactgg gaaaaccctg gcgttaccca acttaatcgc cttgcagcac atccccctt    360 cgccagctgg cgtaatagcg aagaggcccg caccgatcgc ccttcccaac agttgcgcag    420
cctgaatggc gaatggcgcc tgatgcggta ttttctcctt acgcatctgt gcggtatttc    480
acaccgcata tggtgcactc tcagtacaat ctgctctgat gccgcatagt taagccagcc    540
```

```
ccgacacccg ccaacacccg ctgacgcgcc ctgacgggct tgtctgctcc cggcatccgc    600
ttacagacaa gctgtgacgg tctcacgctt tacttgtctt ctgcacgaag tggtttaaac    660
tatcagtgtt tgacaggata tattggcggg taaacctaag agaaagagc gtttattaga     720 ataatcggat atttaaaagg gcgtgaaaag gtttatccgt tcgtccattt gtatgtgcat    780
gccaaccaca gggttcccca gatcaggcgc tggctgctga acccccagcc ggaactgacc    840
ccacaaggcc ctagcgtttg caatgcacca ggtcatcatt gacccaggcg tgttccacca    900
ggccgctgcc tcgcaactct tcgcaggctt cgccgacctg ctcgcgccac ttcttcacgc    960
gggtggaatc cgatccgcac atgaggcgga aggtttccag cttgagcggg tacggctccc    1020
ggtgcgagct gaaatagtcg aacatccgtc gggccgtcgg cgacagcttg cggtacttct    1080
cccatatgaa tttcgtgtag tggtcgccag caaacagcac gacgatttcc tcgtcgatca    1140
ggacctggca acgggacgtt ttcttgccac ggtccaggac gcggaagcgg tgcagcagcg    1200
acaccgattc caggtgccca cgcggtcgg acgtgaagcc catcgccgtc gcctgtaggc     1260
gcgacaggca ttcctcggcc ttcgtgtaat accggccatt gatcgaccag cccaggtcct    1320
ggcaaagctc gtagaacgtg aaggtgatcg gctcgccgat aggggtgcgc ttcgcgtact    1380
ccaacacctg ctgccacacc agttcgtcat cgtcggcccg cagctcgacg ccggtgtagg    1440
tgatcttcac gtccttgttg acgtggaaaa tgaccttgtt ttgcagcgcc tcgcgcggga    1500
ttttcttgtt gcgcgtggtg aacagggcag agcgggccgt gtcgtttggc atcgctcgca    1560
tcgtgtccgg ccacggcgca atatcgaaca aggaaagctg catttccttg atctgctgct    1620
tcgtgtgttt cagcaacgcg gcctgcttgg cctcgctgac ctgttttgcc aggtcctcgc    1680
cggcggtttt tcgcttcttg gtcgtcatag ttcctcgcgt gtcgatggtc atcgacttcg    1740
ccaaacctgc cgcctcctgt tcaagacgac gcgaacgctc cacggcggcc gatgcgcgg     1800 gcagggcagg gggagccagt tgcacgctgt cgcgctcgat cttggccgta gcttgctgga    1860
ccatcgagcc gacggactgg aaggtttcgc ggggcgcacg catgacgtg cggcttgcga     1920 tggtttcggc atcctcggcg gaaaaccccg cgtcgatcag ttcttgcctg tatgccttcc    1980
ggtcaaacgt ccgattcatt caccctcctt gcgggattgc cccgactcac gccggggcaa    2040
tgtgccctta ttcctgattt gacccgcctg gtgccttggt gtccagataa tccaccttat    2100
cggcaatgaa gtcggtcccg tagaccgtct ggccgtcctt ctcgtacttg gtattccgaa    2160
tcttgccctg cacgaatacc agcgacccct tgcccaaata cttgccgtgg gcctcggcct    2220
gagagccaaa acacttgatg cggaagaagt cggtgcgctc ctgcttgtcg ccggcatcgt    2280
tgcgccacat ctaggatctg ccaggaaccg taaaaaggcc gcgttgctgg cgttttttcca   2340 taggctccgc ccccctgacg agcatcacaa aaatcgacgc tcaagtcaga ggtggcgaaa    2400
cccgacagga ctataaagat accaggcgtt tcccctgga agctccctcg tgcgctctcc     2460
tgttccgacc ctgccgctta ccggatacct gtccgccttt ctcccttcgg gaagcgtggc    2520
gctttctcat agctcacgct gtaggtatct cagttcggtg taggtcgttc gctccaagct    2580
gggctgtgtg cacgaacccc ccgttcagcc cgaccgctgc gccttatccg gtaactatcg    2640
tcttgagtcc aacccggtaa gacacgactt atcgccactg gcagcagcca ctggtaacag    2700
gattagcaga gcgaggtatg taggcggtgc tacagagttc ttgaagtggt ggcctaacta    2760
cggctacact agaaggacag tatttggtat ctgcgctctg ctgaagccag ttaccttcgg    2820
aaaaagagtt ggtagctctt gatccggcaa acaaaccacc gctggtagcg gtggtttttt    2880
tgtttgcaag cagcagatta cgcgcagaaa aaaaggatct caagaagatc ctttgatctt    2940
```

```
ttctacgggg tctgacgctc agtggaacga aaactcacgt taagggattt tggtcatgag    3000
attatcaaaa aggatcttca cctagatcct tttaaattaa aaatgaagtt ttaaatcaat    3060
ctaaagtata tatgagtaaa cttggtctga cagttaccaa tgcttaatca gtgaggcacc    3120
tatctcagcg atctgtctat ttcgttcatc catagttgcc tgactccccg tcgtgtagat    3180
aactacgata cgggagggct taccatctgg ccccagtgct gcaatgatac cgcgagaacc    3240
acgctcaccg gctccagatt tatcagcaat aaaccagcca gccggaaggg ccgagcgcag    3300
aagtggtcct gcaactttat ccgcctccat ccagtctatt aattgttgcc gggaagctag    3360
agtaagtagt tcgccagtta atagtttgcg caacgttgtt gccattgcta caggcatcgt    3420
ggtgtcacgc tcgtcgtttg gtatggcttc attcagctcc ggttcccaac gatcaaggcg    3480
agttacatga tcccccatgt tgtgcaaaaa agcggttagc tccttcggtc ctccgatcgt    3540
tgtcagaagt aagttggccg cagtgttatc actcatggtt atggcagcac tgcataattc    3600
tcttactgtc atgccatccg taagatgctt ttctgtgact ggtgagtact caaccaagtc    3660
attctgagaa tagtgtatgc ggcgaccgag ttgctcttgc ccggcgtcaa tacgggataa    3720
taccgcgcca catagcagaa ctttaaaagt gctcatcatt ggaaaacgtt cttcggggcg    3780
aaaactctca aggatcttac cgctgttgag atccagttcg atgtaaccca ctcgtgcacc    3840
caactgatct tcagcatctt ttactttcac cagcgtttct gggtgagcaa aacaggaag    3900
gcaaaatgcc gcaaaaaagg gaataagggc gacacggaaa tgttgaatac tcatactctt    3960
cctttttcaa tattattgaa gcatttatca gggttattgt ctcatgagcg gatacatatt    4020
tgaatgtatt tagaaaaata aacaaatagg ggttccgcgc acgaattggc cagcgctgcc    4080
atttttgggg tgaggccgtt cgcggccgag gggcgcagcc cctgggggga tgggaggccc    4140
gcgttagcgg gccgggaggg ttcgagaagg ggggcaccc ccttcggcg tgcgcggtca    4200
cgcgcacagg gcgcagccct ggttaaaaac aaggtttata aatattggtt taaaagcagg    4260
ttaaaagaca ggttagcggt ggccgaaaaa cgggcggaaa cccttgcaaa tgctggattt    4320
tctgcctgtg gacagcccct caaatgtcaa taggtgcgcc cctcatctgt cagcactctg    4380
cccctcaagt gtcaaggatc gcgcccctca tctgtcagta gtcgcgcccc tcaagtgtca    4440
ataccgcagg gcacttatcc ccaggcttgt ccacatcatc tgtgggaaac tcgcgtaaaa    4500
tcaggcgttt tcgccgattt gcgaggctgg ccagctccac gtcgccggcc gaaatcgagc    4560
ctgcccctca tctgtcaacg ccgcgccggg tgagtcggcc cctcaagtgt caacgtccgc    4620
ccctcatctg tcagtgaggg ccaagttttc cgcgaggtat ccacaacgcc ggcggccgcg    4680
gtgtctcgca cacggcttcg acggcgtttc tggcgcgttt gcagggccat agacggccgc    4740
cagcccagcg gcgagggcaa ccagcccggt gagcgtcgca aaggagatcc tgatctgact    4800
gatgggctgc ctgtatcgag tggtgatttt gtgccgagct gccggtcggg gagctgttgg    4860
ctggctggtg gcaggatata ttgtggtgta aacaaattga cgcttagaca acttaataac    4920
acattgcgga cgtttttaat gtactggggt ggatgcagtg ggccccac                 4968
```

<210> SEQ ID NO 61
<211> LENGTH: 790
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
gccaggaacc gtaaaaaggc cgcgttgctg gcgttttcc ataggctccg cccccctgac    60
gagcatcaca aaaatcgacg ctcaagtcag aggtggcgaa acccgacagg actataaaga   120
taccaggcgt ttccccctgg aagctccctc gtgcgctctc ctgttccgac cctgccgctt   180
accggatacc tgtccgcctt tctcccttcg ggaagcgtgg cgctttctca tagctcacgc   240
tgtaggtatc tcagttcggt gtaggtcgtt cgctccaagc tgggctgtgt gcacgaaccc   300
cccgttcagc ccgaccgctg cgccttatcc ggtaactatc gtcttgagtc caacccggta   360
agacacgact tatcgccact ggcagcagcc actggtaaca ggattagcag agcgaggtat   420
gtaggcggtg ctacagagtt cttgaagtgg tggcctaact acggctacac tagaaggaca   480
gtatttggta tctgcgctct gctgaagcca gttaccttcg gaaaaagagt tggtagctct   540
tgatccggca aacaaaccac cgctggtagc ggtggttttt ttgtttgcaa gcagcagatt   600
acgcgcagaa aaaaggatc tcaagaagat cctttgatct tttctacggg gtctgacgct   660
cagtggaacg aaaactcacg ttaagggatt ttggtcatga gattatcaaa aaggatcttc   720
acctagatcc ttttaaatta aaaatgaagt tttaaatcaa tctaaagtat atatgagtaa   780
acttggtctg                                                           790
```

<210> SEQ ID NO 62
<211> LENGTH: 618
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 62

```
ccgggagggt tcgagaaggg ggggcacccc ccttcggcgt gcgcggtcac gcgcacaggg    60
cgcagccctg gttaaaaaca aggtttataa atattggttt aaaagcaggt taaaagacag   120
gttagcggtg gccgaaaaac gggcggaaac ccttgcaaat gctggatttt ctgcctgtgg   180
acagcccctc aaatgtcaat aggtgcgccc ctcatctgtc agcactctgc ccctcaagtg   240
tcaaggatcg cgcccctcat ctgtcagtag tcgcgcccct caagtgtcaa taccgcaggg   300
cacttatccc caggcttgtc cacatcatct gtgggaaact cgcgtaaaat caggcgtttt   360
cgccgatttg cgaggctggc cagctccacg tcgccggccg aaatcgagcc tgcccctcat   420
ctgtcaacgc cgcgccgggt gagtcggccc tcaagtgtc aacgtccgcc cctcatctgt   480
cagtgagggc caagttttcc gcgaggtatc cacaacgccg gcggccgcgg tgtctcgcac   540
acggcttcga cggcgtttct ggcgcgtttg cagggccata acggccgcc agcccagcgg   600
cgagggcaac cagcccgg                                                 618
```

<210> SEQ ID NO 63
<211> LENGTH: 537
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 63

```
ccgactggaa agcgggcagt gagcgcaacg caattaatgt gagttagctc actcattagg    60
caccccaggc tttacacttt atgcttccgg ctcgtatgtt gtgtggaatt gtgagcggat   120
```

| | |
|---|---|
| aacaatttca cacaggaaac agctatgacc atgattacgc caagcttgca tgcctgcagg | 180 |
| tcgactctag aggatccccg ggtaccgagc tcgaattcac tggccgtcgt tttacaacgt | 240 |
| cgtgactggg aaaaccctgg cgttacccaa cttaatcgcc ttgcagcaca tccccctttc | 300 |
| gccagctggc gtaatagcga agaggcccgc accgatcgcc cttcccaaca gttgcgcagc | 360 |
| ctgaatggcg aatggcgcct gatgcggtat tttctcctta cgcatctgtg cggtatttca | 420 |
| caccgcatat ggtgcactct cagtacaatc tgctctgatg ccgcatagtt aagccagccc | 480 |
| cgacacccgc caacacccgc tgacgcgccc tgacgggctt gtctgctccc ggcatcc | 537 |

<210> SEQ ID NO 64
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

| | |
|---|---|
| aaactatcag tgtttgacag gatatattgg cgggtaaacc taagagaaaa gagcgtttat | 60 |
| tagaataatc ggatatttaa aagggcgtga aaaggtttat ccgttcgtcc atttgtatgt | 120 |
| gcatgcca | 128 |

<210> SEQ ID NO 65
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65

| | |
|---|---|
| cacgacgaat tgtaa | 15 |

<210> SEQ ID NO 66
<211> LENGTH: 1674
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

| | |
|---|---|
| ctagatttac tcccccgact ggagcgacgt ggagcgcgtc cgtctggcga accaggatgt | 60 |
| tcttgtgcgc aaccagctgc ggaagtcgct gcgccaggtt gggcacaagt tcgagggagg | 120 |
| cctggggagc caccagctgc tagctccgct gcgggcgatg ccggatggcc aaataaacac | 180 |
| actctaagaa tactacagga cttctcaagc gaccctcct ctaatctctc atcacactca | 240 |
| cttgagaagt tacctcccgc agccgagccg gccgagcgag cgcttagggg gcgtgacccc | 300 |
| ggggcattac gacctcacga tcctgcacac aggcctttgt tacgtgatcc agggccgcga | 360 |
| agaagcgaat cccctcctgg acccggaggc gacgcatccc ttctggcgag gttatttgaa | 420 |
| cacccattgt acagagtcgc cgtgcctccc ctgactgaag aggacgtctt gttcaacgtt | 480 |
| aactctgaca ccagacttag tcctaaagcg gccgagaatc ctgattggcc gcatgccggg | 540 |
| gcagagggcg ctgagttcct tagcccagga gaggccgcgg tggactccta tccgaactgg | 600 |
| ttgaaattcc atattggaat aaatcgatac gaactatatt ctcgacacaa tccggccatc | 660 |
| gaggccctat tacatgatct gtcctcacaa cgtattacgt cagtggccat gaagagcggc | 720 |

```
ggcacgcaac taaagctgat tatgacattt caaaactatg gtcaagccct gtttaagcca      780
atgaagcaga caagagaaca ggagacgcct cccgacttct tctactttag tgattatgaa      840
cgacataatg ctgaaatagc ggcctttcac ctagacagga tcttagactt ccgtagggtt      900
cccccagttg caggtaggat ggttaacatg actaaagaga taagggatgt aaccagggat      960
aagaagctat ggaggacgtt ctttatttct cctgcgaaca atatctgttt ttacggcgag     1020
tgctcctact attgcagcac agaacatgca ctatgtggaa agcctgacca gattgaaggt     1080
tccctggcgg cctttcttcc agacctctct cttgcgaaac gtaaacttg gcgtaatcca      1140 tggagacgaa gctatcacaa acgtaagaaa gcggagtggg aggtagaccc cgattactgc     1200
gaggaggtta agcaaacccc gccgtatgac tctagccacc gaatattaga cgttatggat     1260
atgacgatct ttgattttct tatgggcaac atggatcgtc accactacga aacgttcgag     1320
aagtttggaa atgagacgtt tattatccat ctggacaacg gcagaggctt tgggaaatat     1380
agtcatgacg aattatccat tcttgttcct ttacagcaat gctgcagaat caggaaatca     1440
acgtatttac gtctccaact cctggcaaaa gaggaatata agcttagcct cctaatggct     1500
gagtctctga ggggcgacca agttgcgcct gttctgtatc aaccacattt agaagcactt     1560
gatagacgtt tgcgtgttgt acttaaagct gtccgagact gtgtcgagag aaatggcctt     1620
cattcagttg tggacgacga tctagatacc gaacataggg cagcgtccgc acgt           1674
```

<210> SEQ ID NO 67
<211> LENGTH: 1524
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
caactcaggc caagggaacg tccccgtggg tgcccgtgta ccggaagggc atctagtttg       60
gcgcgagatt ctgctgctgc ggcgtcagac ccagggacaa ttgtgcataa ttttccccgt      120
actgagccaa gaacagagcc ggccggtggg agccatagcg gaagttcatc taagttgcaa      180
gcactattcg cgcatccttt gtataatgta cctgaagaac ctcctctttt aggagcggag      240
gactcactct tagccagcca ggaagcccct agatactacc gtagaaaggt tgcccgatgg      300
aaccgtaggc ataaaatgta ccgtgagcaa atgaatttaa ctagtcttga tcctcctctc      360
caactgaggc ttgaggctag ttgggttcag ttccatttgg gtatcaatcg acacggcctt      420
tactctaggt caagtcctgt ggtatctaaa cttcttcaag acatgcgtca ttttccgaca      480
atatctgccg attactccca ggatgagaag gctttgcttg gagcatgtga ctgtacccag      540
atagtaaaac ctagtggcgt ccacttaaaa ctggtcctcc gttttagcga ttttgggaaa      600
gctatgttta aacccatgcg acaacaacgt gatgaagaaa cgccagttga tttcttctac      660
ttcattgact ccagcgtca caacgcggag atagcagcat ccacttaga cagaattcta       720 gactttcgtc gagtccccc taccgttggc cgtatagtga atgtaactaa agagattttg      780
gaggtgacaa aaaacgagat cttacaaagc gtcttttttg tatccccggc ctccaacgtc      840 tgttttttg cgaaatgtcc ctatatgtgc aaaactgaat atgcggtctg cggcaacccc      900
catttactcg aaggtagtct cagtgcattt ctccccagtc tcaacttagc tccacgtcta      960
agcgtgccaa acccttggat taggagctat acgctagcgg gcaaggagga gtgggaggtg     1020
aacccacttt attgtgacac agtcaagcaa atctatcctt ataataactc acagagacta     1080
```

| | |
|---|---|
| ctcaatgtca ttgatatggc tatcttcgat ttcctgatag gaaacatgga taggcaccat | 1140 |
| tatgagatgt tcaccaagtt cggggacgat ggttttctga tacatctaga caacgcgcgt | 1200 |
| ggcttcgggc gacactccca cgacgaaatc tccattctta gcccctgag ccagtgttgc | 1260 |
| atgatcaaaa agaaaacact tctgcatctt cagctcctcg ctcaagctga ctatcgactt | 1320 |
| tccgacgtga tgcgagaatc actgcttgaa gatcagctca gcccagtgct tactgaaccg | 1380 |
| cacctactgg cactagatcg tagattacag acgatcttga ggacagtcga ggggtgcatc | 1440 |
| gttgctcacg gccaacaaag cgtcatagtt gatgggcctg tggaacagct agctccggat | 1500 |
| tccggacaag caaatttaac cagc | 1524 |

<210> SEQ ID NO 68
<211> LENGTH: 1674
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

| | |
|---|---|
| ctcctaccca aattagaacg atctgctgca cgtccgagcg gcgaacctgg ctgtagctgc | 60 |
| gcacagccag ctgccgaagc tgccgcgcct ggatgggctc aagctagggg tcatcccggt | 120 |
| ggagaacttg aagcggccgc tagcgccgcc ggggatgcag gctggccaaa taagcacact | 180 |
| ctgaggattc tgcaagactt cagttccgac cccagttcca acctaacgag ccactcactg | 240 |
| gaaaagctgc ctccggctgc cgaagctgcg gaaggtgcac cgccaggcca agatccagga | 300 |
| gttcgtagac ctcccgaccc agcgcatagg ccactcccgc gagatccggg tcctagaggc | 360 |
| cctgtcttgc ccccaggtct tagcggagac gggtccttac ttacgcgtct tttccaacac | 420 |
| ccgctatacc aggtgcccat accgccccta acagaaggcg atgttctctt taatgtcaat | 480 |
| agcgatataa gattcaaccc caaagctgca accgccgaga acccagattg gccacacgag | 540 |
| gggccggaag atgagttttt acctactggt gaagcggcag ttgactctta cccgaattgg | 600 |
| ctgaagtttc atattgggat caatagatac gagctttaca gccgacataa tccggccgtg | 660 |
| ggagcgctct tacaagacct cgggacgcaa aagattactt ctgtcgctat gaaatctggc | 720 |
| gggacacagc tcaaacttat tatgactttc cagaattatg ccaagctct gttcaagccg | 780 |
| atgaagcaga ctagagagca ggagacaccc cctgacttct tctacttcag cgactatgaa | 840 |
| aggcataatg cagaaattgc ggcattccac cttgatagga tcttagactt ccgaagggta | 900 |
| ccaccggtag caggtagact agtcaatatg actaaagaga ttagagatgt cactcgtgac | 960 |
| aagaaactat ggcgtacatt ctttataagc cctgctaaca atgtatgctt ttatggcgaa | 1020 |
| tgttcttact attgctctac agaacatgca ctgtgtggaa acccgaccca gattgagggg | 1080 |
| tcactagccg catttctgcc agacttggca ttggccaagc gtaagacgtg gcgtaatccg | 1140 |
| tggcgacgta gttaccacaa gagaaagaag gcggagtggg aagtagaccc agactactgc | 1200 |
| gaggaggtta gacaaacacc tccatatgat tctagtcata gactgttgga tgttatggac | 1260 |
| atgacaattt ttgattttct catggggaac atggatcgtc accactacga aacctttgag | 1320 |
| aaattcggca atgagacatt cattatccac ttagataatg tcgaggtttt ggcaaacac | 1380 |
| agccatgacg aactatctat attagtgcct ttacaacagt gctgtagaat ccgaaggtct | 1440 |
| acctatttga gacttcaact gttggcccaa gaggagcatc gtctatcact tttaatggcc | 1500 |
| gaggctctaa gggctgatcg tgtggctccc gtactctttc agcctcactt agaggcttta | 1560 |

```
gatcgtcgac ttcgtatagt gcttcgagcg gtaggcgatt gcgtggagaa agatggactg    1620
cacagtgttg tagaggatga tttggggcct gagcacaggg cggccgcggg acgt          1674
```

<210> SEQ ID NO 69
<211> LENGTH: 1503
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
caccttggtc ccagggtacg atccagactg caaccgaggg aacgaccgtt ggggtgccct     60
tgtgcgcgtc gtgccgctag tcctgctccg ggacctgccc cgagtgcgcc caggcgtgtg    120
gaaccaagcg gcggtggcga tccagggtcc aaactcaggg cacttttcgc acacccattg    180
tataacgaac cagaggaacc tccgctgctt gggcccgagg atagcctgct ggcgggtccc    240
gaagcattac gttattaccg aagaaaagta gcaaggtgga atagacgtcg aaagatgtac    300
aaagaacaat taaacctaac cagcccagaa ccgccggtgc aattgagaca agaggcatca    360
tgggtacaat ttcacttggg gatcaatagg catgggctgt atcctcgtag ctctccggtg    420
gtttctaaac tccttcagga tatgagacac ttccctacga tcagcgcgga ttatagccag    480
gacgaaaagg ctcttcttgg cgcatgtgac tgttctcaaa ttgttaagcc ctccggcgtt    540
catctgaagc tcgtacttcg ttttctgat tttgggaagg cgatgtttaa acccatgaga    600
cagcagaggg acgaggagac gccggaggac ttcttctatt tcatcgactt ccagagacat    660
aatgccgaaa ttgctgcctt ccatctagat cgtattttgg actttagacg tgtcccgcca    720
acagtaggga ggctcgtaaa tgtgacaagg gaaatactag aagtcactcg taatgagatt    780
ttacaaagcg tgtttttcgt gagtccggca aacaatgtgt gcttctttgc gaaatgccct    840
tatatgtgca agacggagta tgctgtttgc gggtcacccc acctactaga aggttcttta    900
agtgccttcc ttcccagcct caacctcgct ccacgtttca gtatgcctag tccatggatc    960
aggtcatatt ccctagctgg tcgtgaagag tgggaggtaa acccgctata ctgcgaagcg   1020
gtgaaacagg cttaccccca caatagcagt tcacgtctat aaatattat cgatatggcg   1080 atcttcgact ttctaatagg gaacatggac aggcaccact acgaaatgtt cactaagttc   1140
ggtgaggacg ggttcctaat acatttggat aatgcccgtg gtttgggag acattcacac    1200 gatgaagtct ctatttttagc ccctttattc caatgttgta ggataaaaag aaaaaccctg   1260
ctgcatcttc aactcctggc tcaggctgat taccgtcttt cagacgttat gcgtgagtct   1320
ttgctagagg accaattgag tcctgtacta acagaaccac atctgctagc tttggacaga   1380
cgtttgcaga ctgtgctaag aacggtccag gattgcatcg aggcccatgg ggaacaatca   1440
gtggtagccg acggcccggt gggccaatgg gctcccgaca gtagtagagc gaacgcaact   1500
tct                                                                 1503
```

<210> SEQ ID NO 70
<211> LENGTH: 383
<212> TYPE: DNA
<213> ORGANISM: Unknown
<220> FEATURE:
<223> OTHER INFORMATION: Description of Unknown:
      Agrobacterium tumefaciens sequence -continued

<400> SEQUENCE: 70

```
attttttcaaa tcagtgcgca agacgtgacg taagtatccg agtcagtttt tattttcta      60
ctaatttggt cgtttatttc ggcgtgtagg acatggcaac cgggcctgaa tttcgcgggt    120
attctgtttc tattccaact ttttcttgat ccgcagccat taacgacttt tgaatagata    180
cgctgacacg ccaagcctcg ctagtcaaaa gtgtaccaaa caacgcttta cagcaagaac    240
ggaatgcgcg tgacgctcgc ggtgacgcca tttcgccttt tcagaaatgg ataaatagcc    300
ttgcttccta ttatatcttc ccaaattacc aatacattac actagcatct gaatttcata    360
accaatctcg ataccaaa tcg                                              383
```

<210> SEQ ID NO 71
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71

```
atgagttcta gctttttatc atccactgcg ttcttcctgc tcctttgctt aggcttctgc      60
catgtgtcat ct                                                         72
```

<210> SEQ ID NO 72
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72

```
atggcaaaca agctcttcct cgtctgcgca actttcgccc tctgcttcct cctcaccaac      60
gct                                                                   63
```

<210> SEQ ID NO 73
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73

```
tcgtaccct acgacgttcc tgactacgcc catcatcacc atcaccacca tgatgagttg      60
tag                                                                   63
```

<210> SEQ ID NO 74
<211> LENGTH: 714
<212> TYPE: DNA
<213> ORGANISM: Unknown
<220> FEATURE:
<223> OTHER INFORMATION: Description of Unknown:
      Agrobacterium tumefaciens sequence

<400> SEQUENCE: 74

```
gtcctgcttt aatgagatat gcgagaagcc tatgatcgca tgatatttgc tttcaattct      60
gttgtgcacg ttgtaaaaaa cctgagcatg tgtagctcag atccttaccg ccggtttcgg    120
ttcattctaa tgaatatatc acccgttact atcgtatttt tatgaataat attctccgtt    180
```

```
caatttactg attgtacccct actacttata tgtacaatat taaaatgaaa acaatatatt    240
gtgctgaata ggtttatagc gacatctatg atagagcgcc acaataacaa acaattgcgt    300
tttattatta caaatccaat tttaaaaaaa gcggcagaac cggtcaaacc taaaagactg    360
attacataaa tcttattcaa atttcaaaag tgccccaggg gctagtatct acgacacacc    420
gagcggcgaa ctaataacgc tcactgaagg gaactccggt tccccgccgg cgcgcatggg    480
tgagattcct tgaagttgag tattggccgt ccgctctacc gaaagttacg ggcaccattc    540
aacccggtcc agcacggcgg ccgggtaacc gacttgctgc cccgagaatt atgcagcatt    600 ttttttggtgt atgtgggccc caaatgaagt gcaggtcaaa ccttgacagt gacgacaaat    660
cgttgggcgg gtccagggcg aattttgcga caacatgtcg aggctcagca ggac          714
```

<210> SEQ ID NO 75
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
atgggtggtg gaggaagtgg aggtggagga agtgtcagta aaggagaagc tgtcataaag    60
gagttcatga ggtttaaggt acacatgaaa gggtcaatga acgggcatga atttgagatc   120 gaggggggagg gagaaggaag gccttatgag ggcactcaaa ctgctaagtt gaaggtcact   180
aagggggggc ctcttccttt ttcttgggac atactcagcc ctcagttcat gtatggctca   240 agggcctttta caaaacaccc tgccgatatc cccgattact ataagcagag ctttcccgaa   300
ggcttcaagt gggagagggt tatgaatttt gaagatggcg gtgctgttac agtcacacag   360
gacacaagtc ttgaggatgg gaccctgatt tataaagtta agctcagggg gacaaatttc   420
ccaccagatg gaccagtcat gcagaagaaa actatgggat gggaagcctc taccgagcgt   480
ctttatcccg aagatggcgt tcttaaaggc gatattaaga tggctttgag gctcaaagat   540
ggcggtcgtt acctggccga tttcaaaacc acttacaaag ccaaaaaacc agtacagatg   600
ccaggcgctt acaacgttga tcgtaagctg gacatcactt cccacaacga ggattacaca   660
gttgttgaac agtatgagag atcagagggt agacatagta ccggcggaat ggatgagctg   720
tacaaaagtt cg                                                        732
```

<210> SEQ ID NO 76
<211> LENGTH: 263
<212> TYPE: DNA
<213> ORGANISM: Unknown
<220> FEATURE:
<223> OTHER INFORMATION: Description of Unknown:
      Agrobacterium tumefaciens sequence

<400> SEQUENCE: 76

```
gtcaagcaga tcgttcaaac atttggcaat aaagtttctt aagattgaat cctgttgccg    60
gtcttgcgat gattatcata taatttctgt tgaattacgt taagcatgta ataattaaca   120
tgtaatgcat gacgttattt atgagatggg ttttttatgat tagagtcccg caattataca   180
tttaatacgc gatagaaaac aaaatatagc gcgcaaacta ggataaatta tcgcgcgcgg   240
tgtcatctat gttactagat cga                                            263
```

<210> SEQ ID NO 77
<211> LENGTH: 627

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
agagaacttg aagaattgaa tgttccagga gagattgttg aaagtctctc ctcttctgag      60
gaaagcatca caagaatcaa caagaaaatt gagaagtttc agagtgaaga gcaacaacag    120
actgaagatg aattacaaga taagattcat ccttttgctc aaacacagtc acttgtgtat    180
ccattccctg gaccaattcc aaattcttta ccacaaaaca ttcctcctct gactcaaact    240
cctgtcgttg ttcctccgtt cttgcaacca gaagttatgg gagtttcaaa ggttaaagaa    300
gcaatggctc aaagcataa agagatgcca ttcccaaaat accctgtgga gcctttcaca    360
gaatctcaaa gcttgactct cactgatgtt gagaatcttc atttgcctct tccattgctt    420
caatcatgga tgcatcaacc tcatcagcct ttgccaccaa cagtgatgtt tccacctcaa    480
tctgttctct ctctttctca gtctaaagtt cttccggttc cgcagaaagc tgtgccttat    540
cctcagagag atatgcctat tcaagctttt cttctctacc aagaaccagt tttgggtcct    600
gttcgtggtc catttcccat catagtt                                         627
```

<210> SEQ ID NO 78
<211> LENGTH: 507
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

```
caggagcaaa accaagagca acctattcgt tgtgaaaaag acgagagatt ttttagtgat      60
aaaattgcaa agtacatccc aatccagtac gttttaagtc gatatccgag ctacggtctt    120
aattactatc aacagaagcc agttgccttg ataaacaacc agtttctccc atatccctac    180
tatgctaagc cggccgccgt ccgttctcct gctcagatat tgcagtggca ggttttatcc    240
aacactgtcc cggcgaagtc ttgccaggcg caacccacca ccatggctag acaccgcat     300
ccgcaccttt cctttatggc tattcctccc aaaaagaacc aagacaagac agagatcccg    360
accataaata ctatcgcttc tggtgagcca acttcaacac cgactattga agcggtggag    420
agcacggtcg ccacacttga agcatcccca gaggtgactg aatcaccccc ggagataaac    480
acggtacagg tcacctcaac ggctgtt                                         507
```

<210> SEQ ID NO 79
<211> LENGTH: 507
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
caggagcaaa accaagagca acctattcgt tgtgaaaaag acgagagatt ttttagtgat      60
aaaattgcaa agtacatccc aatccagtac gttttaagtc gatatccgag ctacggtctt    120
aattactatc aacagaagcc agttgccttg ataaacaacc agtttctccc atatccctac    180
tatgctaagc cggccgccgt ccgttctcct gctcagatat tgcagtggca ggttttatcc    240
aacactgtcc cggcgaagtc ttgccaggcg caacccacca ccatggctag acaccgcat     300
```

```
ccgcaccttt cctttatggc tattcctccc aaaaagaacc aagacaagac agagatcccg    360
accataaata ctatcgcttc tggtgagcca acttcaacac cgactattga agcggtggag    420
agcacggtcg ccacacttga agcatcccca gaggtgactg aatcacccc ggagataaac     480 acggtacagg tcacctcaac ggctgtt                                       507
```

<210> SEQ ID NO 80
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Met Ala Asn Lys Leu Phe Leu Val Cys Ala Thr Phe Ala Leu Cys Phe
1               5                   10                  15

Leu Leu Thr Asn Ala Arg Pro Lys His Pro Ile Lys His Gln Gly Leu
            20                  25                  30

Pro Gln Glu Val Leu Asn Glu Asn Leu Leu Arg Phe Phe Val Ala Pro
        35                  40                  45

Phe Pro Glu Val Phe Gly Lys Glu Lys Val Asn Glu Leu Ser Lys Asp
    50                  55                  60

Ile Gly Ser Glu Ser Thr Glu Asp Gln Ala Met Glu Asp Ile Lys Gln
65                  70                  75                  80

Met Glu Ala Glu Ser Ile Ser Ser Ser Glu Glu Ile Val Pro Asn Ser
                85                  90                  95

Val Glu Gln Lys His Ile Gln Lys Glu Asp Val Pro Ser Glu Arg Tyr
            100                 105                 110

Leu Gly Tyr Leu Glu Gln Leu Leu Arg Leu Lys Lys Tyr Lys Val Pro
        115                 120                 125

Gln Leu Glu Ile Val Pro Asn Ser Ala Glu Glu Arg Leu His Ser Met
    130                 135                 140

Lys Glu Gly Ile His Ala Gln Gln Lys Glu Pro Met Ile Gly Val Asn
145                 150                 155                 160

Gln Glu Leu Ala Tyr Phe Tyr Pro Glu Leu Phe Arg Gln Phe Tyr Gln
                165                 170                 175

Leu Asp Ala Tyr Pro Ser Gly Ala Trp Tyr Tyr Val Pro Leu Gly Thr
            180                 185                 190

Gln Tyr Thr Asp Ala Pro Ser Phe Ser Asp Ile Pro Asn Pro Ile Gly
        195                 200                 205

Ser Glu Asn Ser Glu Lys Thr Thr Met Pro Leu Trp Ser Ser Tyr Pro
    210                 215                 220

Tyr Asp Val Pro Asp Tyr Ala His His His His His His Asp Glu
225                 230                 235                 240

Leu
```

<210> SEQ ID NO 81
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Met Ala Asn Lys Leu Phe Leu Val Cys Ala Thr Phe Ala Leu Cys Phe
1               5                   10                  15

Leu Leu Thr Asn Ala Arg Glu Leu Glu Glu Leu Asn Val Pro Gly Glu
            20                  25                  30

Ile Val Glu Ser Leu Ser Ser Ser Glu Glu Ser Ile Thr Arg Ile Asn
        35                  40                  45

Lys Lys Ile Glu Lys Phe Gln Ser Glu Gln Gln Gln Thr Glu Asp
50                  55                  60

Glu Leu Gln Asp Lys Ile His Pro Phe Ala Gln Thr Gln Ser Leu Val
65                  70                  75                  80

Tyr Pro Phe Pro Gly Pro Ile Pro Asn Ser Leu Pro Gln Asn Ile Pro
                85                  90                  95

Pro Leu Thr Gln Thr Pro Val Val Val Pro Pro Phe Leu Gln Pro Glu
            100                 105                 110

Val Met Gly Val Ser Lys Val Lys Glu Ala Met Ala Pro Lys His Lys
        115                 120                 125

Glu Met Pro Phe Pro Lys Tyr Pro Val Glu Pro Phe Thr Glu Ser Gln
130                 135                 140

Ser Leu Thr Leu Thr Asp Val Glu Asn Leu His Leu Pro Leu Pro Leu
145                 150                 155                 160

Leu Gln Ser Trp Met His Gln Pro His Gln Pro Leu Pro Pro Thr Val
                165                 170                 175

Met Phe Pro Pro Gln Ser Val Leu Ser Leu Ser Gln Ser Lys Val Leu
            180                 185                 190

Pro Val Pro Gln Lys Ala Val Pro Tyr Pro Gln Arg Asp Met Pro Ile
        195                 200                 205

Gln Ala Phe Leu Leu Tyr Gln Glu Pro Val Leu Gly Pro Val Arg Gly
210                 215                 220

Pro Phe Pro Ile Ile Val Ser Tyr Pro Tyr Asp Val Pro Asp Tyr Ala
225                 230                 235                 240

His His His His His His His Asp Glu Leu
                245                 250
```

<210> SEQ ID NO 82
<211> LENGTH: 210
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Met Ala Asn Lys Leu Phe Leu Val Cys Ala Thr Phe Ala Leu Cys Phe
1               5                   10                  15

Leu Leu Thr Asn Ala Gln Glu Gln Asn Gln Glu Gln Pro Ile Arg Cys
            20                  25                  30

Glu Lys Asp Glu Arg Phe Phe Ser Asp Lys Ile Ala Lys Tyr Ile Pro
        35                  40                  45

Ile Gln Tyr Val Leu Ser Arg Tyr Pro Ser Tyr Gly Leu Asn Tyr Tyr
    50                  55                  60

Gln Gln Lys Pro Val Ala Leu Ile Asn Asn Gln Phe Leu Pro Tyr Pro
65                  70                  75                  80

Tyr Tyr Ala Lys Pro Ala Ala Val Arg Ser Pro Ala Gln Ile Leu Gln
                85                  90                  95
```

```
Trp Gln Val Leu Ser Asn Thr Val Pro Ala Lys Ser Cys Gln Ala Gln
            100                 105                 110

Pro Thr Thr Met Ala Arg His Pro His Pro His Leu Ser Phe Met Ala
        115                 120                 125

Ile Pro Pro Lys Lys Asn Gln Asp Lys Thr Glu Ile Pro Thr Ile Asn
130                 135                 140

Thr Ile Ala Ser Gly Glu Pro Thr Ser Thr Pro Thr Ile Glu Ala Val
145                 150                 155                 160

Glu Ser Thr Val Ala Thr Leu Glu Ala Ser Pro Val Thr Glu Ser
                165                 170                 175

Pro Pro Glu Ile Asn Thr Val Gln Val Thr Ser Thr Ala Val Ser Tyr
            180                 185                 190

Pro Tyr Asp Val Pro Asp Tyr Ala His His His His His His Asp
            195                 200                 205

Glu Leu
    210

<210> SEQ ID NO 83
<211> LENGTH: 559
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Leu Leu Pro Lys Leu Glu Arg Ser Ala Ala Arg Pro Ser Gly Glu
1               5                   10                  15

Pro Gly Cys Ser Cys Ala Gln Pro Ala Ala Glu Ala Ala Ala Pro Gly
            20                  25                  30

Trp Ala Gln Ala Arg Gly His Pro Gly Gly Glu Leu Glu Ala Ala Ala
        35                  40                  45

Ser Ala Ala Gly Asp Ala Gly Trp Pro Asn Lys His Thr Leu Arg Ile
    50                  55                  60

Leu Gln Asp Phe Ser Ser Asp Pro Ser Ser Asn Leu Thr Ser His Ser
65                  70                  75                  80

Leu Glu Lys Leu Pro Pro Ala Ala Glu Ala Ala Glu Gly Ala Pro Pro
                85                  90                  95

Gly Gln Asp Pro Gly Val Arg Arg Pro Pro Asp Pro Ala His Arg Pro
            100                 105                 110

Leu Pro Arg Asp Pro Gly Pro Arg Gly Pro Val Leu Pro Pro Gly Leu
        115                 120                 125

Ser Gly Asp Gly Ser Leu Leu Thr Arg Leu Phe Gln His Pro Leu Tyr
    130                 135                 140

Gln Val Pro Ile Pro Pro Leu Thr Glu Gly Asp Val Leu Phe Asn Val
145                 150                 155                 160

Asn Ser Asp Ile Arg Phe Asn Pro Lys Ala Ala Thr Ala Glu Asn Pro
                165                 170                 175

Asp Trp Pro His Glu Gly Pro Asp Glu Phe Leu Pro Thr Gly Glu
            180                 185                 190

Ala Ala Val Asp Ser Tyr Pro Asn Trp Leu Lys Phe His Ile Gly Ile
        195                 200                 205

Asn Arg Tyr Glu Leu Tyr Ser Arg His Asn Pro Ala Val Gly Ala Leu
    210                 215                 220
```

Leu Gln Asp Leu Gly Thr Gln Lys Ile Thr Ser Val Ala Met Lys Ser
225                 230                 235                 240

Gly Gly Thr Gln Leu Lys Leu Ile Met Thr Phe Gln Asn Tyr Gly Gln
            245                 250                 255

Ala Leu Phe Lys Pro Met Lys Gln Thr Arg Glu Gln Glu Thr Pro Pro
        260                 265                 270

Asp Phe Phe Tyr Phe Ser Asp Tyr Glu Arg His Asn Ala Glu Ile Ala
    275                 280                 285

Ala Phe His Leu Asp Arg Ile Leu Asp Phe Arg Arg Val Pro Pro Val
290                 295                 300

Ala Gly Arg Leu Val Asn Met Thr Lys Glu Ile Arg Asp Val Thr Arg
305                 310                 315                 320

Asp Lys Lys Leu Trp Arg Thr Phe Phe Ile Ser Pro Ala Asn Asn Val
                325                 330                 335

Cys Phe Tyr Gly Glu Cys Ser Tyr Tyr Cys Ser Thr Glu His Ala Leu
            340                 345                 350

Cys Gly Lys Pro Asp Gln Ile Glu Gly Ser Leu Ala Ala Phe Leu Pro
        355                 360                 365

Asp Leu Ala Leu Ala Lys Arg Lys Thr Trp Arg Asn Pro Trp Arg Arg
    370                 375                 380

Ser Tyr His Lys Arg Lys Lys Ala Glu Trp Glu Val Asp Pro Asp Tyr
385                 390                 395                 400

Cys Glu Glu Val Arg Gln Thr Pro Pro Tyr Asp Ser Ser His Arg Leu
                405                 410                 415

Leu Asp Val Met Asp Met Thr Ile Phe Asp Phe Leu Met Gly Asn Met
            420                 425                 430

Asp Arg His His Tyr Glu Thr Phe Glu Lys Phe Gly Asn Glu Thr Phe
        435                 440                 445

Ile Ile His Leu Asp Asn Gly Arg Gly Phe Gly Lys His Ser His Asp
    450                 455                 460

Glu Leu Ser Ile Leu Val Pro Leu Gln Gln Cys Cys Arg Ile Arg Arg
465                 470                 475                 480

Ser Thr Tyr Leu Arg Leu Gln Leu Leu Ala Gln Glu Glu His Arg Leu
                485                 490                 495

Ser Leu Leu Met Ala Glu Ala Leu Arg Ala Asp Arg Val Ala Pro Val
            500                 505                 510

Leu Phe Gln Pro His Leu Glu Ala Leu Asp Arg Arg Leu Arg Ile Val
        515                 520                 525

Leu Arg Ala Val Gly Asp Cys Val Glu Lys Asp Gly Leu His Ser Val
    530                 535                 540

Val Glu Asp Asp Leu Gly Pro Glu His Arg Ala Ala Ala Gly Arg
545                 550                 555

<210> SEQ ID NO 84
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met His Val Ser Ser His Leu Gly Pro Arg Val Arg Ser Arg Leu Gln
1               5                   10                  15

```
Pro Arg Glu Arg Pro Leu Gly Cys Pro Cys Ala Arg Arg Ala Ala Ser
            20                  25                  30

Pro Ala Pro Gly Pro Ala Pro Ser Ala Pro Arg Arg Val Glu Pro Ser
        35                  40                  45

Gly Gly Gly Asp Pro Gly Ser Lys Leu Arg Ala Leu Phe Ala His Pro
50                  55                  60

Leu Tyr Asn Glu Pro Glu Pro Pro Leu Leu Gly Pro Glu Asp Ser
65                  70                  75                  80

Leu Leu Ala Gly Pro Glu Ala Leu Arg Tyr Tyr Arg Arg Lys Val Ala
                85                  90                  95

Arg Trp Asn Arg Arg Lys Met Tyr Lys Glu Gln Leu Asn Leu Thr
                100                 105                 110

Ser Pro Glu Pro Pro Val Gln Leu Arg Gln Glu Ala Ser Trp Val Gln
            115                 120                 125

Phe His Leu Gly Ile Asn Arg His Gly Leu Tyr Pro Arg Ser Ser Pro
    130                 135                 140

Val Val Ser Lys Leu Leu Gln Asp Met Arg His Phe Pro Thr Ile Ser
145                 150                 155                 160

Ala Asp Tyr Ser Gln Asp Glu Lys Ala Leu Leu Gly Ala Cys Asp Cys
                165                 170                 175

Ser Gln Ile Val Lys Pro Ser Gly Val His Leu Lys Leu Val Leu Arg
            180                 185                 190

Phe Ser Asp Phe Gly Lys Ala Met Phe Lys Pro Met Arg Gln Gln Arg
    195                 200                 205

Asp Glu Glu Thr Pro Glu Asp Phe Phe Tyr Phe Ile Asp Phe Gln Arg
    210                 215                 220

His Asn Ala Glu Ile Ala Ala Phe His Leu Asp Arg Ile Leu Asp Phe
225                 230                 235                 240

Arg Arg Val Pro Pro Thr Val Gly Arg Leu Val Asn Val Thr Arg Glu
            245                 250                 255

Ile Leu Glu Val Thr Arg Asn Glu Ile Leu Gln Ser Val Phe Phe Val
            260                 265                 270

Ser Pro Ala Asn Asn Val Cys Phe Phe Ala Lys Cys Pro Tyr Met Cys
        275                 280                 285

Lys Thr Glu Tyr Ala Val Cys Gly Ser Pro His Leu Leu Glu Gly Ser
    290                 295                 300

Leu Ser Ala Phe Leu Pro Ser Leu Asn Leu Ala Pro Arg Phe Ser Met
305                 310                 315                 320

Pro Ser Pro Trp Ile Arg Ser Tyr Ser Leu Ala Gly Arg Glu Glu Trp
            325                 330                 335

Glu Val Asn Pro Leu Tyr Cys Glu Ala Val Lys Gln Ala Tyr Pro His
            340                 345                 350

Asn Ser Ser Ser Arg Leu Leu Asn Ile Ile Asp Met Ala Ile Phe Asp
        355                 360                 365

Phe Leu Ile Gly Asn Met Asp Arg His His Tyr Glu Met Phe Thr Lys
    370                 375                 380

Phe Gly Glu Asp Gly Phe Leu Ile His Leu Asp Asn Ala Arg Gly Phe
385                 390                 395                 400

Gly Arg His Ser His Asp Glu Val Ser Ile Leu Ala Pro Leu Phe Gln
                405                 410                 415

Cys Cys Arg Ile Lys Arg Lys Thr Leu Leu His Leu Gln Leu Leu Ala
            420                 425                 430
```

```
Gln Ala Asp Tyr Arg Leu Ser Asp Val Met Arg Glu Ser Leu Leu Glu
            435                 440                 445

Asp Gln Leu Ser Pro Val Leu Thr Glu Pro His Leu Leu Ala Leu Asp
450                 455                 460

Arg Arg Leu Gln Thr Val Leu Arg Thr Val Gln Asp Cys Ile Glu Ala
465                 470                 475                 480

His Gly Glu Gln Ser Val Val Ala Asp Gly Pro Val Gly Gln Trp Ala
            485                 490                 495

Pro Asp Ser Ser Arg Ala Asn Ala Thr Ser
            500                 505

<210> SEQ ID NO 85
<211> LENGTH: 382
<212> TYPE: PRT
<213> ORGANISM: Bacillus subtilus

<400> SEQUENCE: 85

Met Lys Val Pro Lys Thr Met Leu Leu Ser Thr Ala Ala Gly Leu Leu
1               5                   10                  15

Leu Ser Leu Thr Ala Thr Ser Val Ser Ala His Tyr Val Asn Glu Glu
            20                  25                  30

His His Phe Lys Val Thr Ala His Thr Glu Thr Asp Pro Val Ala Ser
        35                  40                  45

Gly Asp Ala Ala Asp Asp Pro Ala Ile Trp Val His Glu Lys His
50                  55                  60

Pro Glu Lys Ser Lys Leu Ile Thr Thr Asn Lys Lys Ser Gly Leu Val
65                  70                  75                  80

Val Tyr Asp Leu Asp Gly Lys Gln Leu His Ser Tyr Glu Phe Gly Lys
                85                  90                  95

Leu Asn Asn Val Asp Leu Arg Tyr Asp Phe Pro Leu Asn Gly Glu Lys
            100                 105                 110

Ile Asp Ile Ala Ala Ala Ser Asn Arg Ser Glu Gly Lys Asn Thr Ile
        115                 120                 125

Glu Val Tyr Ala Ile Asp Gly Asp Lys Gly Lys Leu Lys Ser Ile Thr
130                 135                 140

Asp Pro Asn His Pro Ile Ser Thr Asn Ile Ser Glu Val Tyr Gly Phe
145                 150                 155                 160

Ser Leu Tyr His Ser Gln Lys Thr Gly Ala Phe Tyr Ala Leu Val Thr
                165                 170                 175

Gly Lys Gln Gly Glu Phe Glu Gln Tyr Glu Ile Val Asp Gly Gly Lys
            180                 185                 190

Gly Tyr Val Thr Gly Lys Lys Val Arg Glu Phe Lys Leu Asn Ser Gln
        195                 200                 205

Thr Glu Gly Leu Val Ala Asp Asp Glu Tyr Gly Asn Leu Tyr Ile Ala
210                 215                 220

Glu Glu Asp Glu Ala Ile Trp Lys Phe Asn Ala Glu Pro Gly Gly Gly
225                 230                 235                 240

Ser Lys Gly Gln Val Val Asp Arg Ala Thr Gly Asp His Leu Thr Ala
                245                 250                 255

Asp Ile Glu Gly Leu Thr Ile Tyr Tyr Ala Pro Asn Gly Lys Gly Tyr
            260                 265                 270

Leu Met Ala Ser Ser Gln Gly Asn Asn Ser Tyr Ala Met Tyr Glu Arg
        275                 280                 285

Gln Gly Lys Asn Arg Tyr Val Ala Asn Phe Glu Ile Thr Asp Gly Glu
290                 295                 300
```

```
Lys Ile Asp Gly Thr Ser Asp Thr Asp Gly Ile Asp Val Leu Gly Phe
305                 310                 315                 320

Gly Leu Gly Pro Lys Tyr Pro Tyr Gly Ile Phe Val Ala Gln Asp Gly
            325                 330                 335

Glu Asn Ile Asp Asn Gly Gln Ala Val Asn Gln Asn Phe Lys Ile Val
        340                 345                 350

Ser Trp Glu Gln Ile Ala Gln His Leu Gly Glu Met Pro Asp Leu His
        355                 360                 365

Lys Gln Val Asn Pro Arg Lys Leu Lys Asp Arg Ser Asp Gly
    370                 375                 380

<210> SEQ ID NO 86
<211> LENGTH: 467
<212> TYPE: PRT
<213> ORGANISM: Aspergillus niger

<400> SEQUENCE: 86

Met Gly Val Ser Ala Val Leu Leu Pro Leu Tyr Leu Leu Ser Gly Val
1               5                   10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Lys Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Asn Asn
            195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285
```

```
Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Val Gly Tyr Ala
305                 310                 315                 320

Asn Glu Leu Ile Ala Arg Leu Thr His Ser Pro Val His Asp Asp Thr
                    325                 330                 335

Ser Ser Asn His Thr Leu Asp Ser Ser Pro Ala Thr Phe Pro Leu Asn
                340                 345                 350

Ser Thr Leu Tyr Ala Asp Phe Ser His Asp Asn Gly Ile Ile Ser Ile
                355                 360                 365

Leu Phe Ala Leu Gly Leu Tyr Asn Gly Thr Lys Pro Leu Ser Thr Thr
370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
                420                 425                 430

Leu His Gly Cys Pro Val Asp Ala Leu Gly Arg Cys Thr Arg Asp Ser
                435                 440                 445

Phe Val Arg Gly Leu Ser Phe Ala Arg Ser Gly Gly Asp Trp Ala Glu
450                 455                 460

Cys Phe Ala
465

<210> SEQ ID NO 87
<211> LENGTH: 479
<212> TYPE: PRT
<213> ORGANISM: Aspergillus niger

<400> SEQUENCE: 87

Met Pro Arg Thr Ser Leu Leu Thr Leu Ala Cys Ala Leu Ala Thr Gly
1               5                   10                  15

Ala Ser Ala Phe Ser Tyr Gly Ala Ala Ile Pro Gln Ser Thr Gln Glu
                20                  25                  30

Lys Gln Phe Ser Gln Glu Phe Arg Asp Gly Tyr Ser Ile Leu Lys His
            35                  40                  45

Tyr Gly Gly Asn Gly Pro Tyr Ser Glu Arg Val Ser Tyr Gly Ile Ala
    50                  55                  60

Arg Asp Pro Pro Thr Gly Cys Glu Val Asp Gln Val Ile Met Val Lys
65                  70                  75                  80

Arg His Gly Glu Arg Tyr Pro Ser Pro Ser Ala Gly Lys Ser Ile Glu
                85                  90                  95

Glu Ala Leu Ala Lys Val Tyr Ser Ile Asn Thr Thr Glu Tyr Lys Gly
            100                 105                 110

Asp Leu Ala Phe Leu Asn Asp Trp Thr Tyr Tyr Val Pro Asn Glu Cys
        115                 120                 125

Tyr Tyr Asn Ala Glu Thr Thr Ser Gly Pro Tyr Ala Gly Leu Leu Asp
    130                 135                 140

Ala Tyr Asn His Gly Asn Asp Tyr Lys Ala Arg Tyr Gly His Leu Trp
145                 150                 155                 160

Asn Gly Glu Thr Val Val Pro Phe Phe Ser Ser Gly Tyr Gly Arg Val
                165                 170                 175
```

```
Ile Glu Thr Ala Arg Lys Phe Gly Glu Gly Phe Phe Gly Tyr Asn Tyr
            180                 185                 190

Ser Thr Asn Ala Ala Leu Asn Ile Ile Ser Glu Ser Glu Val Met Gly
            195                 200                 205

Ala Asp Ser Leu Thr Pro Thr Cys Asp Thr Asp Asn Asp Gln Thr Thr
210                 215                 220

Cys Asp Asn Leu Thr Tyr Gln Leu Pro Gln Phe Lys Val Ala Ala Ala
225                 230                 235                 240

Arg Leu Asn Ser Gln Asn Pro Gly Met Asn Leu Thr Ala Ser Asp Val
            245                 250                 255

Tyr Asn Leu Ile Val Met Ala Ser Phe Glu Leu Asn Ala Arg Pro Phe
            260                 265                 270

Ser Asn Trp Ile Asn Ala Phe Thr Gln Asp Glu Trp Val Ser Phe Gly
            275                 280                 285

Tyr Val Glu Asp Leu Asn Tyr Tyr Cys Ala Gly Pro Gly Asp Lys
            290                 295                 300

Asn Met Ala Ala Val Gly Ala Val Tyr Ala Asn Ala Ser Leu Thr Leu
305                 310                 315                 320

Leu Asn Gln Gly Pro Lys Glu Ala Gly Pro Leu Phe Phe Asn Phe Ala
            325                 330                 335

His Asp Thr Asn Ile Thr Pro Ile Leu Ala Ala Leu Gly Val Leu Ile
            340                 345                 350

Pro Asn Glu Asp Leu Pro Leu Asp Arg Val Ala Phe Gly Asn Pro Tyr
            355                 360                 365

Ser Ile Gly Asn Ile Val Pro Met Gly Gly His Leu Thr Ile Glu Arg
370                 375                 380

Leu Ser Cys Gln Ala Thr Ala Leu Ser Asp Lys Gly Thr Tyr Val Arg
385                 390                 395                 400

Leu Val Leu Asn Glu Ala Val Leu Pro Phe Asn Asp Cys Thr Ser Gly
            405                 410                 415

Pro Gly Tyr Ser Cys Pro Leu Ala Asn Tyr Thr Ser Ile Leu Asn Lys
            420                 425                 430

Asn Leu Pro Asp Tyr Thr Thr Thr Cys Asn Val Ser Ala Ser Tyr Pro
            435                 440                 445

Gln Tyr Leu Ser Phe Trp Trp Asn Tyr Asn Thr Thr Glu Leu Asn
450                 455                 460

Tyr Arg Ser Ser Pro Ile Ala Cys Gln Glu Gly Asp Ala Met Asp
465                 470                 475

<210> SEQ ID NO 88
<211> LENGTH: 532
<212> TYPE: PRT
<213> ORGANISM: Arabidopsis thaliana

<400> SEQUENCE: 88

Met Thr Phe Leu Leu Leu Leu Phe Cys Phe Leu Ser Pro Ala Ile
1               5                   10                  15

Ser Ser Ala His Ser Ile Pro Ser Thr Leu Asp Gly Pro Phe Val Pro
            20                  25                  30

Val Thr Val Pro Leu Asp Thr Ser Leu Arg Gly Gln Ala Ile Asp Leu
            35                  40                  45

Pro Asp Thr Asp Pro Arg Val Arg Arg Val Ile Gly Phe Glu Pro
50                  55                  60
```

```
Glu Gln Ile Ser Leu Ser Leu Ser Asp His Asp Ser Ile Trp Val
65                  70                  75                  80

Ser Trp Ile Thr Gly Glu Phe Gln Ile Gly Lys Lys Val Lys Pro Leu
                85                  90                  95

Asp Pro Thr Ser Ile Asn Ser Val Val Gln Phe Gly Thr Leu Arg His
            100                 105                 110

Ser Leu Ser His Glu Ala Lys Gly His Ser Leu Val Tyr Ser Gln Leu
            115                 120                 125

Tyr Pro Phe Asp Gly Leu Leu Asn Tyr Thr Ser Gly Ile Ile His His
130                 135                 140

Val Arg Ile Thr Gly Leu Lys Pro Ser Thr Ile Tyr Tyr Arg Cys
145                 150                 155                 160

Gly Asp Pro Ser Arg Arg Ala Met Ser Lys Ile His His Phe Arg Thr
                165                 170                 175

Met Pro Val Ser Ser Pro Ser Ser Tyr Pro Gly Arg Ile Ala Val Val
                180                 185                 190

Gly Asp Leu Gly Leu Thr Tyr Asn Thr Thr Asp Thr Ile Ser His Leu
            195                 200                 205

Ile His Asn Ser Pro Asp Leu Ile Leu Leu Ile Gly Asp Val Ser Tyr
210                 215                 220

Ala Asn Leu Tyr Leu Thr Asn Gly Thr Ser Ser Asp Cys Tyr Ser Cys
225                 230                 235                 240

Ser Phe Pro Glu Thr Pro Ile His Glu Thr Tyr Gln Pro Arg Trp Asp
                245                 250                 255

Tyr Trp Gly Arg Phe Met Glu Asn Leu Thr Ser Lys Val Pro Leu Met
                260                 265                 270

Val Ile Glu Gly Asn His Glu Ile Glu Leu Gln Ala Glu Asn Lys Thr
                275                 280                 285

Phe Glu Ala Tyr Ser Ser Arg Phe Ala Phe Pro Phe Asn Glu Ser Gly
290                 295                 300

Ser Ser Ser Thr Leu Tyr Tyr Ser Phe Asn Ala Gly Gly Ile His Phe
305                 310                 315                 320

Val Met Leu Gly Ala Tyr Ile Ala Tyr Asp Lys Ser Ala Glu Gln Tyr
                325                 330                 335

Glu Trp Leu Lys Lys Asp Leu Ala Lys Val Asp Arg Ser Val Thr Pro
                340                 345                 350

Trp Leu Val Ala Ser Trp His Pro Pro Trp Tyr Ser Ser Tyr Thr Ala
                355                 360                 365

His Tyr Arg Glu Ala Glu Cys Met Lys Glu Ala Met Glu Glu Leu Leu
                370                 375                 380

Tyr Ser Tyr Gly Thr Asp Ile Val Phe Asn Gly His Val His Ala Tyr
385                 390                 395                 400

Glu Arg Ser Asn Arg Val Tyr Asn Tyr Glu Leu Asp Pro Cys Gly Pro
                405                 410                 415

Val Tyr Ile Val Ile Gly Asp Gly Gly Asn Arg Glu Lys Met Ala Ile
                420                 425                 430

Glu His Ala Asp Asp Pro Gly Lys Cys Pro Glu Pro Leu Thr Thr Pro
                435                 440                 445

Asp Pro Val Met Gly Gly Phe Cys Ala Trp Asn Phe Thr Pro Ser Asp
                450                 455                 460

Lys Phe Cys Trp Asp Arg Gln Pro Asp Tyr Ser Ala Leu Arg Glu Ser
465                 470                 475                 480
```

```
Ser Phe Gly His Gly Ile Leu Glu Met Lys Asn Glu Thr Trp Ala Leu
                485                 490                 495

Trp Thr Trp Tyr Arg Asn Gln Asp Ser Ser Glu Val Gly Asp Gln
            500                 505                 510

Ile Tyr Ile Val Arg Gln Pro Asp Arg Cys Pro Leu His His Arg Leu
            515                 520                 525

Val Asn His Cys
        530

<210> SEQ ID NO 89
<211> LENGTH: 512
<212> TYPE: PRT
<213> ORGANISM: Glycine max

<400> SEQUENCE: 89

Met Trp Leu Ala Ser Phe Arg Ser Leu Leu Cys Lys Cys Phe Ile Pro
1               5                   10                  15

Arg Trp Leu Gly Leu Cys Arg Leu Ile Lys Thr Thr Leu Ile Pro Leu
            20                  25                  30

Glu Arg Arg Met Leu Leu Ala Met Leu Leu Asn Leu Val Leu Ala Ser
        35                  40                  45

Phe Val Phe Leu Ser Phe Ile Arg Asp Gly Ser Ala Gly Ile Thr Ser
    50                  55                  60

Ser Phe Ile Arg Ser Glu Trp Pro Ala Val Asp Ile Pro Leu Asp His
65                  70                  75                  80

Glu Ala Phe Ala Val Pro Lys Gly Tyr Asn Ala Pro Gln Gln Val His
                85                  90                  95

Ile Thr Gln Gly Asp Tyr Asp Gly Lys Ala Val Ile Ile Ser Trp Val
            100                 105                 110

Thr Thr Glu Glu Pro Gly His Ser His Ile Gln Tyr Gly Thr Ser Glu
        115                 120                 125

Asn Lys Phe Gln Thr Ser Glu Glu Gly Thr Val Thr Asn Tyr Thr Phe
    130                 135                 140

His Lys Tyr Lys Ser Gly Tyr Ile His His Cys Leu Ile Glu Gly Leu
145                 150                 155                 160

Glu Tyr Glu Thr Lys Tyr Tyr Tyr Arg Ile Gly Ser Gly Asp Ser Ser
                165                 170                 175

Arg Glu Phe Trp Phe Lys Thr Pro Pro Lys Val Asp Pro Asp Ser Pro
            180                 185                 190

Tyr Lys Phe Gly Ile Ile Gly Asp Leu Gly Gln Thr Phe Asn Ser Leu
        195                 200                 205

Ser Thr Leu Glu His Tyr Ile Gln Ser Gly Ala Gln Thr Val Leu Phe
    210                 215                 220

Val Gly Asp Leu Ser Tyr Ala Asp Arg Tyr Gln Tyr Asn Asp Val Gly
225                 230                 235                 240

Leu Arg Trp Asp Thr Trp Gly Arg Phe Val Glu Arg Ser Thr Ala Tyr
                245                 250                 255

His Pro Trp Leu Trp Ser Ala Gly Asn His Glu Ile Asp Tyr Met Pro
            260                 265                 270

Tyr Met Gly Glu Val Val Pro Phe Lys Asn Tyr Leu Tyr Arg Tyr Thr
        275                 280                 285

Thr Pro Tyr Leu Ala Ser Asn Ser Ser Pro Leu Trp Tyr Ala Val
    290                 295                 300

Arg Arg Ala Ser Ala His Ile Ile Val Leu Ser Ser Tyr Ser Pro Phe
305                 310                 315                 320
```

```
Val Lys Tyr Thr Pro Gln Tyr Met Trp Leu Lys Glu Leu Lys Arg
                325                 330                 335

Val Glu Arg Glu Lys Thr Pro Trp Leu Ile Val Leu Met His Val Pro
            340                 345                 350

Leu Tyr Asn Ser Asn Gly Ala His Tyr Met Glu Gly Ser Met Arg
                355                 360                 365

Ser Val Phe Glu Ser Trp Phe Ile Glu Tyr Lys Val Asp Val Ile Phe
    370                 375                 380

Ala Gly His Val His Ala Tyr Glu Arg Ser Tyr Arg Tyr Ser Asn Val
385                 390                 395                 400

Asp Tyr Asn Ile Thr Gly Gly Asn Arg Tyr Pro Leu Pro Asn Lys Ser
                405                 410                 415

Ala Pro Val Tyr Ile Thr Val Gly Asp Gly Asn Gln Glu Gly Leu
                420                 425                 430

Ala Ser Arg Phe Leu Asp Pro Gln Pro Glu Tyr Ser Ala Phe Arg Glu
            435                 440                 445

Ala Ser Tyr Gly His Ser Thr Leu Glu Ile Lys Asn Arg Thr His Ala
            450                 455                 460

Ile Tyr His Trp Asn Arg Asn Asp Asp Gly Lys Lys Val Pro Thr Asp
465                 470                 475                 480

Ser Phe Val Leu His Asn Gln Tyr Trp Gly His Asn Arg Arg Arg
                485                 490                 495

Lys Leu Lys His Phe Leu Leu Lys Val Ile Asp Glu Val Ala Ser Met
                500                 505                 510

<210> SEQ ID NO 90
<211> LENGTH: 385
<212> TYPE: PRT
<213> ORGANISM: Bacillus subtilis

<400> SEQUENCE: 90

Met Lys Lys Gln Asn Asp Ile Pro Gln Pro Ile Arg Gly Asp Lys Gly
1               5                   10                  15

Ala Thr Val Lys Ile Pro Arg Asn Ile Glu Arg Asp Arg Gln Asn Pro
                20                  25                  30

Asp Met Leu Val Pro Pro Glu Thr Asp His Gly Thr Val Ser Asn Met
            35                  40                  45

Lys Phe Ser Phe Ser Asp Thr His Asn Arg Leu Glu Lys Gly Gly Tyr
        50                  55                  60

Ala Arg Glu Val Thr Val Arg Glu Leu Pro Ile Ser Glu Asn Leu Ala
65                  70                  75                  80

Ser Val Asn Met Arg Leu Lys Pro Gly Ala Ile Arg Glu Leu His Trp
                85                  90                  95

His Lys Glu Ala Glu Trp Ala Tyr Met Ile Tyr Gly Ser Ala Arg Val
                100                 105                 110

Thr Ile Val Asp Glu Lys Gly Arg Ser Phe Ile Asp Asp Val Gly Glu
            115                 120                 125

Gly Asp Leu Trp Tyr Phe Pro Ser Gly Leu Pro His Ser Ile Gln Ala
        130                 135                 140

Leu Glu Glu Gly Ala Glu Phe Leu Leu Val Phe Asp Asp Gly Ser Phe
145                 150                 155                 160

Ser Glu Asn Ser Thr Phe Gln Leu Thr Asp Trp Leu Ala His Thr Pro
                165                 170                 175
```

```
Lys Glu Val Ile Ala Ala Asn Phe Gly Val Thr Lys Glu Glu Ile Ser
            180                 185                 190

Asn Leu Pro Gly Lys Glu Lys Tyr Ile Phe Glu Asn Gln Leu Pro Gly
            195                 200                 205

Ser Leu Lys Asp Asp Ile Val Glu Gly Pro Asn Gly Glu Val Pro Tyr
210                 215                 220

Pro Phe Thr Tyr Arg Leu Leu Glu Gln Glu Pro Ile Glu Ser Glu Gly
225                 230                 235                 240

Gly Lys Val Tyr Ile Ala Asp Ser Thr Asn Phe Lys Val Ser Lys Thr
                245                 250                 255

Ile Ala Ser Ala Leu Val Thr Val Glu Pro Gly Ala Met Arg Glu Leu
            260                 265                 270

His Trp His Pro Asn Thr His Glu Trp Gln Tyr Tyr Ile Ser Gly Lys
            275                 280                 285

Ala Arg Met Thr Val Phe Ala Ser Asp Gly His Ala Arg Thr Phe Asn
            290                 295                 300

Tyr Gln Ala Gly Asp Val Gly Tyr Val Pro Phe Ala Met Gly His Tyr
305                 310                 315                 320

Val Glu Asn Ile Gly Asp Glu Pro Leu Val Phe Leu Glu Ile Phe Lys
                325                 330                 335

Asp Asp His Tyr Ala Asp Val Ser Leu Asn Gln Trp Leu Ala Met Leu
            340                 345                 350

Pro Glu Thr Phe Val Gln Ala His Leu Asp Leu Gly Lys Asp Phe Thr
            355                 360                 365

Asp Val Leu Ser Lys Glu Lys His Pro Val Val Lys Lys Lys Cys Ser
            370                 375                 380

Lys
385

<210> SEQ ID NO 91
<211> LENGTH: 472
<212> TYPE: PRT
<213> ORGANISM: Aspergillus niger

<400> SEQUENCE: 91

Met Lys Pro Ser Thr Leu Tyr Ser Ser Leu Pro Trp Val Ile Thr Ser
1               5                   10                  15

Leu Leu Thr Val Ala Val His Gly Ala Pro Thr Gly Thr Lys Ser Asn
            20                  25                  30

Pro Pro Leu Arg Gly Ser Glu Asn Leu Leu Gly Tyr Ser Ala Ser Asn
            35                  40                  45

Thr Val Thr Asp Gln Ser Thr Asp Glu Ile Pro Tyr Val Pro Val Pro
50                  55                  60

Gly Gln Thr Asp Ala Ala Asp Leu Gly Val Tyr Leu Asp Phe Glu Asp
65                  70                  75                  80

Ile Glu Asn Pro Gln Pro Val Arg Gly Ser Thr Gly Gly Thr Asp Pro
            85                  90                  95

Gly Pro Arg Asn Asp Tyr Tyr Arg Ile Asn Ser Asp Lys Leu Ala
            100                 105                 110

Pro Pro Gly Thr Asp Asn Gly Gln Thr Ile Asn Ala Gln Trp Pro Met
            115                 120                 125

Gly Leu Ser His Asn Arg Leu Gly Leu Asn Glu Ser Gly Trp Ala Arg
            130                 135                 140
```

```
Gln Glu Asn Glu Val Val Met Pro Gly Ala Thr Glu Met Ala Gly Val
145                 150                 155                 160

Asp Met Arg Leu Glu Ala Gly Ala Tyr Arg Glu Leu His Trp His Val
            165                 170                 175

Ala Ser Glu Trp Ser Leu Val Leu Asn Gly Ser Cys Arg Ile Glu Ala
        180                 185                 190

Val Asn Glu Asn Gly Gln Thr Phe Val Asp Asp Val Ser Ala Gly Asp
    195                 200                 205

Val Trp Phe Phe Pro Pro Gly Val Pro His Ser Ile Gln Ala Leu Asp
210                 215                 220

Ser Gly Val Glu Phe Leu Leu Ile Phe Asp Asp Gly Ser Phe Ser Glu
225                 230                 235                 240

Asp Asn Thr Phe Leu Ala Thr Glu Val Phe Ala His Gln Pro Arg Glu
            245                 250                 255

Val Leu Ala Lys Asn Phe Asp Leu Pro Val Ala Ala Phe Asp Asp Ile
        260                 265                 270

Pro Glu Asp Glu Leu Tyr Ile Phe Pro Gly Thr Pro Ala Pro Gln Asn
    275                 280                 285

Ile Glu Glu Gln Asn Val Thr Gly Ser Ala Gly Val Leu Pro Lys Ser
290                 295                 300

Gln Ser Tyr Ser Tyr His Phe Ser Gln Pro Ala His Glu Val Gln
305                 310                 315                 320

Gly Gly Ser Val Lys Ile Val Asp Ser Leu Thr Phe Pro Ile Ser Thr
            325                 330                 335

Asn Thr Ala Ala Ala Leu Val Thr Val His Pro Gly Gly Met Arg Glu
        340                 345                 350

Ile His Trp His Pro Ser Ser Asp Glu Trp Thr Phe Phe Ile Ser Gly
    355                 360                 365

Lys Ala Arg Ala Thr Leu Phe Thr Ala Pro Ser Thr Ala Thr Thr Phe
370                 375                 380

Asp Tyr Arg Pro Gly Asp Val Gly Tyr Phe Pro Gln Ser Asn Ser His
385                 390                 395                 400

Tyr Ile Glu Asn Thr Gly Asp Glu Asp Leu Val Phe Leu Glu Val Leu
            405                 410                 415

Gln Thr Glu Gln Phe Ser Asp Ile Ser Leu Gly Gln Trp Ile Gly Ser
        420                 425                 430

Thr Pro Lys Gln Ile Val Ser Asp Thr Leu Asn Leu Pro Gln Ser Ala
    435                 440                 445

Leu Asp Arg Leu Lys Thr Glu Lys Met Tyr Val Ala Gly Ser Asn
450                 455                 460

Glu Thr Asp Val Ala Ala Thr Ala
465                 470

<210> SEQ ID NO 92
<211> LENGTH: 447
<212> TYPE: PRT
<213> ORGANISM: Flammulina velutipes

<400> SEQUENCE: 92

Met Phe Asn Asn Phe Gln Arg Leu Leu Thr Val Ile Leu Leu Ser Gly
1               5                   10                  15

Phe Thr Ala Gly Val Pro Leu Ala Ser Thr Thr Gly Thr Gly Thr
            20                  25                  30
```

```
Ala Thr Gly Thr Ser Thr Ala Ala Glu Pro Ser Ala Thr Val Pro Phe
        35                  40                  45

Ala Ser Thr Asp Pro Asn Pro Val Leu Trp Asn Glu Thr Ser Asp Pro
 50                  55                  60

Ala Leu Val Lys Pro Glu Arg Asn Gln Leu Gly Ala Thr Ile Gln Gly
 65                  70                  75                  80

Pro Asp Asn Leu Pro Ile Asp Leu Gln Asn Pro Asp Leu Leu Ala Pro
                85                  90                  95

Pro Thr Thr Asp His Gly Phe Val Gly Asn Ala Lys Trp Pro Phe Ser
            100                 105                 110

Phe Ser Lys Gln Arg Leu Gln Thr Gly Gly Trp Ala Arg Gln Gln Asn
            115                 120                 125

Glu Val Val Leu Pro Leu Ala Thr Asn Leu Ala Cys Thr Asn Met Arg
        130                 135                 140

Leu Glu Ala Gly Ala Ile Arg Glu Leu His Trp His Lys Asn Ala Glu
145                 150                 155                 160

Trp Ala Tyr Val Leu Lys Gly Ser Thr Gln Ile Ser Ala Val Asp Asn
                165                 170                 175

Glu Gly Arg Asn Tyr Ile Ser Thr Val Gly Pro Gly Asp Leu Trp Tyr
            180                 185                 190

Phe Pro Pro Gly Ile Pro His Ser Leu Gln Ala Thr Ala Asp Asp Pro
            195                 200                 205

Glu Gly Ser Glu Phe Ile Leu Val Phe Asp Ser Gly Ala Phe Asn Asp
        210                 215                 220

Asp Gly Thr Phe Leu Leu Thr Asp Trp Leu Ser His Val Pro Met Glu
225                 230                 235                 240

Val Ile Leu Lys Asn Phe Arg Ala Lys Asn Pro Ala Ala Trp Ser His
                245                 250                 255

Ile Pro Ala Gln Gln Leu Tyr Ile Phe Pro Ser Glu Pro Pro Ala Asp
            260                 265                 270

Asn Gln Pro Asp Pro Val Ser Pro Gln Gly Thr Val Pro Leu Pro Tyr
        275                 280                 285

Ser Phe Asn Phe Ser Ser Val Glu Pro Thr Gln Tyr Ser Gly Gly Thr
        290                 295                 300

Ala Lys Ile Ala Asp Ser Thr Thr Phe Asn Ile Ser Val Ala Ile Ala
305                 310                 315                 320

Val Ala Glu Val Thr Val Glu Pro Gly Ala Leu Arg Glu Leu His Trp
                325                 330                 335

His Pro Thr Glu Asp Glu Trp Thr Phe Phe Ile Ser Gly Asn Ala Arg
            340                 345                 350

Val Thr Ile Phe Ala Ala Gln Ser Val Ala Ser Thr Phe Asp Tyr Gln
            355                 360                 365

Gly Gly Asp Ile Ala Tyr Val Pro Ala Ser Met Gly His Tyr Val Glu
        370                 375                 380

Asn Ile Gly Asn Thr Thr Leu Thr Tyr Leu Glu Val Phe Asn Thr Asp
385                 390                 395                 400

Arg Phe Ala Asp Val Ser Leu Ser Gln Trp Leu Ala Leu Thr Pro Pro
                405                 410                 415

Ser Val Val Gln Ala His Leu Asn Leu Asp Asp Glu Thr Leu Ala Glu
            420                 425                 430

Leu Lys Gln Phe Ala Thr Lys Ala Thr Val Val Gly Pro Val Asn
        435                 440                 445
```

<210> SEQ ID NO 93
<211> LENGTH: 514
<212> TYPE: PRT
<213> ORGANISM: Arabidopsis thaliana

<400> SEQUENCE: 93

| | | | | | | | | | | | | | | | |
|---|---|---|---|---|---|---|---|---|---|---|---|---|---|---|---|
| Met | Asp | Ser | Asp | Thr | Leu | Ser | Gly | Leu | Leu | Glu | Asn | Val | Ala | Lys | Lys |
| 1 | | | | 5 | | | | | 10 | | | | | 15 | |
| Phe | Pro | Asp | Arg | Arg | Ala | Leu | Ser | Val | Ser | Gly | Lys | Phe | Asn | Leu | Thr |
| | | | 20 | | | | | 25 | | | | | 30 | | |
| His | Ala | Arg | Leu | His | Asp | Leu | Ile | Glu | Arg | Ala | Ala | Ser | Arg | Leu | Val |
| | | 35 | | | | | 40 | | | | | 45 | | | |
| Ser | Asp | Ala | Gly | Ile | Lys | Pro | Gly | Asp | Val | Val | Ala | Leu | Thr | Phe | Pro |
| 50 | | | | | 55 | | | | | 60 | | | | | |
| Asn | Thr | Val | Glu | Phe | Val | Ile | Met | Phe | Leu | Ala | Val | Ile | Arg | Ala | Arg |
| 65 | | | | 70 | | | | | 75 | | | | | 80 | |
| Ala | Thr | Ala | Ala | Pro | Leu | Asn | Ala | Ala | Tyr | Thr | Ala | Glu | Glu | Phe | Glu |
| | | | | 85 | | | | | 90 | | | | | 95 | |
| Phe | Tyr | Leu | Ser | Asp | Ser | Asp | Ser | Lys | Leu | Leu | Thr | Ser | Lys | Glu |
| | | | 100 | | | | | 105 | | | | | 110 | | |
| Gly | Asn | Ala | Pro | Ala | Gln | Glu | Ala | Ala | Ser | Lys | Leu | Lys | Ile | Ser | His |
| | | 115 | | | | | 120 | | | | | 125 | | | |
| Val | Thr | Ala | Thr | Leu | Leu | Asp | Ala | Gly | Ser | Asp | Leu | Val | Leu | Ser | Val |
| | 130 | | | | | 135 | | | | | 140 | | | | |
| Ala | Asp | Ser | Asp | Ser | Val | Val | Asp | Ser | Ala | Thr | Glu | Leu | Val | Asn | His |
| 145 | | | | | 150 | | | | | 155 | | | | | 160 |
| Pro | Asp | Asp | Gly | Ala | Leu | Phe | Leu | His | Thr | Ser | Gly | Thr | Thr | Ser | Arg |
| | | | | 165 | | | | | 170 | | | | | 175 | |
| Pro | Lys | Gly | Val | Pro | Leu | Thr | Gln | Leu | Asn | Leu | Ala | Ser | Ser | Val | Lys |
| | | | 180 | | | | | 185 | | | | | 190 | | |
| Asn | Ile | Lys | Ala | Val | Tyr | Lys | Leu | Thr | Glu | Ser | Asp | Ser | Thr | Val | Ile |
| | | | | 195 | | | | | 200 | | | | | 205 | |
| Val | Leu | Pro | Leu | Phe | His | Val | His | Gly | Leu | Leu | Ala | Gly | Leu | Leu | Ser |
| | 210 | | | | | 215 | | | | | 220 | | | | |
| Ser | Leu | Gly | Ala | Gly | Ala | Val | Thr | Leu | Pro | Ala | Ala | Gly | Arg | Phe |
| 225 | | | | | 230 | | | | | 235 | | | | | 240 |
| Ser | Ala | Thr | Thr | Phe | Trp | Pro | Asp | Met | Lys | Lys | Tyr | Asn | Ala | Thr | Trp |
| | | | | 245 | | | | | 250 | | | | | 255 | |
| Tyr | Thr | Ala | Val | Pro | Thr | Ile | His | Gln | Ile | Ile | Leu | Asp | Arg | His | Ala |
| | | | 260 | | | | | 265 | | | | | 270 | | |
| Ser | His | Pro | Glu | Thr | Glu | Tyr | Pro | Lys | Leu | Arg | Phe | Ile | Arg | Ser | Cys |
| | | 275 | | | | | 280 | | | | | 285 | | | |
| Ser | Ala | Ser | Leu | Ala | Pro | Val | Ile | Leu | Ser | Arg | Leu | Glu | Glu | Ala | Phe |
| | 290 | | | | | 295 | | | | | 300 | | | | |
| Gly | Ala | Pro | Val | Leu | Glu | Ala | Tyr | Ala | Met | Thr | Glu | Ala | Thr | His | Leu |
| 305 | | | | | 310 | | | | | 315 | | | | | 320 |
| Met | Ser | Ser | Asn | Pro | Leu | Pro | Glu | Glu | Gly | Pro | His | Lys | Pro | Gly | Ser |
| | | | | 325 | | | | | 330 | | | | | 335 | |
| Val | Gly | Lys | Pro | Val | Gly | Gln | Glu | Met | Ala | Ile | Leu | Asn | Glu | Lys | Gly |
| | | | 340 | | | | | 345 | | | | | 350 | | |
| Glu | Ile | Gln | Glu | Pro | Asn | Asn | Lys | Gly | Glu | Val | Cys | Ile | Arg | Gly | Pro |
| | | | | 355 | | | | | 360 | | | | | 365 | |
| Asn | Val | Thr | Lys | Gly | Tyr | Lys | Asn | Asn | Pro | Glu | Ala | Asn | Lys | Ala | Gly |
| | 370 | | | | | 375 | | | | | 380 | | | | |

```
Phe Glu Phe Gly Trp Phe His Thr Gly Asp Ile Gly Tyr Phe Asp Thr
385                 390                 395                 400

Asp Gly Tyr Leu His Leu Val Gly Arg Ile Lys Glu Leu Ile Asn Arg
            405                 410                 415

Gly Gly Glu Lys Ile Ser Pro Ile Glu Val Asp Ala Val Leu Leu Thr
        420                 425                 430

His Pro Asp Val Ser Gln Gly Val Ala Phe Gly Val Pro Asp Glu Lys
            435                 440                 445

Tyr Gly Glu Glu Ile Asn Cys Ala Val Ile Pro Arg Glu Gly Thr Thr
        450                 455                 460

Val Thr Glu Glu Asp Ile Lys Ala Phe Cys Lys Lys Asn Leu Ala Ala
465                 470                 475                 480

Phe Lys Val Pro Lys Arg Val Phe Ile Thr Asp Asn Leu Pro Lys Thr
                485                 490                 495

Ala Ser Gly Lys Ile Gln Arg Arg Ile Val Ala Gln His Phe Leu Glu
            500                 505                 510

Lys Pro

<210> SEQ ID NO 94
<211> LENGTH: 523
<212> TYPE: PRT
<213> ORGANISM: Glycine max

<400> SEQUENCE: 94

Met Lys Asp Thr Met Glu Thr Pro Thr Thr Leu Thr Thr Leu Leu Arg
1               5                   10                  15

His Val Ala Ala Lys Phe Pro Ser Arg Arg Ala Ile Ser Val Ala Ala
                20                  25                  30

Lys Phe Asp Leu Thr His Ser Arg Leu His Arg Leu Val Glu Ser Ala
            35                  40                  45

Ala Ala Gln Leu Val Ser Ala Gly Val Lys Pro Gly Asp Val Val Ala
        50                  55                  60

Leu Thr Phe Pro Asn Thr Ile Glu Phe Val Val Met Phe Leu Ala Val
65                  70                  75                  80

Ile Arg Ala Arg Ala Thr Ala Ala Pro Leu Asn Ser Ala Tyr Thr Ala
                85                  90                  95

Glu Glu Phe Glu Phe Tyr Leu Ser Asp Ser Glu Ser Lys Leu Leu Leu
            100                 105                 110

Thr Ser Pro Glu Gly Asn Lys Pro Ala Gln Ala Ala Ser Lys Leu
        115                 120                 125

Ser Ile Pro His Ala Thr Ala Ser Ile Thr Lys Ala Glu Asn Glu Glu
        130                 135                 140

Ala Glu Leu Ser Leu Ser Leu Asn His Pro Glu Leu Asn Ser Val
145                 150                 155                 160

Asn Ser Val Glu Ser Leu Val Asn Asp Pro Asp Asp Val Ala Leu Phe
                165                 170                 175

Leu His Thr Ser Gly Thr Thr Ser Arg Pro Lys Gly Val Pro Leu Thr
            180                 185                 190

Gln Tyr Asn Leu Leu Ser Val Lys Asn Ile Asp Ser Val Tyr Arg
        195                 200                 205

Leu Thr Glu Ser Asp Ser Thr Val Ile Val Leu Pro Leu Phe His Val
210                 215                 220

His Gly Leu Ile Ala Gly Leu Leu Ser Ser Leu Gly Ala Gly Ala Ala
225                 230                 235                 240
```

-continued

```
Val Ala Leu Pro Ala Ala Gly Arg Phe Ser Ala Ser Ala Phe Trp Lys
                245                 250                 255

Asp Met Ile Lys Tyr Ser Ala Thr Trp Tyr Thr Ala Val Pro Thr Ile
                260                 265                 270

His Gln Ile Ile Leu Asp Arg His Ser Ser Asn Pro Glu Pro Val Tyr
                275                 280                 285

Pro Arg Leu Arg Phe Ile Arg Ser Cys Ser Ala Ser Leu Ala Pro Val
            290                 295                 300

Ile Leu Gly Lys Leu Glu Glu Ala Phe Gly Ala Pro Val Leu Glu Ala
305                 310                 315                 320

Tyr Ala Met Thr Glu Ala Ser His Leu Met Ala Ser Asn Pro Leu Pro
                325                 330                 335

Gln Asp Gly Ala His Lys Ser Gly Ser Val Gly Lys Pro Val Gly Gln
            340                 345                 350

Glu Met Gly Ile Leu Asp Glu Ser Gly Arg Val Gln Glu Ala Gly Ile
        355                 360                 365

Ser Gly Glu Val Cys Ile Arg Gly Ser Asn Val Thr Lys Gly Tyr Lys
    370                 375                 380

Asn Asn Val Ala Ala Asn Thr Ala Ser Phe Leu Phe Asp Trp Phe His
385                 390                 395                 400

Thr Gly Asp Ile Gly Tyr Phe Asp Ser Asp Gly Tyr Leu His Leu Val
                405                 410                 415

Gly Arg Ile Lys Glu Leu Ile Asn Arg Gly Gly Glu Lys Ile Ser Gly
            420                 425                 430

Arg Glu Val Asp Ala Val Leu Leu Ser His Pro Glu Ile Ala Gln Ala
        435                 440                 445

Val Ala Phe Gly Val Pro Asp Ala Lys Tyr Gly Glu Glu Ile Tyr Cys
    450                 455                 460

Ala Val Ile Pro Arg Glu Gly Ser Asn Val Asp Glu Ala Glu Val Leu
465                 470                 475                 480

Arg Phe Ser Lys Thr Asn Leu Ala Ser Phe Lys Val Pro Lys Lys Val
                485                 490                 495

Phe Ile Thr Asp Ser Leu Pro Lys Thr Ala Thr Gly Lys Ile Leu Arg
            500                 505                 510

Arg Leu Val Ala Glu His Phe Val Ser Gln Ile
        515                 520

<210> SEQ ID NO 95
<211> LENGTH: 523
<212> TYPE: PRT
<213> ORGANISM: Glycine max

<400> SEQUENCE: 95

Met Lys Asp Thr Met Glu Thr Pro Thr Thr Leu Thr Thr Leu Leu Arg
1               5                   10                  15

His Val Ala Ala Lys Phe Pro Ser Arg Arg Ala Ile Ser Val Ala Ala
                20                  25                  30

Lys Phe Asp Leu Thr His Ser Arg Leu His Arg Leu Val Glu Ser Ala
            35                  40                  45

Ala Ala Gln Leu Val Ser Ala Gly Val Lys Pro Gly Asp Val Val Ala
        50                  55                  60

Leu Thr Phe Pro Asn Thr Ile Glu Phe Val Val Met Phe Leu Ala Val
65                  70                  75                  80
```

```
Ile Arg Ala Arg Ala Thr Ala Ala Pro Leu Asn Ser Ala Tyr Thr Ala
                85                  90                  95

Glu Glu Phe Glu Phe Tyr Leu Ser Asp Ser Glu Ser Lys Leu Leu Leu
            100                 105                 110

Thr Ser Pro Glu Gly Asn Lys Pro Ala Gln Ala Ala Ser Lys Leu
        115                 120                 125

Ser Ile Pro His Ala Thr Ala Ser Ile Thr Lys Ala Glu Asn Glu Glu
    130                 135                 140

Ala Glu Leu Ser Leu Ser Leu Leu Asn His Pro Glu Leu Asn Ser Val
145                 150                 155                 160

Asn Ser Val Glu Ser Leu Val Asn Asp Pro Asp Val Ala Leu Phe
                165                 170                 175

Leu His Thr Ser Gly Thr Thr Ser Arg Pro Lys Gly Val Pro Leu Thr
                180                 185                 190

Gln Tyr Asn Leu Leu Ser Ser Val Lys Asn Ile Asp Ser Val Tyr Arg
            195                 200                 205

Leu Thr Glu Ser Asp Ser Thr Val Ile Val Leu Pro Leu Phe His Val
    210                 215                 220

His Gly Leu Ile Ala Gly Leu Leu Ser Ser Leu Gly Ala Gly Ala Ala
225                 230                 235                 240

Val Ala Leu Pro Ala Ala Gly Arg Phe Ser Ala Ser Ala Phe Trp Lys
                245                 250                 255

Asp Met Ile Lys Tyr Ser Ala Thr Trp Tyr Thr Ala Val Pro Thr Ile
            260                 265                 270

His Gln Ile Ile Leu Asp Arg His Ser Ser Asn Pro Glu Pro Val Tyr
        275                 280                 285

Pro Arg Leu Arg Phe Ile Arg Ser Cys Ser Ala Ser Leu Ala Pro Val
    290                 295                 300

Ile Leu Gly Lys Leu Glu Glu Ala Phe Gly Ala Pro Val Leu Glu Ala
305                 310                 315                 320

Tyr Ala Met Thr Glu Ala Ser His Leu Met Ala Ser Asn Pro Leu Pro
                325                 330                 335

Gln Asp Gly Ala His Lys Ser Gly Ser Val Gly Lys Pro Val Gly Gln
            340                 345                 350

Glu Met Gly Ile Leu Asp Glu Ser Gly Arg Val Gln Glu Ala Gly Ile
        355                 360                 365

Ser Gly Glu Val Cys Ile Arg Gly Ser Asn Val Thr Lys Gly Tyr Lys
    370                 375                 380

Asn Asn Val Ala Ala Asn Thr Ala Ser Phe Leu Phe Asp Trp Phe His
385                 390                 395                 400

Thr Gly Asp Ile Gly Tyr Phe Asp Ser Asp Gly Tyr Leu His Leu Val
                405                 410                 415

Gly Arg Ile Lys Glu Leu Ile Asn Arg Gly Gly Glu Lys Ile Ser Pro
            420                 425                 430

Ile Glu Val Asp Ala Val Leu Leu Ser His Pro Glu Ile Ala Gln Ala
        435                 440                 445

Val Ala Phe Gly Val Pro Asp Ala Lys Tyr Gly Glu Glu Ile Tyr Cys
    450                 455                 460

Ala Val Ile Pro Arg Glu Gly Ser Asn Val Asp Glu Ala Glu Val Leu
465                 470                 475                 480
```

Arg Phe Ser Lys Thr Asn Leu Ala Ser Phe Lys Val Pro Lys Lys Val
            485                 490                 495

Phe Ile Thr Asp Ser Leu Pro Lys Thr Ala Thr Gly Lys Ile Leu Arg
            500                 505                 510

Arg Leu Val Ala Glu His Phe Val Ser Gln Ile
            515                 520

<210> SEQ ID NO 96
<211> LENGTH: 1533
<212> TYPE: DNA
<213> ORGANISM: Glycine max

<400> SEQUENCE: 96

| | |
|---|---:|
| atgttcatcg agaattttaa ggttgagtgt cctaatgtga agtacaccga gactgagatt | 60 |
| cagtccgtgt acaactacga aaccaccgaa cttgttcacg agaacaggaa tggcacctat | 120 |
| cagtggattg tcaaacccaa atctgtcaaa tacgaattta aaccaacatc catgttcct | 180 |
| aaattagggg taatgcttgt gggttggggt ggaaacaacg gctcaaccct caccggtggt | 240 |
| gttattgcta accgagaggg catttcatgg gctacaaagg acaagattca acaagccaat | 300 |
| tactttggct ccctcaccca agcctcagct atccgagttg gtccttcca gggagaggaa | 360 |
| atctatgccc cattcaagag cctgcttcca atggttaacc ctgacgacat tgtgtttggg | 420 |
| ggatgggata tcagcaacat gaacctggct gatgccatgg ccagggcaaa ggtgtttgac | 480 |
| atcgatttgc agaagcagtt gaggccttac atggaatcca tgcttccact ccccggaatc | 540 |
| tatgacccgg atttcattgc tgccaaccaa gaggagcgtg ccaacaacgt catcaagggc | 600 |
| acaaagcaag agcaagttca acaaatcatc aaagacatca aggcgtttaa ggaagccacc | 660 |
| aaagtggaca aggtggttgt actgtggact gccaacacag agaggtacag taatttggtt | 720 |
| gtgggcctta atgacaccat ggagaatctc ttggctgctg tggacagaaa tgaggctgag | 780 |
| atttctcctt ccaccttgta tgccattgct tgtgttatgg aaaatgttcc tttcattaat | 840 |
| ggaagccctc agaacacttt tgtaccaggg ctgattgatc ttgccatcgc gaggaacact | 900 |
| ttgattggtg gagatgactt caagagtggt cagaccaaaa tgaaatctgt gttggttgat | 960 |
| ttccttgtgg gggctggtat caagccaaca tctatagtca gttacaacca tctgggaaac | 1020 |
| aatgatggta tgaatctttc ggctccacaa actttccgtt ccaaggaaat ctccaagagc | 1080 |
| aacgttgttg atgatatggt caacagcaat gccatcctct atgagcctgg tgaacatcca | 1140 |
| gaccatgttg ttgttattaa gtatgtgcct tacgtagggg acagcaagag agccatggat | 1200 |
| gagtacactt cagagatatt catgggtgga aagagcacca ttgttttgca caacacatgc | 1260 |
| gaggattccc tcttagctgc tcctattatc ttggacttgg tccttcttgc tgagctcagc | 1320 |
| actagaatcg agtttaaagc tgaaaatgag ggaaaattcc actcattcca cccagttgct | 1380 |
| accatcctca gctacctcac caaggctcct ctggttccac cgggtacacc agtggtgaat | 1440 |
| gcattgtcaa agcagcgtgc aatgctggaa aacataatga gggcttgtgt tggattggcc | 1500 |
| ccagagaata acatgattct cgagtacaag tga | 1533 |

RECOMBINANT MICELLE AND METHOD OF IN VIVO ASSEMBLY

CROSS REFERENCE TO RELATED APPLICATIONS

This application is continuation-in-part (CIP) of U.S. application Ser. No. 17/717,000 filed on Apr. 8, 2022, which is a continuation of U.S. application Ser. No. 16/741,680, filed on Jan. 13, 2020, now patented as U.S. Pat. No. 11,326,176, issued on May 10, 2022, which claims the benefit of U.S. Provisional Patent Application No. 62/939,247, filed on Nov. 22, 2019, all of which are incorporated herein by reference in their entireties. This application also claims the benefit of U.S. Provisional Patent Application No. 63/281,069, filed on Nov. 18, 2021, which is incorporated herein by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on May 26, 2022, is named 62162-701_401_SL.txt and is 188,951 bytes in size.

TECHNICAL FIELD

An embodiment of the present disclosure relates generally to a micelle and more particularly to recombinant micelle and method of in vivo assembly in a plant cell.

BACKGROUND

Casein micelles account for more than 80% of the protein in bovine milk and are a key component of all dairy cheeses. Casein micelles include individual casein proteins are produced in the mammary glands of bovines and other ruminants. The industrial scale production of the milk that is processed to yield these casein micelles, primarily in the form of curds for cheese production, typically occurs on large-scale dairy farms and is often inefficient, damaging to the environment, and harmful to the animals. Dairy cows contribute substantially to greenhouse gasses, consume significantly more water than the milk they produce, and commonly suffer from dehorning, disbudding, mastitis, routine forced insemination, and bobby calf slaughter.

Accordingly, there is a need for an in vivo plant-based casein expression system which allows for purification of biologically active casein proteins that is cost effective at industrial scale.

Protein phosphorylation is a post-translational modification of proteins in which a phosphate group is added to an amino acid in the protein. Chemical phosphorylation of food proteins can be achieved by using chemicals. However, chemical phosphorylation disrupts the native structure of food proteins because of the harsh reaction conditions. Moreover, unwanted chemical reagents from the final product can be difficult to remove. Enzymatic phosphorylation with ATP is a more desirable method to phosphorylate food proteins due to improved food safety. However, this method does not fit the needs of industrial-scale production due to the high cost of ATP and enzymes.

Solutions to these problems have been long sought but prior developments have not taught or suggested any solutions and, thus, solutions to these problems have long eluded those skilled in the art.

SUMMARY

An embodiment of the present disclosure provides a method of in vivo assembly of a recombinant micelle including: introducing a plasmid into a plant cell, wherein: the plasmid includes a segment of deoxyribonucleic acid (DNA) for encoding a ribonucleic acid (RNA) for a protein in a casein micelle, the segment of DNA is transcribed and translated; forming recombinant casein proteins in the plant cell, wherein: the recombinant casein proteins include a κ-casein and at least one of an $\alpha S_1$-casein, an $\alpha S_2$-casein, and a β-casein; and assembling in vivo a recombinant micelle within the plant cell, wherein: an outer layer of the recombinant micelle is enriched with the κ-casein, an inner matrix of the recombinant micelle include at least one of the $\alpha S_1$-casein, the $\alpha S_2$-casein, the β-casein.

An embodiment of the present disclosure provides a recombinant micelle including: an outer layer enriched with a κ-casein; and an inner matrix including at least one of a $\alpha S_1$-casein, a $\alpha S_2$-casein, and a β-casein.

An embodiment of the present disclosure provides a plasmid including a segment of deoxyribonucleic acid (DNA) for encoding a protein in a casein micelle wherein the segment of DNA includes a promoter and a N-terminal signal peptide.

Certain embodiments of the disclosure have other steps or elements in addition to or in place of those mentioned above. The steps or elements will become apparent to those skilled in the art from a reading of the following detailed description when taken with reference to the accompanying drawings.

Some aspects of the present disclosure provide methods of in vivo assembly of a recombinant micelle comprising introducing a plasmid into a plant cell, wherein the plasmid includes a segment of deoxyribonucleic acid (DNA) for encoding a ribonucleic acid (RNA) for a protein in a casein micelle, the segment of DNA is transcribed and translated; forming recombinant casein proteins in the plant cell, wherein the recombinant casein proteins include a κ-casein and at least one of an αS1-casein, an αS2-casein, and a β-casein; and assembling in vivo a recombinant micelle within the plant cell, wherein an outer layer of the recombinant micelle is enriched with the κ-casein and an inner matrix of the recombinant micelle include at least one of the αS1-casein, the αS2-casein, the β-casein.

In some cases, the plasmid includes a further segment of DNA encoding a N-terminal signal peptide that targets the recombinant casein proteins to a vacuole in the plant cell. In some cases, the plasmid includes a further segment of DNA encoding a selectable marker or a screenable marker. In some cases, the plasmid includes a further segment of DNA encoding interference RNA to suppress expression of a native protein or a native peptide in the plant cell. In some cases, the plasmid includes a further segment of DNA encoding a protein capable of altering an intracellular environment of the plant cell.

In some cases, the disclosed method further comprises introducing a further plasmid into the plant cell; wherein the further plasmid includes a further segment of DNA for encoding a further RNA for a further protein in the casein micelle; the further segment of DNA is transcribed and translated; and the further segment of DNA is at least one of the encoding a N-terminal signal peptide that targets the recombinant casein proteins to an endoplasmic reticulum in the plant cell, a further N-terminal signal peptide that targets the recombinant casein proteins to a vacuole in the plant cell, a selectable marker or a screenable marker, and a protein capable of altering an intracellular environment of the plant cell. In some cases, the plasmid includes a further segment of DNA including one or more nucleotide sequences selected from SEQ ID NO:36 to SEQ ID NO:43.

Some aspects of the present disclosure provides a recombinant micelle comprising an outer layer enriched with a κ-casein; and an inner matrix including at least one of a αS1-casein, a αS2-casein, a β-casein. In some cases, the inner matrix includes a calcium and a phosphate.

Some aspects of the present disclosure provide plasmids comprising a segment of deoxyribonucleic acid (DNA) for encoding a protein in a casein micelle wherein the segment of DNA includes a promoter and a N-terminal signal peptide. In some cases, the plasmid includes a further segment of DNA encoding a N-terminal signal peptide that targets the recombinant casein proteins to a vacuole in a plant cell. In some cases, the plasmid includes a further segment of DNA encoding a selectable marker or a screenable marker. In some cases, the plasmid includes a further segment of DNA encoding interference RNA to suppress expression of a native protein or a native peptide in a plant cell. In some cases, the plasmid includes the plasmid includes a further segment of DNA encoding a protein capable of altering an intracellular environment of a plant cell. In some cases, the plasmid includes a further segment of DNA including one or more nucleotide sequences selected from SEQ ID NO:36 to SEQ ID NO:43.

Some aspects of the present disclosure provide methods of isolating a recombinant micelle comprising processing a seed including a cytoplasm with the recombinant micelle; microfiltering the cytoplasm to remove a particulate above 2 um; ultrafiltering the cytoplasm microfiltered to a further particulate greater than 100 nm; and collecting the recombinant micelle from the cytoplasm ultrafiltered. In some cases, the disclosed methods further comprise processing the seed includes cleaning, and deshelling or dehulling the seed, flaking the seed cleaned to 0.005-0.02 inch thickness, extracting with a solvent of oil from the seed flaked, desolventizing the seed flaked without cooking and collecting the de-oiled, cleaned separating the recombinant micelle into a slurry by hydrating, agitating and wet milling the seed flaked, passing the slurry through a mesh screen to remove a particulate above 0.5 mm in size and collecting a permeate; and microfiltering the cytoplasm includes microfiltering the permeate.

In some cases, the disclosed methods further comprise microfiltering the cytoplasm includes microfiltering a permeate; ultrafiltering the cytoplasm microfiltered includes ultrafiltering the permeate microfiltered; and collecting the recombinant micelle from the cytoplasm ultrafiltered includes collecting a retentate from the permeate ultrafiltered.

In some cases, the disclosed methods further comprise microfiltering the cytoplasm includes microfiltering a permeate; ultrafiltering the cytoplasm microfiltered includes ultrafiltering the permeate microfiltered; collecting the recombinant micelle from the cytoplasm ultrafiltered includes collecting a retentate from the permeate ultrafiltered; and diafiltering the retentate at a rate that the permeate is collected and passing the retentate through the ultrafiltering. In some cases, the disclosed methods further comprise processing the seed milled from a maize, a rice, a sorghum, a cowpea, a soybean, a cassava, a coyam, a sesame, a peanut, a pea, a cotton, a yam, or a combination thereof.

The current disclosure provides compositions, methods and systems for phosphorylation of proteins in plants. Described herein, in some aspects, are vectors for expressing a phosphorylated payload protein in a plant, wherein a vector may comprise at least one of a polynucleotide sequence encoding: a first kinase, a second kinase, a first payload protein, a promoter sequence, a terminator sequence, a second payload protein, and combinations thereof. In some instances, described herein are vectors for expressing a phosphorylated payload protein in a plant, wherein a vector may comprise, for example, a polynucleotide sequence encoding: a first kinase, a second kinase, a first payload protein, a promoter sequence, a terminator sequence, and optionally a second payload protein.

Contemplated promoters include CaMV 35S, AtuMas Pro+5'UTR, RbcS2 promoter, a soybean GY1 Promoter, soybean CG1 Promoter, or other suitable promoters.

Contemplated terminator sequence can be octopine synthase terminator (Ocst), Octopine (OCS) terminator, NOS terminator or other suitable terminator sequences. It is contemplated that the first or the second kinase can be a human kinase or a non-human kinase, for example, a bovine kinase. In some instances, at least one of the first and the second kinase is FAM20A, FAM20C, casein Kinase II or a tyrosine kinase. In some instances, at least one of the first kinase and the second kinase has at least 50%, 60%, 70%, 80%, 85%, 90%, 95%, or 99% sequence identity to SEQ ID NO: 40, SEQ ID NO: 41, SEQ ID NO: 43, SEQ ID NO: 83, or SEQ ID NO: 84. In some instances, the first kinase is different from the second kinase. For example, the first kinase can any one of the kinases mentioned herein, and the second kinase can be a different kinase mentioned herein.

In some instances, the first or second payload (e.g., casein) protein is a mammalian protein, for example, a human protein, a ruminant protein, a primate protein. In some instances, the ruminant animal includes, for example, a cow, a buffalo, a yak, a deer, a bovine, a goat, and a sheep.

In some instances, the first or second payload protein comprises a whey protein, including, for example, α-lactalbumin, β-lactoglobulin, serum albumin, immunoglobulins, and proteose peptone. In some instances, the payload protein comprises an egg white protein, including, for example, ovalbumin, ovotransferrin, ovomucoid, ovoglobulin g2, ovoglobulin g3, ovomucin, lysozyme, ovoinhibitor, ovoglycoprotein, flavoprotein, ovomacroglobulin, avidin, and cystatin. In some instances, the egg white protein has at least 50%, 60%, 70%, 80%, 85%, 90%, 95%, or 99% sequence identity to the amino acid SEQ ID NO: 80, SEQ ID NO: 81, SEQ ID NO: 82, SEQ ID NO: 83, SEQ ID NO: 86, SEQ ID NO: 87, SEQ ID NO: 88, SEQ ID NO: 90, SEQ ID NO: 91, or SEQ ID NO: 92.

In some instances, the payload protein is a collagen protein, including, for example, Collagen I, Collagen II, Collagen III, Collagen IV, Collagen V, Collagen VI, Collagen VII, Collagen VIII, Collagen IX, Collagen X, Collagen XI, Collagen XII, Collagen XIII, Collagen XIV, Collagen XV, Collagen XVI, Collagen XVII, Collagen XVIII, Collagen XIX, Collagen XX, Collagen XXI, Collagen XXII, Collagen XXIII, Collagen XXIV, Collagen XXV, Collagen XXVI, Collagen XXVII, and Collagen XXVIII. In some instances, the collagen protein comprises one or more a chains, for example, wild type Bovine Collagen Alpha-1(I)

Chain. In some instances, the collagen protein expressed has at least 50%, 60%, 70%, 80%, 85%, 90%, 95%, or 99% sequence identity to the amino acid SEQ ID NO: 49.

In some instances, the first or second payload protein is a casein protein, including, for example, αS1-casein, αS2-casein, β-casein, and κ-casein. The casein protein can be from any mammalian species (including human) including from a ruminant animal. In some instances, the casein protein has at least 50%, 60%, 70%, 80%, 85%, 90%, 95%, or 99% sequence identity to the amino acid SEQ ID NO:36, SEQ ID NO:37, SEQ ID NO:38, SEQ ID NO:39, SEQ ID NO:77, SEQ ID NO:78, SEQ ID NO:79, SEQ ID NO:80, SEQ ID NO:81, or SEQ ID NO: 82. In some instances, the second payload protein is different from the first payload protein. For example, the first payload protein is κ-casein, and the second payload protein is at least one of αS1-casein, αS2-casein, and β-casein. It is contemplated that the same vector can express casein proteins from different species, for example, the first pay load protein is human κ-casein, and second pay load protein is a bovine αS1-casein, αS2-casein, or β-casein. As another example, the first pay load protein κ-casein is a bovine casein, and second pay load protein is a human β-casein.

TABLE 1

Examples of certain proteins used in the current disclosure and their sequences.

| | | |
|---|---|---|
| SEQ ID NO: 36 | Wild type Bovine k-casein | MMKSFFLVVTILALTLPFLGAQEQN QEQPIRCEKDERFFSDKIAKYIPIQ YVLSRYPSYGLNYYQQKPVALINNQ FLPYPYYAKPAAVRSPAQILQWQVL SNTVPAKSCQAQPTTMARHPHPHLS FMAIPPKKNQDKTEIPTINTIASGE PTSTPTTEAVESTVATLEDSPEVIE SPPEINTVQVTSTAV |
| SEQ ID NO: 37 | Wild type Bovine αs1-casein | MKLLILTCLVAVALARPKHPIKHQG LPQEVLNENLLRFFVAPFPEVFGKE KVNELSKDIGSESTEDQAMEDIKQM EAESISSSEEIVPNSVEQKHIQKED VPSERYLGYLEQLLRLKKYKVPQLE IVPNSAEERLHSMKEGIHAQQKEPM IGVNQELAYFYPELFRQFYQLDAYP SGAWYYVPLGTQYTDAPSFSDIPNP IGSENSEKTTMPLW |
| SEQ ID NO: 38 | Wild type Bovine αS2-casein | MKFFIFTCLLAVALAKNTMEHVSSS EESIISQETYKQEKNMAINPSKENL CSTFCKEVVRNANEEEYSIGSSSEE SAEVATEEVKITVDDKHYQKALNEI NQFYQKFPQYLQYLYQGPIVLNPWD QVKRNAVPITPTLNREQLSTSEENS KKTVDMESTEVFTKKTKLTEEEKNR LNFLKKISQRYQKFALPQYLKTVYQ HQKAMKPWIQPKTKVIPYVRYL |
| SEQ ID NO: 39 | Wild type Bovine β-casein | MKVLILACLVALALARELEELNVPG EIVESLSSSEESITRINKKIEKFQS EEQQQTEDELQDKIHPFAQTQSLVY PFPGPIPNSLPQNIPPLTQTPVVVP PFLQPEVMGVSKVKEAMAPKHKEMP FPKYPVEPFTESQSLTLTDVENLHL PLPLLQSWMHQPHQPLPPTVMFPPQ SVLSLSQSKVLPVPQKAVPYPQRDM PIQAFLLYQEPVLGPVRGPFPIIV |
| SEQ ID NO: 40 | FAM20A | MSSSFLSSTAFFLLLCLGFCHVSSQ LRPRERPRGCPCTGRASSLARDSAA AASDPGTIVHNFSRTEPRTEPAGGS HSGSSSKLQALFAHPLYNVPEEPPL LGAEDSLLASQEALRYYRRKVARWN RRHKMYREQMNLTSLDPPLQLRLEA SWVQFHLGINRHGLYSRSSPVVSKL LQDMRHFPTISADYSQDEKALLGAC DCTQIVKPSGVHLKLVLRFSDFGKA MFKPMRQQRDEETPVDFFYFIDFQR HNAEIAAFHLDRILDFRRVPPTVGR IVNVTKEILEVTKNEILQSVFFVSP ASNVCFFAKCPYMCKTEYAVCGNPH LLEGSLSAFLPSLNLAPRLSVPNPW IRSYTLAGKEEWEVNPLYCDTVKQI YPYNNSQRLLNVIDMAIFDFLIGNM DRHHYEMFTKFGDDGFLIHLDNARG FGRHSHDEISILSPLSQCCMIKKKT LLHLQLLAQADYRLSDVMRESLLED QLSPVLTEPHLLALDRRLQTILRTV EGCIVAHGQQSVIVDGPVEQLAPDS GQANLTSHDEL |
| SEQ ID NO: 41 | FAM20C | MSSSFLSSTAFFLLLCLGFCHVSSL DLLPRLERRGARPSGEPGCSCAQPA AEVAAPGWAQVRGRPGEPPAASSAA GDAGWPNKHTLRILQDFSSDPSSNL SSHSLEKLPPAAEPAERALRGRDPG ALRPHDPAHRPLLRDPGPRRSESPP GPGGDASLLARLFEHPLYRVAVPPL TEEDVLFNVNSDTRLSPKAAENPDW PHAGAEGAEFLSPGEAAVDSYPNWL KFHIGINRYELYSRHNPAIEALLHD LSSQRITSVAMKSGGTQLKLIMTFQ NYGQALFKPMKQTREQETPPDFFYF SDYERHNAEIAAFHLDRILDFRRVP PVAGRMVNMTKEIRDVTRDKKLWRT FFISPANNICFYGECSYYCSTEHAL CGKPDQIEGSLAAFLPDLSLAKRKT WRNPWRRSYHKRKKAEWEVDPDYCE EVKQTPPYDSSHRILDVMDMTIFDF LMGNMDRHYETFEKFGNETFIIHL DNGRGFGKYSHDELSILVPLQQCCR IRKSTYLRLQLLAKEEYKLSLLMAE SLRGDQVAPVLYQPHLEALDRRLRV VLKAVRDCVERNGLHSVVDDDLDTE HRAASARHDEL |
| SEQ ID NO: 42 | CaMV 35S Promoter | GTCAACATGGTGGAGCACGACACTC TGGTCTACTCCAAAAATGTCAAAGA TACAGTCTCAGAAGATCAAAGGGCT ATTGAGACTTTTCAACAAAGGATAA TTTCGGGAAACCTCCTCGGATTCCA TTGCCCAGCTATCTGTCACTTCATC GAAAGGACAGTAGAAAAGGAAGGTG GCTCCTACAAATGCCATCATTGCGA TAAAGGAAAGGCTATCATTCAAGAT CTCTCTGCCGACAGTGGTCCCAAAG ATGGACCCCCACCCACGAGGAGCAT CGTGGAAAAAGAAGAGGTTCCAACC ACGTCTACAAAGCAAGTGGATTGAT GTGACATCTCCACTGACGTAAGGGA TGACGCACAATCCCACTATCCTTCG CAAGACCCTTCCTCTATATAAGGAA GTTCATTTCATTTGGAGAGGACACG C |
| SEQ ID NO: 43 | Wild Type Human Casein Kinase II | MSGPVPSRARVYTDVNTHRPREYWD YESHVVEWGNQDDYQLVRKLGRGKY SEVFEAINITNNEKVVVKILKPVKK KKIKREIKILENLRGGPNIITLADI VKDPVSRTPALVFEHVNNTDFKQLY QTLTDYDIRFYMYEILKALDYCHSM GIMHRDVKPHNVMIDHEHRKLRLID WGLAEFYHPGQEYNVRVASRYFKGP ELLVDYQMYDYSLDMWSLGCMLASM IFRKEPFFHGHDNYDQLVRIAKVLG TEDLYDYIDKYNIELDPRFNDILGR HSRKRWERFVHSENQHLVSPEALDF LDKLLRYDHQSRLTAREAMEHPYFY TVVKDQARMGSSSMPGGSTPVSSAN MMSGISSVPTPSPLGPLAGSPVIAA ANPLGMPVPAAAGAQQ |

TABLE 1-continued

Examples of certain proteins used in the current disclosure and their sequences.

| SEQ ID NO: 44 | octopine synthase terminator | GTCCTGCTTTAATGAGATATGCGAG AAGCCTATGATCGCATGATATTTGC TTTCAATTCTGTTGTGCACGTTGTA AAAAACCTGAGCAGTGTAGCTCAG ATCCTTACCGCCGGTTTCGGTTCAT TCTAATGAATATATCACCCGTTACT ATCGTATTTTTATGAATAATATTCT CCGTTCAATTTACTGATTGTACCCT ACTACTTATATGTACAATATTAAAA TGAAAACAATATATTGTGCTGAATA GGTTTATAGCGACATCTATGATAGA GCGCCACAATAACAAACAATTGCT TTTATTATTACAAATCCAATTTTAA AAAAAGCGGCAGAACCGGTCAAACC TAAAAGACTGATTACATAAATCTTA TTCAAATTTCAAAAGTGCCCCAGGG GCTAGTATCTACGACACACCGAGCG GCGAACTAATAACGCTCACTGAAGG GAACTCCGGTTCCCCGCCGGCGCGC ATGGGTGAGATTCCTTGAAGTTGAG TATTGGCCGTCCGCTCTACCGAAAG TTACGGGCACCATTCAACCCGGTCC AGCACGGCGGCGGGTAACCGACTT GCTGCCCCGTGCAGGTCAAACCTTG ACAGTGACGACAAATCGTTGGGCGG GTCCAGGGCGAATTTTGCGACAACA TGTCGAGGCTCAGCAGGAC |
| SEQ ID NO: 45 | Ovalbumin | MGSIGAASMEFCFDVFKELKVHHAN ENIFYCPIAIMSALAMVYLGAKDST RTQINKVVRFDKLPGFGDSIEAQCG TSVNVHSSLRDILNQITKPNDVYSF SLASRLYAEERYPILPEYLQCVKEL YRGGLEPINFQTAADQARELINSWV ESQTNGIIRNVLQPSSVDSQTAMVL VNAIVFKGLWEKAFKDETQAMPFR VTEQESKPVQMMYQIGLFRVASMAS EKMKILELPFASGTMSMLVLLPDEV SGLEQLESIINFEKLTEWTSSNVME ERKIKVYLPRMKMEEKYNLTSVLMA MGITDVFSSSANLSGISSAESLKIS QAVHAAHAEINEAGREVVGSAEAGV DAASVSEEFRADHPFLFCIKHIATN AVLFFGRCVSP |
| SEQ ID NO: 46 | Ovotransferrin | MKLILCTVLSLGIAAVCFAAPPKSV IRWCTISSPEEKKCNNLRDLTQQER ISLTCVQRATYLDCTKAIANNEADA ISLDGGQAFEAGLAPYKLKPIAAEV YEHTEGSTTSYYAVAVVKKGTEFTV NDLQGKTSCHTGLGRSAGWNIPIGT LLHRGAIEWEGIESGSVEQAVARFF SASCVPGATIEQKLCRQCKGDPKTK CARNAPYSGYSGAFHCLKDGKGDVA FVKHTTVNENAPDQKDEYELLCLDG SRQPVDNYKTCNWARVAAHAVVARD DNKVEDIWSFLSKAQSDFGVDTKSD FHLFGPPGKKDPVLKDLLFKDSAIM LKRVPSLMDSQLYLGFEYYSAIQSM RKDQLTPSPRENRIQWCAVGKDEKS KCDRWSVVSNGDVECTVVDETKDCI IKIMKGEADAVALDGGLVYTAGVCG LVPVMAERYDDESQCSKTDERPASY FAVAVARKDSNYNWNNLKGKKSCHT AVGRTAGWVIPMGLIHNRTGTCNFD EYFSEGCAPGSPPNSRLCQLCQGSG GIPPEKCVASSHEKYFGYTGALRCL VEKGDVAFIQHSTVEENTGGKNKAD WAKNLQMDDFELLCTDGRRANVMDY RECNLAEVPTHAVVVRPEKANKIRD LLERQEKRFGVNGSEKSKFMMFESQ NKDLLFKDLTKCLFKVREGTTYKEF LGDKFYTVISSLKTCNPSDILQMCS FLEGK |
| SEQ ID NO: 47 | Ovomucoid | MAMAGVFVLFSFVLCGFLPDAAFGA EVDCSRFPNATDKEGKDVLVCNKDL RPICGTDGVTYTNDCLLCAYSIEFG TNISKEHDGECKETVPMNCSSYANT TSEDGKVMVLCNRAFNPVCGTDGVT YDNECLLCAHKVEQGASVDKRHDGG CRKELAAVSVDCSEYPKPDCTAEDR PLCGSDNKTYGNKCNFCNAVVESNG TLTLSHFGKC |
| SEQ ID NO: 48 | Ovoglobulin G2 | MGALLALLDPVQPTRAPDCGGILTP LGLSYLAEVSKPHAEVVLRQDLMAQ RASDLFLGSMEPSRNRITSVKVADL WLSVIPEAGLRLGIEVELRVAPLHA VPMPVRISIRADLHVDMGPDGNLQL LTSACRPTVQAQSTREAESKSSRSI LDKVVDVDKLCLDVSKLLLFPNEQL MSLTALFPVTPNCQLQYLPLAAPVF SKQGIALSLQTTFQVAGAVVPVPVS PVPFSMPELASTSTSHLILALSEHF YTSLYFTLERAGAFNMTI PSMLTTATLAQKITQVGSLYHEDLP ITLSAALRSSPRVVLEEGRAALKLF LTVHIGAGSPDFQSFLSVSADVTAG LQLSVSDTRMMISTAVIEDAELSLA ASNVGLVRAALLEELFLAPVCQQVP AWMMDDVLREGVHLPHLSHFTYTDVS VVVHKDYVLVPCKLKLRSTMA |
| SEQ ID NO: 49 | Wild type Bovine Collagen Alpha-1(I) Chain | MFSFVDLRLLLLLAATALLTHGQEE GQEEGQEEDIPPVTCVQNGLRYHDR DVWKPVPCQICVCDNGNVLCDDVIC DELKDCPNAKVPTDECCPVCPEGQE SPTDQETTGVEGPKGDTGPRGPRGP AGPPGRDGIPGQPGLPGPPGPPGPP GPPGLGGNFAPQLSYGYDEKSTGIS VPGPMGPSGPRGLPGPPGAPGPQGF QGPPGEPGEPGASGPMGPRGPPGPP GKNGDDGEAGKPGRPGERGPPGPQG ARGLPGTAGLPGMKGHRGFSGLDGA KGDAGPAGPKGEPGSPGENGAPGQM GPRGLPGERGRPGAPGPAGARGNDG ATGAAGPPGPTGPAGPPGFPGAVGA KGEGGPQGPRGSEGPQGVRGEPGPP GPAGAAGPAGNPGADGQPGAKGANG APGIAGAPGFPGARGRPSGPQGPSGP PGPKGNSGEPGAPGSKGDTGAKGEP GPTGIQGPPGPAGEEGKRGARGEPG PAGLPGPPGERGGPGSRGFPGADGV AGPKGPA GERGAPGPAGPKGSPGEAGRPGEAGL PGAKGLTGSPGSPGPDGKTGPPGPA GQDGRPGPPGPPGARGQAGVMGFPG PKGAAGEPGKAGERGVPGPPGAVGP AGKDGEAGAQGPPGPAGPAGERGEQ GPAGSPGFQGLPGPAGPPGEAGKPG EQGVPGDLGAPGPSGARGERGFPGE RGVQGPPGPAGPRGANGAPGNDGAK GDAGAPGAPGSQGAPGLQGMPGERG AAGLPGPKGDRGDAGPKGADGAPGK DGVRGLTGPIGPPGPAGAPGDKGEA GPSGPAGPTGARGAPGDRGEPGPPG PAGFPPGADGQPGAKGEPGDAGA KGDAGPPGPAGPAGPPGPIGNVGAP GPKGARGSAGPPGATGFPGAAGRVG PPGPSGNAGPPGPPGPAGKEGSKGP RGETGPAGRPGEVGPPGPPGPAGEK GAPGADPGAGAPGTPGPQGIAGQRG VVGLPGQRGERGFPGLPGPSGEPGK QGPSGASGERGPPGPMGPPGLAGPP GESGREGAPGAEGSPGRDGSPGAKG DRGETGPAGPPGAPGAPGAPGPVGP AGKSGDRGETGPAGPAGPIGPVGAR GPAGPQGPRGDKGETGEQGDRGIKG HRGFSGLQGPPGPPGSPGEQGPSGA SGPAGPRGPPGSAGSPGKDGLNGLP |

TABLE 1-continued

Examples of certain proteins used in the current disclosure and their sequences.

| | | |
|---|---|---|
| | | GPIGPPGPRGRTGDAGPAGPPGPPG PPGPPGPPSSGGYDLSFLPQPPQEKA HDGGRYYRADDANVVRDRDLEVDTT LKSLSQQIENIRSPEGSRKNPARTC RDLKMCHSDWKSGEYWIDPNQGCNL DAIKVFCNMETGETCVYPTQPSVAQ KNWYISKNPKEKJRFIVWYGESMTG GFQFEYGGQGSDPADVAIQLTFLRL MSTEASQNITYHCKNSVAYMDQQTG NLKKALLLQGSNEIEIRAEGNSRFT YSVTYDGCTSHTGAWGKTVIEYKTT KTSRLPIIDVAPLDVGAPDQEFGFD VGPACFL |
| SEQ ID NO: 50 | Soybean GY1 Promoter | ggttcaacaacacaagcttcaagtt ttaaaaggaaaaatgtcagccaaaa acttttaaataaaatggtaacaagat ctagttccaccttattttataagaa gaagaaactaatatataagaactaa aaaacagaagaatagaaaaaaaaag tattgacaggaaagaaaaagtagct gtatgcttataagtactttgaggat ttgaattctctcttataaaacacaa acacaattttttagattttattaaa taatcatcaatccgattataattat ttatatattttctattttcaaaga agtaaatcatgagcttttccaactc aacatctatttttttctctcaacc ttttttcacatcttaagtagtctcac ccttatatatataacttatttctt acctttttacattatgtaacttttat caccaaaaccaacaactttaaaatt ttattaaatagactccacaagtaac ttgacactcttacattcatcgacat taactttttatctgttttataaatat tattgtgatataatttaatcaaaat aaccacaaactttcataaaaggttc ttattaagcatggcatttaataagc aaaaacaactcaatcactttcatat aggaggtagcctaagtacgtactca aaatgccaacaaataaaaaaaaagt tgctttaataatgccaaaacaaatt aataaaacacttacaacaccggatt tttttttaattaaaatgtgccattta ggataaatagttaatattttttaata attatttaaaagccgtatctacta aaatgattttttatttggttgaaaat attaatatgtttaaatcaacacaat ctatcaagaaattgaaagcgagtct aatttttaaattatgaacctgcata tataaaaggaaagaaagaatccagg aagaaaagaaatgaaaccatgcatg gtccctcgtcatcacgagtttctg ccatttgcaatagaaacactgaaac acctttctctttgtcacttaattga gatgccgaagccacctcacaccatg aacttcatgaggtgtagcacccaag gcttccatagccatgcatactgaag aatgtctcaagctcagcaccctact tctgtgacgtgtccctcattcacct tcctctcttccctataaataaccac gcctcaggttctccgcttc |
| SEQ ID NO:51 | Wild Type Chicken Lysozyme | MRSLLILVLCFLPLAALGKVFGRCE LAAAMKRHGLDNYRGYSLGNWVCAA KFESNFNTQATNRNTDGSTDYGILQ INSRWWCNDGRTPGSRNLCNIPCSA LLSSDITASVNCAKKIVSDGNGMNA WVAWRNRCKGTDVQAWIRGCRL |
| SEQ ID NO: 52 | Ovoinhibitor | MTDWVLHHKVGPLDMTTRYIFPLLP LPFLPHSESKRAVCAPRCSAMRTAR QFVQVALALCCFADIAFGIEVNCSL YASGIGKDGTSWVACPRNLKPVCGT DGSTYSNECGICLYNREHGANVEKE YDGECRPKHVTIDCSPYLQVVRDGN TMVACPRILKPVCGSDSFTYDNECG ICAYNAEHHTNISKLHDGECKLEIG SVDCSKYPSTVSKDGRTLVACPRIL SPVCGTDGFTYDNECGICAHNAEQR THVSKKHDGKCRQEIPEIDCDQYPT RKTTGGKLLVRCPRILLPVCGTDGF TYDNECGICAHNAQHGTEVKKSHDG RCKERSTPLDCTQYLSNTQNGEAIT ACPFILQEVCGTDGVTYSNDCSLCA HNIELGTSVAKKHDGRCREEVPELD CSKYKTSTLKDGRQVVACTMIYDPV CATNGVTYASECTLCAHNLEQRTNL GKRKNGRCEEDITKEHCREFQKVSP ICTMEYVPHCGSDGVTYSNRCFFCN AYVQSNRTLNLVSMAAC |
| SEQ ID NO: 53 | Ovoglycoprotein | VVSTAAPTDPRRRMAVSVLLFISVA LAGVLSTASQACKLEPVKIDLANPQ LAGKWYFIQVATEVELYQARFANID NSYFISTPDVKLNKTNIKEYSQLGD LCLSTNTDYVVLENGYEFTDGAKNI NNFRIIKSKIDNMLIIDYQYQIEKM DYHMLTLFKRNPTASKEEMEIFESY TKCLGLDKDKIKAFPRNKSECKEEK QINSFNATTQAQDFLEEKVLQNRNI |
| SEQ ID NO: 54 | Soybean CGI Promoter | gtgtgttgtaagtataaautaaaat aaaaataaaaacaattattatatca aaatggcaaaaacatuaatacgtat tatttaagaaaaaatatgtaataa tatatttatatttaatatctattc ttatgtattttttaaaaatctatta tatattgatcaactaaaatatttt atatctacacttatttgcattttt atcaattttcttgcgtttttttggca tatttaataatgactattctttaat aatcaatcattattcttacatggta catattgttggaaccatatgaagtg tccattgcatttgactatgtggata gtgttttgatccaggcctccatttg ccgcttattaattaatttggtaaca gtccgtactaatcagttacttatcc ttcctccatcataattaatcttggt agtctgaatgccacaacactgact agtctcttggatcataagaaaaagc caaggaacaaaagatcacaaaacac aatgagagtatcctttgcatagcaa tgtctaagttcataaaattcaaaca aaaacgcaatcacacacagtggaca tcacttatccactagctgatcagga tcgccgcgtcaagaaaaaaaactg gaccccaaaagccatgcacaacaac acgtactcacaaaggtgtcaatcga gcagcccaaaacattcaccaactca acccatcatgagcccacacatttgt tgttctaacccaacctcaaactcg tattctcttccgccacctcattttt gtttatttcaacacccgtcaaactg catgccaccccgtggccaaatgtcc atgcatgttaacaagacctatgact ataaatatctgcaatctcggcccag gttttcatc |
| SEQ ID NO: 55 | Ovomacroglobulin | ALTSGLGPDVYQFLQDMGMKFFTNS KJRQPTVCTRETVRPPSYFLNAGFT ASTHHVKLSAEVAREERGKRHILET IREFFPETWIWDIILINSTGKASVS YTIPDTITEWKASAFCVLPPNVVEE SARASVSVLGDILGSAMQNTQNLLQ MPYGCGEQNMVLFAPNIYVLDYLNE TQQLSEDMKSKTIGYLESGYQKQLS YKHPDGSY |
| SEQ ID NO: 56 | Avidin | MVHATSPLLLLLLLSLALVAPGLSA RKCSLTGKWTNDLGSNMTIGAVNSR GEFTGTYITAVTATSNEIKESPLHG TQNTINKRTQPTFGFTVNWKFSEST TVFTGQCFIDRNGKEVLKTMWLLRS |

TABLE 1-continued

Examples of certain proteins used in the current disclosure and their sequences.

| | | |
|---|---|---|
| SEQ ID NO: 57 | Cystatin | MVGSPRAPLLLLASLIVALALAV SPAAAQGPRKGRLLGGLMEADVNEE GVQEALSFAVSEFNKRSNDAYQSRV VRVVRARKQVVSGMNYFLDVELGRT TCTKSQANLDSCPFHNQPHLKREKL CSFQVYVVPWMNTINLVKFSCQD SVNDIGDDWKATRVGINIFTRLRTQ KE |
| SEQ ID NO: 58 | TMV Omega | ATTTTTACAACAATTACCAACAACA ACAAACAACAAACAACATTACAATT ACATTTACAATT |
| SEQ ID NO: 59 | AtRbcS2 Promoter | TTGCTTCTTCTCTCTTTTTTTGGTT CAATATGAACCTTTTGATGTCCACT ATCCTTTTATATAATGAAATGATAA GGTTTTTGATATGTTATGTGGTTCT TGATAACATTATACAATTACTTAAT ATCTACATATGAAAGGTTGGAATTT TTTTTAAGTCACCACAATAGAGGTG ACACGTGTAAGCACCTCGTTAATCT TATCTCATCCAAGATGGGGGTAGGA AGAGGATATGAATGTATGATTGAGG TTGGTTTTGAGTTTTTTTTTTTTTT TTTTTTGAGTCCTTCAACTTGTTAT TTTAATTTTTTTTTGGTGGGGGAGG AGGGGGGTTGAAATATTTATCATAT AGTAGTCCAAAGTAAATTGATAGCT AGAGTACTTGTTTGCTTGCTTATAT TGTCCTCAACTTTATGTAATACCAT GATTCCAACTTAGACACTCTTTTAA GTTGTAATTTTCATTATTTTCTTTT TTTAGAGTTTTATGTTGAATTCGCA TAATTTTCAATCGGATAATACAAGA AAAATAATATTTTAGTATAATTTTA TACATGAAATTTCGGGAAGGTAGGA TATACGGATTGTTTGTCGGATCAGA GACTTTACTCGTACCTTTGTAACTG TTGATCCCAAATACAGATAGTGACT CCAGAGTTATATATTATACCTATAG AGACTAATATGATTTAGTGTTATTA AAATTAGTATTACTAATTAATTGTA ATGCCCCATGAATT |
| SEQ ID NO:60 | Vector backbone | tctgtgaagacaaactagaattcga gctcggagtgagacgcagctggca cgacaggtttgccgactggaaagcg ggcagtgagcgcaacgcaattaatg tgagttagctcactcattaggcacc ccaggctttacactttatgcttccg gctcgtatgttgtgtggaattgtga gcggataacaatttcacacaggaaa cagctatgaccatgattacgccaag cttgcatgcctgcaggtcgactcta gaggatccccgggtaccgagctcga attcactggccgtcgttttacaacg tcgtgactgggaaaaccctggcgtt acccaacttaatcgccttgcagcac atccccctttcgccagctggcgtaa tagcgaagaggcccgcaccgatcgc ccttcccaacagttgcgcagccctga atggcgaatggcgcctgatgcggta ttttctccttacgcatctgtgcggt atttcacaccgcatatggtgcactc tcagtacaatctgctctgatgccgc atagttaagccagccccgacacccg ccaacacccgctgacgcgccctgac gggcttgtctgctcccggcatccgc ttacagacaagctgtgacggtctca cgctttacttgtcttctgcacgaag tggtttaaactatcagtgtttgaca ggatatattggcgggtaaacctaag agaaaagagcgtttattagaataat cggatatttaaagggcgtgaaaag gtttatccgttcgtccatttgtatg tgcatgccaaccacagggttcccca gatcaggcgctggctgctgaacccc cagccggaactgaccccacaaggcc ctagcgtttgcaatgcaccaggtca tcattgacccaggcgtgttccacca ggccgctgcctcgcaactcttcgca ggcttcgccgacctgctcgcgccac ttcttcacgcgggtggaatccgatc cgcacatgaggcggaaggtttccag cttgagcgggtacggctcccggtgc gagctgaaatagtcgaacatccgtc gggccgtcggcgacagcttgcggta cttctcccatatgaatttcgtgtag tggtcgccagcaaacagcacgacga tttcctcgtcgatcaggacctggca acgggacgttttcttgccacggtcc aggacgcggaagcggtgcagcagcg acaccgattccaggtgcccaacgcg gtcggacgtgaagcccatcgccgtc gcctgtaggcgcgacaggcattcct cggccttcgtgtaataccggccatt gatcgaccagcccaggtcctggcaa agctcgtagaacgtgaaggtgatcg gctcgccgatagggtgcgcttcgc gtactccaacacctgctgccacacc agttcgtcatcgtcggcccgcagct cgacgccggtgtaggtgatcttcac gtccttgttgacgtggaaaatgacc ttgtttttgcagcgcctcgcgcggga ttttcttgttgcgcgtggtgaacag ggcagagcgggccgtgtcgtttggc atcgctcgcatcgtgtccggccacg gcgcaatatcgaacaaggaaagctg catttcttgatctgctgcttcgtg tgtttcagcaacgcggcctgcttgg cctcgctgacctgttttgccaggtc ctcgccggcggttttttcgcttcttg gtcgtcatagttcctcgcgtgtcga tggtcatcgacttcgccaaacctgc cgcctcctgttcaagacgacgcgaa cgctccacggcggccgatggcgcgg gcagggcaggggagccagttgcac gctgtcgcgctcgatcttggccgta gcttgctggaccatcgagccgacgg actggaaggtttcgcggggcgcacg catgacggtgcggcttgcgatggtt tcggcatcctcggcggaaaacccg cgtcgatcagttcttgcctgtatgc cttccggtcaaacgtccgattcatt caccctccttgcgggattgccccga ctcacgccggggcaatgtgccctta ttcctgatttgacccgcctggtgcc ttggtgtccagataatccaccttat cggcaatgaagtcggtcccgtagac cgtctggccgtccttctcgtacttg gtattccgaattcttgccctgcacga ataccagcgaccccttgcccaaata cttgccgtgggcctcggcctgagag ccaaaacacttgatgcggaagaagt cggtgcgctcctgcttgtcgccggc atcgttgcgccacatctaggatctg ccaggaaccgtaaaaaggccgcgtt gctggcgttttccataggctccgc cccctgacgagcatcacaaaaatc gacgctcaagtcagaggtggcgaaa cccgacaggactataaagataccag gcgtttccccctggaagctccctcg tgcgctctcctgttccgaccctgcc gcttaccggatacctgtccgcctt ctcccttcgggaagcgtggcgcttt ctcatagctcacgctgtaggtatct cagttcggtgtaggtcgttcgctcc aagctgggctgtgtgcacgaacccc ccgttcagcccgaccgctgcgcctt atccggtaactatcgtcttgagtcc aacccggtaagacacgacttatcgc cactggcagcagccactggtaacag gattagcagagcgaggtatgtaggc |

TABLE 1-continued

Examples of certain proteins used in the current disclosure and their sequences.

| | | |
|---|---|---|
| | | ggtgctacagagttcttgaagtggt |
| | | ggcctaactacggctacactagaag |
| | | gacagtatttggtatctgcgctctg |
| | | ctgaagccagttaccttcggaaaaa |
| | | gagttggtagctcttgatccggcaa |
| | | acaaaccaccgctggtagcggtggt |
| | | ttttttgtttgcaagcagcagatta |
| | | cgcgcagaaaaaaggatctcaaga |
| | | agatcctttgatcttttctacgggg |
| | | tctgacgctcagtggaacgaaaact |
| | | cacgttaagggattttggtcatgag |
| | | attatcaaaaaggatcttcacctag |
| | | atccttttaaattaaaaatgaagtt |
| | | ttaaatcaatctaaagtatatatga |
| | | gtaaacttggtctgacagttaccaa |
| | | tgcttaatcagtgaggcacctatct |
| | | cagcgatctgtctatttcgttcatc |
| | | catagttgcctgactccccgtcgtg |
| | | tagataactacgatacgggagggct |
| | | taccatctggccccagtgctgcaat |
| | | gataccgcgagaaccacgctcaccg |
| | | gctccagatttatcagcaataaacc |
| | | agccagccggaagggccgagcgcag |
| | | aagtggtcctgcaactttatccgcc |
| | | tccatccagtctattaattgttgcc |
| | | gggaagctagagtaagtagttcgcc |
| | | agttaatagttgcgcaacgttgtt |
| | | gccattgctacaggcatcgtggtgt |
| | | cacgctcgtcgtttggtatggcttc |
| | | attcagctccggttcccaacgatca |
| | | aggcgagttacatgatccccccatgt |
| | | tgtgcaaaaaagcggttagctcctt |
| | | cggtcctccgatcgttgtcagaagt |
| | | aagttggccgcagtgttatcactca |
| | | tggttatggcagcactgcataattc |
| | | tcttactgtcatgccatccgtaaga |
| | | tgcttttctgtgactggtgagtact |
| | | caaccaagtcattctgagaatagtg |
| | | tatgcggcgaccgagttgctcttgc |
| | | ccggcgtcaatacgggataataccg |
| | | cgccacatagcagaactttaaaagt |
| | | gctcatcattggaaaacgttcttcg |
| | | gggcgaaaactctcaaggatcttac |
| | | cgctgttgagatccagttcgatgta |
| | | acccactcgtgcacccaactgatct |
| | | tcagcatcttttactttcaccagcg |
| | | tttctgggtgagcaaaaacaggaag |
| | | gcaaaatgccgcaaaaaagggaata |
| | | agggcgacacggaaatgttgaatac |
| | | tcatactcttcctttttcaatatta |
| | | ttgaagcatttatcagggttattgt |
| | | ctcatgagcggatacatatttgaat |
| | | gtatttagaaaaataaacaaatagg |
| | | ggttccgcgcacgaattggccagcg |
| | | ctgccatttttggggtgaggccgtt |
| | | cgcggccgaggggcgcagcccctgg |
| | | ggggatgggaggcccgcgttagcgg |
| | | gccgggagggttcgagaagggggg |
| | | cacccccttcggcgtgcgcggtca |
| | | cgcgcacagggcgcagccctggtta |
| | | aaaacaaggtttataaatattggtt |
| | | taaaagcaggttaaaagacaggtta |
| | | gcggtggccgaaaaacgggcggaaa |
| | | cccttgcaaatgctggattttctgc |
| | | ctgtggacagcccctcaaatgtcaa |
| | | taggtgcgccctcatctgtc |
| | | agcactctgcccctcaagtgtcaag |
| | | gatcgcccctcatctgtcagtag |
| | | tcgcgccctcaagtgtcaataccg |
| | | cagggcacttatccccaggcttgtc |
| | | cacatcatctgtgggaaactcgcgt |
| | | aaaatcaggcgttttcgccgatttg |
| | | cgaggctggccagctccacgtcgcc |
| | | ggccgaaatcgagcctgcccctcat |
| | | ctgtcaacgccgcgccgggtgagtc |
| | | ggcccctcaagtgtcaacgtccgcc |
| | | cctcatctgtcagtgagggccaagt |

TABLE 1-continued

Examples of certain proteins used in the current disclosure and their sequences.

| | | |
|---|---|---|
| | | tttccgcgaggtatccacaacgccg |
| | | gcggccgcggtgtctcgcacacggc |
| | | ttcgacggcgtttctggcgcgtttg |
| | | cagggccatagacggccgccagccc |
| | | agcggcgagggcaaccagcccggtg |
| | | agcgtcgcaaaggagatcctgatct |
| | | gactgatgggctgcctgtatcgagt |
| | | ggtgattttgtgccgagctgccgt |
| | | cggggagctgttggctggctggtgg |
| | | caggatatattgtggtgtaaacaaa |
| | | ttgacgcttagacaacttaataaca |
| | | cattgcggacgttttaatgtactg |
| | | gggtggatgcagtgggcccac |
| SEQ ID NO:61 | pUC Origin | gccaggaaccgtaaaaaggccgcgt |
| | | tgctggcgtttttccataggctccg |
| | | cccccctgacgagcatcacaaaaat |
| | | cgacgctcaagtcagaggtggcgaa |
| | | acccgacaggactataaagatacca |
| | | ggcgtttccccctggaagctccctc |
| | | gtgcgctctcctgttccgaccctgc |
| | | cgcttaccggatacctgtccgcctt |
| | | tctcccttcgggaagcgtggcgctt |
| | | tctcatagctcacgctgtaggtatc |
| | | tcagttcggtgtaggtcgttcgctc |
| | | caagctgggctgtgtgcacgaaccc |
| | | cccgttcagcccgaccgctgcgcct |
| | | tatccggtaactatcgtcttgagtc |
| | | caacccggtaagacacgacttatcg |
| | | ccactggcagcagccactggtaaca |
| | | ggattagcagagcgaggtatgtagg |
| | | cggtgctacagagttcttgaagtgg |
| | | tggcctaactacggctacactagaa |
| | | ggacagtatttggtatctgcgctct |
| | | gctgaagccagttaccttcggaaaa |
| | | agagttggtagctcttgatccggca |
| | | aacaaaccaccgctggtagcggtgg |
| | | tttttttgtttgcaagcagcagatt |
| | | acgcgcagaaaaaaggatctcaag |
| | | aagatcctttgatctttctacggg |
| | | gtctgacgctcagtggaacgaaaac |
| | | tcacgttaagggattttggtcatga |
| | | gattatcaaaaaggatcttcaccta |
| | | gatccttttaaattaaaaatgaagt |
| | | tttaaatcaatctaaagtatatatg |
| | | agtaaacttggtctg |
| SEQ ID NO: 62 | oriV | ccgggagggttcgagaaggggggc |
| | | acccccccttcggcgtgcgcggtcac |
| | | gcgcacagggcgcagccctggttaa |
| | | aaacaaggtttataaatattggttt |
| | | aaaagcaggttaaaagacaggttag |
| | | cggtggccgaaaaacgggcggaaac |
| | | ccttgcaaatgctggattttctgcc |
| | | tgtggacagcccctcaaatgtcaat |
| | | aggtgcgcccctcatctgtcagcac |
| | | tctgcccctcaagtgtcaaggatcg |
| | | cgccctcatctgtcagtagtcgcg |
| | | cccctcaagtgtcaataccgcaggg |
| | | cacttatccccaggcttgtccacat |
| | | catctgtgggaaactcgcgtaaaat |
| | | caggcgttttcgccgatttgcgagg |
| | | ctggccagctccacgtcgccggccg |
| | | aaatcgagcctgcccctcatctgtc |
| | | aacgccgcgccgggtgagtcggccc |
| | | ctcaagtgtcaacgtccgcccctca |
| | | tctgtcagtgagggccaagttttcc |
| | | gcgaggtatccacaacgccggcggc |
| | | cgcggtgtctcgcacacggcttcga |
| | | cggcgtttctggcgcgtttgcaggg |
| | | ccatagacggccgccagcccagcgg |
| | | cgagggcaaccagcccgg |
| SEQ ID NO: 63 | lacZ | ccgactggaaagcgggcagtgagcg |
| | | caacgcaattaatgtgagttagctc |
| | | actcattaggcaccccaggctttac |
| | | actttatgcttccggctcgtatgtt |

TABLE 1-continued

Examples of certain proteins used in the current disclosure and their sequences.

| | | |
|---|---|---|
| | | gtgtggaattgtgagcggataacaa |
| | | tttcacacaggaaacagctatgacc |
| | | atgattacgccaagcttgcatgcct |
| | | gcaggtcgactctagaggatcccg |
| | | ggtaccgagctcgaattcactggcc |
| | | gtcgttttacaacgtcgtgactggg |
| | | aaaaccctggcgttacccaacttaa |
| | | tcgccttgcagcacatcccccttc |
| | | gccagctggcgtaatagcgaagagg |
| | | cccgcaccgatcgcccttcccaaca |
| | | gttgcgcagcctgaatggcgaatgg |
| | | cgcctgatgcggtattttctcctta |
| | | cgcatctgtgcggtatttcacaccg |
| | | catatggtgcactctcagtacaatc |
| | | tgctctgatgccgcatagttaagcc |
| | | agccccgacacccgccaacacccgc |
| | | tgacgcgccctgacgggcttgtctg |
| | | ctcccggcatcc |
| SEQ ID NO: 64 | RB | aaactatcagtgtttgacaggatat |
| | | attggcgggtaaacctaagagaaaa |
| | | gagcgtttattagaataatcggata |
| | | tttaaaagggcgtgaaaaggtttat |
| | | ccgttcgtccatttgtatgtgcatg |
| | | cca |
| SEQ ID NO: 65 | HDEL | CACGACGAATTGTAA |
| SEQ ID NO: 66 | HsFam20C | CTAGATTTACTCCCCGACTGGAGC |
| | | GACGTGGAGCGCGTCCGTCTGGCGA |
| | | ACCAGGATGTTCTTGTGCGCAACCA |
| | | GCTGCGGAAGTCGCTGCGCCAGGTT |
| | | GGGCACAAGTTCGAGGGAGGCCTGG |
| | | GGAGCCACCAGCTGCTAGCTCCGCT |
| | | GCGGGCGATGCCGGATGGCCAAATA |
| | | AACACACTCTAAGAATACTACAGGA |
| | | CTTCTCAAGCGACCCTTCCTCTAAT |
| | | CTCTCATCACACTCACTTGAGAAGT |
| | | TACCTCCCGCAGCCGAGCCGGCCGA |
| | | GCGAGCGCTTAGGGGGCGTGACCCC |
| | | GGGGCATTACGACCTCACGATCCTG |
| | | CACACAGGCCTTTGTTACGTGATCC |
| | | AGGGCCGCGAAGAAGCGAATCCCTT |
| | | CCTGGACCCGGAGGCGACGCATCCC |
| | | TTCTGGCGAGGTTATTTGAACACCC |
| | | ATTGTACAGAGTCGCCGTGCCTCCC |
| | | CTGACTGAAGAGGACGTCTTGTTCA |
| | | ACGTTAACTCTGACACCAGACTTAG |
| | | TCCTAAAGCGGCCGAGAATCCTGAT |
| | | TGGCCGCATGCCGGGGCAGAGGGCG |
| | | CTGAGTTCCTTAGCCCAGGAGAGGC |
| | | CGCGGTGGACTCCTATCCGAACTGG |
| | | TTGAAATTCCATATTGGAATAAATC |
| | | GATACGAACTATATTCTCGACACAA |
| | | TCCGGCCATCGAGGCCCTATTACAT |
| | | GATCTGTCCTCACAACGTATTACGT |
| | | CAGTGGCCATGAAGAGCGGCGGCAC |
| | | GCAACTAAAGCTGATTATGACATTT |
| | | CAAAACTATGGTCAAGCCCTGTTTA |
| | | AGCCAATGAAGCAGACAAGAGAACA |
| | | GGAGACGCCTCCCGACTTCTTCTAC |
| | | TTTAGTGATTATGAACGACATAATG |
| | | CTGAAATAGCGGCCTTTCACCTAGA |
| | | CAGGATCTTAGACTTCCGTAGGGTT |
| | | CCCCCAGTTGCAGGTAGGATGGTTA |
| | | ACATGACTAAAGAGATAAGGGATGT |
| | | AACCAGGGATAAGAAGCTATGGAGG |
| | | ACGTTCTTTATTTCTCCTGCGAACA |
| | | ATATCTGTTTTTACGGCGAGTGCTC |
| | | CTACTATTGCAGCACAGAACATGCA |
| | | CTATGTGGAAAGCCTGACCAGATTG |
| | | AAGGTTCCCTGGCGGCCTTTCTTCC |
| | | AGACCTCTCTCTTGCGAAACGTAAA |
| | | ACTTGGCGTAATCCATGGAGACGAA |
| | | GCTATCACAAACGTAAGAAAGCGGA |

TABLE 1-continued

Examples of certain proteins used in the current disclosure and their sequences.

| | | |
|---|---|---|
| | | GTGGGAGGTAGACCCCGATTACTGC |
| | | GAGGAGGTTAAGCAAACCCCGCCGT |
| | | ATGACTCTAGCCACCGAATATTAGA |
| | | CGTTATGGATATGACGATCTTTGAT |
| | | TTTCTTATGGGCAACATGGATCGTC |
| | | ACCACTACGAAACGTTCGAGAAGTT |
| | | TGGAAATGAGACGTTTATTATCCAT |
| | | CTGGACAACGGCAGAGGCTTTGGGA |
| | | AATATAGTCATGACGAATTATCCAT |
| | | TCTTGTTCCTTTACGACAATGCTGC |
| | | AGAATCAGGAAATCAACGTATTTAC |
| | | GTCTCCAACTCCTGGCAAAAGAGGA |
| | | ATATAAGCTTAGCCTCCTAATGGCT |
| | | GAGTCTCTGAGGGGCGACCAAGTTG |
| | | CGCCTGTTCTGTATCAACCACATTT |
| | | AGAAGCACTTGATAGACGTTTGCGT |
| | | GTTGTACTTAAAGCTGTCCGAGACT |
| | | GTGTCGAGAGAAATGGCCTTCATTC |
| | | AGTTGTGGACGACGATCTAGATACC |
| | | GAACATAGGGCAGCGTCCGCACGT |
| SEQ ID NO: 67 | HsFam20A | CAACTCAGGCCAAGGGAACGTCCCC |
| | | GTGGGTGCCCGTGTACCGGAAGGGC |
| | | ATCTAGTTTGGCGCGAGATTCTGCT |
| | | GCTGCGGCGTCAGACCCAGGGACAA |
| | | TTGTGCATAATTTTTCCCGTACTGA |
| | | GCCAAGAACAGAGCCGGCCGGTGGG |
| | | AGCCATAGCGGAAGTTCATCTAAGT |
| | | TGCAAGCACTATTCGCGCATCCTTT |
| | | GTATAATGTACCTGAAGAACCTCCT |
| | | CTTTTAGGAGCGGAGGACTCACTCT |
| | | TAGCCAGCCAGGAAGCCCTTAGATA |
| | | CTACCGTAGAAAGGTTGCCCGATGG |
| | | AACCGTAGGCATAAAATGTACCGTG |
| | | AGCAAATGAATTTAACTAGTCTTGA |
| | | TCCTCCTCTCCAACTGAGGCTTGAG |
| | | GCTAGTTGGGTTCAGTTCCATTTGG |
| | | GTATCAATCGACACGGCCTTTACTC |
| | | TAGGTCAAGTCCTGTGGTATCTAAA |
| | | CTTCTTCAAGACATGCGTCATTTTC |
| | | CGACAATATCTGCCGATTACTCCCA |
| | | GGATGAGAAGGCTTTGCTTGGAGCA |
| | | TGTGACTGTACCCAGATAGTAAAAC |
| | | CTAGTGGCGTCCACTTAAAACTGGT |
| | | CCTCCGTTTTAGCGATTTTGGGAAA |
| | | GCTATGTTTAAACCCATGCGACAAC |
| | | AACGTGATGAAGAAACGCCAGTTGA |
| | | TTTCTTCTACTTCATTGACTTCCAG |
| | | CGTCACAACGCGGAGATAGCAGCAT |
| | | TCCACTTAGACAGAATTCTAGACTT |
| | | TCGTCGAGTCCCCCCTACCGTTGGC |
| | | CGTATAGTGAATGTAACTAAAGAGA |
| | | TTTTGGAGGTGACAAAAAACGAGAT |
| | | CTTACAAAGCGTCTTTTTTGTATCC |
| | | CCGGCCTCCAACGTCTGTTTTTTTG |
| | | CGAAATGTCCCTATATGTGCAAAAC |
| | | TGAAATATGCGGTCTGCGGCAACCCC |
| | | CATTTACTCGAAGGTAGTCTCAGTG |
| | | CATTTCTCCCCAGTCTCAACTTAGC |
| | | TCCACGTCTAAGCGTGCCAAACCCT |
| | | TGGATTAGGAGCTATACGCTAGCGG |
| | | GCAAGGAGGAGTGGGAGGTGAACCC |
| | | ACTTTATTGTGACACAGTCAAGCAA |
| | | ATCTTCCTTATAATAACTCACAGA |
| | | GACTACTCAATGTCATTGATATGGC |
| | | TATCTTCGATTTCCTGATAGGAAAC |
| | | ATGGATAGGCACCATTATGAGATGT |
| | | TCACCAAGTTCGGGGACGATGGTTT |
| | | TCTGATACATCTAGACAACGCGCGT |
| | | GGCTTCGGGCGACACTCCCACGACG |
| | | AAATCTCCATTCTTAGCCCCCTGAG |
| | | CCAGTGTTGCATGATCAAAAAGAAA |
| | | ACACTTCTGCATCTTCAGCTCCTCG |
| | | CTCAAGCTGACTATCGACTTTCCGA |
| | | CGTGATGCGAGAATCACTGCTTGAA |
| | | GATCAGCTCAGCCCAGTGCTTACTG |
| | | AACCGCACCTACTGGCACTAGATCG |

TABLE 1-continued

Examples of certain proteins used in the current disclosure and their sequences.

| | | |
|---|---|---|
| | | TAGATTACAGACGATCTTGAGGACA |
| | | GTCGAGGGGTGCATCGTTGCTCACG |
| | | GCCAACAAAGCGTCATAGTTGATGG |
| | | GCCTGTGGAACAGCTAGCTCCGGAT |
| | | TCCGGACAAGCAAATTTAACCAGC |
| SEQ ID NO: 68 | BtFam20C | CTCCTACCCAAATTAGAACGATCTG CTGCACGTCCGAGCGGCGAACCTGG CTGTAGCTGCGCACAGCCAGCTGCC GAAGCTGCCGCGCCTGGATGGGCTC AAGCTAGGGGTCATCCCGGTGGAGA ACTTGAAGCGGCCGCTAGCGCCGCC GGGGATGCAGGCTGGCCAAATAAGC ACACTCTGAGGATTCTGCAAGACTT CAGTTCCGACCCCAGTTCCAACCTA ACGAGCCACTCACTGGAAAAGCTGC CTCCGGCTGCCGAAGCTGCGGAAGG TGCACCGCCAGGCCAAGATCCAGGA GTTCGTAGACCTCCCGACCCAGCGC ATAG GCCACTCCCGCGAGATCCGGGTCCT AGAGGCCCTGTCTTGCCCCCAGGTC TTAGCGGAGACGGGTCCTTACTTAC GCGTCTTTTCCAACACCCGCTATAC CAGGTGCCCATACCGCCCCTAACAG AAGGCGATGTTCTCTTTAATGTCAA TAGCGATATAAGATTCAACCCCAAA GCTGCAACCGCCGAGAACCCAGATT GGCCACACGAGGGGCCGGAAGATGA GTTTTTACCTACTGGTGAAGCGGCA GTTGACTCTTACCCGAATTGGCTGA AGTTTCATATTGGGATCAATAGATA CGAGCTTTACAGCCGACATAATCCG GCCGTGGGAGCGCTCTTACAAGACC TCGGGACGCAAAAGATTACTTCTGT CGCTATGAAATCTGGCGGGACACAG CTCAAACTTATTATGACTTTCCAGA ATTATGGCCAAGCTCTGTTCAAGCC GATGAAGCAGACTAGAGAGCAGGAG ACACCCCCTGACTTCTTCTACTTCA GCGACTATGAAAGGCATAATGCAGA AATTGCGGCATTCCACCTTGATAGG ATCTTAGACTTCCGAAGGGTACCAC CGGTAGCAGGTAGACTAGTCAATAT GACTAAAGAGATTAGAGATGTCACT CGTGACAAGAAACTATGGCGTACAT TCTTTATAAGCCCTGCTAACAATGT ATGCTTTTATGGCGAATGTTCTTAC TATTGCTCTACAGAACATGCACTGT GTGGAAAACCCGACCAGATTGAGGG GTCACTAGCCGCATTTCTGCCAGAC TTGGCATTGGCCAAGCGTAAGACGT GGCGTAATCCGTGGCGACTAGTTA CCACAAGAGAAGAAGGCGGAGTGG GAAGTAGACCCAGACTACTGCGAGG AGGTTAGACAAACACCTCCATATGA TTCTAGTCATAGACTGTTGGATGTT ATGGACATGACAATTTTTGATTTTC TCATGGGAACATGGATCGTCACCA CTACGAAACCTTTGAGAAATTCGGC AATGAGACATTCATTATCCACTTAG ATAATGGTCGAGGTTTTGGCAAACA CAGCCATGACGAACTATCTATATTA GTGCCTTTACAACAGTGCTGTAGAA TCCGAAGGTCTACCTATTTGAGACT TCAACTGTTGGCCCAAGAGGAGCAT CGTCTATCACTTTTAATGGCCGAGG CTCTAAGGGCTGATCGTGTGGCTCC CGTACTCTTTCAGCCTCACTTAGAG GCTTTAGATCGTCGACTTCGTATAG TGCTTCGAGCGGTAGGCGATTGCGT GGAGAAAGATGGACTGCACAGTGTT GTAGAGGATGATTTGGGGCCTGAGC ACAGGGCGGCCGCGGGACGT |
| SEQ ID | BtFam20A | CACCTTGGTCCCAGGGTACGATCCA GACTGCAACCGAGGGAACGACCGTT |

TABLE 1-continued

Examples of certain proteins used in the current disclosure and their sequences.

| | | |
|---|---|---|
| NO: 69 | | GGGGTGCCCTTGTGCGCGTCGTGCC GCTAGTCCTGCTCCGGGACCTGCCC CGAGTGCGCCCAGGCGTGTGGAACC AAGCGGCGGTGGCGATCCAGGGTCC AAACTCAGGGCACTTTTCGCACACC CATTGTATAACGAACCAGAGGAACC TCCGCTGCTTGGGCCCGAGGATAGC CTGCTGGCGGGTCCCGAAGCATTAC GTTATTACCGAAGAAAAGTAGCAAG GTGGAATAGACGTCGAAAGATGTAC AAAGAACAATTAAACCTAACCAGCC CAGAACCGCCGGTGCAATTGAGACA AGAGGCATCATGGGTACAATTTCAC TTGGGGATCAATAGGCATGGGCTGT ATCCTCGTAGCTCTCCGGTGGTTTC TAAACTCCTTCAGGATATGAGACAC TTCCCTACGATCAGCGCGGATTATA GCCAGGACGAAAAGGCTCTTCTTGG CGCATGTGACTGTTCTCAAATTGTT AAGCCCTCCGGCGTTCATCTGAAGC TCGTACTTCGTTTTTCTGATTTTGG GAAGGCGATGTTTAAACCCATGAGA CAGCAGAGGGACGAGGAGACGCCGG AGGACTTCTTCTATTTCATCGACTT CCAGAGACATAATGCCGAAATTGCT GCCTTCCATCTAGATCGTATTTTGG ACTTTAGACGTGTCCCGCCAACAGT AGGGAGGCTCGTAAATGTGACAAGG GAAATACTAGAAGTCACTCGTAATG AGATTTTACAAAGCGTGTTTTTCGT GAGTCCGGCAAACAATGTGTGCTTC TTTGCGAAATGCCCTTATATGTGCA AGACGGAGTATGCTGTTTGCGGGTC ACCCCACCTACTAGAAGGTTCTTTA AGTGCCTTCCTTCCCAGCCTCAACC TCGCTTCCACGTTTCAGTATGCCTAG TCCATGGATCAGGTCATATTCCCTA GCTGGTCGTGAAGAGTGGGAGGTAA ACCCGCTATACTGCGAAGCGGTGAA ACAGGCTTACCCCACAATAGCAGT TCACGTCTATTAAATATTATCGATA TGGCGATCTTCGACTTTCTAATAGG GAACATGGACAGGCACCACTACGAA ATGTTCACTAAGTTCGGTGAGGACG GGTTCCTAATACATTTGGATAATGC CCGTGGTTTTGGGAGACATTCACAC GATGAAGTCTCTATTTTAGCCCCTT TATTCCAATGTTGTAGGATAAAAAG AAAAACCCTGCTGCATCTTCAACTC CTGGCTCAGGCTGATTACCGTCTTT CAGACGTTATGCGTGAGTCTTTGCT AGAGGACCAATTGAGTCCTGTACTA ACAGAACCACATCTGCTAGCTTTGG ACAGACGTTTGCAGACTGTGCTAAG AACGGTCCAGGATTGCATCGAGGCC CATGGGAACAATCAGTGGTAGCCG ACGGCCCGGTGGGCCAATGGGCTCC CGACAGTAGTAGAGCGAACGCAACT TCT |
| SEQ ID NO: 70 | AtuMAS | ATTTTTCAAATCAGTGCGCAAGACG TGACGTAAGTATCCGAGTCAGTTTT TATTTTCTACTAATTTGGTCGTTT ATTTCGGCGTGTAGGA CATGGCAACCGGGCCTGAATTTCGC GGGTATTCTGTTTCTATTCCAACTT TTTCTTGATCCGCAGCCATTAACGA CTTTTGAATAGATACGCTGACACGC CAAGCCTCGCTAGTCAAAAGTGTAC CAAACAACGCTTTACAGCAAGAACG GAATGCGCGTGACGCTCGCGGTGAC GCCATTTCGCCTTTTCAGAAATGGA TAAATAGCCTTGCTTCCTATTATAT CTTCCCAAATTACCAATACATTACA CTAGCATCTGAATTTCATAACCAAT CTCGATACACCCAAATCG |

TABLE 1-continued

Examples of certain proteins used in the current disclosure and their sequences.

| SEQ ID NO: | Name | Sequence |
|---|---|---|
| SEQ ID NO: 71 | ARA12 Signal Peptide | ATGAGTTCTAGCTTTTTATCATCCACTGCGTTCTTCCTGCTCCTTTGCTTAGGCTTCTGCCATGTGTCATCT |
| SEQ ID NO: 72 | A12S2 Signal Peptide | ATGGCAAACAAGCTCTTCCTCGTCTGCGCAACTTTCGCCCTCTGCTTCCTCCTCACCAACGCT |
| SEQ ID NO: 73 | HA Tag, 6His Tag, HDEL | TCGTACCCCTACGACGTTCCTGACTACGCCCATCATCACCATCACCACATGATGAGTTGTAG |
| SEQ ID NO: 74 | Octopine (OCS) Terminator | GTCCTGCTTTAATGAGATATGCGAGAAGCCTATGATCGCATGATATTTGCTTTCAATTCTGTTGTGCACGTTGTAAAAAACCTGAGCATGTGTAGCTCAGATCCTTACCGCCGGTTTCGGTTCATTCTAATGAATATATCACCCGTTACTATCGTATTTTTATGAATAATATTCTCCGTTCAATTTACTGATTGTACCCTACTACTTATATGTACAATATTAAAATGAAACAATATATTGTGCTGAATAGGTTTATAGCGACATCTATGATAGAGCGCCACAATAACAAACAATTGCGTTTTATTATTACAAATCCAATTTTAAAAAAAGCGGCAGAACCGGTCAAACCTAAAAGACTGATTACATAAATCTTATTCAAATTTCAAAAGTGCCCCAGGGGCTAGTATCTACGACACACCGAGCGGCGAACTAATAACGCTCACTGAAGGGAACTCCGGTTCCCCGCCGGCGCGCATGGGTGAGATTCCTTGAAGTTGAGTATTGGCCGTCCGCTCTACCGAAAGTTACGGGCACCATTCAACCCGGTCCAGCACGGCGGCCGGGTAACCGACTTGCTGCCCCGTGCAGGTCAAACCTTGACAGTGACGACAAATCGTTGGGCGGGTCCAGGGCGAATTTTGCGACAACATGTCGAGGCTCAGCAGGAC |
| SEQ ID NO: 75 | mScarlet Coding Sequence | ATGGGTGGTGGAGGAAGTGGAGGTGGAGGAAGTGTCAGTAAAGGAGAAGCTGTCATAAAGGAGTTCATGAGGTTTAAGGTACACATGGAAGGGTCAATGAACGGGCATGAATTTGAGATCGAGGGGGAGGGAGAAGGAAGGCCTTATGAGGGCACTCAAACTGCTAAGTTGAAGGTCACTAAGGGGGGGCCTCTTCCTTTTTCTTGGGACATACTCAGCCCTCAGTTCATGTATGGCTCAAGGGCCTTTACAAAACACCCTGCCGATATCCCCGATTACTATAAGCAGAGCTTTCCCGAAGGCTTCAAGTGGGAGAGGGTTATGAATTTTGAAGATGGCGGTGCTGTTACAGTCACACAGGACACAAGTCTTGAGGATGGGACCCTGATTTATAAAGTTAAGCTCAGGGGGACAAATTTCCCACCAGATGGACCAGTCATGCAGAAGAAAACTATGGGATGGGAAGCCTCTACCGAGCGTCTTTATCCCGAAGATGGCGTTCTTAAAGGCGATATTAAGATGGCTTTGAGGCTCAAAGATGGCGGTCGTTACCTGGCCGATTTCAAAACCACTTACAAGCCAAAAAACCAGTACAGATGCCAGGCGCTTACAACGTTGATCGTAAGCTGGACATCACTTCCCACAACGAGGATTACACAGTTGTTGAACAGTATGAGAGATCAGAGGGTAGACATAGTACCGGCGGAATGGATGAGCTGTACAAAGTTCG |
| SEQ ID NO: 76 | NOS Terminator | GTCAAGCAGATCGTTCAAACATTTGGCAATAAAGTTTCTTAAGATTGAATCCTGTTGCCGGTCTTGCGATGATTATCTATATAATTTCTGTTGAATTACGTTAAGCATGTAATAATTAACATGTAATGCATGACGTTATTTATGAGATGGGTTTTTATGATTAGAGTCCCGCAATTATACATTTAATACGCGATAGAAAACAAAATATAGCGCGCAAACTAGGATAATTATCGCGCGCGGTGTCATCTATGTTACTAGATCGA |
| SEQ ID NO: 77 | β-casein codon optimized for N. benthamiana | AGAGAACTTGAAGAATTGAATGTTCCAGGAGAGATTGTTGAAAGTCTCTCCTCTTCTGAGGAAAGCATCACAAGAATCAACAAGAAAATTGAGAAGTTTCAGAGTGAAGAGCAACAACAGACTGAAGATGAATTACAAGATAAGATTCATCCTTTTGCTCAAACACAGTCACTTGTGTATCCATTCCCTGGACCAATTCCAAATTCTTTACCACAAAACATTCCTCCTCTGACTCAAACTCCTGTCGTTGTTCCTCCGTTCTTGCAACCAGAAGTTATGGGAGTTTCAAAGGTTAAAGAAGCAATGGCTCCAAAGCATAAGAGATGCCATTCCCAAAATACCCTGTGGAGCCTTTCACAGAATCTCAAAGCTTGACTCTCACTGATGTTGAGAATCTTCATTTGCCTCTTCCATTGCTTCAATCATGGATGCATCAACCTCATCAGCCTTTGCCACCAACAGTGATGTTTCCACCTCAATCTGTTCTCTCTCTTCTCAGTCTAAAGTTCTTCCGGTTCCGCAGAAAGCTGTGCCTTATCCTCAGAGAGATATGCCTATTCAAGCTTTTCTTCTCTACCAAGAACCAGTTTTGGGTCCTGTTCGTGGTCCATTTCCCATCATAGTT |
| SEQ ID NO: 78 | K-casein codon optimized for N. benthamiana | CAGGAGCAAAACCAAGAGCAACCTATTCGTTGTGAAAAAGACGACGTTTTAAGTCGATATCCGAGCTACGGTCTTAATTACTATCAACAGAAGCCAGTTGCCTTGATAAACAACCAGTTTCTCCCATATCCCTACTATGCTAAGCCGGCCGCCGTCCGTTCTCCTGCTCAGATATTGCAGTGGCAGGTTTTATCCAACACTGTCCCGGCGAAGTCTTGCCAGGCGCAACCCACCACCATGCCTAGAACACCCGCATCCGCACCTTTCCTTTATGGCTATTCCTCCCAAAAAGAACCAAGACAAGACAGAGATCCCGACCATAAATACTATCGCTTCTGGTGAGCCAACTTCAACACCGACTATTGAAGCGGTGGAGAGCACGGTCGCCACACTTGAAGCATCCCCAGAGGTGACTGAATCACCCCCGGAGATAAACACGGTACAGGTCACCTCAACGGCTGTT |
| SEQ ID NO: 79 | αS1-casein codon optimized for N. benthamiana | CAGGAGCAAAACCAAGAGCAACCTATTCGTTGTGAAAAAGACGACGTTTTAAGTCGATATCCGAGCTACGGTCTTAATTACTATCAACAGAAGCCAGTTGCCTTGATAAACAACCAGTTTCTCCCATATCCCTACTATGCTAAGCCGGCCGCCGTCCGTTCTCCTGCTCAGATATTGCAGTGGCAGGTTTTATCCAACACTGTCCCGGCGAAGTCTTGCCAGGCGCAACCCACCACCATGCCTAGAACACCCGCATCCGCACCTTTCCTTTATGGCTATTCCTCCCAAAAAGAACCAAGACAAGACAGAGATCCCGACCATAAATACTATCGCTTCTGGTGAGCCAACTTCAACACCGACTATTGAAGCGGTGGAGAGCACGGTCGCCACACTTGAAGCATCCCCAGAGGTGACTGAATCACCCCCGGAGATAAACACGGTACAGGTCACCTCAACGGCTGTT |
| SEQ ID NO: 80 | Protein produced by pMOZ701 | MANKLFLVCATFALCFLLTNARPKHPIKHQGLPQEVLNENLLRFFVAPFPEVFGKEKVNELSKDIGSESTEDQAM |

TABLE 1-continued

Examples of certain proteins used in the current disclosure and their sequences.

| | | |
|---|---|---|
| | (aS1-HA-6His-HDEL) | EDIKQMEAESISSSEEIVPNSVEQK HIQKEDVPSERYLGYLEQLLRLKKY KVPQLEIVPNSAEERLHSMKEGIHA QQKEPMIGVNQELAYFYPELFRQFY QLDAYPSGAWYYVPLGTQYTDAPSF SDIPNPIGSENSEKTTMPLWSSYPY DVPDYAHHHHHHDEL |
| SEQ ID NO: 81 | Protein produced by pMOZ702 (β-HA-6His-HDEL) | MANKLFLVCATFALCFLLTNARELE ELNVPGEIVESLSSSEESITRINKK IEKFQSEEQQQTEDELQDKIHPFAQ TQSLVYPFPGPIPNSLPQNIPPLTQ TPVVVPPFLQPEVMGVSKVKEAMAP KHKEMPFPKYPVEPFTESQSLTLTD VENLHLPLPLLQSWMHQPHQPLPPT VMFPPQSVLSLSQSKVLPVPQKAVP YPQRDMPIQAFLLYQEPVLGPVRGP FPIIVSYPYDVPDYAHHHHHHDEL |
| SEQ ID NO: 82 | Protein produced by pMOZ700 (K-HA-6His-HDEL) | MANKLFLVCATFALCFLLTNAQEQN QEQPIRCERDERFFSDKJAKYIPIQ YVLSRYPSYGLNYYQQKPVALINNQ FLPYPYYAKPAAVRSPAQILQWQVL SNTVPAKSCQAQPTTMARHPHPHLS FMAIPPKKNQDKTEIPTINTIASGE PTSTPTIEAVESTVATLEASPEVTE SPPEINTVQVTSTAVSYPYDVPDYA HHHHHHDEL |
| SEQ ID NO: 83 | Cow Fam20C | MLLPKLERSAARPSGEPGCSCAQPA AEAAAPGWAQARGHPGGELEAAASA AGDAGWPNKHTLRILQDFSSDPSSN LTSHSLEKLPPAAEAAEGAPPGQDP GVRRPPDPAHRPLPRDPGPRGPVLP PGLSGDGSLLTRLFQHPLYQVPIPP LTEGDVLFNVNSDIRFNPKAATAEN PDWPHEGPEDEFLPTGEAAVDSYPN WLKFHIGINRYELYSRHNPAVGALL QDLGTQKITSVAMKSGGTQLKLIMT FQNYGQALFKPMKQTREQETPPDFF YFSDYERHNAEIAAFHLDRILDFRR VPPVAGRLVNMTKEIRDVTRDKKLW RTFFISPANNVCFYGECSYYCSTEH ALCGKPDQIEGSLAAFLPDLALAKR KTWRNPWRRSYHKRKKAEWEVDPDY CEEVRQTPPYDSSHRLLDVMDMTIF DPLMGNMDRHHYETFEKFGNETFII HLDNGRGFGKHSHDELSILVPLQQC CRIRRSTYLRLQLLAQEEHRLSLLM AEALRADRVAPVLFQPHLEALDRRL RIVLRAVGDCVEKDGLHSVVEDDLG PEHRAAAGR |
| SEQ ID NO: 84 | Cow Fam20A | MHVSSHLGPRVRSRLQPRERPLGCP CARRAASPAPGPAPSAPRRVEPSGG GDPGSKLRALFAHPLYNEPEEPPLL GPEDSLLAGPEALRYYRRKVARWNR RRKMYKEQLNLTSPEPPVQLRQEAS WVQFHLGINRHGLYPRSSPVVSKLL QDMRHFPTISADYSQDEKALLGACD CSQIVKPSGVHLKLVLRFSDFGKAM FKPMRQQRDEETPEDFFYFIDFQRH NAEIAAFHLDRILDFRRVPPTVGRL VNVTREILEVTRNEILQSVFFVSPA NNVCFFAKCPYMCKTEYAVCGSPHL LEGSLSAFLPSLNLAPRFSMPSPWI RSYSLAGREEWEVNPLYCEAVKQAY PHNSSSRLLNIIDMAIFDFLIGNMD RHHYEMFTKFGEDGFLIHLDNARGF GRHSHDEVSILAPLFQCCRIKRKTL LHLQLLAQADYRLSDVMRESLLEDQ LSPVLTEPHLLALDRRLOTVLRTVO DCIEAHGEQSVVADGPVGQWAPDSS RANATS |

In some aspects, the current disclosure also provides methods for expressing a phosphorylated payload protein in a plant, comprising transforming the plant with a vector as described herein, and growing the transformed plant, wherein the payload protein is phosphorylated by the first or second kinase. In some instances, phosphorylation using the methods described herein leads to a higher yield or improved quality of food protein production in plants, compared to using an alternative method that does not use vectors described herein.

In some aspects, the current disclosure also provides methods of expressing a phosphorylated payload protein in a plant, comprising transforming the plant with a first vector, a second vector, and a third vector; and growing the transformed plant, wherein the payload protein is phosphorylated by the kinase; wherein the first vector comprises a first polynucleotide sequence encoding a first kinase, the second vector comprises a second polynucleotide sequence encoding a second kinase, and the third vector comprises a third polynucleotide sequence encoding the payload protein.

In some aspects, the current disclosure also provides food products and food product substitutes comprising the phosphorylated payload protein made using the method describe above. Contemplated food products include dairy products or products that resembles a dairy product (i.e., dairy product substitutes). The term "dairy product" as used herein refers to milk (e.g., whole milk (at least 3.25% milk fat), partly skimmed milk (from 1% to 2% milk fat), skim milk (less than 0.2% milk fat), cooking milk, condensed milk, flavored milk, goat milk, sheep milk, dried milk, evaporated milk, milk foam), and products derived from milk, including but not limited to yogurt (e.g., whole milk yogurt (at least 6 grams of fat per 170 g), low-fat yogurt (between 2 and 5 grams of fat per 170 g), nonfat yogurt (0.5 grams or less of fat per 170 g), greek yogurt (strained yogurt with whey removed), whipped yogurt, goat milk yogurt, Labneh (labne), sheep milk yogurt, yogurt drinks (e.g., whole milk Kefir, low-fat milk Kefir), Lassi), cheese (e.g., whey cheese such as ricotta; pasta filata cheese such as mozzarella; semi-soft cheese such as Havarti and Muenster; medium-hard cheese such as Swiss and Jarlsberg; hard cheese such as Cheddar and Parmesan; washed curd cheese such as Colby and Monterey Jack; soft ripened cheese such as Brie and Camembert; fresh cheese such as cottage cheese, feta cheese, cream cheese, and curd; processed cheese; processed cheese food; processed cheese product; processed cheese spread; enzyme-modulated cheese; cold-pack cheese), dairy-based sauces (e.g., fresh, frozen, refrigerated, or shelf stable), dairy spreads (e.g., low-fat spread, low-fat butter), cream (e.g., dry cream, heavy cream, light cream, whipping cream, half-and-half, coffee whitener, coffee creamer, sour cream, creme fraiche), frozen confections (e.g., ice cream, smoothie, milk shake, frozen yogurt, sundae, gelato, custard), dairy desserts (e.g., fresh, refrigerated, or frozen), butter (e.g., whipped butter, cultured butter), dairy powders (e.g., whole milk powder, skim milk powder, fat-filled milk powder (i.e., milk powder comprising plant fat in place of all or some animal fat), infant formula, milk protein concentrate (i.e., protein content of at least 80% by weight), milk protein isolate (i.e., protein content of at least 90% by weight), whey protein concentrate, whey protein isolate, demineralized whey protein concentrate, demineralized whey protein concentrate, .beta.-lactoglobulin concentrate, .beta.-lactoglobulin isolate, .alpha.-lactalbumin concentrate, .alpha.-lactalbumin isolate, glycomacropeptide concentrate, glycomacropeptide isolate, casein concentrate, casein isolate, nutritional supplements, texturizing blends, flavoring blends, coloring blends), ready-to-drink or ready-to-mix products (e.g., fresh, refrigerated, or shelf stable dairy protein beverages, weight loss beverages, nutritional beverages, sports recovery beverages, and energy drinks), puddings, gels, chewables, crisps, and bars. As used herein, the term "food product substitute" (e.g., "dairy product substitute") refers to a food product that resembles a conventional food product (e.g., can be used in place of the conventional food product). Such resemblance can be due to any physical, chemical, or functional attribute. In some embodiments, the resemblance of the food product provided herein to a conventional food product is due to a physical attribute. Non-limiting examples of physical attributes include color, shape, mechanical characteristics (e.g., hardness, G' storage modulus value, shape retention, cohesion, texture (i.e., mechanical characteristics that are correlated with sensory perceptions (e.g., mouthfeel, fattiness, creaminess, homogenization, richness, smoothness, thickness), viscosity, and crystallinity. In some embodiments, the resemblance of the food product provided herein and a conventional food product is due to a chemical/biological attribute. Non-limiting examples of chemical attributes include nutrient content (e.g., type and/or amount of amino acids (e.g., PDCAAS score), type and/or amount of lipids, type and/or amount of carbohydrates, type and/or amount of minerals, type and/or amount of vitamins), pH, digestibility, shelf-life, hunger and/or satiety regulation, taste, and aroma. In some embodiments, the resemblance of the food product provided herein to a conventional food product is due to a functional attribute. Non-limiting examples of functional attributes include gelling/agglutination behavior (e.g., gelling capacity (i.e., time required to form a gel (i.e., a protein network with spaces filled with solvent linked by hydrogen bonds to the protein molecules) of maximal strength in response to a physical and/or chemical condition (e.g., agitation, temperature, pH, ionic strength, protein concentration, sugar concentration, ionic strength)), agglutination capacity (i.e., capacity to form a precipitate (i.e., a tight protein network based on strong interactions between protein molecules and exclusion of solvent) in response to a physical and/or chemical condition), gel strength (i.e., strength of gel formed, measured in force/unit area (e.g., pascal (Pa))), water holding capacity upon gelling, syneresis upon gelling (i.e., water weeping over time)), foaming behavior (e.g., foaming capacity (i.e., amount of air held in response to a physical and/or chemical condition), foam stability (i.e., half-life of foam formed in response to a physical and/or chemical condition), foam seep), thickening capacity, use versatility (i.e., ability to use the food product in a variety of manners and/or to derive a diversity of other compositions from the food product; e.g., ability to produce food products that resemble milk derivative products such as yoghurt, cheese, cream, and butter), and ability to form protein dimers.

In some aspects, the current disclosure also provides plants transformed with a vector as described herein, wherein the payload protein is phosphorylated by the first or the second kinase in vivo in the plant. Contemplated plants can be a dicot plant, for example, *Arabidopsis*, tobacco, tomato, potato, sweet potato, cassava, alfalfa, lima bean, pea, chick pea, soybean, carrot, strawberry, lettuce, oak, maple, walnut, rose, mint, squash, daisy, quinoa, buckwheat, mung bean, cow pea, lentil, lupin, peanut, fava bean, French beans, mustard, and cactus. Contemplated plants can also be a monocot plant, for example, turf grass, corn, rice, oat, wheat, barley, sorghum, orchid, iris, lily, onion, palm, and duckweed.

Described herein, in some aspects, are vectors for expressing a phosphorylated casein protein in a plant. For example, a vector can comprise polynucleotide sequences encoding a kinase, κ-casein, and at least one of αS1-casein, αS2-casein, and β-casein. In some instances, the casein protein has at least 50%, 60%, 70%, 80%, 85%, 90%, 95%, or 99% sequence identity to the amino acid SEQ ID NO:36, SEQ ID NO:37, SEQ ID NO:38, SEQ ID NO:39, SEQ ID NO:77, SEQ ID NO:78, SEQ ID NO:79, SEQ ID NO:80, SEQ ID NO:81, or SEQ ID NO:82.

In some aspects, the current disclosure also provides methods of enhancing casein micelle formation in a plant, comprising transforming the plant with a vector as described herein and growing the transformed plant, wherein at least one of κ-casein, αS1-casein, αS2-casein, and β-casein is phosphorylated by the kinase.

In some aspects, the current disclosure also provides methods of enhancing casein micelle formation in a plant, comprising transforming the plant with a first vector and a second vector, and growing the transformed plant; wherein the first vector comprises a first polynucleotide sequence encoding a kinase, wherein the second vector comprises a second polynucleotide sequence encoding a κ-casein and at least one of αS1-casein, αS2-casein, and β-casein; wherein at least one of κ-casein, αS1-casein, αS2-casein, and β-casein is phosphorylated by the kinase, and wherein the κ-casein and at least one of αS1-casein, αS2-casein, and β-casein form the casein micelle in the plant in vivo.

In some aspects, the current disclosure also provides methods of enhancing casein micelle formation in a plant, comprising transforming the plant with a first vector, a second vector, and a third vector, and growing the transformed plant; wherein the first vector comprises a first polynucleotide sequence encoding a kinase, wherein the second vector comprises a second polynucleotide sequence encoding a κ-casein, wherein the third vector comprises a third polynucleotide sequence encoding at least one of αS1-casein, αS2-casein, and β-casein; wherein at least one of κ-casein, αS1-casein, αS2-casein, and β-casein is phosphorylated by the kinase, and wherein the κ-casein and at least one of αS1-casein, αS2-casein, and β-casein form the casein micelle in the plant in vivo.

In some aspects, phosphorylation using the methods described herein leads to improved micelle formation in plant cells, for example, in terms of increased number of micelles, micelles becoming more stable, and increased solubility of casein proteins. As a result, food products containing phosphorylated caseins made using the methods described herein have superior quality, including, for example, increased viscosity, melting point, and binding to calcium (e.g., calcium phosphate) than food products without phosphorylated caseins.

In some aspects, phosphorylation of a casein protein in a plant by using the vectors and methods described herein increases the expression level of the casein protein in the plant, wherein the casein protein is selected form the group consisting of κ-casein, αS1-casein, αS2-casein, and β-casein, and wherein phosphorylation of a casein protein increases expression level of the casein protein by at least 10%, 20%, 30%, 40%, 50%, 60%, 70%, 80%, 90%, or even 100%.

In some aspects, phosphorylation of a casein protein in a plant by using the vectors and methods described herein increases its ability to aggregate or bind to another casein protein, wherein the casein protein is selected form the group consisting of κ-casein, αS1-casein, αS2-casein, and β-casein. In some aspects, phosphorylation of a casein protein in a plant by using the vectors and methods described herein improves casein micelle formation, by increasing the number of micelles, or by stabilizing the micelles, or both. In some aspects, phosphorylation of a casein protein in a plant by using the vectors and methods described herein increases its binding to calcium by at least 10%, 20%, 30%, 40%, 50%, 60%, 70%, 80%, 90%, or even 100%.

In some aspects, phosphorylation of a casein protein in a plant by using the vectors and methods described herein increases the viscosity of a liquid containing the phosphorylated casein proteins, compared to a solution containing same amount of unphosphorylated casein proteins.

In some aspects, the current disclosure also provides a plant cell co-expressing at least one casein protein and at least one kinase. In some cases, the at least one casein protein comprises at least one of κ-casein, αS1-casein, αS2-casein, and β-casein. In some cases, the at least one casein protein comprises κ-casein and at least one of αS1-casein, αS2-casein, and β-casein. In some cases, the at least one kinase is a mammalian kinase. In some cases, the at least one kinase comprises two different kinases. In some cases, the at least one kinase is at least one of FAM20A, FAM20C, or human Casein kinase 2 (CK2), or any combination thereof. In some cases, the at least one kinase has at least 80% sequence identity to SEQ ID NO: 40, SEQ ID NO: 41, SEQ ID NO: 43, SEQ ID NO: 83, or SEQ ID NO: 84.

In some cases, the plant cell is co-transformed with one or more plasmids comprising polynucleotide sequences encoding at least one casein protein and at least one kinase. In some cases, the polynucleotide sequences encoding the at least one casein protein and the at least one kinase are in the same plasmid. In some cases, the polynucleotide sequences encoding the at least one casein protein and the at least one kinase are in different plasmids. In some cases, the at least one casein protein comprises κ-casein and at least one of αS1-casein, αS2-casein, and β-casein and wherein the polynucleotide sequences encoding different casein proteins are in different plasmids.

In some aspects, the current disclosure also provides a plant cell genetically modified to increase free phosphate inside the plant cell. In some cases, the plant cell co-expresses 1) at least one casein protein, 2) at least one kinase, and 3) 3-phytase increase free phosphate inside the plant cell. In some cases, the plant cell co-expresses 1) at least one casein protein, 2) at least one kinase, and 3) purple acid phosphatase increase free phosphate inside the plant cell.

In some aspects, the current disclosure also provides a plant cell genetically modified to increase free calcium in the plant cell. In some cases, the plant cell co-expresses 1) at least one casein protein, 2) at least one kinase, and 3) oxalate decarboxylase to increase free calcium in the plant cell. In some cases, the plant cell co-expressing at least one casein protein and at least one kinase has oxalyl-CoA synthetase gene knocked-out or under-expressed to increase free calcium in the plant cell.

In some cases, the plant cell is genetically modified to increase free phosphate and free calcium inside the plant cell. In some cases, the plant cell co-expresses 1) at least one casein protein, 2) at least one kinase, and 3) at least one of 3-phytase, a purple acid phosphatase, oxalate decarboxylase, or any combination thereof.

In some cases, the 3-phytase has at least 50%, 60%, 70%, 80%, 85%, 90%, 95%, or 99% sequence identity to SEQ ID NO: 85, SEQ ID NO: 86, or SEQ ID NO: 87. In some cases, the purple acid phosphatase has at least 50%, 60%, 70%, 80%, 85%, 90%, 95%, or 99% sequence identity to SEQ ID NO: 88 or SEQ ID NO: 89. In some cases, the oxalate decarboxylase has at least 50%, 60%, 70%, 80%, 85%, 90%, 95%, or 99% sequence identity to SEQ ID NO: 90, SEQ ID NO: 91, or SEQ ID NO: 92. In some cases, the oxalyl-CoA synthetase has at least 50%, 60%, 70%, 80%, 85%, 90%, 95%, or 99% sequence identity to SEQ ID NO: 93, SEQ ID NO: 94, or SEQ ID NO: 95.

Examples certain genes that can modified to increase free calcium or free phosphate are listed in Table 2.

TABLE 2

Examples of genes that can be modified in a plant cell that co-expresses at least one kinase and at least one casein protein, to increase free calcium or free phosphate.

| Protein Family | Specific Protein | Source Species | SEQ ID NO: |
|---|---|---|---|
| 3-Phytase | 168phyA | Bacillus subtilus | 85 |
|  | 3-phytase A | Aspergillus niger | 86 |
|  | 3-phytase B | Aspergillus niger | 87 |
| Purple Acid Phosphatase | PAP15 | Arabidopsis thaliana | 88 |
|  | PAP3 | Glycine max | 89 |
| Oxalate decarboxylase | odxC | Bacillus subtilis | 90 |
|  | ABL_03746 | Aspergillus niger | 91 |
|  | OXDC | Flammulina velutipes | 92 |
| oxalyl-CoA synthetase | AAE3 | Arabidopsis thaliana | 93 |
|  | GLYMA_11G198300 | Glycine max | 94 |
|  | Oxalyl-CoA synthetase | Glycine max | 95 |

In some aspects, the current disclosure also provides a plant cell disclosed herein having Inositol-3-phosphate synthase gene (for example, soybean Inositol-3-phosphate synthase, SEQ ID NO: 94) knocked-out or under-expressed in the plant cell, which can be achieved by RNAi, CRISPR-Cas9, or other suitable genome editing systems.

In some aspects, the current disclosure also provides methods of producing a casein micelle, comprising growing a plant comprising a plant cell disclosed herein, wherein the at least one casein protein comprises κ-casein and at least one of αS1-casein, αS2-casein, or β-casein, wherein the at least one casein protein is phosphorylated by the at least one kinase in vivo, and the κ-casein and at least one of αS1-casein, αS2-casein, or β-casein form a casein micelle in vivo; and collecting the casein micelle from the plant.

In some aspects, the current disclosure also provides methods of producing a micelle, comprising mixing phosphorylated casein proteins in a liquid to form at least one casein micelle, wherein the casein proteins comprises κ-casein and at least one of αS1-casein, αS2-casein, and β-casein, wherein one or more casein proteins are phosphorylated. In some cases, the one or more casein proteins are expressed in different plants of the same species. In some cases, the one or more casein proteins are expressed in different species of plants. In some cases, the same plant produce the one or more casein proteins.

In some cases, the method further comprises adding a salt or phosphate acid to the liquid. The salt comprises at least one of a phosphate salt or a calcium salt (e.g., calcium chloride ($CaCl_2$)). Contemplated phosphate salts include a salt having a phosphate group including dihydrogen phosphate, hydrogen phosphate, or phosphate, for example, sodium phosphate.

In some aspects, the current disclosure also provides food product or food product substitute, comprising a phosphorylated casein protein produced by the plant cell disclosed herein. In some aspects, the food product or food product substitute comprises a product traditionally derived from milk, comprising at least one of yogurt, low-fat yogurt, nonfat yogurt, greek yogurt, whipped yogurt, goat milk yogurt, Labneh (labne), sheep milk yogurt, yogurt drink, Lassi, cheese, dairy-based sauce, dairy spread, cream, frozen confections, dairy desserts, butter, dairy powders, infant formula, milk protein concentrate, milk protein isolate, milk protein concentrate, whey protein isolate, demineralized whey protein concentrate, demineralized whey protein concentrate, beta-lactoglobulin concentrate, beta-lactoglobulin isolate, alpha-lactalbumin concentrate, alpha-lactalbumin isolate, glycomacropeptide concentrate, glycomacropeptide isolate, casein concentrate, casein isolate, nutritional supplements, ready-to-drink or ready-to-mix product, pudding, gel, chewable, crisp, and bar.

BRIEF DESCRIPTION OF THE DRAWINGS

FIG. 3B is an example with additional details for the in vivo formation.

FIG. 3C is an example of a schematic illustration of a transcription of proteins which impart herbicide resistance to the transformed plant.

DETAILED DESCRIPTION

Figure 1:
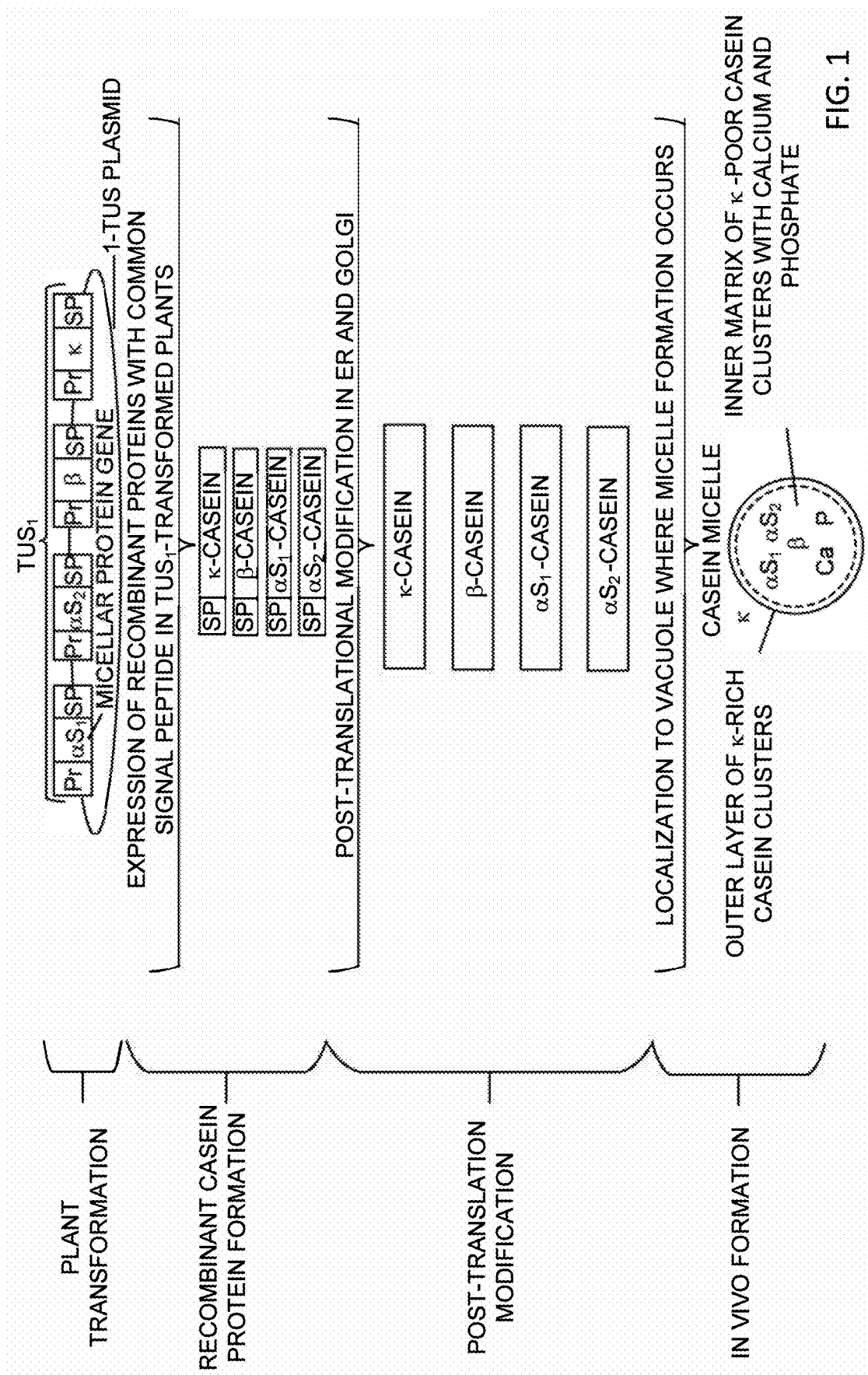
FIG. 1 is an example of a flow for forming in vivo casein micelles in an embodiment.

The following embodiments are described in sufficient detail to enable those skilled in the art to make and use the invention. It is to be understood that other embodiments would be evident based on the present disclosure, and that system, process, or mechanical changes may be made without departing from the scope of an embodiment of the present disclosure.

In the following description, numerous specific details are given to provide a thorough understanding of the invention. However, it will be apparent that the invention may be practiced without these specific details. In order to avoid obscuring an embodiment of the present disclosure, some well-known techniques, system configurations, and process steps are not disclosed in detail.

The drawings showing embodiments of the system are semi-diagrammatic, and not to scale and, particularly, some of the dimensions are for the clarity of presentation and are shown exaggerated in the drawing figures. Similarly, although the views in the drawings for ease of description generally show similar orientations, this depiction in the figures is arbitrary for the most part. Generally, the invention can be operated in any orientation.

The term "invention" or "present disclosure" as used herein is not meant to be limiting to any one specific embodiment of the invention but applies generally to any and all embodiments of the invention as described in the claims and specification.

Referring now to FIG. 1, therein is shown an example of a flow for forming in vivo casein micelles in an embodiment. In this example, FIG. 1 depicts the flow for forming the casein micelles by a plant transformation, a recombinant casein protein formation, a post-translation modification, and an in-vivo formation. As a specific example, FIG. 1 is a schematic illustration of the elements of a plasmid of this embodiment and its use in creation of micelles in vivo in a plant cell.

In this example for the plant transformation, a plant is transformed using a plasmid including a single transcription unit set. As used herein "plasmid" is a deoxyribonucleic acid (DNA) molecule capable of replication in a host cell and to which another DNA segment can be operatively linked so as to bring about replication of the attached DNA segment. As it relates to this example, methods for plant transformation include microprojectile bombardment as illustrated in U.S. Pat. Nos. 5,015,580; 5,550,318; 5,538,880; 6,153,812; 6,160,208; 6,288,312 and 6,399,861, all of which are incorporated herein by reference. Methods for plant transformation also include *Agrobacterium*-mediated transformation as illustrated in U.S. Pat. Nos. 5,159,135; 5,824,877; 5,591,616 and 6,384,301, all of which are incorporated herein by reference. Recipient cells for the plant transformation include, but are not limited to, meristem cells, callus, immature embryos, hypocotyls explants, cotyledon explants, leaf explants, and gametic cells such as microspores, pollen, sperm and egg cells, and any cell from which a fertile plant may be regenerated, as described in U.S. Pat. Nos. 6,194,636; 6,232,526; 6,541,682 and 6,603,061 and U.S. Patent Application publication US 2004/0216189 A1, all of which are incorporated herein by reference.

Continuing this example for the plant transformation, the plasmid including the single transcription unit set is shown and abbreviated in FIG. 1 as 1-TUS PLASMID. The transcription unit set included on this plasmid is transcription unit set 1 shown and abbreviated in FIG. 1 as $TUS_1$. As used herein "transcription unit set" is a segment of DNA including one or more transcription units. The purpose of a transcription unit set includes but is not limited to protein expression, gene suppression, regulatory ribonucleic acid (RNA) production, and herbicide resistance. As used herein "transcription unit" is a segment of DNA including at least a promoter DNA and transcribable DNA. As used herein "promoter" means regulatory DNA for initiating RNA transcription. A "plant promoter" is a promoter capable of initiating transcription in plant cells whether or not its origin is a plant cell. As used herein "terminator" means any DNA sequence that causes RNA transcription to terminate.

Further continuing this example for the plant transformation shown in FIG. 1 as an embodiment, the transcription unit set 1 includes four segments of DNA; each encoding RNA for one of the four proteins found in a casein micelle: an $\alpha S_1$ casein, an $\alpha S_2$ casein, a $\beta$ casein, and a $\kappa$ casein. For clarity and as an example, the genes encoding the $\alpha S_1$ casein, the $\alpha S_2$ casein, the $\beta$ casein, and the $\kappa$ casein are shown and abbreviated in FIG. 1 as $\alpha S_1$, as $\alpha S_2$, as $\beta$, and as $\kappa$, respectively, and shown and annotated in FIG. 1 as MICELLAR PROTEIN GENE. Each DNA segment encoding RNA for one of the four proteins found in a casein micelle is operably linked to a promoter, shown and abbreviated in FIG. 1 as P, and includes a plant-derived, tissue specific, N-terminal signal peptide, shown and abbreviated in FIG. 1 as SP. As used herein "operably linked" is the association of two or more DNA fragments in a DNA construct such that the function of one is controlled by the other, for example DNA encoding a protein associated with DNA encoding a promoter. In some embodiments, the N-terminal signal peptide targets the recombinant casein proteins to the plant vacuoles. In other embodiments, the recombinant casein proteins are targeted to and retained in the endoplasmic reticulum.

As an example for the recombinant casein protein formation, when the four segments of DNA included in transcription unit set 1 are transcribed and translated in a transgenic plant (not shown), four recombinant casein proteins, each including a plant-derived tissue specific signal peptide, are formed in the cytoplasm of the plant cell. The recombinant casein proteins are shown and abbreviated in FIG. 1 as $\alpha S_1$-CASEIN, as $\alpha S_2$-CASEIN, as $\beta$-CASEIN, and as $\kappa$-CASEIN, respectively, and are also referred to herein as "recombinant casein proteins" for brevity. As used herein, "transgenic" plant is a plant whose genome has been altered by the stable integration of recombinant DNA. As an example of stable integration, the transgenic plant includes a plant regenerated from an originally-transformed plant cell and progeny transgenic plants from later generations or crosses of a transformed plant. As used herein "recombinant DNA" refers to DNA which has been synthesized, assembled or constructed outside of a cell. Examples of recombinant DNA can include DNA containing naturally occurring DNA or complementary DNA (cDNA) or synthetic DNA.

As it relates to this example for the post-translation modification shown in FIG. 1 as an embodiment, the four recombinant casein proteins in the cytoplasm of the plant cell include the $\alpha S_1$-casein, the $\alpha S_2$-casein, the $\beta$-casein, and the $\kappa$-casein, each including a signal peptide (SP) that localizes the recombinant casein protein to specific organelles, for example the secretory pathway and protein storage vacuoles, in the plant cell. The signal peptide is removed from the recombinant casein proteins during post-translational modification that occurs in the endoplasmic reticulum and the Golgi apparatus of the plant cell. For clarity in this example, the endoplasmic reticulum and the Golgi apparatus are shown and abbreviated in FIG. 1 as ER, and as GOLGI, respectively. In this embodiment and example, phosphorylation occurs on the recombinant casein proteins prior to, during, or after migration to a specific tissue, shown in FIG. 1 as circles enclosing the letter "P" attached to each of the recombinant casein proteins. In other embodiments and examples, one or more post-translational modifications of the recombinant casein proteins can occur, including phosphorylation, glycosylation, ubiquitination, nitrosylation, methylation, acetylation, lipidation and proteolysis. In other embodiments no post-translational modifications occur on the recombinant casein proteins, or in other words, the post-translation modification is optional.

Continuing this example for the in vivo formation as an embodiment, an outer layer of the micelle is enriched in recombinant $\kappa$-casein shown and abbreviated in FIG. 1 as $\kappa$, and an inner matrix of the micelle includes the recombinant $\alpha S_1$-casein, the recombinant $\alpha S_2$-casein, the recombinant $\beta$-casein, the calcium and the phosphate, shown in and annotated in FIG. 1 as $\alpha S_1$, $\alpha S_2$, as $\alpha S$, and $\beta$, respectively. Micelle formation is enhanced by the presence of intracellular calcium and phosphate, shown and abbreviated in FIG. 1 as Ca and P, respectively.

Figure 2:
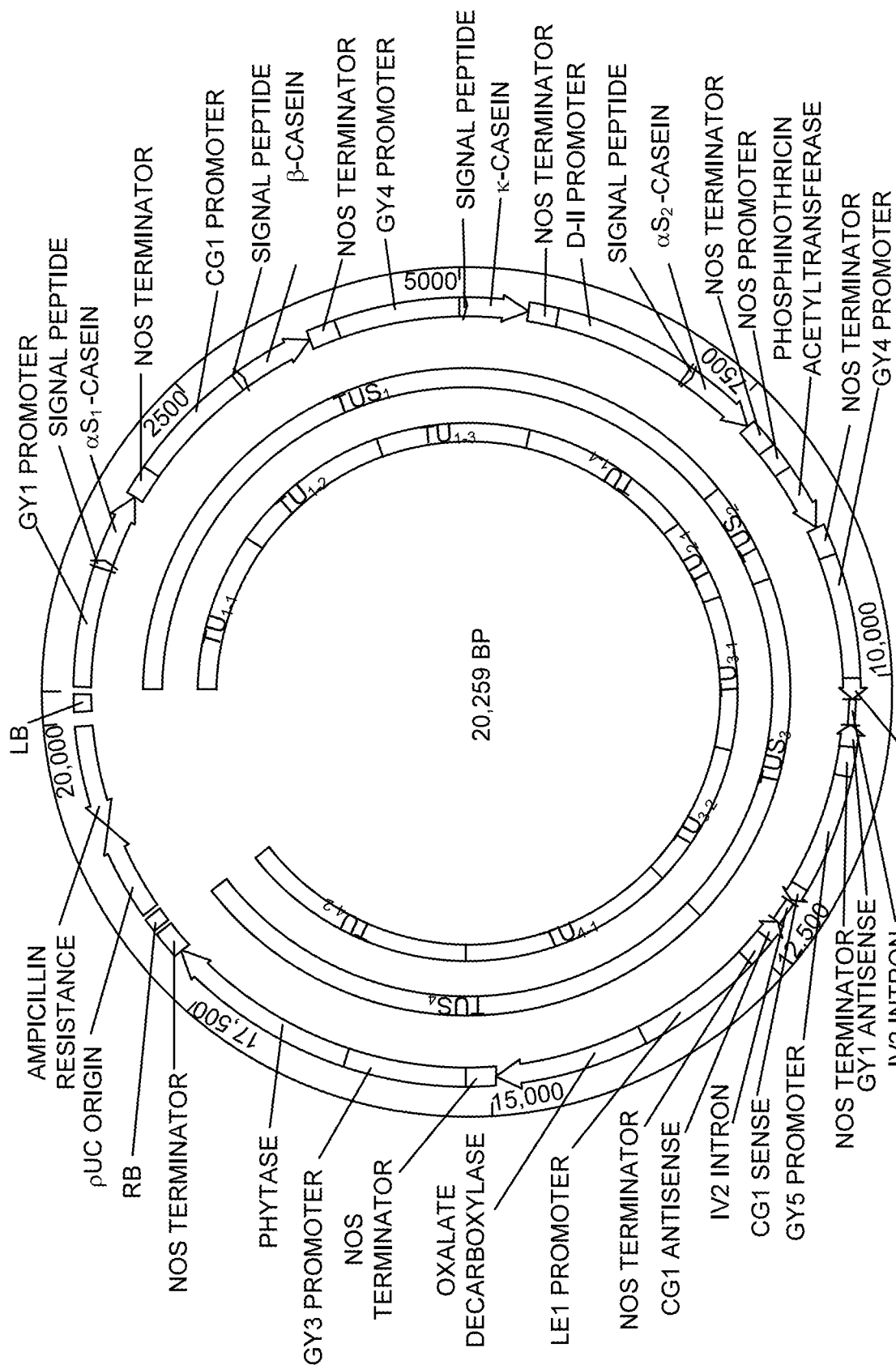
FIG. 2 is an example of a schematic illustration of a plasmid used in FIG. 1.

Referring now to FIG. 2, therein is shown an example of a schematic illustration of a plasmid used in FIG. 1. As a specific example, FIG. 2 is a schematic illustration of the elements of a plasmid of this embodiment.

In this example for the plant transformation of FIG. 1, an embodiment provides a plant that is transformed with one or more transfer DNAs including one or more transcription unit sets. As used herein "transfer DNA" (T-DNA) is DNA which integrates or is integrated into a genome.

For example, an *Agrobacterium*-mediated transformation T-DNA is part of a binary plasmid, which is flanked by T-DNA borders, and the binary plasmid is transferred into an *Agrobacterium tumefaciens* strain carrying a disarmed tumor inducing plasmid. Also for example, for a biolistic mediated transformation a gene gun is used for delivery of T-DNA, which is typically a biolistic construct containing promoter and terminator sequences, reporter genes, and border sequences or signaling peptides, to cells.

Continuing the example of a T-DNA used to transform a plant in an embodiment, the T-DNA includes four transcription unit sets: a transcription unit set 1, a transcription unit set 2, a transcription unit set 3, and a transcription unit set 4. For clarity, the transcription unit set 1, the transcription unit set 2, the transcription unit set 3, and the transcription unit set 4 are shown and abbreviated in FIG. 2 as $TUS_1$, as $TUS_2$, as $TUS_3$, and as $TUS_4$, respectively.

In this example as an embodiment, $TUS_1$ includes one transcription unit for each of the four casein proteins found in a casein micelle of FIG. 2: a transcription unit 1-1 includes DNA encoding $\alpha S_1$-casein, a transcription unit 1-2 includes DNA encoding β-casein, a transcription unit 1-3 includes DNA encoding κ-casein, and a transcription unit 1-4 includes DNA encoding $\alpha S_1$-casein. For clarity and brevity, the transcription unit 1-1, the transcription unit 1-2, the transcription unit 1-3, and the transcription unit 1-4 are shown and abbreviated in FIG. 2 as $TU_{1-1}$, as $TU_{1-2}$, as $TU_{1-3}$, and as $TU_{1-4}$, respectively. Each transcription unit in $TUS_1$ can also include DNA encoding the same plant-derived signal peptide. Additionally, each transcription unit in $TUS_1$ includes a promoter and a transcriptional terminator.

Continuing this example as an embodiment, $TUS_2$ includes one transcription unit, shown and abbreviated in FIG. 2 as $TU_{2-1}$, that includes a promoter, DNA encoding phosphinothricin acetyltransferase, and a transcriptional terminator. In other embodiments, $TUS_2$ can include one or more genes encoding a selectable marker that can impart herbicide or antibiotic resistance which enables the selection of transformed plants that produce micelles in vivo. Genes enabling selection of transformed plants include those conferring resistance to antibiotics, including as examples kanamycin, hygromycin B, gentamicin, and bleomycin. Genes enabling selection of transformed plants also include those conferring resistance to herbicides, including as examples a glyphosate herbicide, a phosphinothricin herbicide, an oxynil herbicide, an imidazolinone herbicide, a dinitroaniline herbicide, a pyridine herbicide, a sulfonylurea herbicide, a bialaphos herbicide, a sulfonamide herbicide, and a glufosinate herbicide. Examples of such selectable markers are illustrated in U.S. Pat. Nos. 5,550,318; 5,633,435; 5,780,708 and 6,118,047, all of which are incorporated herein by reference. In other embodiments, $TUS_2$ includes one or more genes expressing a screenable marker which enables the visual identification of transformed plants that produce micelles in vivo. Genes expressing a screenable marker include genes encoding a colored or fluorescent protein, including as examples luciferase or green fluorescent protein (U.S. Pat. No. 5,491,084, herein incorporated by reference), and genes expressing β-glucuronidase or uidA gene (U.S. Pat. No. 5,599,670, herein incorporated by reference) for which various chromogenic substrates are known. In some embodiments, each of the genes encoding a selectable or screenable marker are operably linked to an inducible promoter, such as for example a NOS promoter, or a tissue-specific promoter, such as for example a promoter from the soybean a' subunit of β-conglycinin, such that the translation of the selectable or screenable markers can be regulated.

Continuing this example as an embodiment, $TUS_3$ includes two transcription units that yield untranslated RNA molecules that suppress native seed protein gene translation. The first transcription unit in $TUS_3$, a transcription unit 3-1, includes the sense strand, or coding strand, of DNA encoding soybean Glycinin1, and the antisense strand, or non-coding strand, of DNA encoding soybean Glycinin1 separated by the potato IV2 intron. For clarity and brevity, the transcription unit 3-1 the sense strand or coding strand of DNA encoding soybean Glycinin1, and the antisense strand or non-coding strand of DNA encoding soybean Glycinin1, the potato IV2 intron are shown and annotated in FIG. 2 as $TU_{3-1}$ as GY1 SENSE, as GY1 ANTISENSE, and as IV2 INTRON, respectively. The second transcription unit in $TUS_3$, a transcription unit 3-2 includes the sense strand, or coding strand, of DNA encoding β-conglycinin 1 and the antisense strand, or non-coding strand, of DNA encoding β-conglycinin 1 separated by the potato IV2 intron. For clarity and brevity, the transcription unit 3-2, the sense strand or coding strand of DNA encoding β-conglycinin 1, the antisense strand or non-coding strand of DNA encoding β-conglycinin 1, and the potato IV2 intron are shown and annotated in FIG. 2 as $TU_{3-2}$ as CG1 SENSE, as CG1 ANTISENSE, and as IV2 INTRON, respectively.

In other embodiments, $TUS_3$ includes other transcription units that yield untranslated RNA molecules that suppress native seed protein gene translation. As an example, in other embodiments, $TUS_3$ includes one transcription unit, a transcription unit 3-1, that includes a promoter from the soybean GY4 gene (SEQ ID NO: 15), a miR319a microRNA from *Arabidopsis thaliana* that has been modified such that the homologous arms of the microRNA hairpin contain 21 nucleotide sequences matching a portion of the soybean GY1 gene sequence (SEQ ID NO:10), and a NOS transcriptional terminator (SEQ ID NO:35) (not shown).

Continuing this example as an embodiment, $TUS_4$ includes two transcription units that encode proteins which alter the intracellular environment in a manner that optimizes the production of micelles having requisite attributes including size, mineral content, protein content, protein distribution, and mass. The first transcription unit in $TUS_4$, a transcription unit 4-1 includes a promoter, DNA encoding oxalate decarboxylase, and a transcriptional terminator. For clarity and brevity, the transcription unit 4-1 is shown and abbreviated in FIG. 2 as $TU_{4-1}$. The second transcription unit in $TUS_4$, a transcription unit 4-2, includes a promoter, DNA encoding phytase, and a transcriptional terminator. For clarity and brevity, the transcription unit 4-2 is shown and abbreviated as $TU_{4-2}$. In this embodiment, transcription and translation of $TU_{4-1}$ yields an oxalate-degrading enzyme which increases the amount of free intracellular calcium available for capture and inclusion during micelle formation. Also in this embodiment, transcription and translation of $TU_{4-2}$ yields a phytase enzyme which increases the amount of free intracellular phosphate available for capture and inclusion during micelle formation. In some embodiments, each of the genes encoding oxalate-degrading enzymes or phytase enzymes are operably linked to a constitutive promoter, tissue specific promoter or an inducible promoter, such as for example, a nopaline synthase promoter or a promoter from the soybean β-conglycinin gene, such that the translation of proteins which alter the intracellular environment can be regulated. In some embodiments, $TUS_4$ includes both a transcription unit 4-1 that increases the intracellular calcium concentration and a transcription unit 4-2 that increases the intracellular phosphate concentration. In other embodiments, TUS$_4$ includes only a transcription unit 4-1 that increases the intracellular calcium concentration. In other embodiments, TUS$_4$ includes only a transcription unit 4-2 that increases the intracellular phosphate concentration.

In other embodiments, TUS$_4$ includes transcription units that increase the intracellular calcium concentration by expressing an oxalate oxidase enzyme (not shown). As an example, in other embodiments, TUS$_4$ includes one transcription unit, a transcription unit 4-1, that includes a promoter from the soybean GY4 gene (SEQ ID NO:15), the coding sequence for the oxalate oxidase 1 coding sequence from wheat that has been codon optimized for expression in soybean (SEQ ID NO:9), and the NOS transcriptional terminator (SEQ ID NO:35) (not shown). In other embodiments, TUS$_4$ includes transcription units that increase the intracellular phosphate concentration by suppressing the expression of the soybean myo-inositol-3-phosphate synthase (MIPS1) gene. As an example, in other embodiments, TUS$_4$ includes one transcription unit, a transcription unit 4-2, that includes a promoter from the soybean GY4 gene (SEQ ID NO:15), a portion of the MIPS1 coding sequence lacking a start codon (SEQ ID NO:21), the IV2 intron from potato (SEQ ID NO:25), the antisense of the MIPS1 sequence (SEQ ID NO:22), and the NOS transcriptional terminator (SEQ ID NO:35) (not shown).

In some embodiments of the disclosure, transcription unit sets are assembled in numeric order. In other embodiments, transcription unit sets can be assembled in any order.

In some embodiments of the disclosure, the plant is transformed with a plasmid that contains transcription unit sets TUS$_1$, TUS$_2$, TUS$_3$, and TUS$_4$. In other embodiments of the disclosure, the plant is transformed with a plasmid that contains only transcription unit set TUS$_1$.

In some embodiments of the disclosure, the plant is transformed with a plasmid that contains transcription unit sets TUS$_1$, and TUS$_2$. In other embodiments of the disclosure, the plant is transformed with a plasmid that contains transcription unit sets TUS$_1$, TUS$_2$, and TUS$_3$. In other embodiments of the disclosure, the plant is transformed with a plasmid that contains transcription unit sets TUS$_1$, TUS$_2$, and TUS$_4$.

In other embodiments of the disclosure, the plant is transformed with a plasmid that contains transcription unit sets TUS$_1$, and TUS$_3$. In other embodiments of the disclosure, the plant is transformed with a plasmid that contains transcription unit sets TUS$_1$, TUS$_3$, and TUS$_4$.

In other embodiments of the disclosure, the plant is transformed with a plasmid that contains transcription unit sets TUS$_1$, and TUS$_4$. In some embodiments of the disclosure, transgenic plants are prepared by crossing a first plant that has been transformed with a plasmid containing one or more transcription unit sets with a second untransformed plant. In other embodiments of the disclosure, transgenic plants are prepared by crossing a first plant that has been transformed with a plasmid containing one or more but not all transcription unit sets required for micelle formation in vivo with a second plant having one or more transcription unit sets, wherein at least one of the transcription unit sets is present in the second plant and not present in the first plant.

In some embodiments of the disclosure, transgenic plants are prepared by crossing a first plant that has been transformed with a plasmid containing one or more transcription unit sets enabling micelle formation in vivo with a second plant having another trait, such as herbicide resistance or pest resistance.

In some embodiments of the disclosure, transgenic plants are prepared by growing progeny generations of a plant that has been transformed with a plasmid containing one or more transcription unit sets enabling micelle formation in vivo. In other embodiments, transgenic plants are prepared by growing progeny generations of a transgenic plant produced by crossing one or more plants that have been transformed with a plasmid containing one or more transcription unit sets enabling micelle formation in vivo.

Further to this example shown in FIG. 2 as an embodiment, the promoters in the four transcription unit sets include the promoters of genes coding for soybean Glycinin1, soybean β-conglycinin1, soybean Glycinin4, soybean Bowman-Birk protease inhibitor, *Agrobacterium* nopaline synthase, soybean Glycinin5, soybean lectin, and soybean Glycinin3. For clarity and brevity, the promoters of genes coding for soybean Glycinin1 is shown and annotated in FIG. 2 as GY1 PROMOTER. Also for clarity and brevity, the soybean β-conglycinin1 is shown and annotated in FIG. 2 as CG1 promoter. Further for clarity and brevity, the soybean Glycinin4 is shown and annotated in FIG. 2 as GY4 promoter. Yet further for clarity and brevity, the Bowman-Birk protease inhibitor promoter is shown and annotated in FIG. 2 as D-II promoter. Yet further for clarity and brevity, the *Agrobacterium* nopaline synthase is shown and annotated in FIG. 2 as NOS promoter. Yet further for clarity and brevity, the soybean Glycinin5 is shown and annotated in FIG. 2 as GY5 promoter. Yet further for clarity and brevity, the soybean lectin is shown and annotated in FIG. 2 as LE1 promoter. Yet further for clarity and brevity, the soybean Glycinin3 is shown and annotated in FIG. 2 as GY3 promoter.

In other embodiments and examples, promoters in one or more of the four transcription unit sets include a promoter capable of initiating transcription in plant cells whether or not an origin of the promoter is a plant cell. For example, *Agrobacterium* promoters are functional in plant cells. The promoters capable of initiating transcription in plant cells include promoters obtained from plants, plant viruses and bacteria such as *Agrobacterium*.

As specific examples of promoters under developmental control include promoters that preferentially initiate transcription in certain tissues, such as leaves, roots, or seeds. Such promoters are referred to as "tissue preferred". Also as specific examples of promoters that initiate transcription only in certain tissues are referred to as "tissue specific". Further as a specific example, a "cell type specific" promoter primarily drives expression in certain cell types in one or more organs, for example, vascular cells in roots or leaves. Yet further a specific example, an "inducible" or "repressible" promoter is a promoter which is under environmental control. Examples of environmental conditions that may affect transcription by inducible or repressible promoters include anaerobic conditions, or certain chemicals, or the presence of light. Tissue preferred, tissue specific, cell type specific, and inducible or repressible promoters constitute the class of "non-constitutive" promoters. A "constitutive" promoter is a promoter which is active under most conditions.

Returning to this example in FIG. 2 as an embodiment, the transcriptional terminators in the four transcription unit sets include the termination sequence of the nopaline synthase gene, shown and annotated in FIG. 2 as NOS terminator. In other embodiments, the transcriptional terminators in one or more of the four transcription unit sets includes transcriptional terminators from the native soybean Glycinin genes, or any other plant transcriptional terminators.

In this example as an embodiment, the T-DNA used to transform a plant also includes DNA encoding an origin of replication, a gene conferring antibiotic resistance, a right boundary for the T-DNA, and a left boundary for the T-DNA, shown and annotated in FIG. 2 as pUC origin, ampicillin resistance, RB, and LB, respectively. In this embodiment, the gene conferring antibiotic resistance is a gene conferring resistance to the antibiotic ampicillin. In other embodiments, the gene conferring antibiotic resistance is a gene conferring resistance to any other antibiotic, including kanamycin and chloramphenicol.

Figure 3A:
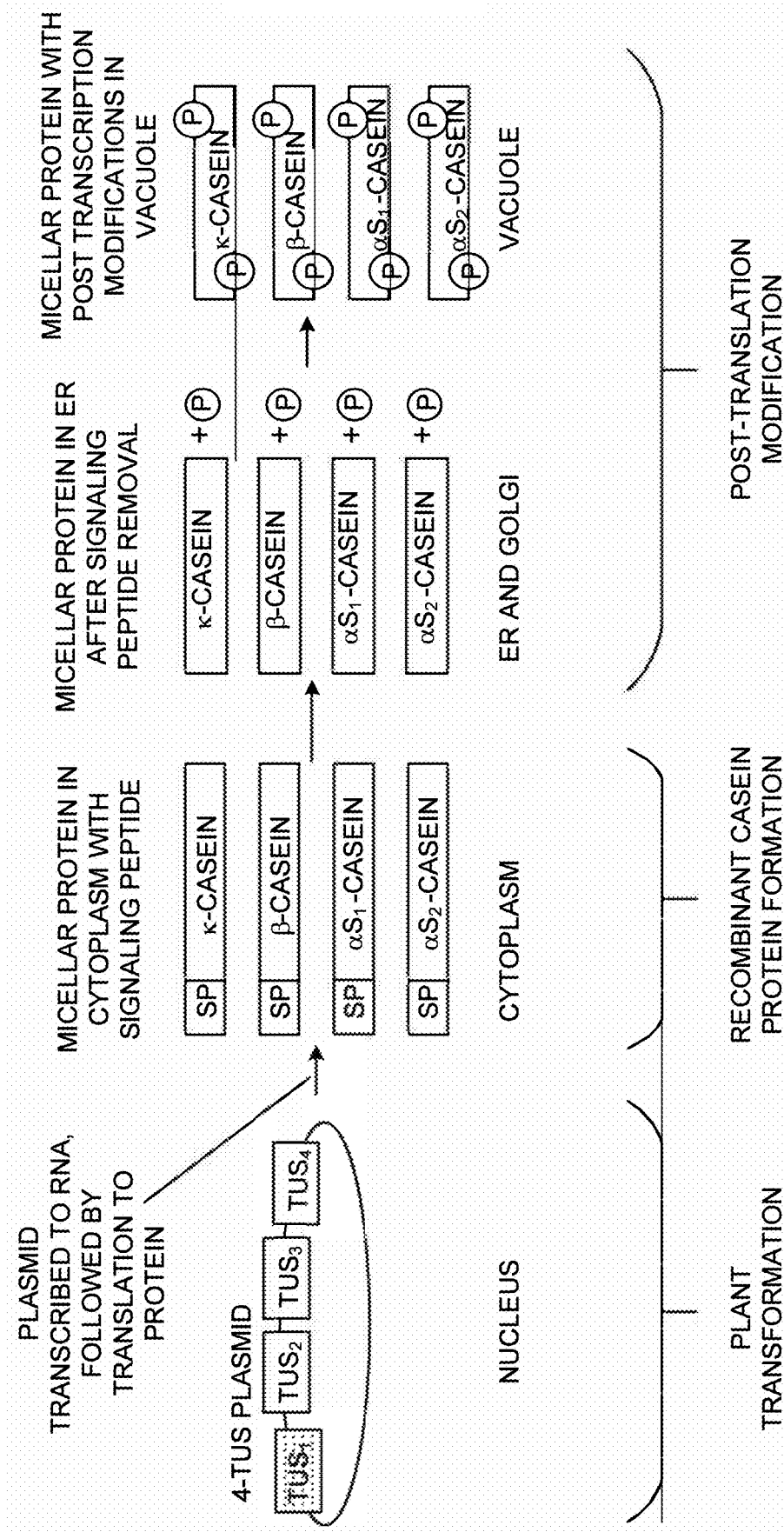
FIG. 3A is an example with additional details from the plant transformation to the post-translation modification.

Referring now to FIG. 3A, therein is shown an example with additional details from the plant transformation to the post-translation modification. The plant transformation and the post-translation modification are also described in FIG. 1. The example depicted in FIG. 3A also depicts the recombinant casein protein formation, also described in FIG. 1. As a specific example, FIG. 3A schematically illustrates the transcription of casein proteins from genes in $TUS_1$ as well as post transcriptional alterations that occur as the proteins move towards their subcellular specific destination encoded by the common signal peptide.

In the example shown in FIG. 3A, the purpose of transcription unit set 1 is forming casein micelles in vivo in an embodiment. In this example, the plant transformation depicts a plant transformed using a T-DNA including four transcription unit sets shown and annotated in FIG. 3A as 4-TUS plasmid. The T-DNA includes transcription unit set 1, shown and abbreviated in FIG. 3A as $TUS_1$, which includes one transcription unit for each of the four casein proteins found in a casein micelle, with each transcription unit including DNA encoding the same plant-derived signal peptide, a promoter and a transcriptional terminator as described in FIG. 2. Upon transcription and translation of $TUS_1$ in the transgenic plant during the recombinant casein protein formation, the four recombinant casein proteins ($\alpha S_1$-casein, $\alpha S_2$-casein, $\beta$-casein, and $\kappa$-casein) are formed in the cytoplasm, each including a signal peptide that localizes the recombinant protein to a specific tissue, for example the secretory pathway and protein storage vacuoles, in the plant cell. In this example, the signal peptide is removed from the recombinant casein proteins during post-translational modification that occurs in the endoplasmic reticulum, abbreviated as ER, of the plant cell.

Continuing this example and embodiment for the post-translation modification, phosphorylation occurs on the recombinant casein proteins prior to, during, or after migration to a specific tissue. The phosphorylation is shown in FIG. 3A as circles enclosing the letter "P" that are added to and then attached to each of the recombinant casein proteins to form phosphorylated casein proteins. The phosphorylated casein proteins are then localized to the vacuole where micelle assembly occurs in vivo. In some embodiments, proteins encoded by $TUS_2$ transcription units (not shown) are also phosphorylated, glycosylated, or a combination thereof. In other embodiments, the casein proteins encoded by $TUS_4$ transcription units (not shown) are also phosphorylated or glycosylated or both. In other embodiments, no post-translational modifications occur to proteins encoded by $TUS_1$, $TUS_2$, $TUS_3$, or $TUS_4$ (not shown). As another example and embodiment, a kinase gene may optionally be included to generate a kinase protein that ensures phosphorylation of the casein proteins encoded by $TUS_4$ transcription units (not shown).

Referring now to FIG. 3B, therein is shown an example with additional details for the in vivo formation. The in vivo formation is also described in FIG. 1. As a specific example, FIG. 3B schematically illustrates the in vivo formation of recombinant micelles inside a plant cell.

Upon localization to the vacuole, each of the four recombinant casein proteins assemble with the other recombinant casein proteins to form micelles in vivo. In this example, the outer layer of the micelle is enriched in recombinant $\kappa$-casein shown and abbreviated in FIG. 3B as $\kappa$, and the inner matrix of the micelle includes recombinant $\alpha S_1$-casein and $\alpha S_2$-casein, shown and abbreviated as $\alpha S_1$ and $\alpha S_2$, respectively, in FIG. 3B, and $\beta$-casein, shown and abbreviated in FIG. 3B as $\beta$.

Referring now to FIG. 3C, therein is shown an example of a schematic illustration of a transcription of proteins which impart herbicide resistance to the transformed plant. FIG. 3C depicts an example of the purpose of transcription unit set 2 in an embodiment.

In this example, a plant is transformed using a T-DNA including four transcription unit sets shown and annotated in FIG. 3C as 4-TUS plasmid. The T-DNA includes transcription unit set 2, shown in FIG. 3C and abbreviated as $TUS_2$ which includes one transcription unit that includes DNA encoding phosphinothricin acetyltransferase that imparts herbicide resistance and allow for selection of transformed cells producing micelles, shown and abbreviated as AC-PT in FIG. 3C, and a promoter and a transcriptional terminator (not shown).

Figures 3D, 3E:
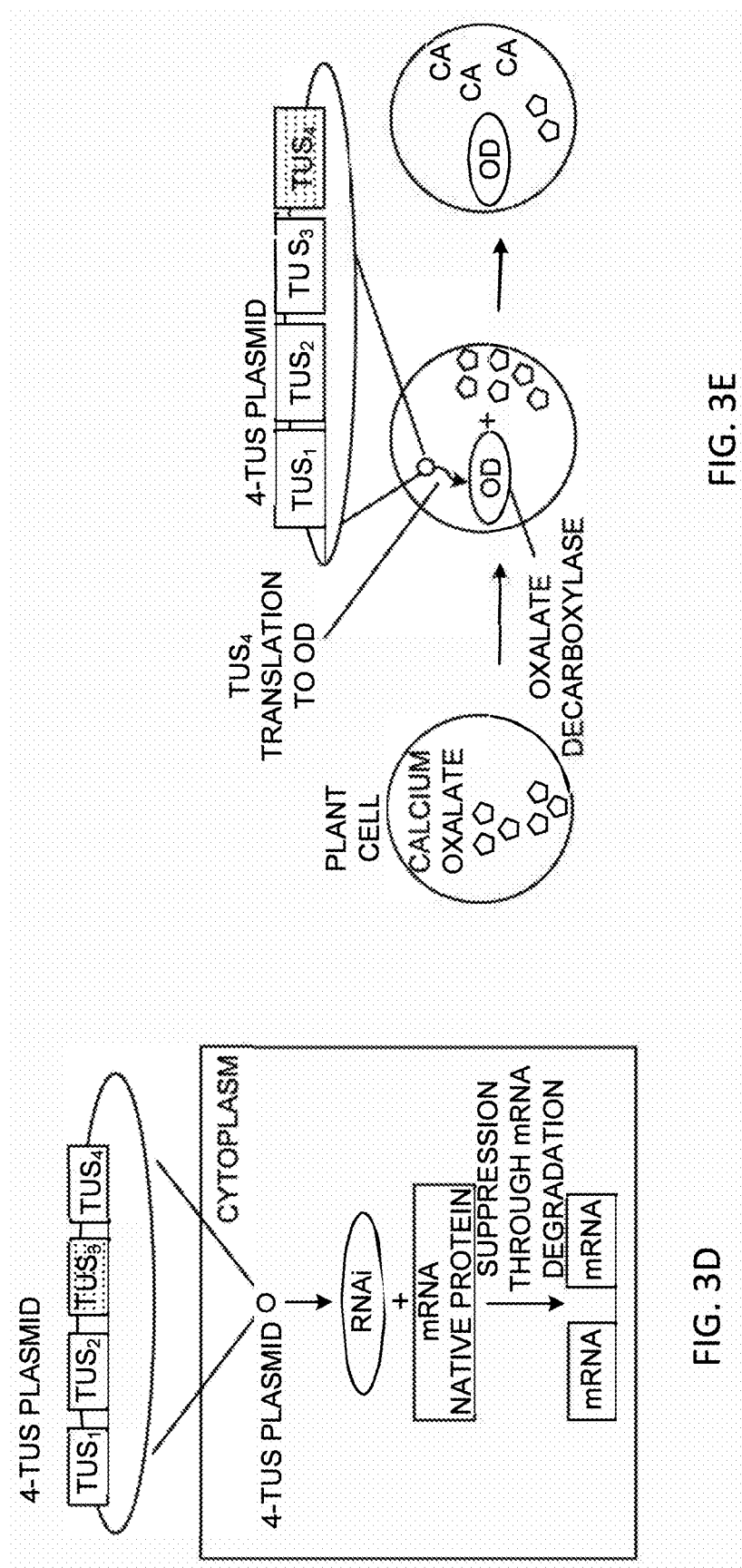
FIG. 3D is an example of a schematic illustration of suppression of native seed storage proteins by RNAi transcribed by a portion of the plasmid of FIG. 1.
FIG. 3E is an example of a schematic illustration of a transcription of a portion of the plasmid of FIG. 1 and resulting proteins used to increase calcium concentrations in the plant cell.

Referring now to FIG. 3D, therein is shown an example of a schematic illustration of suppression of native seed storage proteins by interference RNA (RNAi) transcribed by a portion of the plasmid of FIG. 1. As a specific example, FIG. 3D schematically illustrates suppression of native seed storage proteins by RNAi transcribed by one or more genes in $TUS_3$.

FIG. 3D depicts an example of the purpose of transcription unit set 3 in an embodiment. In this example, a plant is transformed using a T-DNA including four transcription unit sets, shown and annotated in FIG. 3D as 4-TUS plasmid. The T-DNA includes transcription unit set 3, shown and abbreviated in FIG. 3D as $TUS_3$, which includes one or more transcription units that yield untranslated RNA molecules that suppress native seed protein gene translation thereby freeing cellular resources to produce micelles in vivo. Transcription of the DNA in $TUS_3$ yields RNAi, shown and abbreviated in FIG. 3D as RNAi, that targets messenger RNA of native plant proteins or native plant peptides, shown and annotated in FIG. 3D as mRNA NATIVE PROTEIN, and suppresses the expression of those messenger RNAs through messenger RNA degradation such that the recombinant casein proteins encoded by $TUS_1$, described in FIG. 1, FIG. 3A, and FIG. 3B, can be translated at higher quantities, thereby yielding higher concentrations of micelles in vivo (not shown). In some embodiments, DNA encoding RNAi is operably linked to a constitutive promoter or an inducible promoter (not shown), such as for example a nopaline synthase promoter or soybean $\alpha'$ subunit of $\beta$-conglycinin, such that the suppression of native seed protein gene translation by RNAi can be regulated.

Figure 3F:
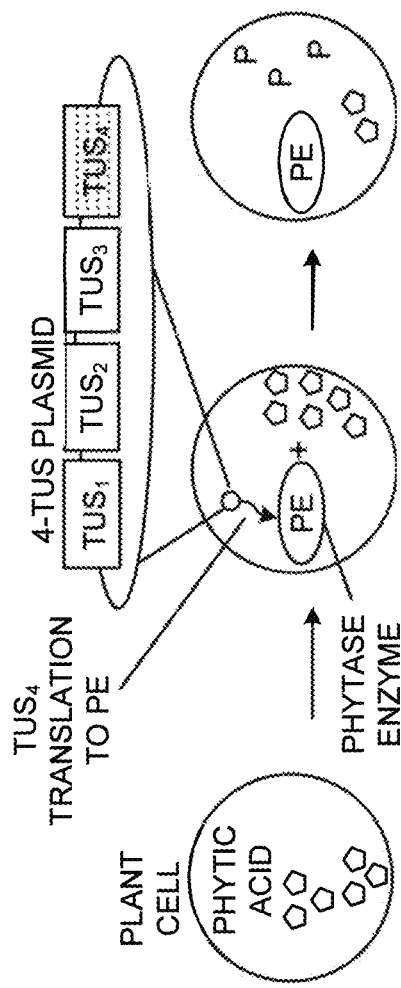
FIG. 3F is an example of a schematic illustration of a transcription of a portion of the plasmid of FIG. 1 and resulting proteins used to increase phosphate concentrations in the plant cell.

Referring now to FIG. 3E and FIG. 3F, therein are shown examples of schematic illustrations of a transcription of a portion of the plasmid of FIG. 1 and resulting proteins used to alter the intracellular conditions of the plant cell. As specific examples, FIG. 3E and FIG. 3F schematically illustrate the transcription of $TUS_4$ genes and the resulting proteins used to alter the conditions in the cytoplasm of the cell.

FIG. 3E depicts an example of the purpose of transcription unit set 4 in an embodiment. In this example, a plant is transformed using a T-DNA including four transcription unit sets, shown and annotated in FIG. 3E as 4-TUS plasmid. The T-DNA includes transcription unit set 4, shown and abbreviated in FIG. 3E as $TUS_4$, which includes one or more transcription units that encode proteins which increase the concentration of intracellular minerals, including calcium and phosphate. In this example, $TUS_4$ includes one transcription unit, a $TU_{4-1}$, that includes a promoter, DNA encoding oxalate decarboxylase, and a transcriptional terminator (not shown). Transcription and translation of $TU_{4-1}$ yields the enzyme oxalate decarboxylase, shown and abbreviated in FIG. 3E as OD, that breaks down the calcium oxalate and increases calcium levels in the plant cell. The increased intracellular calcium enhances the formation of recombinant casein micelles in the plant cell (not shown).

FIG. 3F depicts an example of the purpose of transcription unit set 4 in an embodiment. In this example, a plant is transformed using a T-DNA including four transcription unit sets, shown and annotated in FIG. 3F as 4-TUS plasmid. The T-DNA includes transcription unit set 4, shown and abbreviated in FIG. 3F as $TUS_4$, which includes one or more transcription units that encode proteins which increase the concentration of intracellular minerals, including calcium and phosphate. In this example, $TUS_4$ includes one transcription unit, a $TU_{4-2}$, that includes a promoter, DNA encoding a phytase enzyme, and a transcriptional terminator (not shown). Transcription and translation of $TU_{4-2}$ yields the phytase enzyme, shown and abbreviated in FIG. 3F as PE, that breaks down the phytic acid and increases phosphate levels in the plant cell. The increased intracellular phosphate enhances the formation of recombinant casein micelles in the plant cell (not shown).

Figure 3G:
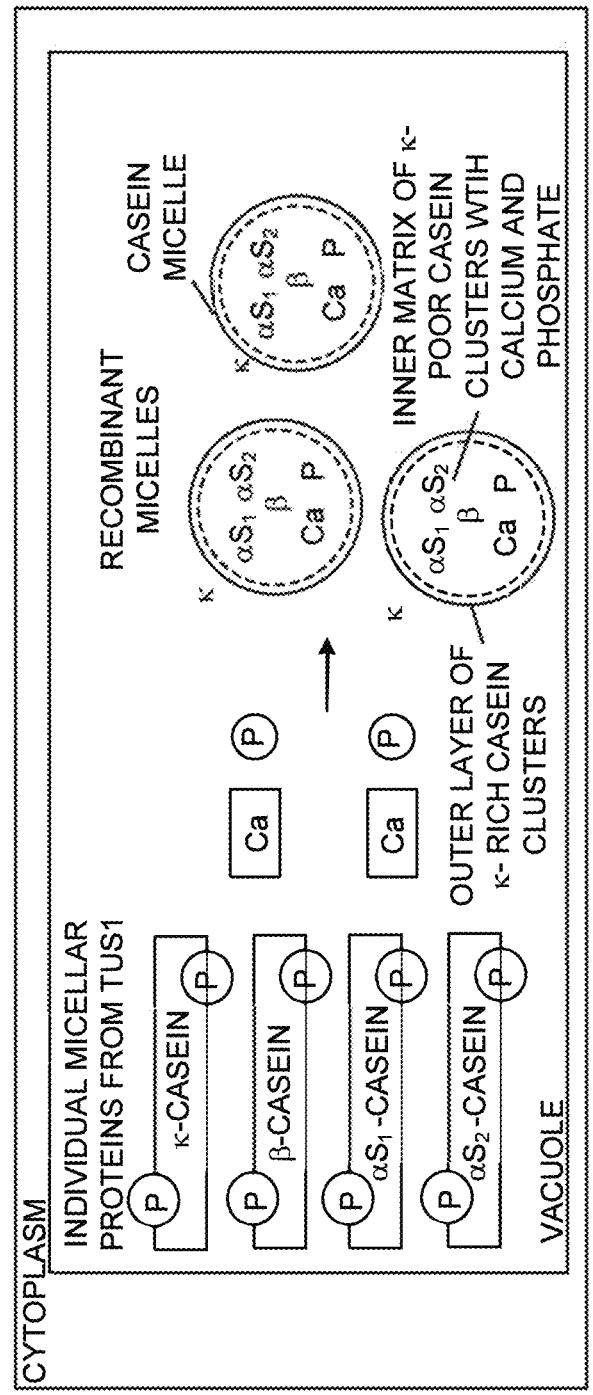
FIG. 3G is an example with further additional details of the in vivo formation.

Referring now to FIG. 3G, therein is shown an example of further additional details of the in vivo formation. The in vivo formation is also described in FIG. 1, FIG. 3A, and FIG. 3B. As a specific example, FIG. 3G schematically illustrates the in vivo formation of recombinant micelles inside a plant cell.

In the example shown in FIG. 3G, the in vivo formation of recombinant micelles inside a plant cell in which the four micellar proteins are produced by transcription and translation of transcription unit set 1 as depicted and described in FIG. 3A. The levels of calcium in plant cell vacuoles is increased by the presence of oxalate decarboxylase produced by transcription and translation of transcription unit set 4 as depicted and described in FIG. 3E. In this example, the four casein proteins encoded by transcription unit 1 are phosphorylated and localized to the plant cell vacuole where the intracellular calcium and the intracellular phosphate enhances the formation of recombinant casein micelles in the plant cell vacuole.

Figure 4:
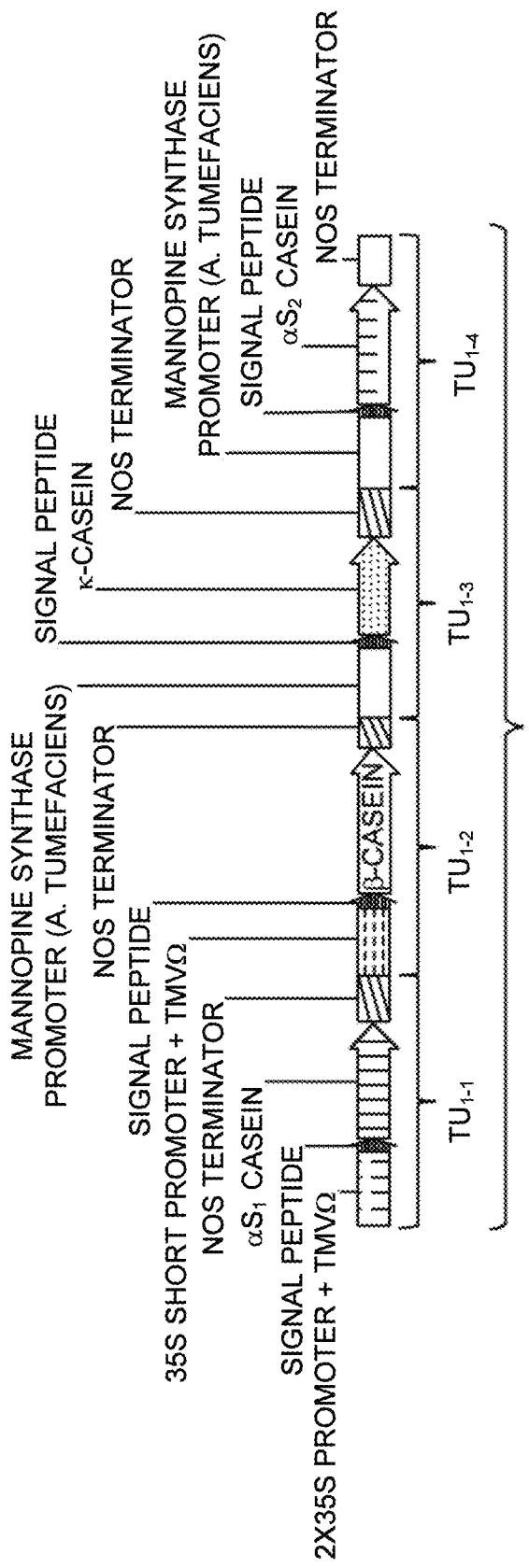
FIG. 4 is an example of a schematic illustration of a portion of a plasmid in *Arabidopsis*.
Figure 5:
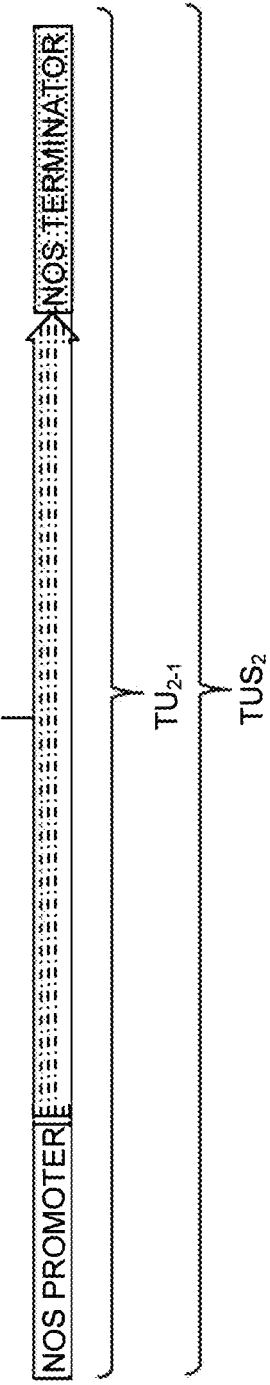
FIG. 5 is an example of a schematic illustration of a portion of a plasmid in *Arabidopsis* for a screenable marker in plants.

Aspects of the disclosure can be further illustrated by a specific embodiment in which a casein micelle is assembled in vivo from its constituent proteins in Arabidopsis thaliana as further described in FIG. 4 and FIG. 5.

Referring now to FIG. 4, therein is shown an example of a schematic illustration of a portion of a plasmid in Arabidopsis. The example shown in FIG. 4 is also described in FIG. 2. As a specific example, FIG. 4 schematically illustrates elements of plasmids that encode micellar component proteins. Transcription units depicted are components of $TUS_1$ in Arabidopsis.

The example in FIG. 4 depicts a transcription unit set which can be used for creation of casein micelles in vivo in Arabidopsis thaliana. The transcription unit set includes one transcription unit for each of the four casein proteins found in a casein micelle, abbreviated and shown in FIG. 4 as $TU_{1-1}$, $TU_{1-2}$, $TU_{1-3}$, and $TU_{1-4}$. The transcription unit set abbreviated and shown in FIG. 4 as $TUS_1$. Each of the four transcription units includes a promoter, a plant-derived N-terminal signal peptide, DNA encoding one of the four proteins found in a casein micelle, and a transcriptional terminator.

Continuing this example, $TU_{1-1}$ includes a double 35S promoter containing the tobacco mosaic virus omega leader sequence (SEQ ID NO:29), a signal peptide from the Arabidopsis CLV3 gene (SEQ ID NO:27), the $\alpha S_1$-casein coding sequence codon optimized for expression in Arabidopsis with a C-terminal HDEL peptide for retention in the endoplasmic reticulum (SEQ ID NO:5), and the nopaline synthase terminator (SEQ ID NO:35), annotated and shown in FIG. 4 as 2X35S promoter+TMVΩ, signal peptide, $\alpha S_1$ casein, and NOS terminator, respectively.

Further continuing this example, $TU_{1-2}$ includes a 35S short promoter containing a truncated version of the cauliflower mosaic virus promoter and the tobacco mosaic virus omega leader sequence (SEQ ID NO:31), a signal peptide (SEQ ID NO:27), the β-casein coding sequence codon optimized for expression in Arabidopsis with a C-terminal HDEL peptide for retention in the endoplasmic reticulum (SEQ ID NO:7), and the nopaline synthase terminator (SEQ ID NO:35), abbreviated and shown in FIG. 4 as 35S SHORT PROMOTER+TMVΩ, SIGNAL PEPTIDE, β-CASEIN, and NOS TERMINATOR, respectively.

Further continuing this example, $TU_{1-3}$ includes the mannopine synthase promoter from Agrobacterium tumefaciens (SEQ ID NO:32), a signal peptide (SEQ ID NO:27), the κ-casein coding sequence codon optimized for expression in Arabidopsis with a C-terminal HDEL peptide for retention in the endoplasmic reticulum (SEQ ID NO:6), and the nopaline synthase terminator (SEQ ID NO:35), abbreviated and shown in FIG. 4 as MANNOPINE SYNTHASE PROMOTER (A. tumefaciens), SIGNAL PEPTIDE, κ-CASEIN, and NOS TERMINATOR, respectively.

Further continuing this example, $TU_{1-4}$ includes the mannopine synthase promoter from Agrobacterium tumefaciens, a signal peptide (SEQ ID NO:32), the $\alpha S_2$-casein coding sequence codon optimized for expression in Arabidopsis with a C-terminal HDEL peptide for retention in the endoplasmic reticulum (SEQ ID NO:8), and the nopaline synthase terminator (SEQ ID NO:35), abbreviated and shown in FIG. 4 as MANNOPINE SYNTHASE PROMOTER (A. tumefaciens), SIGNAL PEPTIDE, $\alpha S_2$ CASEIN, and NOS TERMINATOR, respectively.

Referring now to FIG. 5, therein is shown an example of a schematic illustration of a portion of a plasmid in Arabidopsis for a screenable marker in plants. As a specific example, FIG. 5 schematically illustrates elements of plasmids that provide for a screenable marker in plants. Transcription units depicted are components of $TUS_2$ in Arabidopsis.

The example shown in FIG. 5 depicts a transcription unit set which can be used to identify plant cells that have been transformed. The transcription unit set, abbreviated and shown in FIG. 5 as $TUS_2$, includes a single transcription unit, abbreviated and shown in FIG. 5 as $TU_{2-1}$.

Continuing this example for a portion of the plant transformation shown in FIG. 5 as an embodiment, $TU_{2-1}$ includes the nopaline synthase constitutive promoter (SEQ ID NO:28), the enhanced green fluorescence protein coding sequence modified to enhance fluorescence brightness and codon optimized for expression in *Arabidopsis* (SEQ ID NO:33), and the nopaline synthase terminator (SEQ ID NO:35), abbreviated and shown in FIG. 5 as NOS PROMOTER, EGFP, and NOS TERMINATOR, respectively.

As a specific example, subsequent steps in the plant transformation for creation of casein micelles in vivo in *Arabidopsis thaliana*, a plasmid including $TUS_1$ and $TUS_2$ can be introduced into *Arabidopsis thaliana* cotyledons using *Agrobacterium tumefaciens* and the FAST transient expression method. Seedlings are soaked in a solution containing *Agrobacterium* two days after germination which results in some cotyledon cells being transformed. Transformed *Arabidopsis* cells can be identified as containing the T-DNA by observing fluorescence exhibited by the enhanced green fluorescence protein. Successfully transformed *Arabidopsis* cells display green fluorescence while unsuccessfully transformed cells show little or no green fluorescence.

Also as a specific example of the in vivo formation of micelles in *Arabidopsis thaliana* as an embodiment, immunogold labeling techniques can be used to identify the location and morphology of the casein micelles formed in vivo. For this example for the in vivo formation of micelles as an embodiment, embryonic tissue can be obtained from *Arabidopsis thaliana* that has been transformed with a plasmid including $TUS_1$, and optionally $TUS_2$, shown in FIG. 4 and FIG. 5, respectively. The embryonic tissue can be treated with casein-specific antibodies using immunogold labeling techniques, and imaged with transmission electron microscopy to identify the location and morphology of the micelles formed in vivo. In tissue obtained from the transformed *Arabidopsis thaliana*, the casein micelles are visualized as gold-antibody labeled subcellular structures that range in size from 50 nm to 600 nm, which is similar to the size of bovine casein micelles. As a control, no casein micelles are visualized using immunogold labeling techniques in tissue obtained from untransformed *Arabidopsis thaliana*.

Continuing this specific example of the in vivo formation of micelles in *Arabidopsis thaliana* as an embodiment, protein extraction and high performance liquid chromatography (HPLC) analysis can be used to evaluate the protein composition of the casein micelles formed in vivo. In this example for the in vivo formation of micelles as an embodiment, embryonic tissue can be obtained from *Arabidopsis thaliana* that has been transformed with a plasmid including $TUS_1$, and optionally $TUS_2$, shown in FIG. 4 and FIG. 5, respectively. Proteins extracted from the embryonic tissue can be separated using HPLC and detected by ultraviolet absorbance. Proteins extracted from the transformed *Arabidopsis thaliana* tissue and subjected to HPLC analysis show peaks associated with each four proteins found in a casein micelle, including $\alpha S_1$ casein, $\alpha S_2$ casein, $\beta$ casein, and $\kappa$ casein, that display retention times similar to those reported by Bordin et al. for each of the four casein proteins found in bovine casein micelles. As a control, proteins extracted from the untransformed *Arabidopsis thaliana* tissue and subjected to HPLC analysis do not show peaks associated with any of the four casein proteins.

Further continuing this specific example of the in vivo formation of micelles in *Arabidopsis thaliana* as an embodiment, the amount of each casein protein found in micelles formed in vivo can be quantified by measuring the area under the peaks produced upon HPLC analysis. Quantification of the peaks produced upon HPLC analysis of proteins extracted from transformed *Arabidopsis thaliana* produces measurements showing that $\alpha S_1$ casein is the most abundant, followed by $\beta$ casein as the next most abundant, then $\alpha S_2$ casein and $\kappa$ casein as the least abundant casein proteins, which correlates to the relative abundances of each of the four casein proteins in bovine casein micelles as previously reported in the Handbook of Dairy Foods and Nutrition, Table 1.1.

Aspects of the disclosure can be further illustrated by a specific embodiment in which a casein micelle is assembled in vivo from its constituent proteins in soybean and further described in FIG. 6 through FIG. 9.

Figures 6, 7:
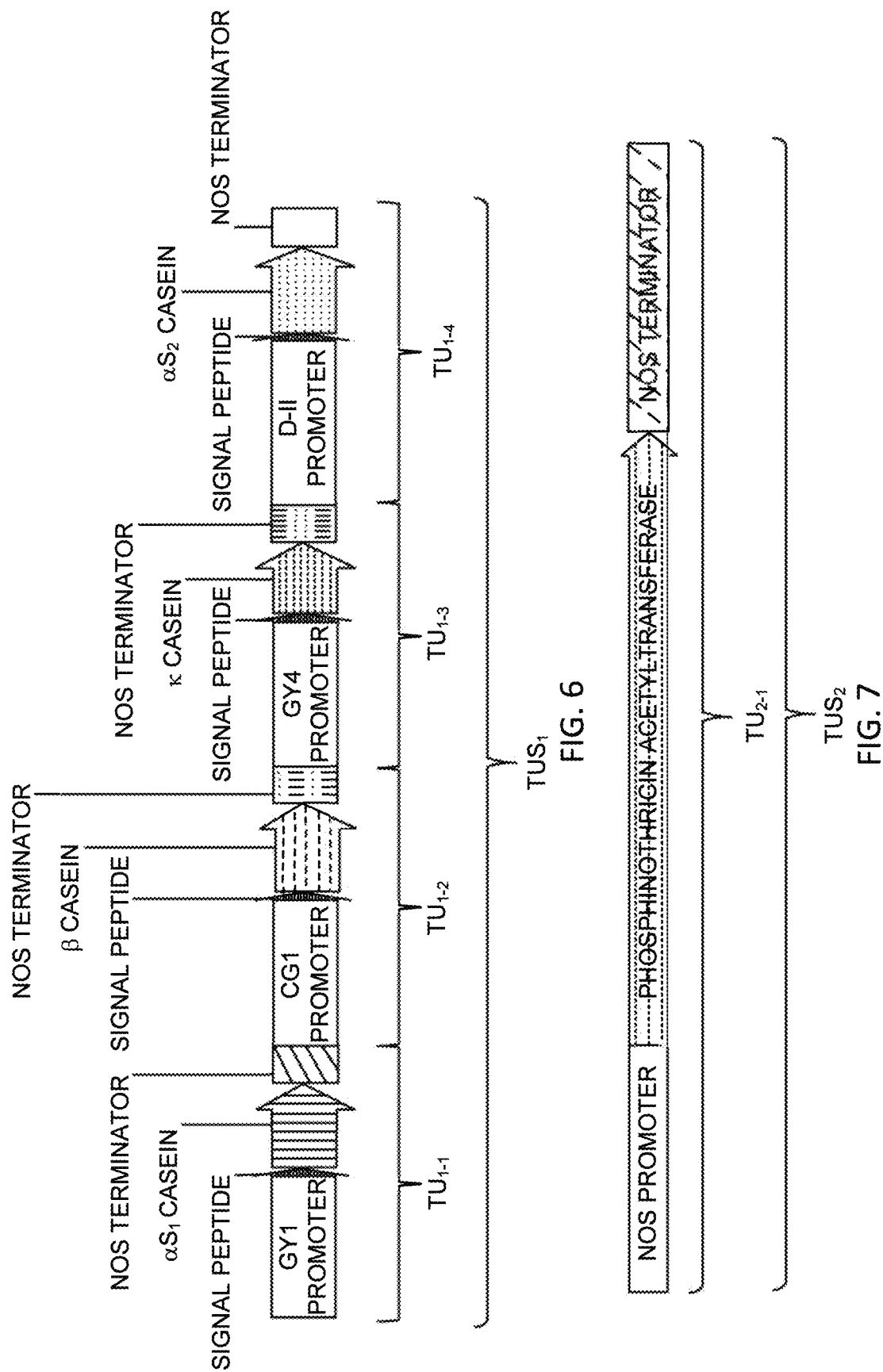
FIG. 6 is an example of a schematic illustration of a portion of a plasmid in soybean.
FIG. 7 is an example of a schematic illustration of a portion of a plasmid in soybean for herbicide resistance in plants.

Referring now to FIG. 6, therein is shown an example of a schematic illustration of a portion of a plasmid in soybean. As a specific example, FIG. 6 schematically illustrates elements of plasmids that encode micellar component proteins. Transcription units depicted are components of $TUS_1$ in soybean.

In this example, FIG. 6 depicts a transcription unit set which can be used for creation of casein micelles in vivo in soybean. The transcription unit set includes one transcription unit for each of the four casein proteins found in a casein micelle, abbreviated and shown in FIG. 4 as $TU_{1-1}$, $TU_{1-2}$, $TU_{1-3}$, and $TU_{1-4}$. The first transcription unit set is abbreviated and shown in FIG. 6 as $TUS_1$. Each of the four transcription units includes a promoter, a plant-derived N-terminal signal peptide, DNA encoding one of the four proteins found in a casein micelle, and a transcriptional terminator.

Continuing this example for a portion of the plant transformation shown in FIG. 6 as an embodiment, $TU_{1-1}$ includes a promoter from the soybean glycinin GY1 gene (SEQ ID NO:13), a signal peptide (SEQ ID NO:26), the $\alpha S_1$ casein coding sequence codon optimized for expression in soybean (SEQ ID NO:1), and the nopaline synthase terminator (SEQ ID NO:35), abbreviated and shown in FIG. 6 as GY1 PROMOTER, SIGNAL PEPTIDE, $\alpha S_1$ CASEIN, and NOS TERMINATOR, respectively.

Further continuing this example for a portion of the plant transformation shown in FIG. 6 as an embodiment, $TU_{1-2}$ includes the promoter from the soybean CG1 gene (SEQ ID NO:14), a signal peptide (SEQ ID NO:26), the $\beta$ casein coding sequence codon optimized for expression in soybean (SEQ ID NO:3), and the nopaline synthase terminator (SEQ ID NO:35), abbreviated and shown in FIG. 6 as CG1 PROMOTER, SIGNAL PEPTIDE, $\beta$ CASEIN, and NOS TERMINATOR, respectively.

Further continuing this example for a portion of the plant transformation shown in FIG. 6 as an embodiment, $TU_{1-3}$ includes the promoter from the soybean glycinin GY4 gene (SEQ ID NO:15), a signal peptide (SEQ ID NO:26), the $\kappa$ casein coding sequence codon optimized for expression in soybean (SEQ ID NO:2), and the nopaline synthase terminator (SEQ ID NO:35), abbreviated and shown in FIG. 6 as GY4 PROMOTER, SIGNAL PEPTIDE, $\kappa$ CASEIN, and NOS TERMINATOR, respectively.

Further continuing this example for a portion of the plant transformation shown in FIG. 6 as an embodiment, $TU_{1-4}$ includes the promoter from the soybean D-II Bowman-Birk proteinase isoinhibitor gene (SEQ ID NO:16), a signal peptide (SEQ ID NO:26), the $\alpha S_2$ casein coding sequence codon optimized for expression in soybean (SEQ ID NO:4), and the nopaline synthase terminator (SEQ ID NO:35), abbreviated and shown in FIG. 6 as D-II PROMOTER, SIGNAL PEPTIDE, $\alpha S_2$ CASEIN, and NOS TERMINATOR, respectively.

Referring now to FIG. 7, therein is shown an example of a schematic illustration of a portion of a plasmid in soybean for herbicide resistance in plants. As a specific example, FIG. 7 schematically illustrates elements of plasmids that provide for herbicide resistance in plants. Transcription units depicted are components of $TUS_2$ in soybean.

FIG. 7 is an example of a portion of the plant transformation that depicts a transcription unit set which can be used to select for plant cells that have been transformed. The transcription unit set abbreviated and shown in FIG. 7 as $TUS_2$ includes a single transcription unit abbreviated and shown in FIG. 7 as $TU_{2-1}$.

Continuing this example for a portion of the plant transformation shown in FIG. 7 as an embodiment, $TU_{2-1}$ includes nopaline synthase promoter (SEQ ID NO:28), the phosphinothricin acetyltransferase coding sequence codon optimized for expression in soybean (SEQ ID NO:34) which confers resistance to the herbicide glufosinate, and the nopaline synthase terminator (SEQ ID NO:35), abbreviated and shown in FIG. 7 as NOS PROMOTER, PHOSPHINO-THRICIN ACETYLTRANSFERASE, and NOS TERMINATOR, respectively.

Figure 8:
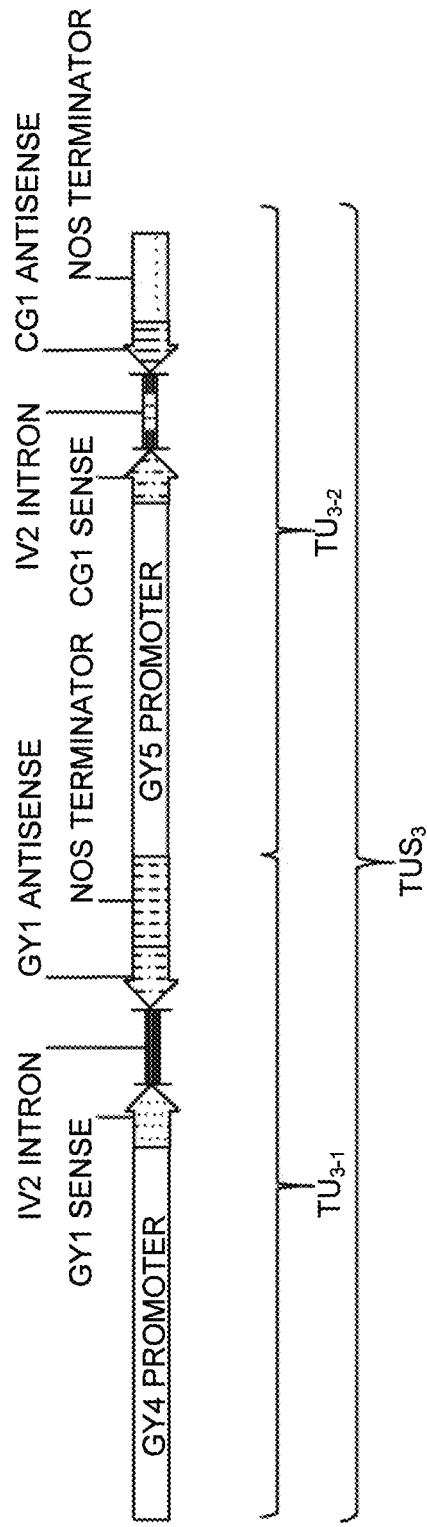
FIG. 8 is an example of a schematic illustration of a portion of the plasmid of FIG. 1 for soybean for suppression of native seed storage proteins in plants.

Referring now to FIG. 8, therein is shown an example of a schematic illustration of a portion of a plasmid in soybean for suppression of native seed storage proteins in plants. As a specific example, FIG. 8 schematically illustrates elements of plasmids that provide for suppression of native seed storage proteins in plants. Transcription units depicted are components of $TUS_3$ in soybean.

FIG. 8 is an example of a portion of the plant transformation that depicts a transcription unit set which can be used for enhancing the creation of casein micelles in vivo in soybean. The third transcription unit set abbreviated and shown in FIG. 8 as $TUS_3$ includes two transcription units abbreviated and shown in FIG. 8 as $TU_{3-1}$ and $TU_{3-2}$. The transcription of $TU_{3-1}$ and $TU_{3-2}$ produces RNA with a hairpin structure where the arms are homologous to a portion of a native soybean gene or gene family and are sufficient to cause down regulation of those native genes or gene families (not shown).

Continuing this example for a portion of the plant transformation shown in FIG. 8 as an embodiment, $TU_{3-1}$ includes a promoter from the soybean glycinin GY4 gene (SEQ ID NO:15), a portion of the soybean glycinin GY1 coding sequence that is lacking a start codon and is highly homologous among the glycinin gene family (SEQ ID NO:24), the potato IV2 intron (SEQ ID NO:25), the antisense of the soybean glycinin GY1 sequence (SEQ ID NO:17), and the nopaline synthase terminator (SEQ ID NO:35), abbreviated and shown in FIG. 8 as GY4 PROMOTER, GY1 SENSE, IV2 INTRON, GY1 ANTISENSE, and NOS TERMINATOR, respectively.

Further continuing this example for a portion of the plant transformation shown in FIG. 8 as an embodiment, $TU_{3-2}$ includes a promoter from the soybean glycinin GY5 gene (SEQ ID NO:18), a portion of the soybean β-conglycinin 1 coding sequence that is lacking a start codon and is highly homologous among the β-conglycinin gene family (SEQ ID NO:19), the potato IV2 intron (SEQ ID NO:25), the antisense of the soybean β-conglycinin 1 sequence (SEQ ID NO:20), and the nopaline synthase terminator (SEQ ID NO:35), abbreviated and shown in FIG. 8 as GY5 PROMOTER, CG1 SENSE, IV2 INTRON, CG1 ANTISENSE, and NOS TERMINATOR, respectively.

Figure 9:
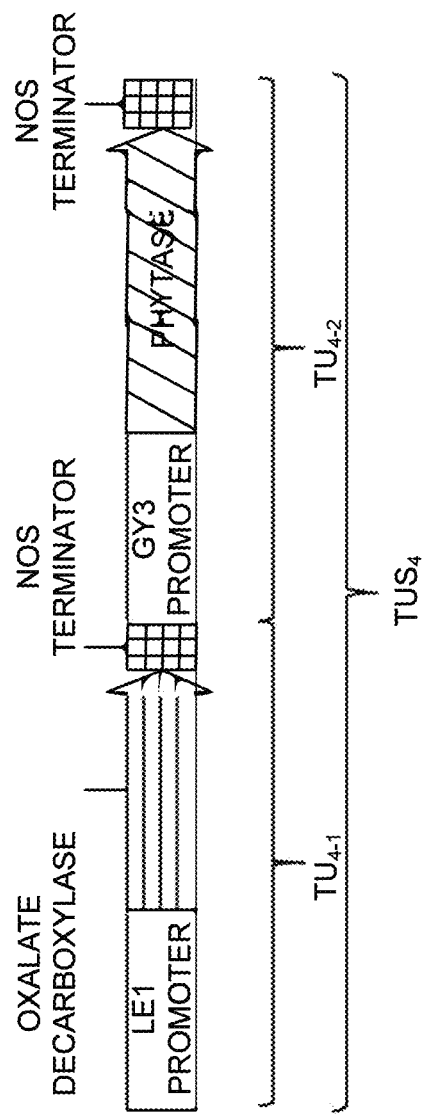
FIG. 9 is an example of a schematic illustration of a portion of a plasmid for soybean to regulate intracellular concentrations of minerals which can enhance micelle formation.

Referring now to FIG. 9, therein is shown an example of a schematic illustration of a portion of a plasmid in soybean for regulating cytoplasmic concentrations of minerals which can enhance micelle formation. As a specific example, FIG. 9 schematically illustrates elements of plasmids that regulate cytoplasmic concentrations of minerals which can enhance micelle formation. Transcription units depicted are components of $TUS_4$ in soybean.

FIG. 9 is an example of a portion of the plant transformation that depicts a transcription unit set which can be used for enhancing the creation of casein micelles in vivo in soybean. The fourth transcription unit set abbreviated and shown in FIG. 9 as $TUS_4$ includes two transcription units abbreviated and shown in FIG. 9 as $TU_{4-1}$ and $TU_{4-2}$. Proteins encoded by $TU_{4-1}$ and $TU_{4-2}$ alter the intracellular environment in a manner that optimizes the formation of micelles in vivo.

Continuing this example for a portion of the plant transformation shown in FIG. 9 as an embodiment, $TU_{4-1}$ includes a promoter from the soybean LE1 gene (SEQ ID NO:23), a coding sequence for oxalate decarboxylase from *Flammulina velutipes* codon optimized for expression in soybean (SEQ ID NO:12), and nopaline synthase terminator (SEQ ID NO:35), abbreviated and shown in FIG. 9 as LE1 PROMOTER, OXALATE DECARBOXYLASE CDS, and NOS TERMINATOR, respectively.

Further continuing this example for a portion of the plant transformation shown in FIG. 9 as an embodiment, $TU_{4-2}$ includes the glycinin GY3 promoter (SEQ ID NO:30), the coding sequence for a soybean phytase enzyme (SEQ ID NO:11), and the nopaline synthase terminator (SEQ ID NO:35), abbreviated and shown in FIG. 9 as GY3 PROMOTER, PHYTASE, and NOS TERMINATOR, respectively.

In this example, subsequent steps in the plant transformation for creation of casein micelles in vivo in soybean, a plasmid including $TUS_1$, $TUS_2$, and optionally $TUS_3$, and optionally $TUS_4$, shown in FIG. 6, FIG. 7, FIG. 8, and FIG. 9, respectively, can be introduced into soybean callus using standard biolistic transformation methods. Transformed soybean plants can be selected on a medium containing glufosinate herbicide, and the genomes of transformed soybean plants can be screened for insertion of the plasmid using standard PCR mapping methods. Transformed soybean plants including $TUS_1$, $TUS_2$, and optionally $TUS_3$, and optionally $TUS_4$ in their genome can be transferred to a greenhouse for seed production.

In the example of the in vivo formation of micelles in soybean as an embodiment, immunogold labeling techniques can be used to identify the location and morphology of the casein micelles formed in vivo. As it relates to this example for the in vivo formation of micelles as an embodiment, tissue can be obtained from soybean plants that have been transformed with a plasmid including $TUS_1$, $TUS_2$, and optionally $TUS_3$, and optionally $TUS_4$, shown in FIG. 6, FIG. 7, FIG. 8, and FIG. 9, respectively. The tissue can be treated with casein-specific antibodies using standard immunogold labeling techniques, and imaged with transmission electron microscopy to identify the location and morphology of the micelles formed in vivo. In tissue obtained from the transformed soybean plants, the casein micelles are visualized as gold-antibody labeled subcellular structures that range in size from 50 nm to 600 nm, which is similar to the size of bovine casein micelles. As a control, no casein micelles are visualized using immunogold labeling techniques in tissue obtained from untransformed soybean plants.

Continuing this example of the in vivo formation of micelles in soybean as an embodiment, protein extraction and polyacrylamide gel electrophoresis analysis can be used to evaluate the protein composition of the casein micelles formed in vivo. For this example for the in vivo formation of micelles as an embodiment, tissue can be obtained from soybean plants that have been transformed with a plasmid including $TUS_1$, $TUS_2$, and optionally $TUS_3$, and optionally $TUS_4$, shown in FIG. 6, FIG. 7, FIG. 8, and FIG. 9, respectively. Proteins extracted from the transformed soybean plant tissue and subjected to polyacrylamide gel electrophoresis analysis show bands on the polyacrylamide gel corresponding in size to each of the four casein proteins found in a casein micelle, including $\alpha S_1$ casein, $\alpha S_2$ casein, R casein, and κ casein. As a control, proteins extracted from untransformed soybean plant tissue and subjected to polyacrylamide gel electrophoresis analysis do not show bands on the polyacrylamide gel corresponding to the four casein proteins.

Further continuing this example of the in vivo formation of micelles in soybean as an embodiment, protein extraction and HPLC analysis can be used to evaluate the protein composition of the casein micelles formed in vivo. For this example for the in vivo formation of micelles as an embodiment, tissue can be obtained from soybean plants that have been transformed with a plasmid including $TUS_1$, $TUS_2$, and optionally $TUS_3$, and optionally $TUS_4$, shown in FIG. 6, FIG. 7, FIG. 8, and FIG. 9, respectively. Proteins extracted from the transformed soybean plant tissue can be separated using HPLC and detected by ultraviolet absorbance. Proteins extracted from the transformed soybean plant tissue and subjected to HPLC analysis show peaks associated with each four proteins found in a casein micelle, including $\alpha S_1$ casein, $\alpha S_2$ casein, β casein, and κ casein, that display retention times similar to those reported by Bordin et al. for each of the four casein proteins found in bovine casein micelles. As a control, proteins extracted from the untransformed soybean plant tissue and subjected to HPLC analysis do not show peaks associated with the four casein proteins.

Further continuing this example of the in vivo formation of micelles in soybean as an embodiment, the amount of each casein protein found in micelles formed in vivo can be quantified by measuring the area under the peaks produced upon HPLC analysis. Quantification of the peaks produced upon HPLC analysis of proteins extracted from transformed soybean plant tissue produces measurements showing that $\alpha S_1$ casein is the most abundant, followed by β casein as the next most abundant, then $\alpha S_2$ casein and κ casein as the least abundant casein proteins, which correlates to the relative abundances of each of the four casein proteins in bovine casein micelles as previously reported in the Handbook of Dairy Foods and Nutrition, Table 1.1.

Further continuing this example of the in vivo formation of micelles in soybean as an embodiment, RNA analysis can be used to evaluate the suppression of native soybean seed genes during the formation of casein micelles in vivo. For this example for the in vivo formation of micelles as an embodiment, soybean plants that have been transformed with a plasmid including $TUS_1$, $TUS_2$, $TUS_3$, and optionally $TUS_4$, shown in FIG. 6, FIG. 7, FIG. 8, and FIG. 9, respectively, can be grown to the flowering stage in a greenhouse and soybean embryos removed from the flowering seed pods at 35 days using standard dissection techniques. The expression levels of native soybean seed genes can be analyzed using standard techniques for RNA extraction and sequencing. RNA analysis of the embryos from transformed soybean plants show at least a 10% reduction in the expression of one or more of the native soybean seed genes, including genes in the glycinin family (Glyma.03g163500, Glyma.19g164900, Glyma.10g037100, Glyma.13g123500, Glyma.19g164800) and genes in the β-conglycinin family (Glyma.10g246300, Glyma.20g148400, Glyma.20g148300, Glyma.20g146200, Glyma.20g148200, Glyma.10g246500, Glyma.10g028300, Glyma.02g145700). As a control, RNA analysis of embryos from untransformed soybean plants do not show a reduction in the expression of native soybean seed genes.

Further continuing this example of the in vivo formation of micelles in soybean as an embodiment, commercially available assays and X-ray fluorescence techniques can be used to evaluate calcium oxalate levels during the formation of casein micelles in vivo. As it relates to this example for the in vivo formation of micelles as an embodiment, soybean plants that have been transformed with a plasmid including $TUS_1$, $TUS_2$, and optionally $TUS_3$, and $TUS_4$, shown in FIG. 6, FIG. 7, FIG. 8, and FIG. 9, respectively, can be grown to the flowering stage in a greenhouse and soybean embryos removed from the flowering seed pods at 27 days using standard dissection techniques. The oxalate concentration can be measured using commercially available assays, and the calcium concentration can be measured using X-ray fluorescence. Embryos from transformed soybean plants show at least a 5% reduction in oxalate concentration and at least a 4% increase in calcium concentration as compared to control embryos from untransformed soybean plants, indicating that embryos from transformed soybean plants have at least 4% more available calcium compared to embryos from untransformed soybean plants.

Further continuing this example of the in vivo formation of micelles in soybean as an embodiment, commercially available assays can be used to evaluate phosphate levels during the formation of casein micelles in vivo. As it relates to this example for the in vivo formation of micelles as an embodiment, soybean plants that have been transformed with a plasmid including $TUS_1$, $TUS_2$, and optionally $TUS_3$, and $TUS_4$, shown in FIG. 6, FIG. 7, FIG. 8, and FIG. 9., respectively, can be grown to the flowering stage in a greenhouse and soybean embryos removed from the flowering seed pods at 27 days using standard dissection techniques. Embryos can be ground with a mortar and pestle, sonicated and centrifuged to produce a supernatant that can be tested for phosphatase levels using commercially available assays. Embryos from transformed soybean plants show at least a 5% increase in phosphatase levels as compared to control embryos from untransformed soybean plants, indicating that embryos from transformed soybean plants have at least 5% more available phosphate compared to embryos from untransformed soybean plants.

Figure 10:
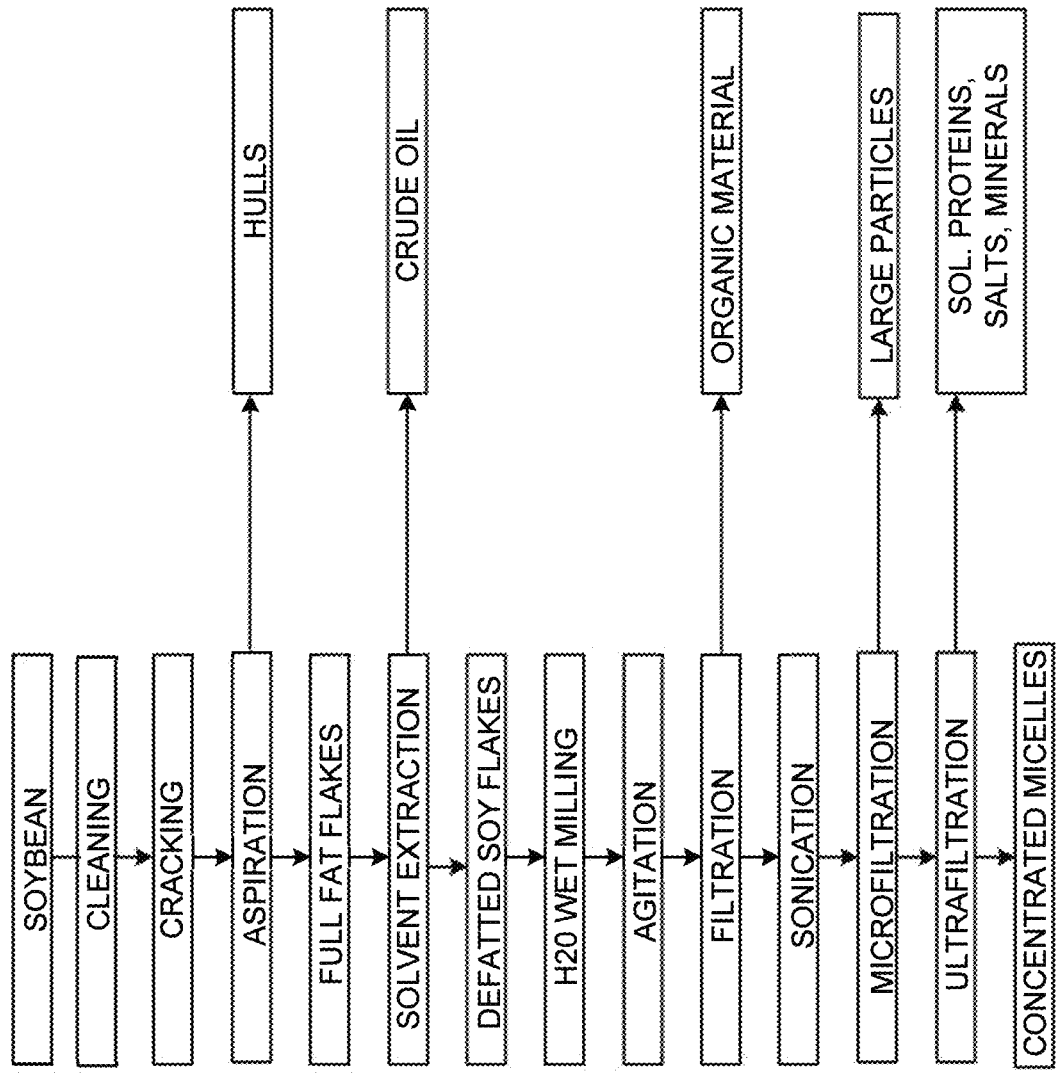
FIG. 10 is an example of a flow for the purification of micelles formed in vivo in soybean.

Aspects of the disclosure can be further illustrated by a specific embodiment in which micelles produced in vivo are purified as further described in FIG. 10.

Referring now to FIG. 10, therein is shown an example of a flow for the purification of micelles formed in vivo in soybean. Also, the flow in FIG. 10 is an example of isolating a recombinant micelle. Further in this example, FIG. 10 depicts a process where casein micelles produced in soybeans are purified from the plant tissue in a way that the micelles are still functional after the purification. The input material for the purification process is dried soybeans harvested from plants that have been transformed with a plasmid containing all four transcription unit sets, $TUS_1$, $TUS_2$, $TUS_3$, and $TUS_4$, described in FIG. 6, FIG. 7, FIG. 8, and FIG. 9, respectively. The input material for the purification process is shown in FIG. 10 and depicted as a rectangle enclosing the word "SOYBEAN".

Continuing this example of the purification of micelles formed in vivo in soybean as an embodiment, the hulls are removed from the dried soybeans in a series of steps including cleaning, cracking, and aspiration, shown in FIG. 10 and depicted as rectangles enclosing the words "CLEANING", "CRACKING" and "ASPIRATION". In this embodiment, the hulls do not contain useful amounts of casein micelles and are discarded, shown in FIG. 10 and depicted as an arrow pointing to a rectangle enclosing the word "HULLS".

Further continuing this example of the purification of micelles formed in vivo in soybean as an embodiment, the remaining material is flaked to increase the surface area and allow for faster aqueous or solvent infiltrations. The resulting flaked material is shown in FIG. 10 and depicted as a rectangle enclosing the words "FULL FAT FLAKES".

Further continuing this example of the purification of micelles formed in vivo in soybean as an embodiment, the flaked material is then defatted with hexane using standard defatting equipment and solvent extraction techniques, shown in FIG. 10 and depicted as a rectangle enclosing the words "SOLVENT EXTRACTION". Defatting can occur using any standard hexane based solvent, followed by desolventizing using flash or vapor-based processes. The resulting oil is removed, shown in FIG. 10 and depicted as an arrow pointing to a rectangle enclosing the words "CRUDE OIL", leaving behind the defatted flakes, shown in FIG. 10 and depicted as an arrow pointing to a rectangle enclosing the words "DEFATTED SOY FLAKES".

Further continuing this example of the purification of micelles formed in vivo in soybean as an embodiment, the defatted flakes are then mixed with water and wet milled, shown in FIG. 10 and depicted as an arrow pointing to a rectangle enclosing the words "H2O WET MILLING". The milling process pulverizes the defatted flakes which releases the casein micelles and allows the micelles to come into contact with an aqueous medium. In addition to the milling process, the defatted flakes are also vigorously agitated to assist in the release of casein micelles into the water, shown in FIG. 10 and depicted as an arrow pointing to a rectangle enclosing the word "AGITATION". The milling process and vigorous agitation of the defatted flakes yields a slurry where soybean material has been finely ground and many of the casein micelles have been released into suspension in the water (not shown). Additionally, many other proteins and carbohydrates are also dissolved in the water (not shown). In some embodiments, wet milling is done using perforated disc or colloid continuous flow mills.

Further continuing this example of the purification of micelles formed in vivo in soybean as an embodiment, the slurry is fed through a series of mesh screens to remove larger particles from the casein micelles, shown in FIG. 10 and depicted as an arrow pointing to a rectangle enclosing the word "FILTRATION". In this embodiment, the slurry is first passed through a screen with 5 mm sieve openings (not shown), and then is passed through a screen with 0.5 mm sieve openings (not shown). The material trapped by the screens is discarded, shown in FIG. 10 and depicted as an arrow pointing to a rectangle enclosing the words "ORGANIC MATERIAL".

Further continuing this example of the purification of micelles formed in vivo in soybean as an embodiment, the remaining material in the slurry that passed through both screens is then sonicated to break up aggregates of casein micelles such that the majority of micelles are not contacting other micelles, shown in FIG. 10 and depicted as an arrow pointing to a rectangle enclosing the word "SONICATION". In some embodiments, continuous flow sonication with multiple sonicators in parallel are used to maximize flow rates.

Further continuing this example of the purification of micelles formed in vivo in soybean as an embodiment, after sonication the slurry is passed through a 2 µm microfiltration unit to eliminate larger particles while allowing casein micelles to pass through, shown in FIG. 10 and depicted as an arrow pointing to a rectangle enclosing the word "MICROFILTRATION". The material trapped by the microfiltration unit is discarded, shown in FIG. 10 and depicted as an arrow pointing to a rectangle enclosing the words "LARGE PARTICLES". The remaining material that passed through the microfiltration unit is largely composed of casein micelles as well as dissolved proteins, salts and carbohydrates (not shown).

Further continuing this example of the purification of micelles formed in vivo in soybean as an embodiment, the material that passed through the microfiltration unit is then processed with an ultrafiltration unit that allows dissolved molecules lower than 100 nm in diameter to pass through while retaining casein micelles, shown in FIG. 10 and depicted as an arrow pointing to a rectangle enclosing the words "ULTRAFILTRATION". In some embodiments, continuous flow ultrafiltration with multiple filters in parallel are used to maximize flow rates. The soluble proteins, salts and minerals that passed through the ultrafiltration unit are discarded, shown in FIG. 10 and depicted as an arrow pointing to a rectangle enclosing the words "SOL. PROTEINS, SALTS, MINERALS".

Further continuing this example of the purification of micelles formed in vivo in soybean as an embodiment, the final output from this process is an aqueous liquid where the most common component after water is casein micelles, shown in FIG. 10 and depicted as an arrow pointing to a rectangle enclosing the words "CONCENTRATED MICELLES". These micelles (not shown) retain their shape and function such that they can be used in downstream processes such as in making synthetic milk or cheese.

As additional examples for FIG. 10, a method of isolating recombinant micelles from a seed of a plant produced can include cleaning, and deshelling or dehulling seeds, flaking cleaned seeds to 0.005-0.02 inch thickness, solvent extraction of oil from the flake, desolventizing the flake without cooking and collecting the defatted, clean flake, separating micelles into an aqueous slurry by hydrating, agitating and wet milling the flake, passing the slurry through a series of mesh screens to remove particulate above 0.5 mm in size and collecting the permeate, sonication of the permeate from previous step, microfiltration of the product from previous step to remove particulate above 2 um in size, ultrafiltration of the permeate from previous step using a device that allows particles >100 nm in diameter to pass through in the ultrafiltration permeate, collecting the retentate of previous step which contains concentrated recombinant micelles.

Continuing with this example, the method of isolating recombinant micelles from a seed further includes centrifuging the retentate of a previous step to separate the micelles from the remainder of the retentate. Also the method continues from the ultrafiltration step to passing the slurry through an ultrafiltration device and collecting a permeate containing protein and other molecules and a retentate containing micelles and thereafter adding a diafiltration fluid to the retentate at substantially the same rate that the permeate is collected and passing said retentate through the ultrafiltration device. Yet further the method continues where the seed is milled from at least one plant selected from the group of plants consisting of maize, rice, sorghum, cowpeas, soybeans, cassava, coyam, sesame, peanuts, peas, cotton and yams.

The resulting method, process, apparatus, device, product, and system is cost-effective, highly versatile, and accurate, and can be implemented by adapting components for ready, efficient, and economical manufacturing, application, production, and utilization. Another important aspect of an embodiment of the present disclosure is that it valuably supports and services the historical trend of reducing costs, simplifying systems, and increasing yield.

Construction of Expression Plasmids for Plant Transformation

Figure 11:
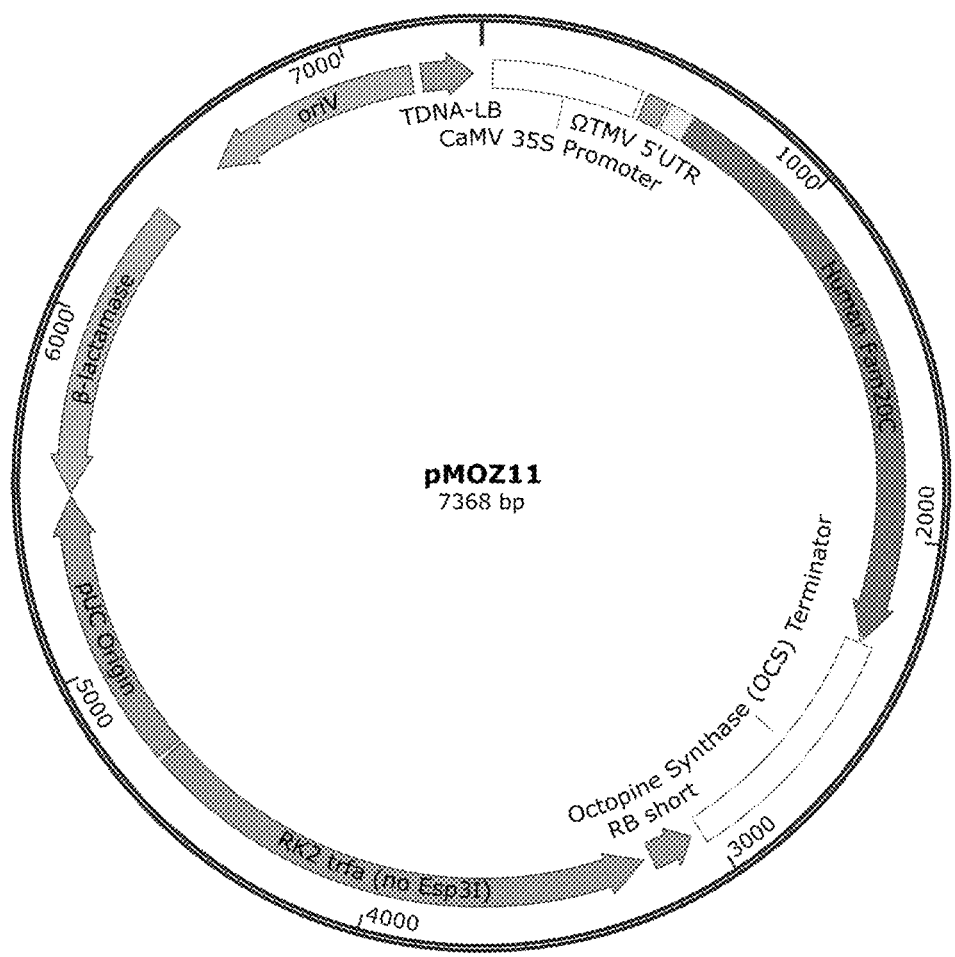
FIG. 11 shows an example of an expression plasmid for the production of kinase proteins in plants.
Figure 18:
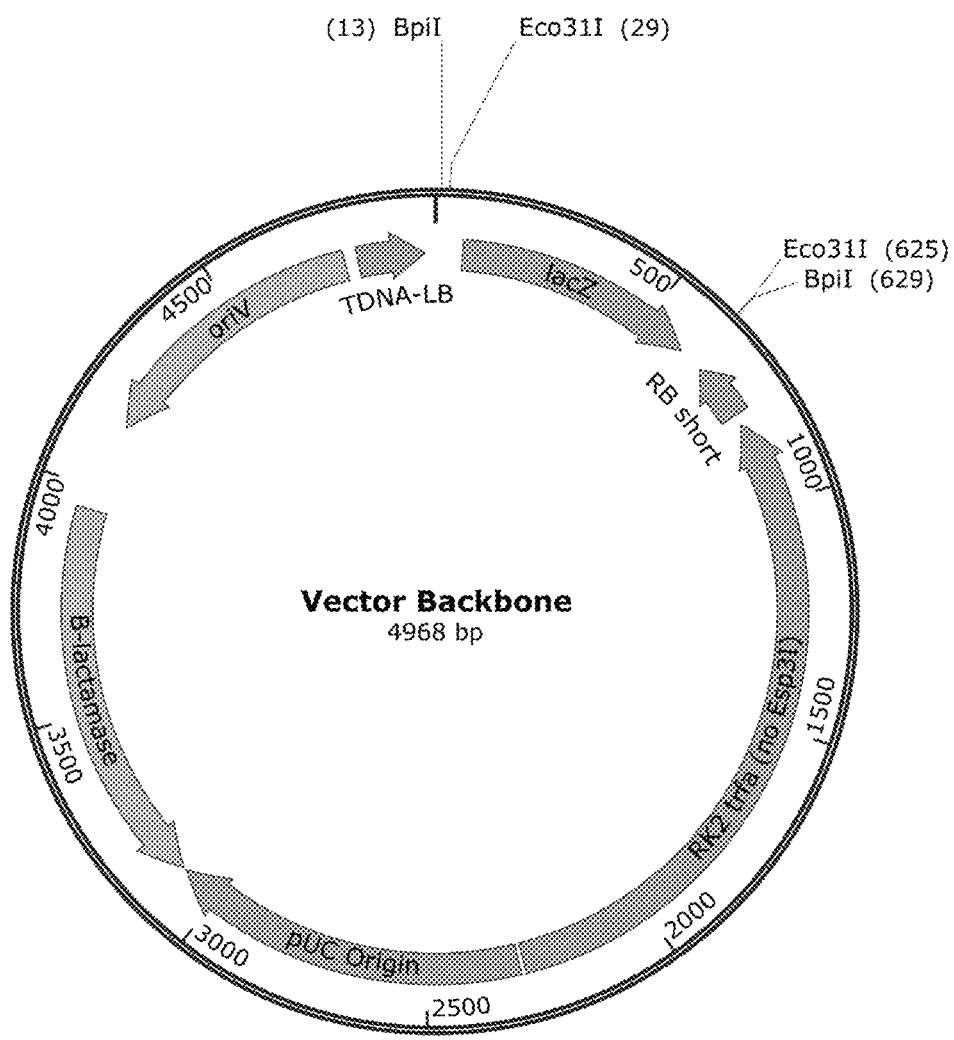
FIG. 18 shows a map of a vector backbone including a nucleic acid sequence encoding a β-lactamase.

Referring now to FIG. 11, therein is shown an example of a pMOZ vector backbone [SEQ ID NO:60], which is an example vector backbone used to construct expression plasmids for the production of casein and kinases in plants. As a specific example, FIG. 18 is a map of a vector backbone including a nucleic acid sequence encoding a β-lactamase conferring resistance to carbenicillin that allows for the plasmid to be selected for in *E. coli*, a first origin of replication (pUC on) [SEQ ID NO:61] that allows for the plasmid to be propagated in *E. coli*, and a second origin of replication (oriV) [SEQ ID NO:62] that allows for the plasmid to be propagated in either *E. coli* or *Agrobacterium*. In this way, expression plasmids can be assembled using standard cloning methods in bacteria and then transferred to *Agrobacterium* for transformation into plants.

Continuing this example, the vector backbone further includes two Eco31I restriction sites that allow for cloning of a single expression cassette into the vector backbone using standard GoldenGate or MoClo methods, an identification nucleic acid sequence encoding the lacZ gene (lacZ) [SEQ ID NO:63] to aid in the identification of correct clones through *E. coli* colony blue/white screening. The Eco31I sites are flanked by a left border repeat (LB) and a right border repeat (RB) from nopaline C58 T-DNA [SEQ ID NO:64] that are recognized by *Agrobacterium* and allow for an expression cassette to be transformed into plant cells and integrated into the plant host genome.

Referring now to FIG. 11, therein is shown an example of an expression plasmid for the production of kinase proteins in plants constructed using the vector backbone using standard GoldenGate or MoClo methods. As a specific example, FIG. 11 is a map of a pMOZ11 expression plasmid, which is an example expression plasmid for the production of recombinant *H. sapiens* Fam20C in plants. Continuing this example, the pMOZ11 expression plasmid includes a 1674 bp nucleic acid sequence encoding *H. sapiens* Fam20C (HsFam20C) [SEQ ID NO:66] that had been synthesized using only coding sequences from the original *H. sapiens* Fam20A gene and was codon optimized for expression in plants using *Nicotiana benthamiana* as the model expression system, operatively linked to a 426 bp sequence encoding the promoter Cauliflower Mosaic Virus 35S promoter (CaMV 35S Promoter) [SEQ ID NO:42], a 62 bp translational enhancer encoding the omega leader sequence of the Tobacco Mosaic Virus (Ω TMV 5UTR) [SEQ ID NO:68], a 57 bp nucleic acid sequence encoding the *Arabidopsis thaliana* ARA12 signal peptide gene (ARA12 Signal Peptide) [SEQ ID NO:71] for localizing the recombinant protein to the endoplasmic reticulum of the plant cell, and a 15 bp sequence coding for the endoplasmic reticulum retention peptide HDEL [SEQ ID NO:65]. PMOZ11 was assembled using the enzyme Eco31I and standard GoldenGate protocols. The resulting plasmid was transformed into *E. coli* and later purified using a standard miniprep protocol. Sanger sequencing was used to verify the correct assembly of the plasmid.

Figure 12:
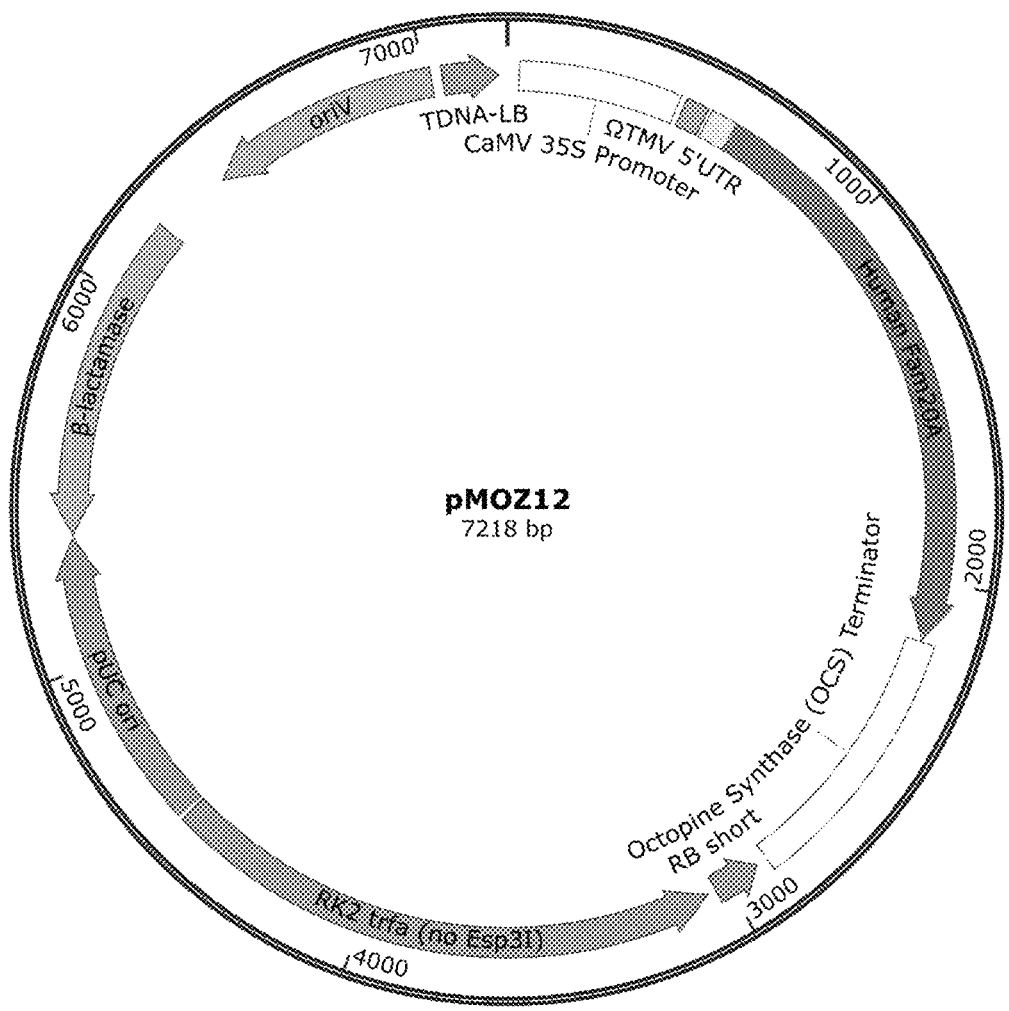
FIG. 12 shows a map of a pMOZ12 expression plasmid, which is an example expression plasmid for the production of recombinant *H. sapiens* Fam20A in plants.

As another specific example, FIG. 12 is a map of a pMOZ12 expression plasmid, which is an example expression plasmid for the production of recombinant *H. sapiens* Fam20A in plants. Continuing this example, the pMOZ12 expression plasmid includes a 1524 bp nucleic acid sequence encoding *H. sapiens* Fam20A (HsFam20A) [SEQ ID NO:67] that had been synthesized using only coding sequences from the original *H. sapiens* Fam20A gene and was codon optimized for expression in plants using *Nicotiana benthamiana* as the model expression system, operatively linked to a 426 bp sequence encoding the promoter Cauliflower Mosaic Virus 35S promoter (CaMV 35S Promoter) [SEQ ID NO:42], a 62 bp translational enhancer encoding the omega leader sequence of the Tobacco Mosaic Virus (Ω TMV 5UTR) [SEQ ID NO:68], a 57 bp nucleic acid sequence encoding the *Arabidopsis thaliana* ARA12 signal peptide gene (ARA12 Signal Peptide) [SEQ ID NO:71] for localizing the recombinant protein to the endoplasmic reticulum of the plant cell, and a 15 bp sequence coding for the endoplasmic reticulum retention peptide HDEL [SEQ ID NO:65]. PMOZ12 was assembled using the enzyme Eco31I and standard GoldenGate protocols. The resulting plasmid was transformed into *E. coli* and later purified using a standard miniprep protocol. Sanger sequencing was used to verify the correct assembly of the plasmid.

Figure 13:
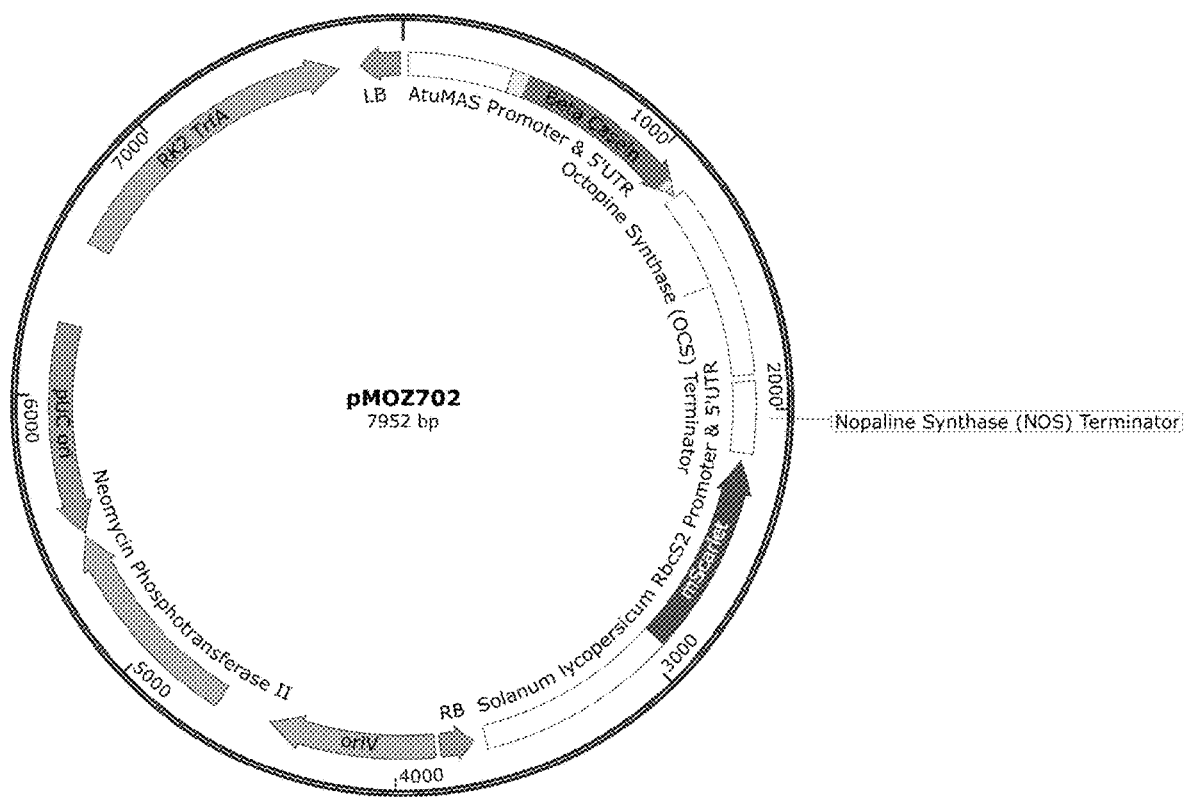
FIG. 13 shows a map of a pMOZ702 expression plasmid, which is an example expression plasmid for the production of recombinant *B. taurus* Beta Casein in plants.

As another specific example, FIG. 13 is a map of a pMOZ702 expression plasmid, which is an example expression plasmid for the production of recombinant *B. taurus* Beta Casein in plants. Continuing this example, the pMOZ702 expression plasmid includes a 627 bp nucleic acid sequence encoding *B. taurus* β-casein [SEQ ID NO:77] that had been synthesized and was codon optimized for expression in plants using *Nicotiana benthamiana* as the model expression system, operatively linked to a 383 bp sequence encoding the promoter *A. tumefaciens* Mannopine Synthase promoter (AtuMAS Promoter) [SEQ ID NO:70], a 63 bp nucleic acid sequence encoding the *Arabidopsis thaliana* S2S signal peptide (AtS2S Signal Peptide) [SEQ ID NO:72] for localizing the recombinant protein to the endoplasmic reticulum of the plant cell, and a 63 bp sequence coding for an HA peptide tag, a 6× histidine peptide tag, and an endoplasmic reticulum retention peptide HDEL [SEQ ID NO:73]. These sequences code for a protein containing a signal peptide, beta casein, HA tag, 6 histidine tag, and HDEL peptide [SEQ ID NO:81]. The plasmid also contains a 732 bp nucleic acid sequence coding for the mScarlet fluorescent protein [SEQ ID NO: 75] that had been synthesized and was codon optimized for expression in plants using *Nicotiana benthamiana* as the model expression system, operatively linked to a 739 bp sequence encoding the *S. lycopersicum* RbcS2 promoter (SlRbcS2 Promoter) [SEQ ID NO: 59], and a 263 bp sequence encoding the *A. tumefaciens* Nopaline Synthase Terminator (NOS Terminator) [SEQ ID NO: 76]. pMOZ702 was assembled using the enzyme BpiI and standard GoldenGate protocols. The resulting plasmid was transformed into *E. coli* and later purified using a standard miniprep protocol. Sanger sequencing was used to verify the correct assembly of the plasmid.

Figure 14:
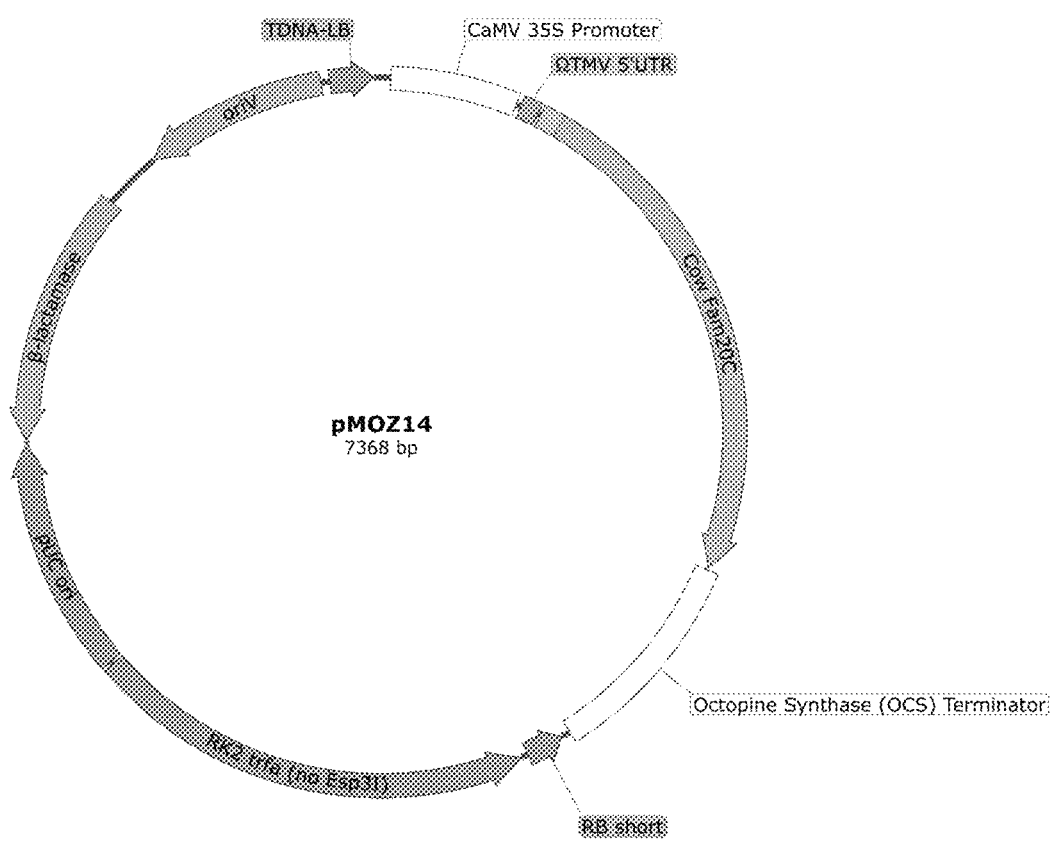
FIG. 14 shows a map of a pMOZ14 expression plasmid, which is an example expression plasmid for the production of recombinant *B. taurus* Fam20C in plants.

As another specific example, FIG. 14 is a map of a pMOZ14 expression plasmid, which is an example expression plasmid for the production of recombinant *B. taurus* Fam20C in plants. Continuing this example, the pMOZ14 expression plasmid includes a 1674 bp nucleic acid sequence encoding *B. taurus* Fam20C (BtFam20C) [SEQ ID NO:68] that had been synthesized using only coding sequences from the original *B. taurus* Fam20C gene and was codon optimized for expression in plants using *Nicotiana benthamiana* as the model expression system, operatively linked to a 426 bp sequence encoding the promoter Cauliflower Mosaic Virus 35S promoter (CaMV 35S Promoter) [SEQ ID NO:42], a 62 bp translational enhancer encoding the omega leader sequence of the Tobacco Mosaic Virus (Ω TMV 5UTR) [SEQ ID NO:58], a 57 bp nucleic acid sequence encoding the *Arabidopsis thaliana* ARA12 signal peptide gene (ARA12 Signal Peptide) [SEQ ID NO:71] for localizing the recombinant protein to the endoplasmic reticulum of the plant cell, and a 15 bp sequence coding for the endoplasmic reticulum retention peptide HDEL [SEQ ID NO:65]. PMOZ14 was assembled using the enzyme Eco31I and standard GoldenGate protocols. The resulting plasmid was transformed into *E. coli* and later purified using a standard miniprep protocol. Sanger sequencing was used to verify the correct assembly of the plasmid.

Figure 15:
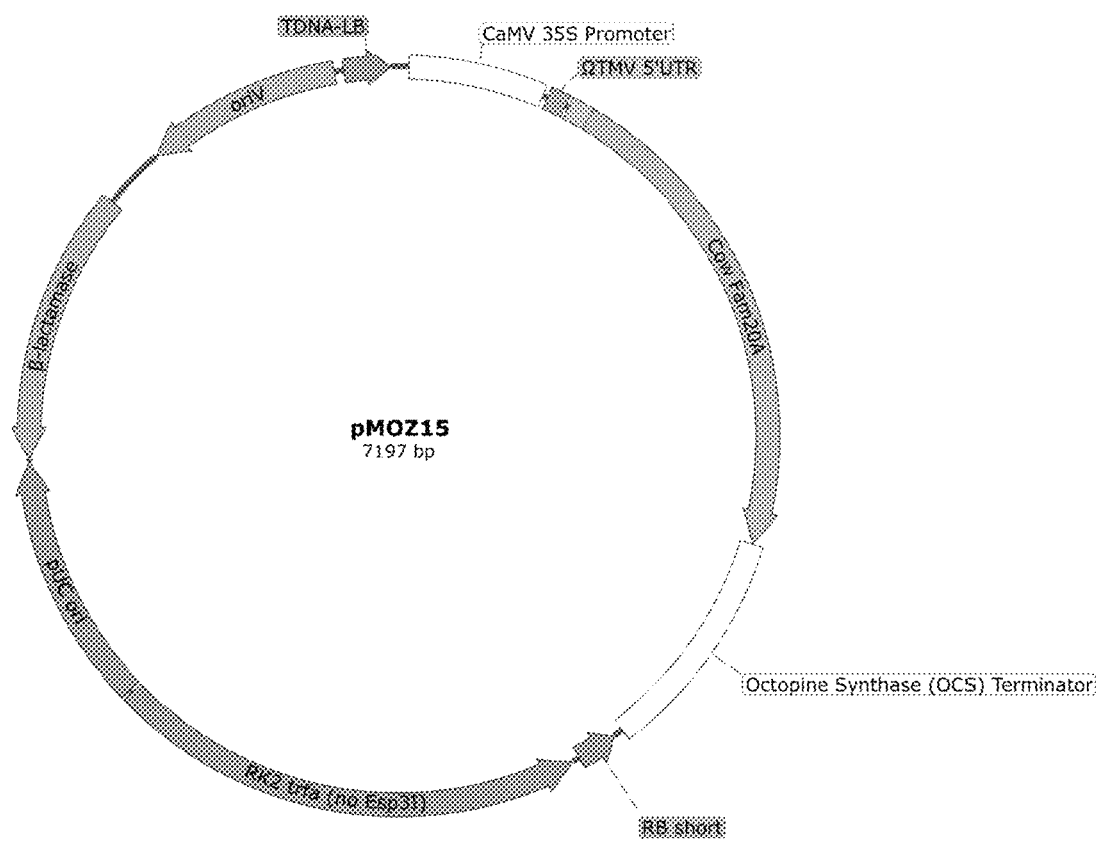
FIG. 15 shows a map of a pMOZ15 expression plasmid, which is an example expression plasmid for the production of recombinant *B. taurus* Fam20A in plants.

As another specific example, FIG. 15 is a map of a pMOZ15 expression plasmid, which is an example expression plasmid for the production of recombinant *B. taurus* Fam20A in plants. Continuing this example, the pMOZ15 expression plasmid includes a 1503 bp nucleic acid sequence encoding *B. taurus* Fam20A (BtFam20A) [SEQ ID NO:69] that had been synthesized using only coding sequences from the original *B. taurus* Fam20A gene and was codon optimized for expression in plants using *Nicotiana benthamiana* as the model expression system, operatively linked to a 426 bp sequence encoding the promoter Cauliflower Mosaic Virus 35S promoter (CaMV 35S Promoter) [SEQ ID NO:42], a 62 bp translational enhancer encoding the omega leader sequence of the Tobacco Mosaic Virus (Ω TMV 5UTR) [SEQ ID NO:58], a 57 bp nucleic acid sequence encoding the *Arabidopsis thaliana* ARA12 signal peptide gene (ARA12 Signal Peptide) [SEQ ID NO:71] for localizing the recombinant protein to the endoplasmic reticulum of the plant cell, and a 15 bp sequence coding for the endoplasmic reticulum retention peptide HDEL [SEQ ID NO:65]. PMOZ15 was assembled using the enzyme Eco31I and standard GoldenGate protocols. The resulting plasmid was transformed into *E. coli* and later purified using a standard miniprep protocol. Sanger sequencing was used to verify the correct assembly of the plasmid.

Figure 16:
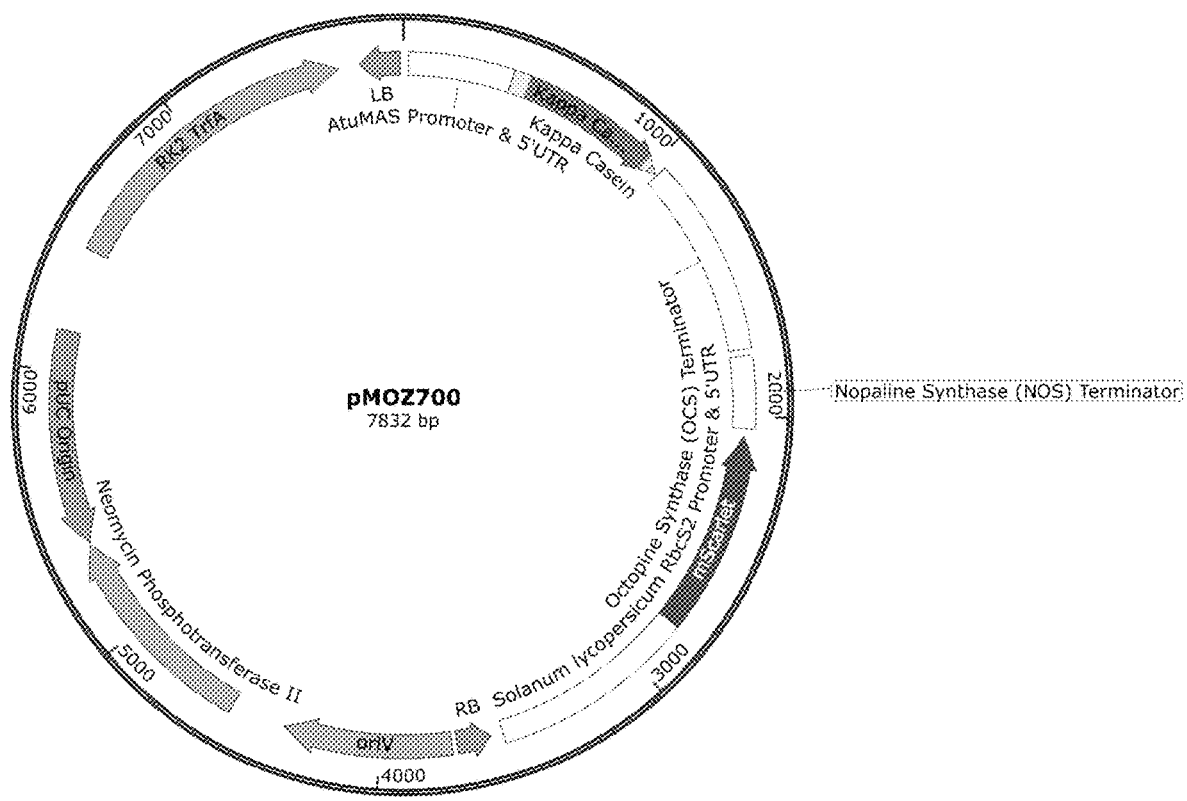
FIG. 16 shows a map of a pMOZ700 expression plasmid, which is an example expression plasmid for the production of recombinant *B. taurus* Kappa Casein in plants.

As another specific example, FIG. 16 is a map of a pMOZ700 expression plasmid, which is an example expression plasmid for the production of recombinant *B. taurus* Kappa Casein in plants. Continuing this example, the pMOZ700 expression plasmid includes a 507 bp nucleic acid sequence encoding *B. taurus* K-casein [SEQ ID NO:78] that had been synthesized and was codon optimized for expression in plants using *Nicotiana benthamiana* as the model expression system, operatively linked to a 383 bp sequence encoding the promoter *A. tumefaciens* Mannopine Synthase promoter (AtuMAS Promoter) [SEQ ID NO:70], a 63 bp nucleic acid sequence encoding the *Arabidopsis thaliana* S2S signal peptide (AtS2S Signal Peptide) [SEQ ID NO:72] for localizing the recombinant protein to the endoplasmic reticulum of the plant cell, and a 63 bp sequence coding for an HA peptide tag, a 6× histidine peptide tag, and an endoplasmic reticulum retention peptide HDEL [SEQ ID NO:73]. These sequences code for a protein containing a signal peptide, beta casein, HA tag, 6 histidine tag, and HDEL peptide [SEQ ID NO:82]. The plasmid also contains a 732 bp nucleic acid sequence coding for the mScarlet fluorescent protein [SEQ ID NO: 75] that had been synthesized and was codon optimized for expression in plants using *Nicotiana benthamiana* as the model expression system, operatively linked to a 739 bp sequence encoding the *S. lycopersicum* RbcS2 promoter (SlRbcS2 Promoter) [SEQ ID NO: 59], and a 263 bp sequence encoding the *A. tumefaciens* Nopaline Synthase Terminator (NOS Terminator) [SEQ ID NO: 76]. pMOZ702 was assembled using the enzyme BpiI and standard GoldenGate protocols. The resulting plasmid was transformed into *E. coli* and later purified using a standard miniprep protocol. Sanger sequencing was used to verify the correct assembly of the plasmid.

Figure 17:
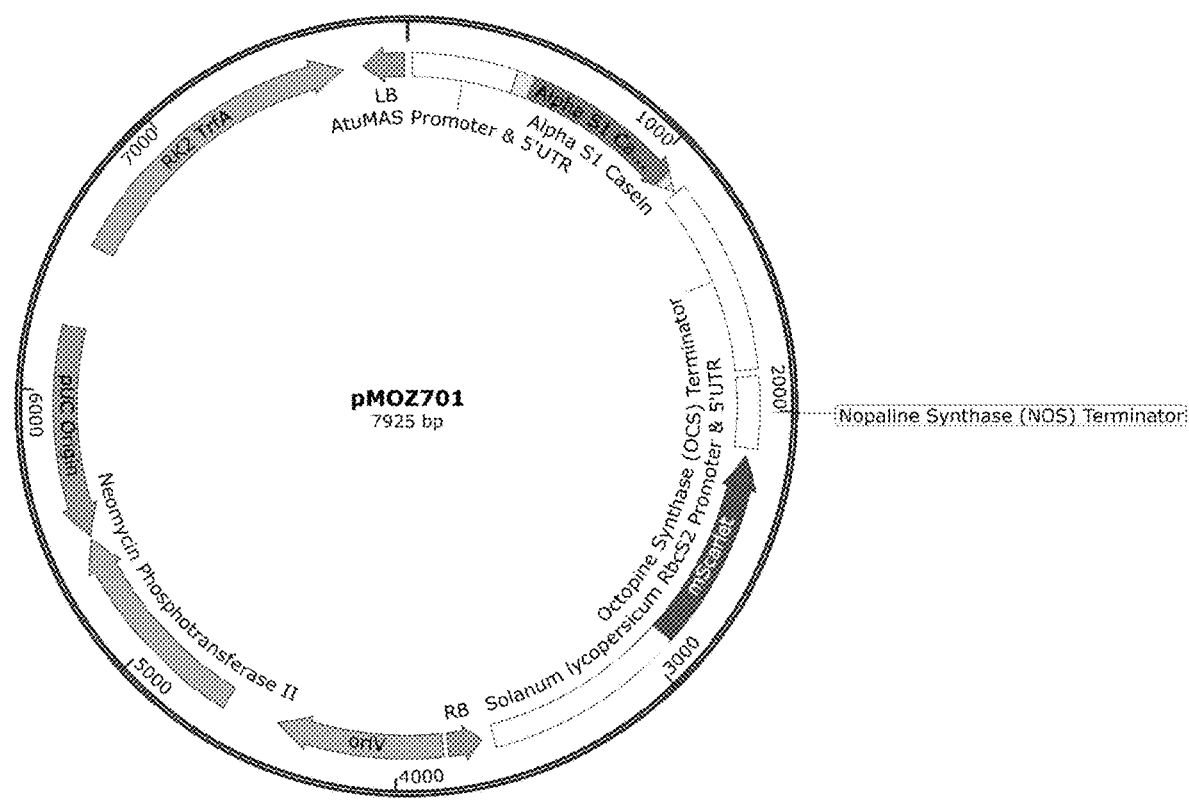
FIG. 17 shows a map of a pMOZ701 expression plasmid, which is an example expression plasmid for the production of recombinant *B. taurus* $\alpha S_1$ Casein in plants.

As another specific example, FIG. 17 is a map of a pMOZ701 expression plasmid, which is an example expression plasmid for the production of recombinant *B. taurus* αS1 Casein in plants. Continuing this example, the pMOZ701 expression plasmid includes a 597 bp nucleic acid sequence encoding *B. taurus* αS1-casein [SEQ ID NO:79] that had been synthesized and was codon optimized for expression in plants using *Nicotiana benthamiana* as the model expression system, operatively linked to a 383 bp sequence encoding the promoter *A. tumefaciens* Mannopine Synthase promoter (AtuMAS Promoter) [SEQ ID NO:70], a 63 bp nucleic acid sequence encoding the *Arabidopsis thaliana* S2S signal peptide (AtS2S Signal Peptide) [SEQ ID NO:72] for localizing the recombinant protein to the endoplasmic reticulum of the plant cell, and a 63 bp sequence coding for an HA peptide tag, a 6× histidine peptide tag, and an endoplasmic reticulum retention peptide HDEL [SEQ ID NO:73]. These sequences code for a protein containing a signal peptide, beta casein, HA tag, 6 histidine tag, and HDEL peptide [SEQ ID NO:80]. The plasmid also contains a 732 bp nucleic acid sequence coding for the mScarlet fluorescent protein [SEQ ID NO: 75] that had been synthesized and was codon optimized for expression in plants using *Nicotiana benthamiana* as the model expression system, operatively linked to a 739 bp sequence encoding the *S. lycopersicum* RbcS2 promoter (SlRbcS2 Promoter) [SEQ ID NO: 59], and a 263 bp sequence encoding the *A. tumefaciens* Nopaline Synthase Terminator (NOS Terminator) [SEQ ID NO: 76]. pMOZ701 was assembled using the enzyme BpiI and standard GoldenGate protocols. The resulting plasmid was transformed into *E. coli* and later purified using a standard miniprep protocol. Sanger sequencing was used to verify the correct assembly of the plasmid.

Coexpression of 1 Casein and 2 Human Kinases

Figure 19:
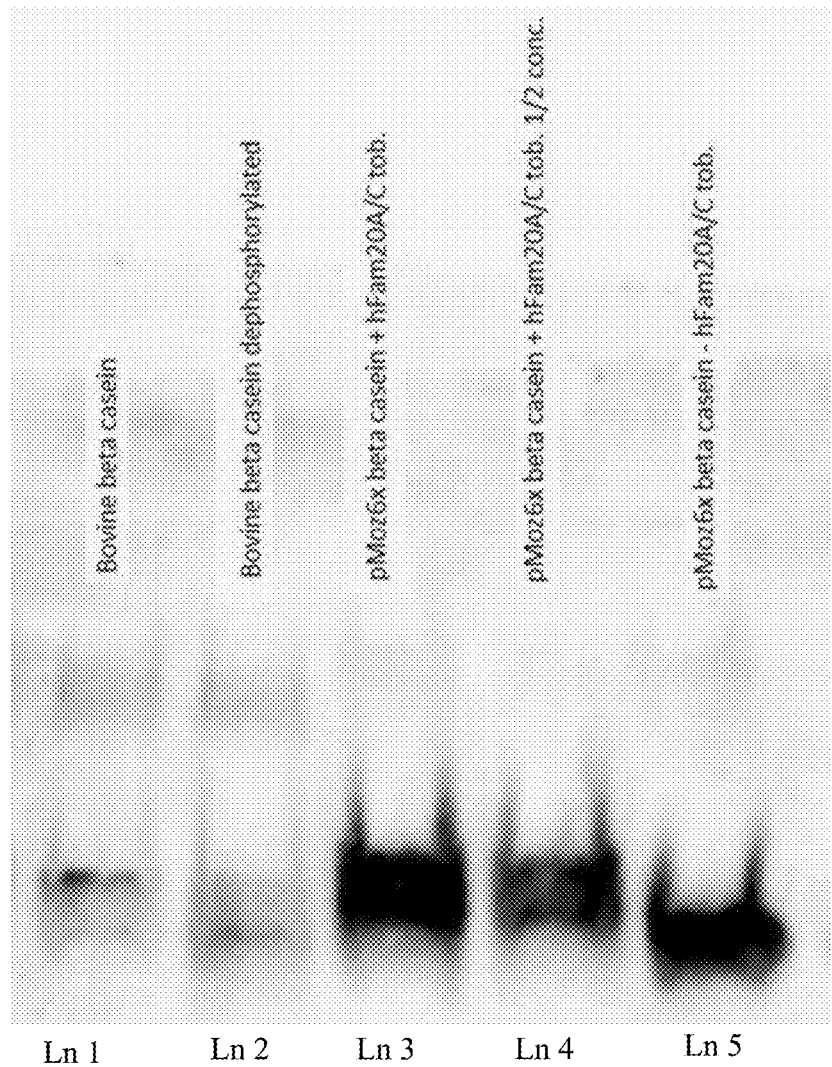
FIG. 19 shows results of Western blot showing the expression of recombinant Beta casein, HsFam20C, and HsFam20A in a systemically-infected *N. benthamiana* plant using combinations of the pMOZ11 (expresses HsFam20C), pMOZ12 (expresses HsFam20A) and pMOZ702 (expresses beta casein) expression plasmids.

Referring to FIG. 19, therein is shown an example of the expression of recombinant Beta casein, HsFam20C, and HsFam20A in a systemically-infected *N. benthamiana* plant using combinations of the pMOZ11 (expresses HsFam20C), pMOZ12 (expresses HsFam20A) and pMOZ702 (expresses beta casein) expression plasmids. In this example, *N. benthamiana* plants were incubated in a growth room at 25° C. with a 16 hour light 8 hour dark cycle for 4 weeks. The 4-week old *N. benthamiana* plants were infiltrated with *A. tumefaciens* strain GV3101 carrying combinations of pMOZ plasmids.

In one condition the plants were infiltrated with three different cultures of *A. tumefaciens* strain GV3101 carrying pMOZ702, pMOZ11, and pMOZ12 all grown to an OD600 of 0.1.

In a second condition the plants were infiltrated with three different cultures of *A. tumefaciens* strain GV3101 carrying pMOZ702, pMOZ11, and pMOZ12 all grown to an OD600 of 0.05.

In a third condition the plants were infiltrated with one culture of *A. tumefaciens* strain GV3101 carrying pMOZ702 grown to an OD600 of 0.1.

Following vacuum infiltration, plants were blot-dried and returned to the growth room for 72 hours before being imaged. Infected leaves were imaged with an epifluorescent microscope with Red Fluorescent Protein (RFP) excitation and emission filters to confirm that the mScarlet protein from pMOZ702 was successfully expressing in the plant cells. Leaves that were expressing mScarlet were harvested, frozen with liquid nitrogen, crushed with a mortar and pestle. 250 mg of crushed plant tissue was transferred to a 1.7 mL tube and 300 uL of protein extraction buffer (800 uL of 500 mM sodium phosphate, 200 uL of 500 mM sodium phosphate dibasic, 1 mL 200 mM Sodium metabisulfite, 50 uL Tween-20, 5 mL 1M Trehalose, 3 mL diH2O) was added. This mixture was incubated on a rotisserie at 4 C for 1 hour and then centrifuged at 400 RPM in with an Eppendorf 5415R centrifuge to pellet the solid plant material. The supernatant containing the extracted protein was transferred to a new 1.7 mL tube.

Further continuing this example, protein samples from the infected plant tissue were analyzed with sodium dodecyl sulfate polyacrylamide gel electrophoresis (SDS PAGE). 10 uL of supernatant was mixed with 30 uL of protein loading buffer (900 uL of 4× Laemmli Sample Buffer [Bio-Rad Laboratories]+100 uL of 2-mercaptoethanol) and heated for 5 minutes at 95 C. These samples were loaded onto Bio-Rad "Any kD" precast polyacrylamide gels along with a standard protein ladder and phosphorylated and dephosphorylated beta casein samples from Sigma Aldrich. The gel was run in 1× Tris/*Glycine*/SDS Buffer (Bio-Rad Laboratories) at 150V for 45 minutes. The gel was removed from the gel box and placed in a PVDF Transfer Pack (Bio-Rad Laboratories), the transfer pack was placed in a Trans-Blot Turbo (Bio-Rad Laboratories) and the proteins were transferred to the PVDF membrane using the "Mini TGX" settings. The PVDF membrane containing the transferred proteins was first washed in 25 mL Protein Free Blocking Buffer (ThermoFisher) for 1 hour, then incubated with 5 mL of Protein Free Blocking Buffer containing 5 uL of anti-beta-casein polyclonal rabbit IgG at room temperature for 4 hours. The membrane was then washed three times with 10 mL TBST (20 mM Tris-HCl, 150 mM NaCl, 0.1% Tween 20) for 10 minutes at room temperature. Then the membrane was washed with 25 mL of Protein Free Blocking Buffer containing 2 uL of anti-rabbit IgG secondary antibody conjugated to horseradish peroxidase for 1 hour at room temperature and then poured off. The membrane was placed in a ChemiDoc MP imaging system (Bio-Rad Laboratories) and 1 mL of SuperSignal West Pico (ThermoFisher) luminescent imaging solution was added to the membrane. Images were captured using the Chemiluminescence setting on the ChemiDoc MP.

Further continuing this example, the casein proteins expressed in plant cells show up on the anti-beta-casein Western blot with varying migration distances (FIG. 19). Lane 1 purified beta casein from milk as standard. Lane 2: dephosphorylated beta casein from milk standard. Lane 3: Beta casein+human Fam20C+human Fam20A expressed in tobacco leaf (Tobacco leaf tissue transformed with pMOZ702+pMOZ11+pMOZ12). Lane 4: same as lane 3, with half as much protein loaded on gel. Lane 5: Beta casein (pMOZ702) expressed in tobacco leaf (no kinase). In lanes containing beta casein coexpressed with the human kinases the bands are shifted upward on the gel relative to the sample transformed with only beta casein, suggesting that the molecular weight of the beta casein has increased due to phosphorylation.

Coexpression of 1 Casein and 1 or 2 Kinases

Figure 20:
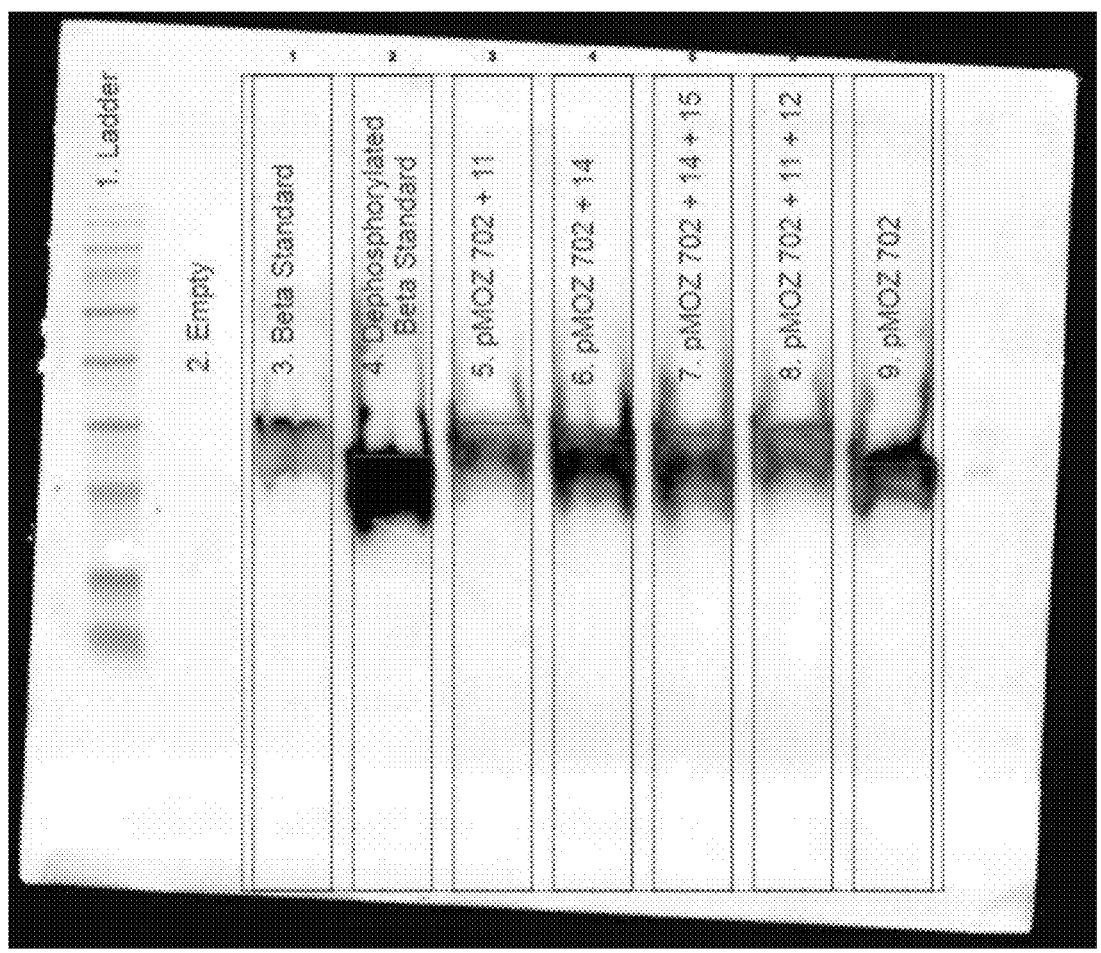
FIG. 20 shows results of Western blot showing the expression of recombinant Beta casein, HsFam20C, and HsFam20A in a systemically-infected *N. benthamiana* plant using combinations of the pMOZ11 (expresses HsFam20C), pMOZ12 (expresses HsFam20A), pMOZ14 (expresses BtFam20C), pMOZ15 (expresses BtFam20A) and pMOZ702 (expresses beta casein) expression plasmids.

Referring to FIG. 20, therein is shown an example of the expression of recombinant Beta casein, HsFam20C, and HsFam20A in a systemically-infected *N. benthamiana* plant using combinations of the pMOZ11 (expresses HsFam20C), pMOZ12 (expresses HsFam20A), pMOZ14 (expresses BtFam20C), pMOZ15 (expresses BtFam20A) and pMOZ702 (expresses beta casein) expression plasmids. In this example, *N. benthamiana* plants were incubated in a growth room at 25° C. with a 16 hour light 8 hour dark cycle for 4 weeks. The 4-week old *N. benthamiana* plants were infiltrated with *A. tumefaciens* strain GV3101 carrying combinations of pMOZ plasmids at an OD600 of 0.1.

In one condition the plants were infiltrated with two different cultures of *A. tumefaciens* strain GV3101 carrying pMOZ702, pMOZ11.

In a second condition the plants were infiltrated with three different cultures of *A. tumefaciens* strain GV3101 carrying pMOZ702, pMOZ11, and pMOZ12.

In a third condition the plants were infiltrated with a single culture of *A. tumefaciens* strain GV3101 carrying pMOZ702.

In a fourth condition the plants were infiltrated with two different cultures of *A. tumefaciens* strain GV3101 carrying pMOZ702, pMOZ14.

In a fifth condition the plants were infiltrated with three different cultures of *A. tumefaciens* strain GV3101 carrying pMOZ702, pMOZ14, and pMOZ15.

Following vacuum infiltration, plants were blot-dried and returned to the growth room for 72 hours before being imaged. Infected leaves were imaged with an epifluorescent microscope with Red Fluorescent Protein (RFP) excitation and emission filters to confirm that the mScarlet protein from pMOZ702 was successfully expressing in the plant cells. Leaves that were expressing mScarlet were harvested, frozen with liquid nitrogen, crushed with a mortar and pestle. 250 mg of crushed plant tissue was transferred to a 1.7 mL tube and 300 uL of protein extraction buffer (800 uL of 500 mM sodium phosphate, 200 uL of 500 mM sodium phosphate dibasic, 1 mL 200 mM Sodium metabisulfite, 50 uL Tween-20, 5 mL 1M Trehalose, 3 mL diH2O) was added. This mixture was incubated on a rotisserie at 4 C for 1 hour and then centrifuged at 400 RPM in with an Eppendorf 5415R centrifuge to pellet the solid plant material. The supernatant containing the extracted protein was transferred to a new 1.7 mL tube.

Further continuing this example, protein samples from the infected plant tissue were analyzed with sodium dodecyl sulfate polyacrylamide gel electrophoresis (SDS PAGE). 10 uL of supernatant was mixed with 30 uL of protein loading buffer (900 uL of 4× Laemmli Sample Buffer [Bio-Rad Laboratories]+100 uL of 2-mercaptoethanol) and heated for 5 minutes at 95 C. These samples were loaded onto Bio-Rad "Any kD" precast polyacrylamide gels along with a standard protein ladder and phosphorylated and dephosphorylated beta casein samples from Sigma Aldrich. The gel was run in 1× Tris/*Glycine*/SDS Buffer (Bio-Rad Laboratories) at 150V for 45 minutes. The gel was removed from the gel box and placed in a PVDF Transfer Pack (Bio-Rad Laboratories), the transfer pack was placed in a Trans-Blot Turbo (Bio-Rad Laboratories) and the proteins were transferred to the PVDF membrane using the "Mini TGX" settings. The PVDF membrane containing the transferred proteins was first washed in 25 mL Protein Free Blocking Buffer (ThermoFisher) for 1 hour, then incubated with 5 mL of Protein Free Blocking Buffer containing 5 uL of anti-beta-casein polyclonal rabbit IgG at room temperature for 4 hours. The membrane was then washed three times with 10 mL TBST (20 mM Tris-HCl, 150 mM NaCl, 0.1% Tween 20) for 10 minutes at room temperature. Then the membrane was washed with 25 mL of Protein Free Blocking Buffer containing 2 uL of anti-rabbit IgG secondary antibody conjugated to horseradish peroxidase for 1 hour at room temperature and then poured off. The membrane was placed in a ChemiDoc MP imaging system (Bio-Rad Laboratories) and 1 mL of SuperSignal West Pico (ThermoFisher) luminescent imaging solution was added to the membrane. Images were captured using the Chemiluminescence setting on the ChemiDoc MP.

Further continuing this example, the casein proteins expressed in plant cells show up on the anti-beta-casein Western blot with varying migration distances (FIG. 20). Lane 1: Molecular weight ladder. Lane 2: Empty. Lane 3: Purified beta casein from milk as standard. Lane 4: dephosphorylated beta casein from milk as standard. Lane 5: beta casein+human Fam20C expressed in tobacco leaf (Tobacco leaf tissue transformed with pMOZ702 and pMOZT1). Lane 6: beta casein+cow Fam20C expressed in tobacco leaf (Tobacco leaf tissue transformed with pMOZ702 and pMOZ14). Lane 7: beta casein+cow Fam20C+cow Fam20A expressed in tobacco leaf (Tobacco leaf tissue transformed with pMOZ702, pMOZ14, and pMOZ15). Lane 8: beta casein+human Fam20C+human Fam20A expressed in tobacco leaf (Tobacco leaf tissue transformed with pMOZ702, pMOZ11, and pMOZ12). Lane 9: Tobacco leaf tissue transformed with only pMOZ702. In lanes containing beta casein coexpressed with 1 human kinase, 2 human kinases, 1 bovine kinase or 2 bovine kinases the bands are shifted upward on the gel relative to the sample transformed with only beta casein, suggesting that the molecular weight of the beta casein has increased due to phosphorylation.

Figure 21:
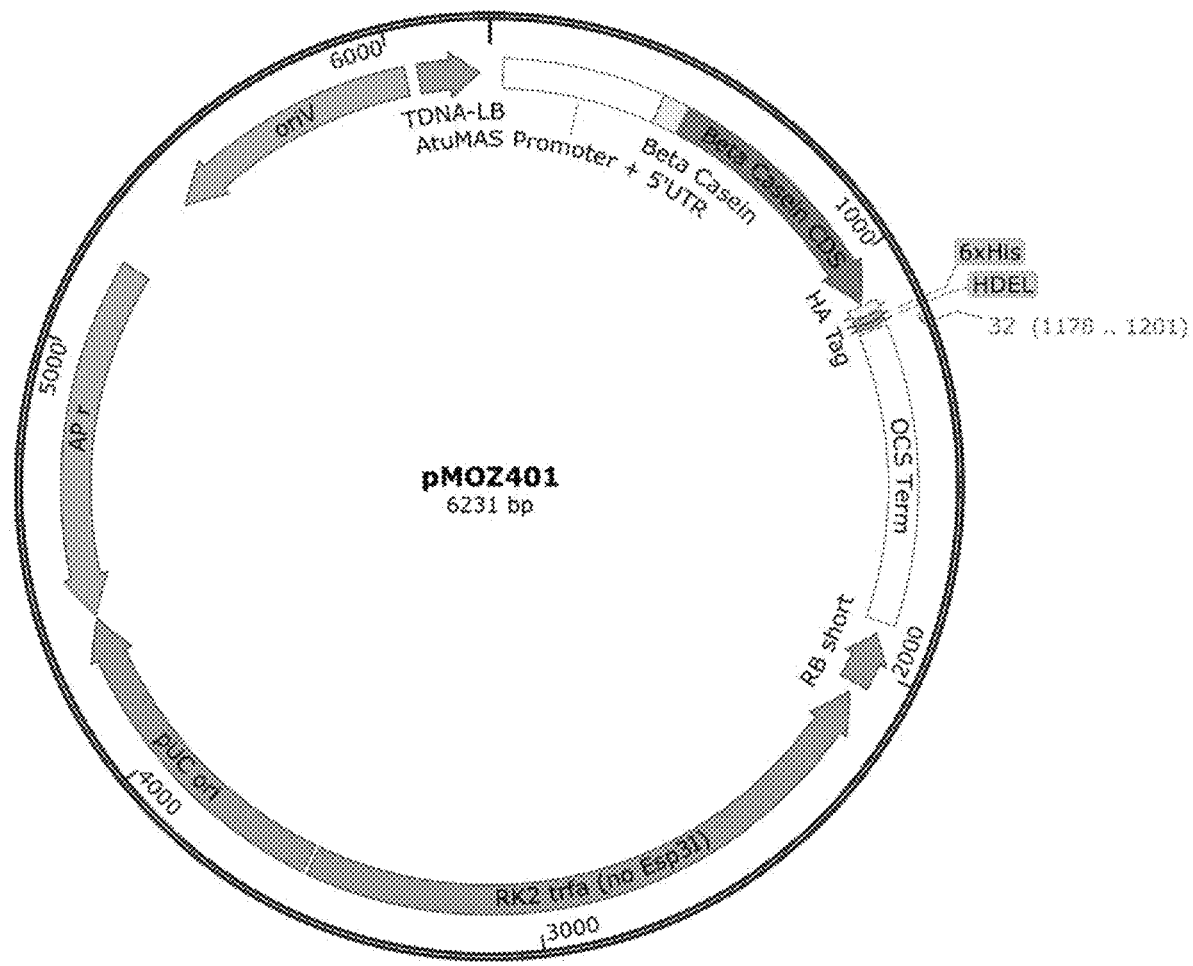
FIG. 21 shows a map of a pMOZ401 expression plasmid, which is an example expression plasmid for the production of recombinant *B. taurus* Beta Casein in plants.

As another specific example, FIG. 21 is a map of a pMOZ401 expression plasmid, which is an example expression plasmid for the production of recombinant *B. taurus* Beta Casein in plants. Continuing this example, the pMOZ401 expression plasmid includes a 627 bp nucleic acid sequence encoding *B. taurus* β-casein [SEQ ID NO:77] that had been synthesized and was codon optimized for expression in plants using *Nicotiana benthamiana* as the model expression system, operatively linked to a 383 bp sequence encoding the promoter *A. tumefaciens* Mannopine Synthase promoter (AtuMAS Promoter) [SEQ ID NO:70], a 63 bp nucleic acid sequence encoding the *Arabidopsis thaliana* S2S signal peptide (AtS2S Signal Peptide) [SEQ ID NO:72] for localizing the recombinant protein to the endoplasmic reticulum of the plant cell, and a 63 bp sequence coding for an HA peptide tag, a 6× histidine peptide tag, and an endoplasmic reticulum retention peptide HDEL [SEQ ID NO:73]. These sequences code for a protein containing a signal peptide, beta casein, HA tag, 6 histidine tag, and HDEL peptide [SEQ ID NO:81]. pMOZ401 was assembled using the enzyme Eco31I and standard GoldenGate protocols. The resulting plasmid was transformed into *E. coli* and later purified using a standard miniprep protocol. Sanger sequencing was used to verify the correct assembly of the plasmid.

Figure 22:
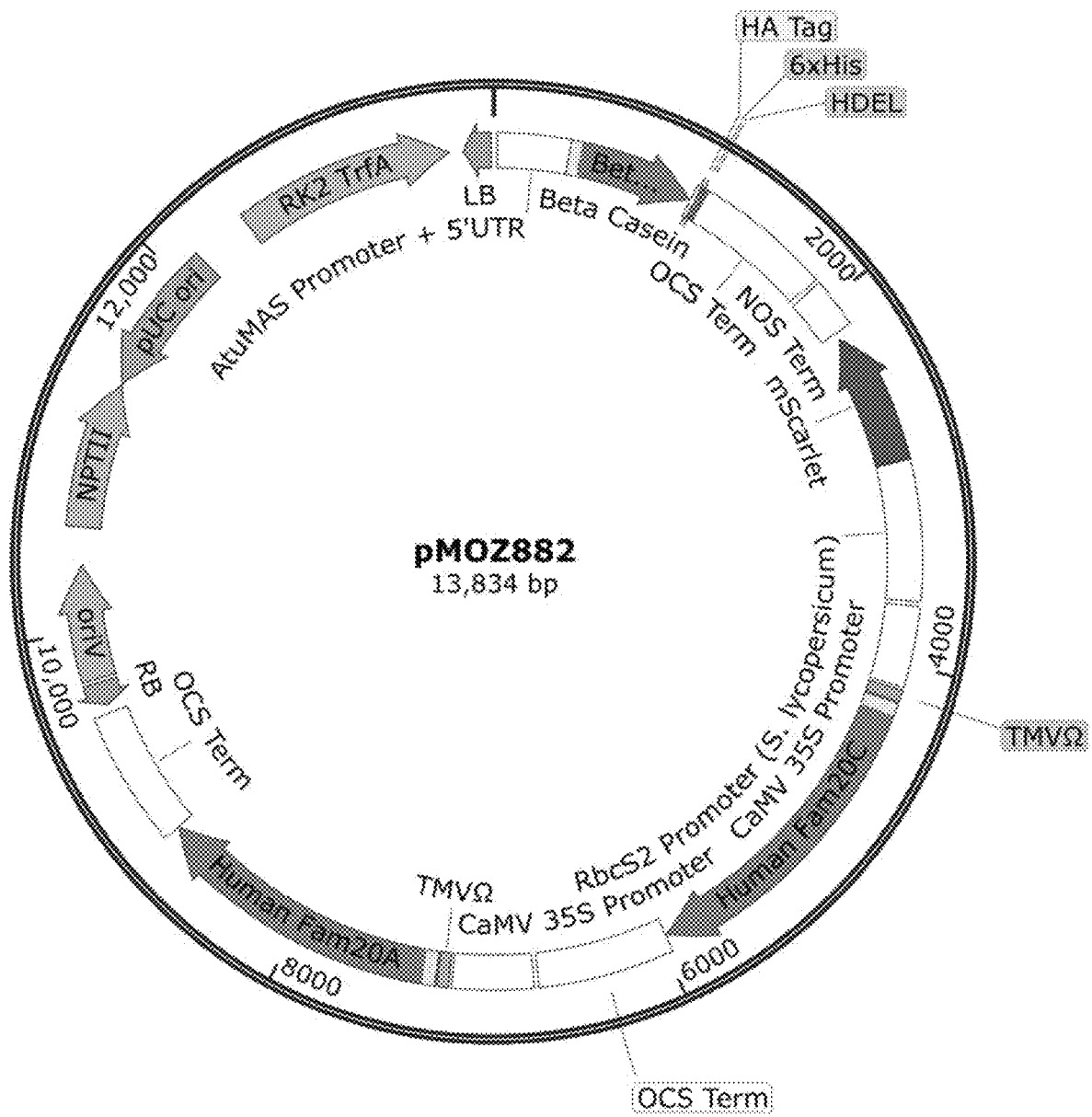
FIG. 22 shows a map of a pMOZ882 expression plasmid, which is an example expression plasmid for the production of recombinant *B. taurus* Beta Casein in plants.

As another specific example, FIG. 22 is a map of a pMOZ882 expression plasmid, which is an example expression plasmid for the production of recombinant *B. taurus* Beta Casein in plants. Continuing this example, the pMOZ882 expression plasmid includes a 627 bp nucleic acid sequence encoding *B. taurus* β-casein [SEQ ID NO:77] that had been synthesized and was codon optimized for expression in plants using *Nicotiana benthamiana* as the model expression system, operatively linked to a 383 bp sequence encoding the promoter *A. tumefaciens* Mannopine Synthase promoter (AtuMAS Promoter) [SEQ ID NO:70], a 63 bp nucleic acid sequence encoding the *Arabidopsis thaliana* S2S signal peptide (AtS2S Signal Peptide) [SEQ ID NO:72] for localizing the recombinant protein to the endoplasmic reticulum of the plant cell, and a 63 bp sequence coding for an HA peptide tag, a 6× histidine peptide tag, and an endoplasmic reticulum retention peptide HDEL [SEQ ID NO:73]. These sequences code for a protein containing a signal peptide, beta casein, HA tag, 6 histidine tag, and HDEL peptide [SEQ ID NO:81]. The plasmid also contains a 732 bp nucleic acid sequence coding for the mScarlet fluorescent protein [SEQ ID NO: 75] that had been synthesized and was codon optimized for expression in plants using *Nicotiana benthamiana* as the model expression system, operatively linked to a 739 bp sequence encoding the *S. lycopersicum* RbcS2 promoter (SlRbcS2 Promoter) [SEQ ID NO: 59], and a 263 bp sequence encoding the *A. tumefaciens* Nopaline Synthase Terminator (NOS Terminator) [SEQ ID NO: 76]. The plasmid also contains a 1674 bp nucleic acid sequence encoding *H. sapiens* Fam20C (HsFam20C) [SEQ ID NO:66] that had been synthesized using only coding sequences from the original *H. sapiens* Fam20C gene and was codon optimized for expression in plants using *Nicotiana benthamiana* as the model expression system, operatively linked to a 426 bp sequence encoding the promoter Cauliflower Mosaic Virus 35S promoter (CaMV 35S Promoter) [SEQ ID NO:42], a 62 bp translational enhancer encoding the omega leader sequence of the Tobacco Mosaic Virus (Ω TMV 5UTR) [SEQ ID NO:58], a 57 bp nucleic acid sequence encoding the *Arabidopsis thaliana* ARA12 signal peptide gene (ARA12 Signal Peptide) [SEQ ID NO:71] for localizing the recombinant protein to the endoplasmic reticulum of the plant cell, and a 15 bp sequence coding for the endoplasmic reticulum retention peptide HDEL [SEQ ID NO:65]. The plasmid also contains a 1524 bp nucleic acid sequence encoding *H. sapiens* Fam20A (HsFam20A) [SEQ ID NO:67] that had been synthesized using only coding sequences from the original *H. sapiens* Fam20A gene and was codon optimized for expression in plants using *Nicotiana benthamiana* as the model expression system, operatively linked to a 426 bp sequence encoding the promoter Cauliflower Mosaic Virus 35S promoter (CaMV 35S Promoter) [SEQ ID NO:42], a 62 bp translational enhancer encoding the omega leader sequence of the Tobacco Mosaic Virus (Ω TMV 5UTR) [SEQ ID NO:58], a 57 bp nucleic acid sequence encoding the *Arabidopsis thaliana* ARA12 signal peptide gene (ARA12 Signal Peptide) [SEQ ID NO:71] for localizing the recombinant protein to the endoplasmic reticulum of the plant cell, and a 15 bp sequence coding for the endoplasmic reticulum retention peptide HDEL [SEQ ID NO:65]. pMOZ882 was assembled using the enzyme BpiI and standard GoldenGate protocols. The resulting plasmid was transformed into *E. coli* and later purified using a standard miniprep protocol. Sanger sequencing was used to verify the correct assembly of the plasmid.

Example 1. Phosphorylation Increased Casein Expression

In this proposed experiment the expression level of casein proteins is shown to increase when phosphorylated. Recombinant Kappa casein and BtFam20C kinase are expressed in a systemically-infected N. benthamiana plant using combinations of the pMOZ14 (expresses BtFam20C) and pMOZ700 (expresses bovine kappa casein) expression plasmids. In this example, N. benthamiana plants were incubated in a growth room at 25° C. with a 16 hour light 8 hour dark cycle for 4 weeks. The 4-week old N. benthamiana plants were infiltrated with A. tumefaciens strain GV3101 carrying combinations of pMOZ plasmids.

In one condition the N. benthamiana plants were infiltrated with two different cultures of A. tumefaciens strain GV3101 carrying pMOZ700, pMOZ14 all grown to an OD600 of 0.1.

In a second condition N. benthamiana plants were infiltrated with a single culture of A. tumefaciens strain GV3101 carrying pMOZ700 grown to an OD600 of 0.1.

Following vacuum infiltration, plants will be blot-dried and returned to the growth room for 72 hours before being imaged. Infected leaves will be imaged with an epifluorescent microscope with Red Fluorescent Protein (RFP) excitation and emission filters to confirm that the mScarlet protein from pMOZ700 was successfully expressed in the plant cells. Leaves that express mScarlet will be harvested, frozen with liquid nitrogen, crushed with a mortar and pestle. 250 mg of crushed plant tissue will be weighed and transferred to a 1.7 mL tube and 300 uL of protein extraction buffer (800 uL of 500 mM sodium phosphate, 200 uL of 500 mM sodium phosphate dibasic, 1 mL 200 mM Sodium metabisulfite, 50 uL Tween-20, 5 mL 1M Trehalose, 3 mL diH2O) will be added. This mixture will be incubated on a rotisserie at 4 C for 1 hour and then centrifuged to pellet the solid plant material. The supernatant containing the extracted protein will be transferred to a new tube.

Continuing this example, extracted protein will be analyzed with SDS PAGE followed by a Western blot with kappa casein antibodies using a typical Western blotting protocol. After incubating with an appropriate secondary antibody conjugated to horseradish peroxidase, luminescent developing solution such as SuperSignal West (ThermoFisher) will be applied to the Western membrane and imaged on a ChemiDoc MP (Bio-Rad Laboratories) imaging system. The brightness of the kappa casein bands will be quantified using functions built into the ChemiDoc MP. Brighter bands in lanes containing protein from the plants transformed with both pMOZ700 (Kappa casein) and pMOZ14 (kinase) compared to protein from plants transformed with only pMOZ700 (kappa casein) shows that phosphorylated casein proteins are expressed at higher concentrations than non-phosphorylated casein.

In a similar experiment, N. benthamiana plants will be transformed with the same casein and kinase plasmids and protein will be extracted the same as just described. Extracted protein supernatants will be analyzed by high pressure liquid chromatography (HPLC). The supernatants will be diluted with acetate buffer and loaded into the HPLC apparatus. Eluted protein will be detected and quantified by UV absorption. Integrals will be calculated for the peaks corresponding to casein proteins to quantify the concentration of casein in each sample. Larger integral values for casein proteins from plants transformed with casein and kinase compared to casein from plants transformed with only casein will show that phosphorylation of casein increases their expression level.

Example 2. Phosphorylation Increased Aggregation of Casein Proteins

In this proposed experiment the aggregation of multiple caseins proteins is shown to be increased when the caseins are phosphorylated compared to non-phosphorylated caseins. Recombinant bovine alpha S1 casein casein, bovine beta casein and BtFam20C kinase will be expressed in a in a systemically-infected N. benthamiana plant using combinations of the pMOZ14 (expresses BtFam20C), pMOZ701 (expresses bovine alpha S1 casein), and pMOZ702 (expresses bovine beta casein) expression plasmids. In this example, N. benthamiana plants will be incubated in a growth room at 25° C. with a 16 hour light 8 hour dark cycle for 4 weeks. The 4-week old N. benthamiana plants will be infiltrated with A. tumefaciens strain GV3101 carrying combinations of pMOZ plasmids.

In one condition the N. benthamiana plants were infiltrated with two different cultures of A. tumefaciens strain GV3101 carrying pMOZ701 and pMOZ14 all grown to an OD600 of 0.1.

In a second condition the N. benthamiana plants were infiltrated with two different cultures of A. tumefaciens strain GV3101 carrying pMOZ702 and pMOZ14 all grown to an OD600 of 0.1.

In a third condition the N. benthamiana plants were infiltrated with a single culture of A. tumefaciens strain GV3101 carrying pMOZ701 grown to an OD600 of 0.1.

In a fourth condition the N. benthamiana plants were infiltrated with a single culture of A. tumefaciens strain GV3101 carrying pMOZ702 grown to an OD600 of 0.1.

Following vacuum infiltration, plants will be blot-dried and returned to the growth room for 72 hours before being imaged. Infected leaves will be imaged with an epifluorescent microscope with Red Fluorescent Protein (RFP) excitation and emission filters to confirm that the mScarlet protein from pMOZ701 or pMOZ702 was successfully expressed in the plant cells. Leaves that express mScarlet will be harvested, frozen with liquid nitrogen, crushed with a mortar and pestle. 250 mg of crushed plant tissue will be weighed and transferred to a 1.7 mL tube and 300 uL of protein extraction buffer (800 uL of 500 mM sodium phosphate, 200 uL of 500 mM sodium phosphate dibasic, 1 mL 200 mM Sodium metabisulfite, 50 uL Tween-20, 5 mL 1M Trehalose, 3 mL diH2O) will be added. This mixture will be incubated on a rotisserie at 4 C for 1 hour and then centrifuged to pellet the solid plant material. The supernatant containing the extracted protein will be transferred to a new tube for further analysis.

Continuing this example, various combinations of protein supernatants from the different transformation conditions will be used in a co-immunoprecipitation (CoIP) assay to measure the amount of protein-protein aggregation. In each CoIP assay protein supernatant from one sample will be mixed with magnetic anti-HA Dynabeads (ThermoFisher catalog #88837) so that the HA peptide tag attached to the casein protein expressed from either pMOZ701 or pMOZ702 plasmid is contacted with anti-HA antibodies attached to the magnetic beads. The quantity of protein added will be great enough to saturate all available HA antibodies on the surface of the beads. The HA-labeled casein proteins will stick to the magnetic beads and the rest of the supernatant will be washed away with wash buffer ((10 mM Tris pH 7.4, 1 mM EDTA, 1 mM EGTA, pH 8.0, 150 mM NaCl, 1% Triton X-100, 0.2 mM sodium orthovanadate) while the casein is retained by the magnetic beads held stationary by an external magnetic force. Protein supernatant from a second sample will then be contacted with the beads and allowed to incubate at room temperature for 1 hour. The supernatant will then be washed with wash buffer while the beads are held stationary by an external magnetic force. Any protein stuck the the beads will then be released from the beads by adding 30 uL of Laemmli buffer (65.8 mM Tris-HCl, pH 6.8, 2.1% SDS, 26.3% glycerol, 2% 2-mercaptoethanol) and incubating at 90 degrees celsius for 20 minutes. The beads will then be removed from the Laemmli buffer using a magnet and the remaining liquid will be analyzed by SDS PAGE and Western blot using standard protocols. The Western blot will be developed using a casein-specific antibody targeting the second casein protein that was added to the CoIP assay. Analyzing the brightness of the bands on the Western blot will show which samples captured more secondary casein protein.

In one condition, the supernatant from plants transformed with pMOZ701 will be first contacted with the beads and then supernatant from plants transformed with pMOZ702 will be contacted second.

In a second condition, the supernatant from plants transformed with pMOZ702 will be first contacted with the beads and then supernatant from plants transformed with pMOZ701 will be contacted second.

In a third condition, the supernatant from plants transformed with pMOZ702 and pMOZ14 will be first contacted with the beads and then supernatant from plants transformed with pMOZ701 and pMOZ14 will be contacted second.

In a third condition, the supernatant from plants transformed with pMOZ701 and pMOZ14 will be first contacted with the beads and then supernatant from plants transformed with pMOZ702 and pMOZ14 will be contacted second.

Further continuing this example, Western blots showing increased amounts of casein eluted from the beads from samples where both casein plasmids (pMOZ701 or pMOZ702) were co-transformed with kinase plasmids (pMOZ14) compared to samples where the casein plasmids were transformed without kinase plasmid will indicate that phosphorylation of caseins increases their ability to aggregate or bind to each other.

Example 3. Phosphorylation Improves Casein Micelle Formation

In this proposed experiment micelles will form in vivo when casein is phosphorylated. Recombinant Beta casein, Kappa casein, Alpha S1 casein, and BtFam20C kinase are expressed in a in a systemically-infected *N. benthamiana* plant using combinations of the pMOZ14 (expresses BtFam20C), pMOZ702 (expresses bovine beta casein), pMOZ701 (expresses alpha casein), and pMOZ700 (expresses bovine kappa casein) expression plasmids. In this example, *N. benthamiana* plants were incubated in a growth room at 25° C. with a 16 hour light 8 hour dark cycle for 4 weeks. The 4-week old *N. benthamiana* plants were infiltrated with *A. tumefaciens* strain GV3101 carrying combinations of pMOZ plasmids.

In one condition the *N. benthamiana* plants were infiltrated with four different cultures of *A. tumefaciens* strain GV3101 carrying pMOZ700, pMOZ701, pMOZ702, and pMOZ14 all grown to an OD600 of 0.1.

In a second condition *N. benthamiana* plants were infiltrated with three different cultures of *A. tumefaciens* strain GV3101 carrying pMOZ700, pMOZ701, and pMOZ702 all grown to an OD600 of 0.1.

Following vacuum infiltration, plants will be blot-dried and returned to the growth room for 72 hours before being imaged. Infected leaves will be imaged with an epifluorescent microscope with Red Fluorescent Protein (RFP) excitation and emission filters to confirm that the mScarlet protein from pMOZ700 or pMOZ701 or pMOZ702 were successfully expressed in the plant cells. Leaves that express mScarlet will be cut from the plant and then fixed in formaldehyde and osmium tetroxide using standard fixation and clearing protocols. The fixed tissue will then be sectioned and imaged on a transmission electron microscope. Comparison of images of leaves transformed with and without pMOZ14 will show that casein micelles form when kinase is present to phosphorylate the casein protein.

Example 4. Phosphorylation Increased Viscosity (Quality/Mouthfeel)

In this proposed experiment the amount of calcium bound to casein proteins is shown to be increased when casein is phosphorylated. Recombinant Kappa casein and BtFam20C kinase are expressed in a in a systemically-infected *N. benthamiana* plant using combinations of the pMOZ14 (expresses BtFam20C) and pMOZ702 (expresses bovine alpha casein) expression plasmids. In this example, *N. benthamiana* plants were incubated in a growth room at 25° C. with a 16 hour light 8 hour dark cycle for 4 weeks. The 4-week old *N. benthamiana* plants were infiltrated with *A. tumefaciens* strain GV3101 carrying combinations of pMOZ plasmids.

In one condition the *N. benthamiana* plants were infiltrated with two different cultures of *A. tumefaciens* strain GV3101 carrying pMOZ702, pMOZ14 all grown to an OD600 of 0.1.

In a second condition *N. benthamiana* plants were infiltrated with a single culture of *A. tumefaciens* strain GV3101 carrying pMOZ702 grown to an OD600 of 0.1.

Following vacuum infiltration, plants will be blot-dried and returned to the growth room for 72 hours before being imaged. Infected leaves will be imaged with an epifluorescent microscope with Red Fluorescent Protein (RFP) excitation and emission filters to confirm that the mScarlet protein from pMOZ700 was successfully expressed in the plant cells. Leaves that express mScarlet will be harvested, frozen with liquid nitrogen, crushed with a mortar and pestle. 250 mg of crushed plant tissue will be weighed and transferred to a 1.7 mL tube and 300 uL of protein extraction buffer (800 uL of 500 mM sodium phosphate, 200 uL of 500 mM sodium phosphate dibasic, 1 mL 200 mM Sodium metabisulfite, 50 uL Tween-20, 5 mL 1M Trehalose, 3 mL diH2O) will be added. This mixture will be incubated on a rotisserie at 4 C for 1 hour and then centrifuged to pellet the solid plant material. The supernatant containing the extracted protein will be transferred to a new tube.

Continuing this example, the viscosity of protein supernatants of samples transformed with and without the kinase encoded by pMOZ14 will be measured and compared. 10 uL of each supernatant will be loaded into RheoSense microVISC viscometer and the viscosities will be measured. Results showing higher values for samples co-transformed with pMOZ14 indicate that phosphorylation of caseins increases viscosity of solutions containing those casein proteins.

Example 5. Phosphorylated Casein Increased Calcium Binding

In this proposed experiment the amount of calcium bound to casein proteins is shown to be increased when casein is phosphorylated. Recombinant Kappa casein and BtFam20C kinase are expressed in a in a systemically-infected *N. benthamiana* plant using combinations of the pMOZ14 (expresses BtFam20C) and pMOZ700 (expresses bovine kappa casein) expression plasmids. In this example, *N.* benthamiana plants were incubated in a growth room at 25° C. with a 16 hour light 8 hour dark cycle for 4 weeks. The 4-week old *N. benthamiana* plants were infiltrated with *A. tumefaciens* strain GV3101 carrying combinations of pMOZ plasmids.

In one condition the *N. benthamiana* plants were infiltrated with two different cultures of *A. tumefaciens* strain GV3101 carrying pMOZ700, pMOZ14 all grown to an OD600 of 0.1.

In a second condition *N. benthamiana* plants were infiltrated with a single culture of *A. tumefaciens* strain GV3101 carrying pMOZ700 grown to an OD600 of 0.1.

Following vacuum infiltration, plants will be blot-dried and returned to the growth room for 72 hours before being imaged. Infected leaves will be imaged with an epifluorescent microscope with Red Fluorescent Protein (RFP) excitation and emission filters to confirm that the mScarlet protein from pMOZ700 was successfully expressed in the plant cells. Leaves that express mScarlet will be harvested, frozen with liquid nitrogen, crushed with a mortar and pestle. 250 mg of crushed plant tissue will be weighed and transferred to a 1.7 mL tube and 300 uL of protein extraction buffer (800 uL of 500 mM sodium phosphate, 200 uL of 500 mM sodium phosphate dibasic, 1 mL 200 mM Sodium metabisulfite, 50 uL Tween-20, 5 mL 1M Trehalose, 3 mL diH2O) will be added. This mixture will be incubated on a rotisserie at 4 C for 1 hour and then centrifuged to pellet the solid plant material. The supernatant containing the extracted protein will be transferred to a new tube.

Continuing this example, protein supernatants will be assayed for calcium content by first purifying the protein using anti-HA magnetic beads, then by a colorimetric assay specific for calcium. Supernatant from either plants transformed with both pMOZ702 and pMOZ14 or plants only transformed with pMOZ702 will be mixed with magnetic anti-HA Dynabeads (ThermoFisher catalog #88837) so that the HA peptide tag attached to the casein protein expressed from either pMOZ702 plasmid is contacted with anti-HA antibodies attached to the magnetic beads. The HA-labeled casein proteins will stick to the magnetic beads and the rest of the supernatant will be washed away with wash buffer ((10 mM Tris pH 7.4, 1 mM EDTA, 1 mM EGTA, pH 8.0, 150 mM NaCl, 1% Triton X-100, 0.2 mM sodium orthovanadate) while the casein is retained by the magnetic beads held stationary by an external magnetic force. Any protein stuck to the beads will then be released from the beads by adding 30 uL Tris buffer (10 mM Tris-HCl, pH 7.5) and incubating at 90 degrees celsius for 20 minutes. The beads will then be removed from the Tris buffer using a magnet. The remaining liquid will be assayed for calcium concentration using a Calcium Assay Kit from Abcam (catalog #ab102505). The protocol provided with the kit will be followed and the color intensity will be read out by a colorimetric plate reader. The values will be compared to a standard curve to calculate calcium concentrations. Results showing increased calcium in samples where both pMOZ702 and pMOZ14 were transformed compared to samples where only pMOZ702 was transformed will indicate that phosphorylated caseins bind calcium to a greater degree than non-phosphorylated caseins.

Example 6 Coexpression of Casein and Human Kinase in Soybean

Example 6 is an example of the expression of recombinant Beta casein, HsFam20A, and HsFam20C in *Glycine max* (l.) merr protoplasts isolated from immature cotyledon nodes using combinations of the pMOZ11 (expresses HsFam20C), pMOZ702 (expresses beta casein), pMOZ401 (expresses beta casein), and pMOZ882 (expresses beta casein, HsFam20A and HsFam20C) expression plasmids. In this example, *Glycine max* (l.) merr plants are incubated in a growth room at 28° C. with a 12 hour light 12 hour dark cycle for about 4 weeks. Seeds are removed from the plant and dissected to reveal the cotyledon tissue. The cotyledons are incubated in an enzyme solution (7.5 g/L cellulase R-10, 5 g/L macerozyme R-10, 1.4 g/L calcium chloride, 1 g/L BSA, 116.75 g/L mannitol, 4.25 g/L MES, and 1.5 g/L potassium chloride) overnight to digest the cell walls and isolate the protoplasts. After incubating in enzyme solution overnight, the protoplasts are strained to remove undigested tissue, spun down for 3 minutes at 0.1 RCF and washed with CPW9M (27.2 mg/L potassium phosphate monobasic, 101 mg/L potassium nitrate, 1.47 g/L calcium chloride dihydrate, 246 mg/L magnesium sulfate heptahydrate, 100 uL of 1 mM stock/L of copper sulfate pentahydrate, 93.2 g/L mannitol, and 980 mg/L MES, pH 5.7) three times. After the washes, the samples are incubated on ice for 30 minutes and then washed 2 times with MMG (90.5 g/L mannitol, 1.428 g/L magnesium chloride, 780 mg/L MES, pH 5.7). After the final wash with MMG, 20 uL of protoplast sample is imaged under an EVOS microscope using DHC-F01 disposable hemocytometers to get an approximate cell count per sample. Each sample is diluted to about 800,000 cells per mL. Once diluted, the protoplasts are incubated with 10 uL of purified DNA from *E. coli*, containing various combinations of pMOZ plasmids and PEG solution (14.8 g/L calcium chloride, 26.6 g/L mannitol, and 400 g/L PEG 4000) to initiate PEG mediated gene transfer.

In one condition the protoplasts are transformed with purified DNA containing pMOZ401. In a second condition the protoplasts are transformed with purified DNA containing pMOZ702 and pMOZ11. In a third condition the protoplasts are transformed with purified DNA containing pMOZ882.

Following incubation with PEG solution and DNA containing pMOZ plasmids, the protoplasts are washed three times with CPW9M and incubated at 25° C. in the dark for 72 hours. After 72 hours, the samples are spun down at 16.1 RCF for 5 minutes. The supernatant is removed and 50 uL of protein extraction buffer (800 uL of 500 mM sodium phosphate, 200 uL of 500 mM sodium phosphate dibasic, 1 mL 200 mM Sodium metabisulfite, 50 uL Tween-20, 5 mL 1M Trehalose, 3 mL diH2O) is added. The samples go through 3 cycles of 2 minutes in liquid nitrogen followed by 3 minutes in a 37° C. water bath. After three freeze-thaw cycles are complete, the mixtures are incubated on a rotisserie at 4 C for 1 hour and then centrifuged at 4000 RPM in with an Eppendorf 5415R centrifuge to pellet the transformed protoplasts. The supernatant containing the extracted protein is transferred to a new 1.7 mL tube.

Further continuing this example, protein samples from transformed protoplasts are analyzed with sodium dodecyl sulfate polyacrylamide gel electrophoresis (SDS PAGE). 20 uL of supernatant is mixed with 6.6 uL of protein loading buffer (900 uL of 4× Laemmli Sample Buffer [Bio-Rad Laboratories]+100 uL of 2-mercaptoethanol) and heated for 5 minutes at 95 C. These samples are loaded onto Bio-Rad "Any kD" precast polyacrylamide gels along with a standard protein ladder and phosphorylated and dephosphorylated beta casein samples from Sigma Aldrich. The gel is run in 1× Tris/*Glycine*/SDS Buffer (Bio-Rad Laboratories) at 150V for 45 minutes. The gel is removed from the gel box and placed in a PVDF Transfer Pack (Bio-Rad Laboratories), the transfer pack is placed in a Trans-Blot Turbo (Bio-Rad Laboratories) and the proteins are transferred to the PVDF membrane using the "Mini TGX" settings. The PVDF membrane containing the transferred proteins is first washed in 25 mL Protein Free Blocking Buffer (ThermoFisher) for 1 hour, then incubated with 5 mL of Protein Free Blocking Buffer containing 5 uL of anti-beta-casein polyclonal rabbit IgG at room temperature for 4 hours. The membrane is then washed three times with 10 mL TBST (20 mM Tris-HCl, 150 mM NaCl, 0.1% Tween 20) for 10 minutes at room temperature. Then the membrane is washed with 25 mL of Protein Free Blocking Buffer containing 2 uL of anti-rabbit IgG secondary antibody conjugated to horseradish peroxidase for 1 hour at room temperature and then poured off. The membrane is placed in a ChemiDoc MP imaging system (Bio-Rad Laboratories) and 1 mL of SuperSignal West Pico (ThermoFisher) luminescent imaging solution is added to the membrane. Images are captured using the Chemiluminescence setting on the ChemiDoc MP.

Further continuing this example, the casein proteins expressed in plant cells are probed on the anti-beta-casein Western blot to measure varying migration distances. In lanes containing beta casein coexpressed with a human kinase, two human kinases, a bovine kinase, or two bovine kinases, the bands are shifted upward on the gel relative to the sample transformed with only beta casein, showing that the molecular weight of the beta casein has increased suggesting the casein proteins are phosphorylated by the kinase or kinases.

As used herein, a "vector" is a plasmid comprising operably linked polynucleotide sequences that facilitate expression of a coding sequence in a particular host organism (e.g., a bacterial expression vector or a plant expression vector). Polynucleotide sequences that facilitate expression in prokaryotes can include, e.g., a promoter, an enhancer, an operator, and a ribosome binding site, often along with other sequences. Eukaryotic cells can use promoters, enhancers, termination and polyadenylation signals and other sequences that are generally different from those used by prokaryotes.

A specified nucleic acid is "derived from" a given nucleic acid when it is constructed using the given nucleic acid's sequence, or when the specified nucleic acid is constructed using the given nucleic acid. For example, a cDNA or EST is derived from an expressed mRNA.

As used herein, the term "plant" includes whole plant, plant organ, plant tissues, and plant cell and progeny of same, but is not limited to angiospems and gymnosperms such as *Arabidopsis*, potato, tomato, tobacco, alfalfa, lemice, carrot, strawberry, sugarbeet, cassava, sweet potato, soybean, lima bean, pea, chick pea, maize (corn), turf grass, wheat, rice, barley, sorghum, oat, oak, *eucalyptus*, walnut, palm and duckweed a well as fern and moss. Thus, a plant may be a monocot, a dicot, a vascular plant reproduced from spores such as fern or a nonvascular plant such as moss, liverwort, hornwort and algae. The term "plant," as used herein, also encompasses plant cells, seeds, plant progeny, propagule whether generated sexually or asexually, and descendants of any of these, such as cuttings or seed. Plant cells include suspension cultures, callus, embryos, meristematic regions, callus tissue, leaves, roots, shoots, gametophytes, sporophytes, pollen, seeds and microspores. Plants may be at various stages of maturity and may be grown in liquid or solid culture, or in soil or suitable media in pots, greenhouses or fields.

As used herein, the term "dicot" refers to a flowering plant whose embryos have two seed leaves or cotyledons. Examples of dicots include *Arabidopsis*, tobacco, tomato, potato, sweet potato, cassava, alfalfa, lima bean, pea, chick pea, soybean, carrot, strawberry, lettuce, oak, maple, walnut, rose, mint, squash, daisy, quinoa, buckwheat, mung bean, cow pea, lentil, lupin, peanut, fava bean, French beans, mustard, or cactus.

As used herein, the term "monocot" refers to a flowering plant whose embryos have one cotyledon or seed leaf. Examples of monocots include turf grass, maize (corn), rice, oat, wheat, barley, sorghum, orchid, iris, lily, onion, palm, and duckweed.

As used herein, the term "transgenic plant" means a plant that has been transformed with one or more exogenous nucleic acids. "Transformation" refers to a process by which a nucleic acid is stably integrated into the genome of a plant cell. "Stably transformed" refers to the permanent, or non-transient, retention, expression, or a combination thereof of a polynucleotide in and by a cell genome. A stably integrated polynucleotide is one that is a fixture within a transformed cell genome and can be replicated and propagated through successive progeny of the cell or resultant transformed plant. Transformation can occur under natural or artificial conditions using various methods. Transformation can rely on any method for the insertion of nucleic acid sequences into a prokaryotic or eukaryotic host cell, including *Agrobacterium*-mediated transformation as illustrated in U.S. Pat. Nos. 5,159,135; 5,824,877; 5,591,616 and 6,384,301, all of which are incorporated herein by reference in its entirety. Methods for plant transformation also include microprojectile bombardment as illustrated in U.S. Pat. Nos. 5,015,580; 5,550,318; 5,538,880; 6,153,812; 6,160,208; 6,288,312 and 6,399,861, all of which are incorporated herein by reference in its entirety. Recipient cells for the plant transformation include meristem cells, callus, immature embryos, hypocotyls explants, cotyledon explants, leaf explants, and gametic cells such as microspores, pollen, sperm and egg cells, and any cell from which a fertile plant can be regenerated, as described in U.S. Pat. Nos. 6,194,636; 6,232,526; 6,541,682 and 6,603,061 and U.S. Patent Application publication US 2004/0216189 A1, all of which are incorporated herein by reference in its entirety.

As used herein, the term "stably expressed" refers to expression and accumulation of a protein in a plant cell over time. As an example, a recombinant protein may accumulate because it is not degraded by endogenous plant proteases. As a further example, a recombinant protein is considered to be stably expressed in a plant if it is present in the plant in an amount of 1% or higher per total protein weight of soluble protein extractable from the plant.

As used herein, the term "recombinant" refers to nucleic acids or proteins formed by laboratory methods of genetic recombination (e.g., molecular cloning) to bring together genetic material from multiple sources, creating sequences that would otherwise not be found in the genome. Recombinant proteins may be expressed in vivo in various types of host cells, including plant cells, bacterial cells, fungal cells, avian cells, and mammalian cells. Recombinant proteins may also be generated in vitro. As used herein, the term "tagged protein" refers to a recombinant protein that includes additional peptides that are not part of the native protein and that remain after post-translational processing.

These and other valuable aspects of the embodiments of the present disclosure consequently further the state of the technology to at least the next level. While the disclosure has been described in conjunction with a specific best mode, it is to be understood that many alternatives, modifications, and variations will be apparent to those skilled in the art in light of the descriptions herein. Accordingly, it is intended to embrace all such alternatives, modifications, and variations that fall within the scope of the included claims. All matters set forth herein or shown in the accompanying drawings are to be interpreted in an illustrative and non-limiting sense.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Use of absolute or sequential terms, for example, "will," "will not," "shall," "shall not," "must," "must not," "first," "initially," "next," "subsequently," "before," "after," "lastly," and "finally," are not meant to limit scope of the present embodiments disclosed herein but as exemplary.

While some instances of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

These and other valuable aspects of the embodiments of the present disclosure consequently further the state of the technology to at least the next level. While the disclosure has been described in conjunction with a specific best mode, it is to be understood that many alternatives, modifications, and variations will be apparent to those skilled in the art in light of the descriptions herein. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. A soybean cell comprising a heterologous ruminant casein protein selected from the group consisting of κ-casein, $\alpha_{s1}$-casein, $\alpha_{s2}$-casein, and β-casein, and a heterologous non-plant kinase, wherein both proteins are expressed in the cell, and wherein the heterologous non-plant kinase phosphorylates the heterologous ruminant casein protein in vivo.

2. The soybean cell of claim 1, wherein the soybean cell comprises at least two heterologous ruminant casein proteins selected from the group consisting of κ-casein, $\alpha_{s1}$-casein, $\alpha_{s2}$-casein, and β-casein.

3. A method of modifying a soybean cell comprising:
   introducing into the soybean cell nucleic acids encoding
      (i) a heterologous ruminant casein protein selected from the group consisting of κ-casein, $\alpha_{s1}$-casein, $\alpha_{s2}$-casein, and β-casein, and (ii) a heterologous non-plant kinase; and
   expressing the heterologous ruminant casein protein and the heterologous non-plant kinase in the soybean cell, wherein the heterologous non-plant kinase phosphorylates the heterologous ruminant casein protein in vivo.

4. The method of claim 3, wherein the nucleic acids encode at least two different heterologous ruminant casein proteins selected from the group consisting of κ-casein, $\alpha_{s1}$-casein, $\alpha_{s2}$-casein, and β-casein.

5. A food composition comprising the phosphorylated heterologous ruminant casein protein produced by the method of claim 3, wherein the phosphorylated heterologous ruminant casein protein is selected from the group consisting of κ-casein, $\alpha_{s1}$-casein, $\alpha_{s2}$-casein, and β-casein.

6. The food composition of claim 5, further comprising one or more additional components selected from the group consisting of carbohydrates, fats, proteins, minerals, vitamins, and flavoring agents.

7. The food composition of claim 5, wherein the food composition is a cheese comprising the phosphorylated heterologous ruminant casein protein.

* * * * *